US009452996B2

(12) United States Patent
Illig et al.

(10) Patent No.: US 9,452,996 B2
(45) Date of Patent: Sep. 27, 2016

(54) INHIBITORS OF C-FMS KINASE

(71) Applicant: Janssen Pharmaceutica NV, Beerse (BE)

(72) Inventors: Carl R. Illig, Phoenixville, PA (US); Shelley K. Ballentine, Lansdale, PA (US); Jinsheng Chen, Exton, PA (US); Renee Louise Desjarlais, Saint Davids, PA (US); Sanath K. Meegalla, Garnet, NJ (US); Mark Wall, Lansdale, PA (US); Kenneth Wilson, Playas Del Coco (CR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/927,855

(22) Filed: Oct. 30, 2015

(65) Prior Publication Data

US 2016/0046602 A1    Feb. 18, 2016

Related U.S. Application Data

(62) Division of application No. 14/168,670, filed on Jan. 30, 2014, now Pat. No. 9,221,797, which is a division of application No. 11/736,635, filed on Apr. 18, 2007, now Pat. No. 8,674,100.

(60) Provisional application No. 60/793,694, filed on Apr. 20, 2006, provisional application No. 60/871,171, filed on Dec. 21, 2006.

(51) Int. Cl.
| C07D 403/02 | (2006.01) |
| C07D 405/12 | (2006.01) |
| C07D 491/056 | (2006.01) |
| C07D 401/12 | (2006.01) |
| C07D 233/90 | (2006.01) |
| C07D 235/24 | (2006.01) |
| C07D 307/68 | (2006.01) |
| C07D 401/14 | (2006.01) |
| C07D 403/12 | (2006.01) |
| C07C 53/18 | (2006.01) |

(52) U.S. Cl.
CPC ............ *C07D 401/12* (2013.01); *C07C 53/18* (2013.01); *C07D 233/90* (2013.01); *C07D 235/24* (2013.01); *C07D 307/68* (2013.01); *C07D 401/14* (2013.01); *C07D 403/12* (2013.01); *C07D 405/12* (2013.01); *C07D 491/056* (2013.01)

(58) Field of Classification Search
USPC ............................ 544/364; 546/272.7, 272.4
See application file for complete search history.

(56) References Cited

U.S. PATENT DOCUMENTS

| 6,100,254 A | 8/2000 | Budde et al. |
| 6,235,746 B1 | 5/2001 | Davis et al. |
| 6,346,625 B1 | 2/2002 | Karabelas et al. |
| 6,383,790 B1 | 5/2002 | Shokat |
| 7,414,050 B2 * | 8/2008 | Illig ................. C07D 401/12 514/222.5 |
| 7,429,603 B2 * | 9/2008 | Player ............... C07D 213/81 514/326 |
| 7,645,755 B2 * | 1/2010 | Illig ................. C07D 307/71 514/235.8 |
| 7,662,837 B2 * | 2/2010 | Illig ................. C07D 307/71 514/326 |
| 7,705,042 B2 * | 4/2010 | Illig ................. C07D 207/34 514/461 |
| 7,790,724 B2 * | 9/2010 | Player ............... C07D 307/68 514/252.05 |
| 8,722,718 B2 * | 5/2014 | Illig ................. C07D 207/34 514/397 |
| 8,815,867 B2 * | 8/2014 | Illig ................. C07D 207/34 514/253.01 |
| 8,859,602 B2 * | 10/2014 | Illig ................. C07D 207/34 514/397 |
| 8,895,584 B2 * | 11/2014 | Illig ................. C07D 401/12 514/318 |
| 9,221,797 B2 * | 12/2015 | Illig ................. C07D 233/90 |
| 9,266,866 B2 * | 2/2016 | Illig ................. C07D 207/34 |
| 9,296,726 B2 * | 3/2016 | Illig ................. C07D 401/12 |
| 2005/0113566 A1 | 5/2005 | Player et al. |
| 2006/0258666 A1 * | 11/2006 | Player ............... C07D 307/68 514/252.05 |

FOREIGN PATENT DOCUMENTS

| WO | WO 00/027820 | 5/2000 |
| WO | WO 01/047897 | 7/2001 |
| WO | WO 02/068406 | 9/2002 |
| WO | WO 2004/096795 | 11/2004 |

OTHER PUBLICATIONS

U.S. Appl. No. 11/736,617, Carl R. Illig et al.
U.S. Appl. No. 11/736,644, Carl R. Illig et al.
U.S. Appl. No. 11/736,650, Carl R. Illig et al.
U.S. Appl. No. 11/736,653, Carl R. Illig et al.
International Search Report dated Sep. 19, 2007 for PCT/US2007/066864.

* cited by examiner

Primary Examiner — Nyeemah A Grazier

(57) ABSTRACT

The invention is directed to compounds of Formula I:

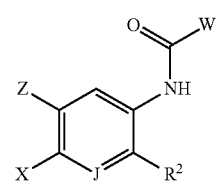

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, colon cancer, stomach cancer, hairy cell leukemia and non-small lung carcinoma; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including arthritis, prosthesis failure, osteolytic sarcoma, myeloma, and tumor metastasis to bone with the compounds of Formula I, are also provided.

16 Claims, No Drawings

INHIBITORS OF C-FMS KINASE

CROSS REFERENCE TO RELATED APPLICATION

This application is a divisional of co-pending U.S. patent application Ser. No. 14/168,670, filed Jan. 30, 2014, which is a divisional of U.S. patent application Ser. No. 11/736,635, filed Apr. 18, 2007, now issued as U.S. Pat. No. 8,674,100, which claims priority to U.S. Provisional Patent Applications 60/793,694, filed Apr. 20, 2006, and 60/871,171, filed Dec. 21, 2006, all of which are incorporated herein in their entirety.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain.

Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R overexpression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

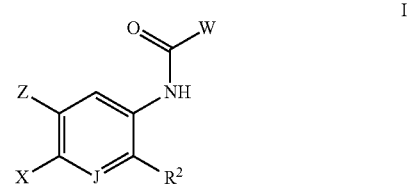

or a solvate, hydrate, tautomer or pharmaceutically acceptable salt thereof, wherein:
W is

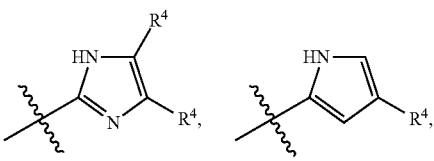

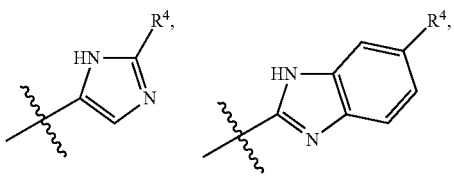

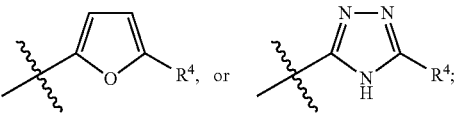

wherein each R⁴ is independently H, F, Cl, Br, I, OH, OCH₃, OCH₂CH₃, SC₍₁₋₄₎alkyl, SOC₍₁₋₄₎alkyl, SO₂C₍₁₋₄₎alkyl, —C₍₁₋₃₎alkyl, —CO₂R$^d$, CONR$^e$R$^f$, C≡CR$^g$, or CN;
  wherein R$^d$ is H, or —C₍₁₋₃₎alkyl;
    R$^e$ is H, or —C₍₁₋₃₎alkyl;
    R$^f$ is H, or —C₍₁₋₃₎alkyl; and
    R$^g$ is H, —CH₂OH, or —CH₂CH₂OH;

R² is cycloalkyl, spiro-substituted cycloalkenyl heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, C₍₁₋₃₎alkyl, and C₍₁₋₄₎alkyl;

Z is H, F, or CH₃;

J is CH, or N;

X is —C₍₁₋₆₎alkylR¹, alkenyl, propenyl-NA¹A², —CH=CH—CO₂R$^a$ (including both E and Z stereochemistry for said CH=CH bond), —C₍₁₋₄₎alkylR³R$^{4a}$, or —CH₂-heteroaryl-C₍₁₋₄₎alkyl-R¹;
  wherein R¹ is —CN, —SO₂NA¹A², —SO₂R$^a$, —SCH₂CH₂NA¹A², —SOCH₂CH₂NA¹A², —SO₂CH₂CH₂NA¹A², —S—C(O)C₍₁₋₄₎alkyl, —S—CH₂-4-methoxy phenyl, —OC₍₁₋₄₎alkylNA¹A², —NA¹A², —NHSO₂R$^a$, —NHCOR$^a$, —NHSO₂CH₂CH₂NA¹A², —NHCOCH₂CH₂NA¹A², —CONH₂, —CONHCH₂CH₂CH₂OH, CONHCH₂CH₂N(C₍₁₋₄₎alkyl)₂, —NHCONH₂, —NHCONHCH₂CH₂OH, —NHCOCONH₂, —NR$_a$CH₂CH₂NA¹A², CO₂R$^a$, pyridyl, 2-methyl pyridyl, —OCH₂CH₂OR$^a$, —OCH₂CH₂OCH₂CH₂NA¹A², —OCH₂CH₂NA¹CH₂CH₂OR$^a$, —NA¹CH₂CH₂OCH₂CH₂OR$^a$, —OCOR$^a$, or —CH₂OCOCH₃;

A¹ is H or —C₍₁₋₄₎alkyl;
A² is —C₍₁₋₄₎alkyl, —CH₂CH₂OR$^a$, —COR$^a$, —CH₂CH₂SC₍₁₋₄₎alkyl, —CH₂CH₂SOC₍₁₋₄₎alkyl, pyridyl, —CH₂CH₂OCH₂CH₂OR$^a$, or —CH₂CH₂SO₂C₍₁₋₄₎alkyl;
  alternatively, A¹ and A² may be taken together with their attached nitrogen to form a heterocyclic ring selected from the following:

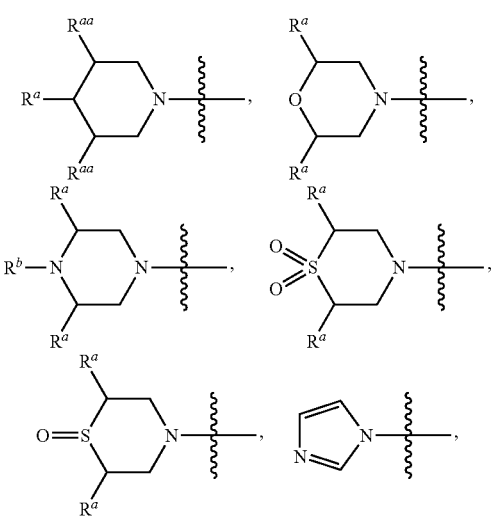

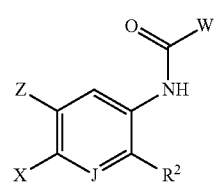

wherein:
R$^a$ is H or C₍₁₋₄₎alkyl;
R$^{aa}$ is H or C₍₁₋₄₎alkyl;
R$^b$ is H, —C₍₁₋₄₎alkyl, alkoxyether, —C(O)C₍₁₋₄₎alkyl, —C₍₁₋₄₎alkyl-OH, —C₍₁₋₄₎alkyl-O—C₍₁₋₄₎alkyl, —C₍₁₋₄₎alkyl-C(O)O—C₍₁₋₄₎alkyl, —C₍₁₋₄₎alkylC(O)OH, —C₍₁₋₄₎alkylC(O)ONa, or —CH₂C(O)C₍₁₋₄₎alkyl; and
R³ and R$^{4a}$ are independently —CH₂OH, —OCH₃, —CH₂OCH₃, —CO₂H, —CO₂C₍₁₋₄₎alkyl, —OC(O)C₍₁₋₄₎ alkyl, or —OH.

Herein and throughout this application, when two substituents appear on an alkyl group, such as —C₍₁₋₄₎alkylR³R$^{4a}$, it is understood that the two substituents may independently be attached the same or different carbon atoms.

Herein and throughout this application, the terms "Me", "Et", "Pr", and "Bu" refer to methyl, ethyl, propyl, and butyl respectively.

DETAILED DESCRIPTION OF THE INVENTION

The invention is directed to the novel compounds of Formula I:

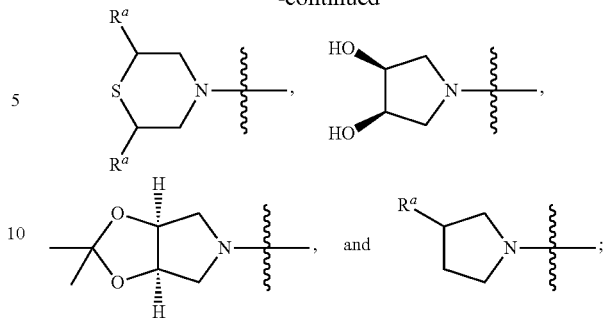

or a solvate, hydrate, tautomer or pharmaceutically acceptable salt thereof, wherein:
W is

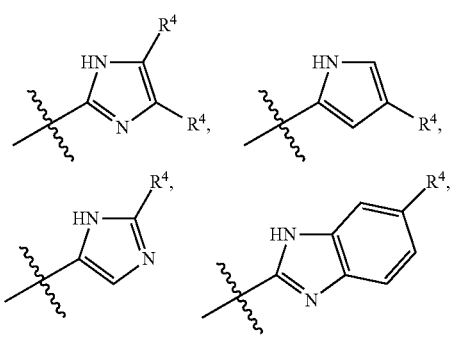

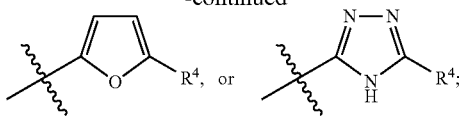

wherein each R⁴ is independently H, F, Cl, Br, I, OH, OCH₃, OCH₂CH₃, SC$_{(1-4)}$alkyl, SOC$_{(1-4)}$alkyl, SO₂C$_{(1-4)}$alkyl, —C$_{(1-3)}$alkyl, —CO₂R$^d$, CONR$^e$R$^f$, C≡CR$^g$, or CN; wherein R$^d$ is H, or —C$_{(1-3)}$alkyl;
R$^e$ is H, or —C$_{(1-3)}$alkyl;
R$^f$ is H, or —C$_{(1-3)}$alkyl; and
R$^g$ is H, —CH₂OH, or —CH₂CH₂OH;
R² is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro[5.5]undec-2-enyl) heterocyclyl (including piperidinyl), spirosubstituted piperidinyl (including 3-aza-spiro[5.5]undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy, C$_{(1-3)}$alkyl, and C$_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);
Z is H, F, or CH₃;
J is CH, or N;
X is —C$_{(1-6)}$alkylR¹ (including —CH₂R¹, —CH₂CH₂R¹, and —C(C$_{(1-4)}$alkyl)₂R¹), alkenyl (including propenyl), propenyl-NA¹A², —CH═CH—CO₂R$^a$ (including both E and Z stereochemistry for said CH═CH bond), —C$_{(1-4)}$alkylR³R$^{4a}$, or —CH₂-heteroaryl-C$_{(1-4)}$alkyl-R¹;
wherein:
R¹ is —CN, —SO₂NA¹A², —SO₂R$^a$, —SCH₂CH₂NA¹A², —SOCH₂CH₂NA¹A², —SO₂CH₂CH₂NA¹A², —S—C(O)C$_{(1-4)}$alkyl (including —S—C(O)CH₃), —S—CH₂-4-methoxy phenyl, —OC$_{(1-4)}$alkylNA¹A² (including —OCH₂CH₂NA¹A²), —NA¹A², —NHSO₂R$^a$ (including —NHSO₂CH₃), —NHCOR$^a$ (including —NHCOCH₃), —NHSO₂CH₂CH₂NA¹A², —NHCOCH₂CH₂NA¹A², —CONH₂, —CONHCH₂CH₂CH₂OH, CONHCH₂CH₂N(C$_{(1-4)}$alkyl)₂ (including CONHCH₂CH₂N(CH₃)₂), —NHCONH₂, —NHCONHCH₂CH₂OH, —NHCOCONH₂, —NR$_a$CH₂CH₂NA¹A², CO₂R$^a$, pyridyl, —OCH₂CH₂OR$^a$, —OCH₂CH₂OCH₂CH₂NA¹A², —OCH₂CH₂NA¹CH₂CH₂OR$^a$, —NA¹CH₂CH₂OCH₂CH₂OR$^a$—OCOR$^a$ (including —OCOCH₃), or —CH₂OCOCH₃;
A¹ is H or —C$_{(1-4)}$alkyl;
A² is —C$_{(1-4)}$alkyl, —CH₂CH₂OR$^a$ (including —CH₂CH₂OCH₃), —COR$^a$ (including —COCH₃), —CH₂CH₂SC$_{(1-4)}$alkyl (including —CH₂CH₂SCH₃), —CH₂CH₂SOC$_{(1-4)}$alkyl (including —CH₂CH₂SOCH₃), pyridyl, 2-methyl pyridyl, —CH₂CH₂OCH₂CH₂OR$^a$, or —CH₂CH₂SO₂C$_{(1-4)}$alkyl (including —CH₂CH₂SO₂CH₃);

alternatively, A¹ and A² may be taken together with their attached nitrogen to form a heterocyclic ring selected from the following:

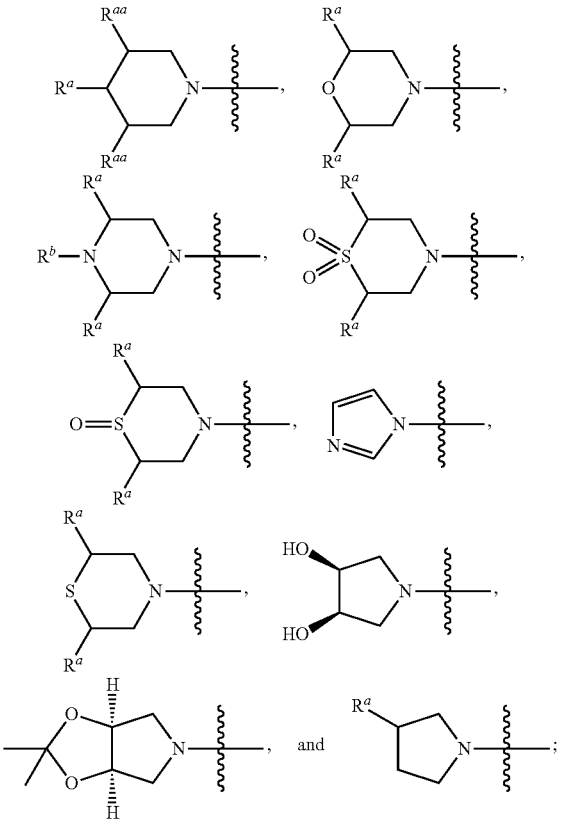

wherein:
R$^a$ is H or C$_{(1-4)}$alkyl;
R$^{aa}$ is H or C$_{(1-4)}$alkyl;
R$^b$ is H, —C$_{(1-4)}$alkyl, alkoxyether, —C(O)C$_{(1-4)}$alkyl, —C$_{(1-4)}$alkyl-OH (including —CH₂CH₂OH), —C$_{(1-4)}$alkyl-O—C$_{(1-4)}$alkyl (including —CH₂CH₂OCH₃), —C$_{(1-4)}$alkyl-C(O)O—C$_{(1-4)}$alkyl (including —CH₂C(O)OCH₂CH₃), —C$_{(1-4)}$alkylC(O)OH (including —CH₂C(O)OH), —C$_{(1-4)}$alkylC(O)ONa (including —CH₂C(O)ONa), or —CH₂C(O)C$_{(1-4)}$alkyl; and
R³ and R$^{4a}$ are independently —CH₂OH, —OCH₃, —CH₂OCH₃, —CO₂H, —CO₂C$_{(1-4)}$alkyl (including —CO₂CH₂CH₃), OC(O)C$_{(1-4)}$alkyl (including —OC(O)CH₃), or —OH.

Preferred compounds of Formula I are those wherein W is substituted with one —CN.

Other preferred compounds of Formula I are those wherein:
W is

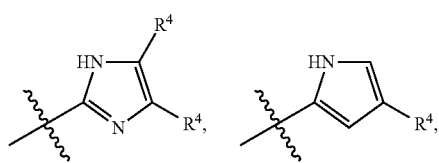

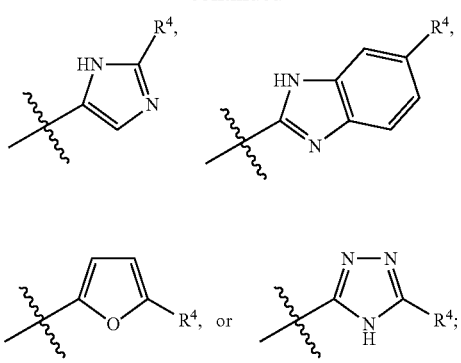

wherein each R⁴ is independently H, F, Cl, Br, I, OH, OCH₃, OCH₂CH₃, SC₍₁₋₄₎alkyl, SOC₍₁₋₄₎alkyl, SO₂C₍₁₋₄₎alkyl, —C₍₁₋₃₎alkyl, CO₂R$^d$, CONR$^e$R$^f$, C≡CR$^g$, or CN;
wherein R$^d$ is H, or —C₍₁₋₃₎alkyl;
R$^e$ is H, or —C₍₁₋₃₎alkyl;
R$^f$ is H, or —C₍₁₋₃₎alkyl; and
R$^g$ is H, —CH₂OH, or —CH₂CH₂OH;
R² is

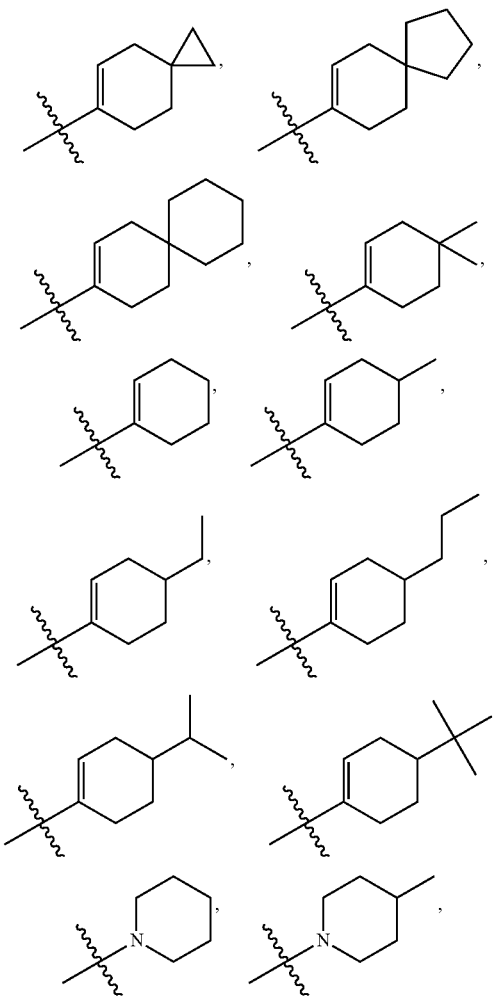

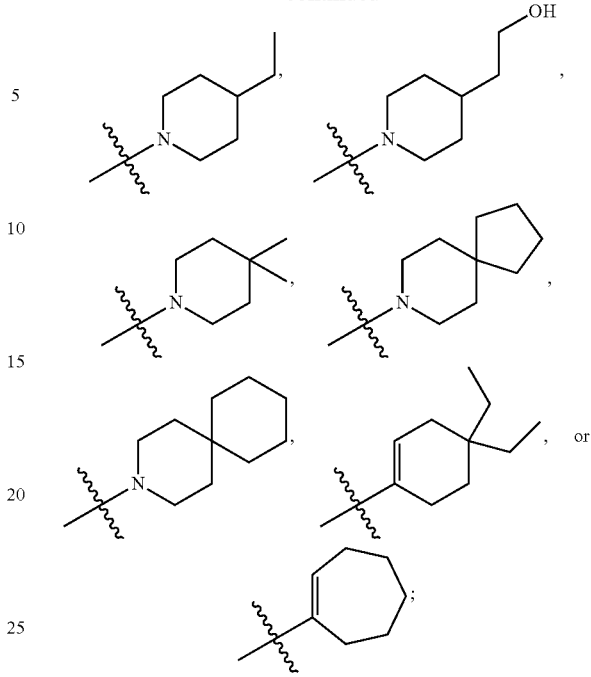

Z is H, F, or CH₃;
J is CH, or N;
X is —C₍₁₋₆₎alkylR¹, alkenyl, propenyl-NA¹A², —CH=CH—CO₂R$^a$, —C₍₁₋₄₎alkylR³R$^{4a}$, or —CH₂-heteroaryl-C₍₁₋₄₎alkyl-R¹;
wherein:
R¹ is —CN, —SO₂NA¹A², —SO₂R$^a$, —SCH₂CH₂NA¹A², —SOCH₂CH₂NA¹A², —SO₂CH₂CH₂NA¹A², —S—C(O)C₍₁₋₄₎alkyl, —S—CH₂-4-methoxy phenyl, —OC₍₁₋₄₎alkylNA¹A², —NA¹A², —NHSO₂CH₃, —NHCOCH₃, —CONH₂, —CONHCH₂CH₂CH₂OH, —CONHCH₂CH₂N(C₍₁₋₄₎alkyl)₂, —NHCONH₂, —NHCONHCH₂CH₂OH, —NHCOCONH₂, —NR$_a$CH₂CH₂NA¹A², —CO₂R$^a$, pyridyl, —OCOCH₃, or —CH₂OCOCH₃;
A¹ is H or —C₍₁₋₄₎alkyl;
A² is —C₍₁₋₄₎alkyl, —CH₂CH₂OR$^a$, —COR$^a$, —CH₂CH₂SC₍₁₋₄₎alkyl, —CH₂CH₂SOC₍₁₋₄₎alkyl, pyridyl, 2-methyl pyridyl, or —CH₂CH₂SO₂C₍₁₋₄₎alkyl;
alternatively, A¹ and A² may be taken together with their attached nitrogen to form a heterocyclic ring selected from the following:

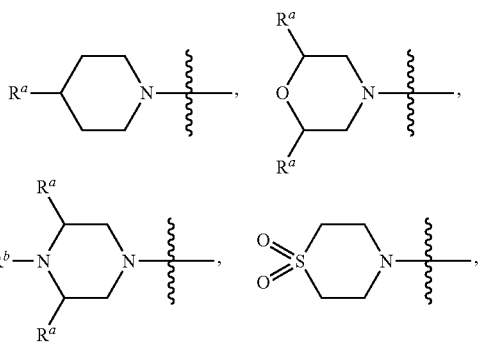

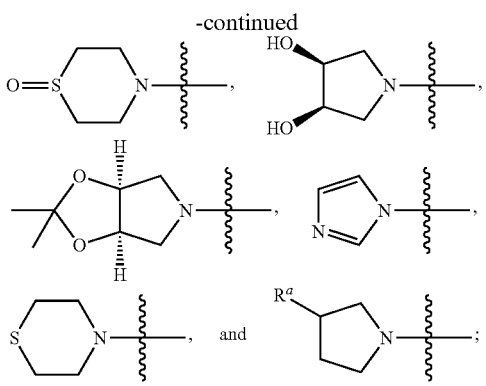

wherein:
$R^a$ is H or $C_{(1-4)}$alkyl;
$R^b$ is H, —$C_{(1-4)}$alkyl, alkoxyether, —C(O)$C_{(1-4)}$ alkyl, —$C_{(1-4)}$alkyl-OH, —$C_{(1-4)}$alkyl-O—$C_{(1-4)}$ alkyl, —$C_{(1-4)}$alkyl-C(O)O—$C_{(1-4)}$alkyl, —$C_{(1-4)}$alkylC(O)OH, —$C_{(1-4)}$alkylC(O)ONa, or —CH$_2$C(O)$C_{(1-4)}$alkyl; and $R^3$ and $R^{4a}$ are independently —CH$_2$OH, —OCH$_3$, —CH$_2$OCH$_3$, —CO$_2$H, —CO$_2C_{(1-4)}$alkyl, OC(O)$C_{(1-4)}$ alkyl, or —OH;

and solvates, hydrates, tautomers and pharmaceutically acceptable salts thereof.

Other preferred compounds of Formula I are those wherein:

W is

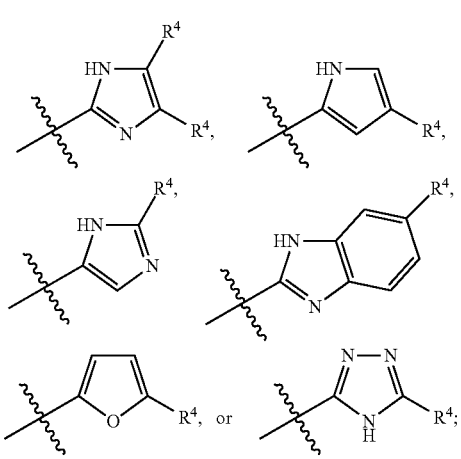

wherein each $R^4$ is independently H, F, Cl, Br, I, OH, OCH$_3$, OCH$_2$CH$_3$, S$C_{(1-4)}$alkyl, SO$C_{(1-4)}$alkyl, SO$_2C_{(1-4)}$alkyl, —$C_{(1-3)}$alkyl, CO$_2R^d$, CONR$^eR^f$, C≡CR$^g$, or CN; wherein $R^d$ is H, or —$C_{(1-3)}$alkyl;
$R^e$ is H, or —$C_{(1-3)}$alkyl;
$R^f$ is H, or —$C_{(1-3)}$alkyl; and
$R^g$ is H, —CH$_2$OH, or —CH$_2$CH$_2$OH;

$R^2$ is

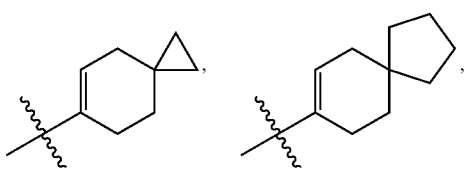

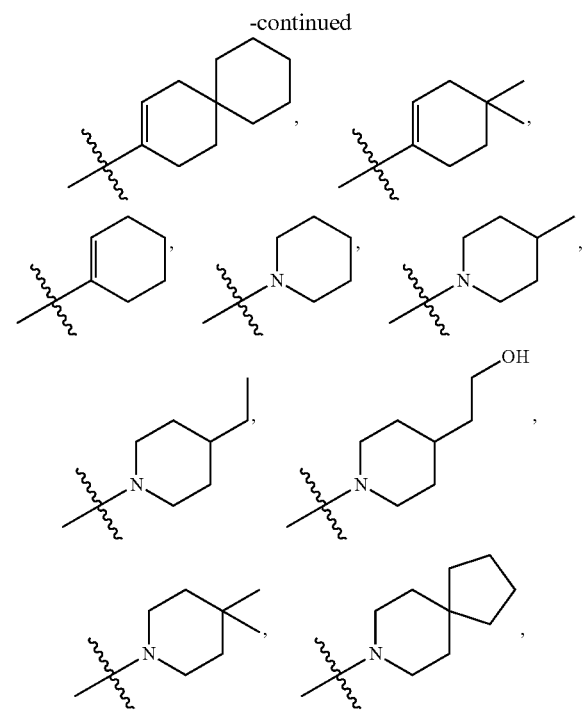

Z is H, F, or CH$_3$;

J is CH, or N;

X is —$C_{(1-5)}$alkylR$^1$, alkenyl, propenyl-NA$^1$A$^2$, —CH=CH—CO$_2R^a$, —$C_{(1-4)}$alkylR$^3$R$^{4a}$, or —CH$_2$-heteroaryl-$C_{(1-4)}$alkyl-R$^1$;

wherein:

$R^1$ is —CN, —SO$_2$NA$^1$A$^2$, —SO$_2R^a$, —SCH$_2$CH$_2$NA$^1$A$^2$, —SOCH$_2$CH$_2$NA$^1$A$^2$, —SO$_2$CH$_2$CH$_2$NA$^1$A$^2$, —S—C(O)$C_{(1-4)}$alkyl, —S—CH$_2$-4-methoxy phenyl, —O$C_{(1-4)}$alkylNA$^1$A$^2$, —NA$^1$A$^2$, —NHSO$_2$CH$_3$, —NHCOCH$_3$, —CONH$_2$, —CONHCH$_2$CH$_2$CH$_2$OH, —CONHCH$_2$CH$_2$N(C$_{(1-4)}$ alkyl)$_2$, —NHCONH$_2$, —NHCONHCH$_2$CH$_2$OH, —NHCOCONH$_2$, —NR$_a$CH$_2$CH$_2$NA$^1$A$^2$, —CO$_2R^a$, pyridyl, —OCOCH$_3$, or —CH$_2$OCOCH$_3$;

$A^1$ is H or —$C_{(1-4)}$alkyl;

$A^2$ is —$C_{(1-4)}$alkyl, —CH$_2$CH$_2$OR$^a$, —COR$^a$, —CH$_2$CH$_2$S$C_{(1-4)}$alkyl, —CH$_2$CH$_2$SO$C_{(1-4)}$alkyl, pyridyl, 2-methyl pyridyl, or —CH$_2$CH$_2$SO$_2C_{(1-4)}$ alkyl;

alternatively, $A^1$ and $A^2$ may be taken together with their attached nitrogen to form a heterocyclic ring selected from the following:

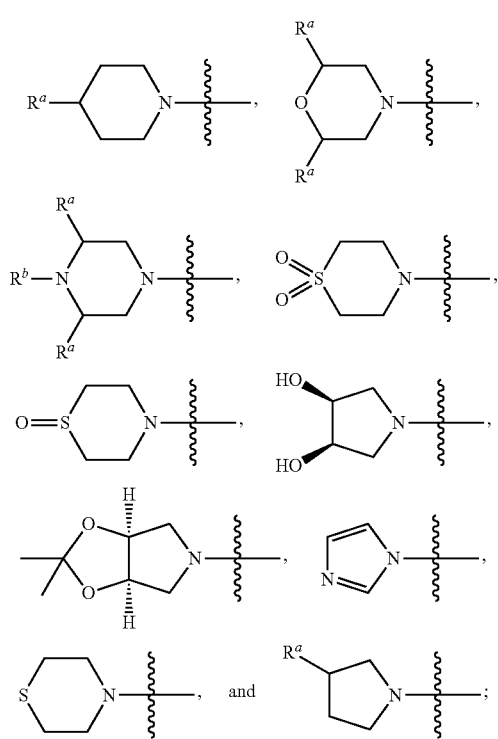

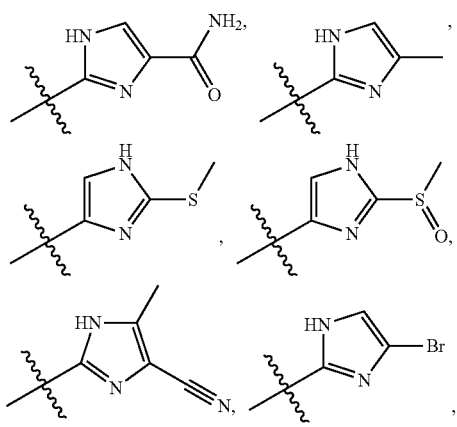

wherein:

R$^a$ is H or C$_{(1-4)}$alkyl;

R$^b$ is H, —C$_{(1-4)}$alkyl, alkoxyether, —C(O)C$_{(1-4)}$alkyl, —C$_{(1-4)}$alkyl-OH, —C$_{(1-4)}$alkyl-O—C$_{(1-4)}$alkyl, —C$_{(1-4)}$alkyl-C(O)O—C$_{(1-4)}$alkyl, —C$_{(1-4)}$alkylC(O)OH, —C$_{(1-4)}$alkylC(O)ONa, or —CH$_2$C(O)—C$_{(1-4)}$alkyl; and R$^3$ and R$^{4a}$ are independently —CH$_2$OH, —OCH$_3$, —CH$_2$OCH$_3$, —CO$_2$H, —CO$_2$C$_{(1-4)}$alkyl, OC(O)C$_{(1-4)}$alkyl, or —OH;

and solvates, hydrates, tautomers and pharmaceutically acceptable salts thereof.

Other preferred compounds of Formula I are those wherein:

W is

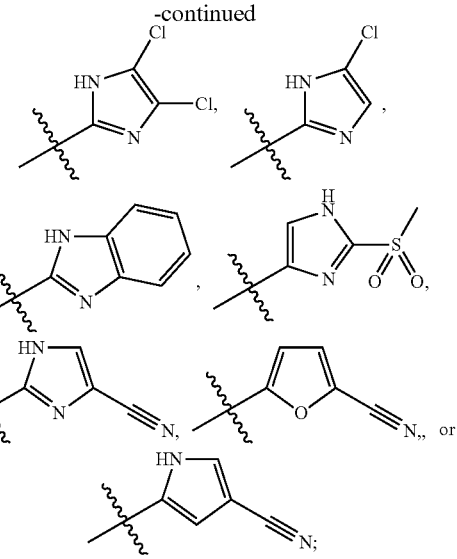

R$^2$ is

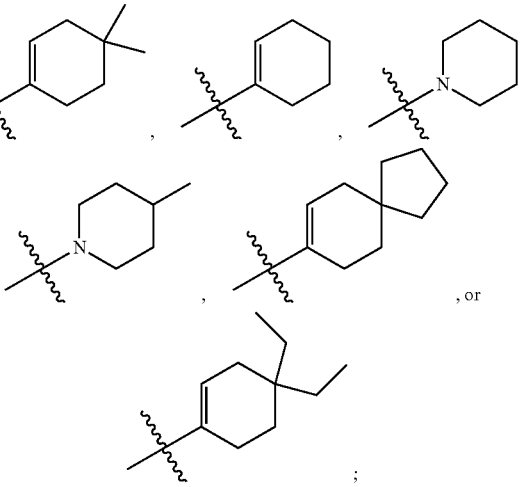

Z is H;

J is CH, or N;

X is —C$_{(1-5)}$alkylR$^1$, —CH═CH—CO$_2$H wherein said CH═CH bond has E stereochemistry, —C$_{(1-4)}$alkylR$^3$R$^{4a}$, propenyl-NA$^1$A$^2$, or propenyl;

wherein:

R$^1$ is —SO$_2$NA$^1$A$^2$, —S—C(O)CH$_3$, —S—CH$_2$-4-methoxy phenyl, —OC$_{(1-4)}$alkylNA$^1$A$^2$, NA$^1$A$^2$, NHCH$_2$CH$_2$NA$^1$A$^2$, NHSO$_2$CH$_3$, NCOCH$_3$, CONH$_2$, CONHCH$_2$CH$_2$OH, CONHCH$_2$CH$_2$N(CH$_3$)$_2$, NHCONH$_2$, NHCONHCH$_2$CH$_2$OH, NHCOCONH$_2$, CO$_2$R$^a$, or pyridyl;

A$^1$ is H or —C$_{(1-4)}$alkyl;

A$^2$ is —C$_{(1-4)}$alkyl, —CH$_2$CH$_2$OR$^a$, —COCH$_3$, —CH$_2$CH$_2$SC$_{(1-4)}$alkyl, pyridyl, 2-methyl pyridyl, or —CH$_2$CH$_2$SO$_2$C$_{(1-4)}$alkyl;

alternatively, A$^1$ and A$^2$ may be taken together with their attached nitrogen to form a heterocyclic ring selected from the following:

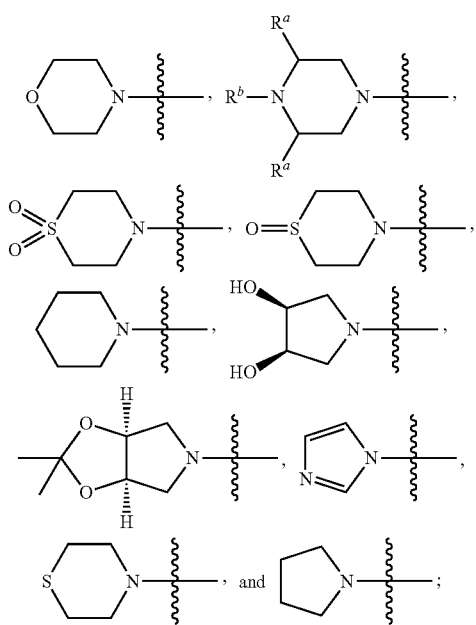

wherein:

$R^a$ is H or $C_{(1-4)}$alkyl;

$R^b$ is H, $CH_2CH_2OH$, —$CH_2CH_2OCH_3$, —$CH_2C(O)OCH_2CH_3$, $CH_2C(O)OH$, —$CH_2C(O)ONa$, $C(O)CH_3$, or —$C_{(1-4)}$alkyl; and $R^3$ and $R^{4a}$ are independently —$OCH_3$, —$CH_2OCH_3$, —$CO_2H$, —$OC(O)CH_3$, or —OH;

and solvates, hydrates, tautomers and pharmaceutically acceptable salts thereof.

Other preferred compounds of Formula I are those wherein:

W is

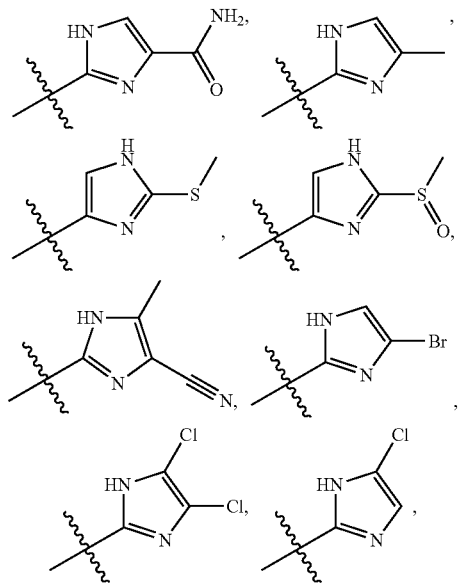

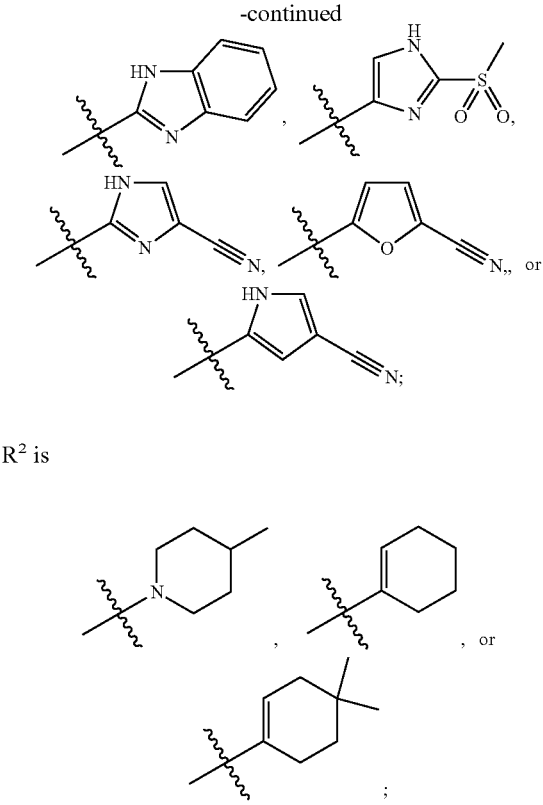

$R^2$ is

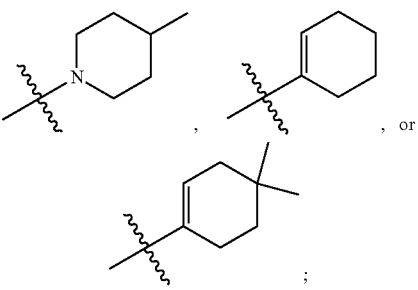

Z is H;

J is CH, or N;

X is —$CH_2R^1$, —$CH_2CH_2R^1$, —$C(CH_3)_2R^1$, —CH=CH—$CO_2H$ wherein said CH=CH bond has E stereochemistry, —$C_{(1-4)}$alkyl$R^3R^{4a}$, propenyl-$NA^1A^2$, or propenyl;

wherein:

$R^1$ is —$SO_2NA^1A^2$, —S—$C(O)CH_3$, —S—$CH_2$-4-methoxy phenyl, —$OCH_2CH_2NA^1A^2$, —$NA^1A^2$, —$NHCH_2CH_2NA^1A^2$, —$NHSO_2CH_3$, —$NHCOCH_3$, —$CONH_2$, —$CONHCH_2CH_2OH$, —$CONHCH_2CH_2N(CH_3)_2$, —$NHCONH_2$, —$NHCONHCH_2CH_2OH$, —$NHCOCONH_2$, or —$CO_2R^a$;

$A^1$ is H or —$C_{(1-4)}$alkyl;

$A^2$ is —$C_{(1-4)}$alkyl, —$C(O)CH_3$, —$CH_2CH_2OCH_3$, —$CH_2CH_2OH$, —$CH_2CH_2SCH_3$, pyridyl, 2-methyl pyridyl, or —$CH_2CH_2SO_2CH_3$;

alternatively, $A^1$ and $A^2$ may be taken together with their attached nitrogen to form a heterocyclic ring selected from the following:

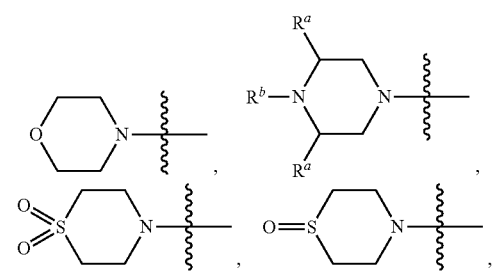

-continued wherein:

R$^a$ is H, CH$_3$, or CH$_2$CH$_3$;

R$^b$ is H, CH$_2$CH$_2$OH, —CH$_2$CH$_2$OCH$_3$, —CH$_2$C(O)OCH$_2$CH$_3$, CH$_2$C(O)OH, —CH$_2$C(O)ONa, CH$_2$CH$_3$, C(O)CH$_3$, or CH$_3$; and R$^3$ and R$^{4a}$ are independently, —OCH$_3$, —CH$_2$OCH$_3$, —CO$_2$H, —OC(O)CH$_3$, or —OH;

and solvates, hydrates, tautomers and pharmaceutically acceptable salts thereof.

Other preferred compounds of Formula I are those wherein:

W is

R$^2$ is

Z is H;

J is CH, or N;

X is —C$_{(1-6)}$alkylR$^1$, or propenyl-NA$^1$A$^2$, wherein:

R$^1$ is —S—C(O)C$_{(1-4)}$alkyl, —S—CH$_2$-4-methoxy phenyl, wherein:

R$^a$ is H or C$_{(1-4)}$alkyl; and

R$^b$ is —C$_{(1-4)}$alkyl-OH, —C$_{(1-4)}$alkyl-O—C$_{(1-4)}$alkyl, —C$_{(1-4)}$alkyl-C(O)O—C$_{(1-4)}$alkyl, —C$_{(1-4)}$alkylC(O)OH, or —C$_{(1-4)}$alkylC(O)ONa;

or a solvate, hydrate, tautomer or pharmaceutically acceptable salt thereof.

Other preferred compounds of Formula I are those wherein:

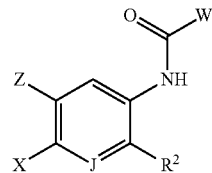

W is

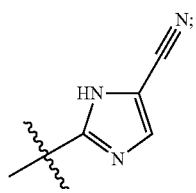 [SMILES: *c1ncc(C#N)[nH]1]

$R^2$ is

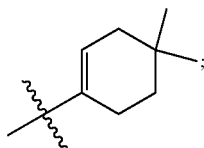 [SMILES: *C1=CCC(C)(C)CC1]

Z is H;
J is CH, or N (preferably, J is CH);
X is —$C_{(1-6)}$alkyl$R^1$ (preferably, —$C_{(1-4)}$alkyl$R^1$) wherein:
  $R^1$ is

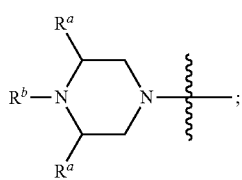

wherein:
  $R^a$ is H or $C_{(1-4)}$alkyl (preferably, H); and
  $R^b$ is —$C_{(1-4)}$alkyl-OH, —$C_{(1-4)}$alkyl-O—$C_{(1-4)}$alkyl, —$C_{(1-4)}$alkyl-C(O)O—$C_{(1-4)}$alkyl, —$C_{(1-4)}$alkylC(O)OH, or —$C_{(1-4)}$alkylC(O)ONa (preferably, —$C_{(1-4)}$alkyl-OH);
and solvates, hydrates, tautomers or pharmaceutically acceptable salts thereof.

Another embodiment is compounds of formula I wherein:
W is

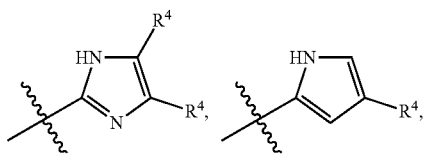

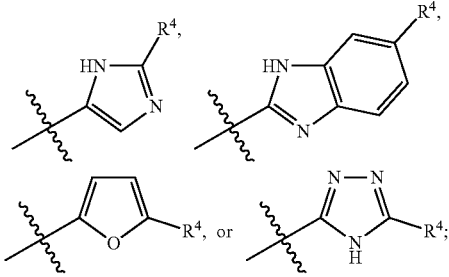

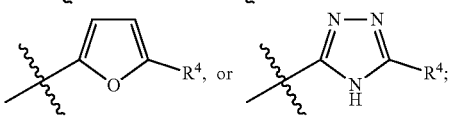

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, $C\equiv CR^g$, or CN;
  wherein $R^d$ is H, or —$C_{(1-3)}$alkyl;
    $R^e$ is H, or —$C_{(1-3)}$alkyl;
    $R^f$ is H, or —$C_{(1-3)}$alkyl; and
    $R^g$ is H, —$CH_2OH$, or —$CH_2CH_2OH$; $R^2$ is cycloalkyl, spiro-substituted cycloalkenyl heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;
Z is H, F, or $CH_3$;
J is CH, or N;
X is —$C_{(1-6)}$alkyl$R^1$, alkenyl, —CH=CH—$CO_2R^a$, —$C_{(1-4)}$ alkyl$R^3R^{4a}$, or —$CH_2$-heteroaryl-$C_{(1-4)}$alkyl-$R^1$;
wherein:
  $R^1$ is —CN, —$SO_2NA^1A^2$, —$SO_2R^a$, —$SCH_2CH_2NA^1A^2$, —$SOCH_2CH_2NA^1A^2$, —$SO_2CH_2CH_2NA^1A^2$, —$OC_{(1-4)}$alkyl$NA^1A^2$, —$NA^1A^2$, —$NHSO_2R^a$, —$NHCOR^a$, —$NHSO_2CH_2CH_2NA^1A^2$, —$NHCOCH_2CH_2NA^1A^2$, —$CONH_2$, —$CONHCH_2CH_2CH_2OH$, $CONHCH_2CH_2N(C_{(1-4)}$alkyl$)_2$, —$NHCONH_2$, —$NHCONHCH_2CH_2OH$, —$NHCOCONH_2$, —$NR_aCH_2CH_2NA^1A^2$, $CO_2R^a$, pyridyl, —$OCH_2CH_2OR^a$, —$OCH_2CH_2OCH_2CH_2NA^1A^2$, —$OCH_2CH_2NA^1CH_2CH_2OR^a$, —$NA^1CH_2CH_2OCH_2CH_2OR^a$—$OCOR^a$, or —$CH_2OCOCH_3$;
  $A^1$ is H or —$C_{(1-4)}$alkyl;
  $A^2$ is —$C_{(1-4)}$alkyl, —$CH_2CH_2OR^a$, —$COR^a$, —$CH_2CH_2SC_{(1-4)}$alkyl, —$CH_2CH_2SOC_{(1-4)}$alkyl, pyridyl, —$CH_2CH_2OCH_2CH_2OR^a$, or —$CH_2CH_2SO_2C_{(1-4)}$alkyl;
  alternatively, $A^1$ and $A^2$ may be taken together with their attached nitrogen to form a heterocyclic ring selected from the following:

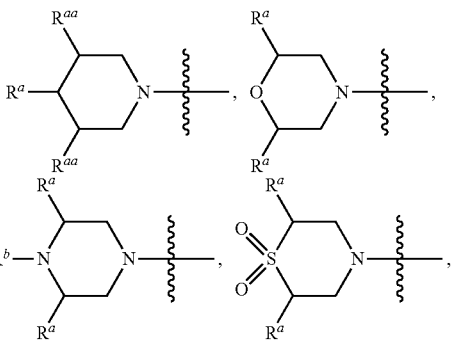

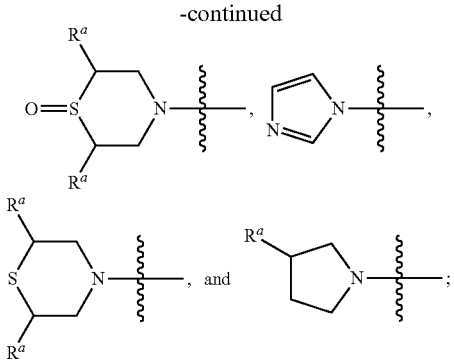

wherein:
R$^a$ is H or C$_{(1-4)}$alkyl;
R$^{aa}$ is H or C$_{(1-4)}$alkyl;
R$^b$ is H, —C$_{(1-4)}$alkyl, alkoxyether, —C(O)C$_{(1-4)}$alkyl, or —CH$_2$C(O)C$_{(1-4)}$alkyl; and
R$^3$ and R$^{4a}$ are independently —CH$_2$OH, —OCH$_3$, —CH$_2$OCH$_3$, —CO$_2$H, —CO$_2$C$_{(1-4)}$alkyl, OC(O)C$_{(1-4)}$alkyl, or —OH;
and solvates, hydrates, tautomers, and pharmaceutically acceptable salts thereof.

Preferred compounds of Formula I are those wherein W is substituted with one —CN.

Other preferred compounds of Formula I are those wherein:
W is

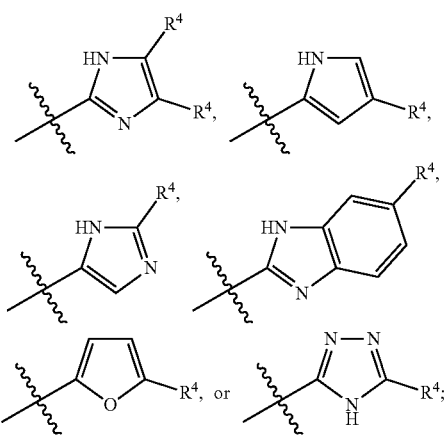

wherein each R$^4$ is independently H, F, Cl, Br, I, OH, OCH$_3$, OCH$_2$CH$_3$, SC$_{(1-4)}$alkyl, SOC$_{(1-4)}$alkyl, SO$_2$C$_{(1-4)}$alkyl, —C$_{(1-3)}$alkyl, CO$_2$R$^d$, CONR$^e$R$^f$, C≡CR$^g$, or CN;
wherein R$^d$ is H, or —C$_{(1-3)}$alkyl;
R$^e$ is H, or —C$_{(1-3)}$alkyl;
R$^f$ is H, or —C$_{(1-3)}$alkyl; and
R$^g$ is H, —CH$_2$OH, or —CH$_2$CH$_2$OH;
R$^2$ is

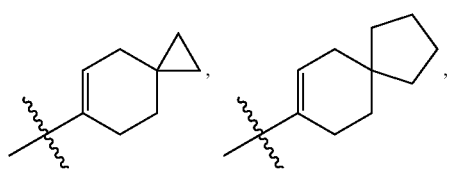

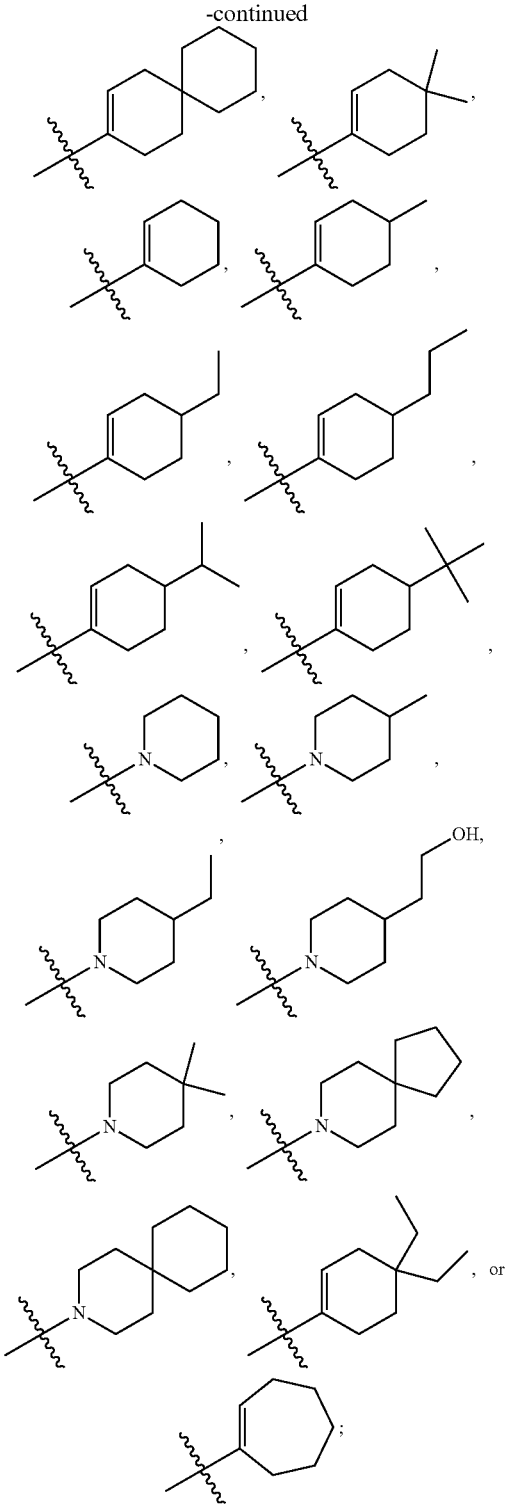

Z is H, F, or CH$_3$;
J is CH, or N;
X is —C$_{(1-6)}$alkylR$^1$, alkenyl, —CH=CH—CO$_2$R$^a$, —C$_{(1-4)}$alkylR$^3$R$^{4a}$, or —CH$_2$-heteroaryl-C$_{(1-4)}$alkyl-R$^1$;
wherein:
R$^1$ is —CN, —SO$_2$NA$^1$A$^2$, —SO$_2$R$^a$, —SCH$_2$CH$_2$NA$^1$A$^2$, —SOCH$_2$CH$_2$NA$^1$A$^2$, —SO$_2$CH$_2$CH$_2$NA$^1$A$^2$, —OC$_{(1-4)}$alkylNA$^1$A$^2$, —NA¹A², —NSO₂CH₃, —NCOCH₃, —CONH₂, —CONHCH₂CH₂CH₂OH, —CONHCH₂CH₂N(C$_{(1-4)}$alkyl)₂, —NHCONH₂, —NHCONHCH₂CH₂OH, —NHCOCONH₂, —NR$_a$CH₂CH₂NA¹A², CO₂R$^a$, pyridyl, —OCOCH₃, or —CH₂OCOCH₃;

A¹ is H or —C$_{(1-4)}$alkyl;

A² is —C$_{(1-4)}$alkyl, —CH₂CH₂OR$^a$, —COR$^a$, —CH₂CH₂SC$_{(1-4)}$alkyl, —CH₂CH₂SOC$_{(1-4)}$alkyl, pyridyl, or —CH₂CH₂SO₂C$_{(1-4)}$alkyl;

alternatively, A¹ and A² may be taken together with their attached nitrogen to form a heterocyclic ring selected from the following:

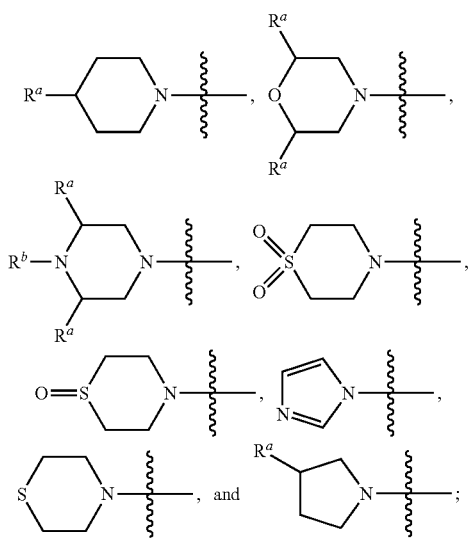

wherein:
R$^a$ is H or C$_{(1-4)}$alkyl;
R$^b$ is H, —C$_{(1-4)}$alkyl, alkoxyether, —C(O)C$_{(1-4)}$alkyl, or —CH₂C(O)C$_{(1-4)}$alkyl; and
R³ and R$^{4a}$ are independently —CH₂OH, —OCH₃, —CH₂OCH₃, —CO₂H, —CO₂C$_{(1-4)}$alkyl, OC(O)C$_{(1-4)}$alkyl, or —OH;
and solvates, hydrates, tautomers and pharmaceutically acceptable salts thereof.

Other preferred compounds of Formula I are those wherein:

W is

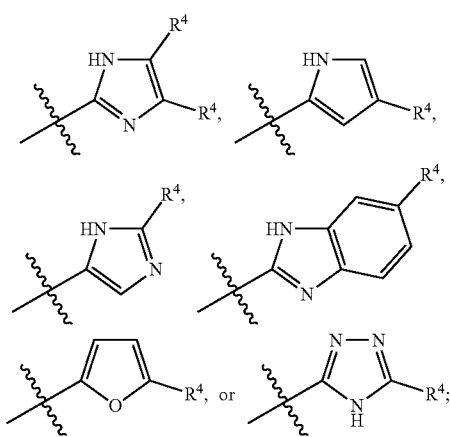

wherein each R⁴ is independently H, F, Cl, Br, I, OH, OCH₃, OCH₂CH₃, SC$_{(1-4)}$alkyl, SOC$_{(1-4)}$alkyl, SO₂C$_{(1-4)}$alkyl, —C$_{(1-3)}$alkyl, CO₂R$^d$, CONR$^e$R$^f$, C≡CR$^g$, or CN;

wherein R$^d$ is H, or —C$_{(1-3)}$alkyl;
R$^e$ is H, or —C$_{(1-3)}$alkyl;
R$^f$ is H, or —C$_{(1-3)}$alkyl; and
R$^g$ is H, —CH₂OH, or —CH₂CH₂OH;

R² is

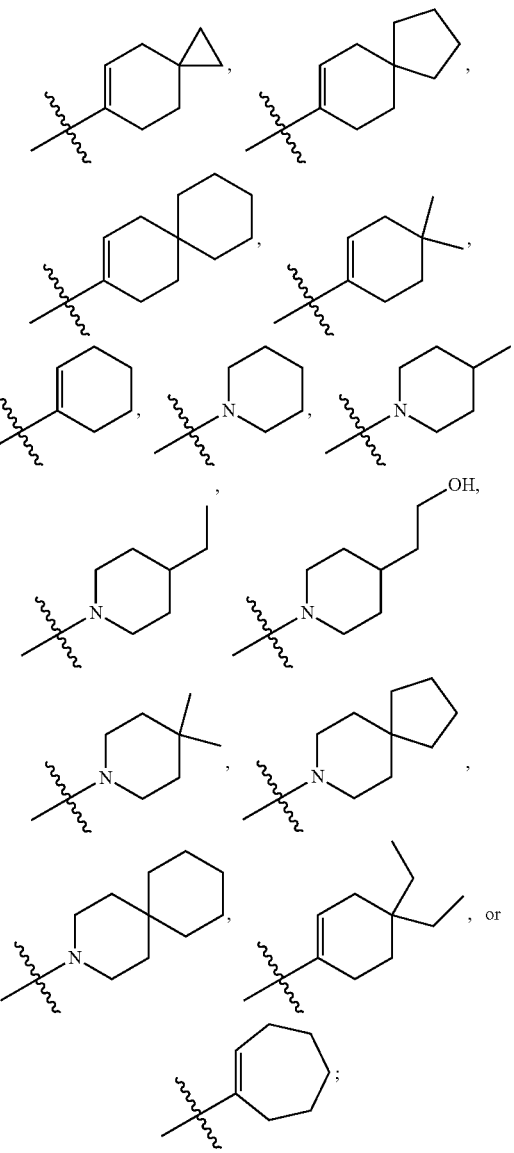

Z is H, F, or CH₃;
J is CH, or N;
X is —C$_{(1-5)}$alkylR¹, alkenyl, —CH=CH—CO₂R$^a$, —C$_{(1-4)}$alkylR³R$^{4a}$, or —CH₂-heteroaryl-C$_{(1-4)}$alkyl-R¹;

wherein:
R¹ is —CN, —SO₂NA¹A², —SO₂R$^a$, —SCH₂CH₂NA¹A², —SOCH₂CH₂NA¹A², —SO₂CH₂CH₂NA¹A², —OC$_{(1-4)}$alkylNA¹A², —NA¹A², —NSO₂CH₃, —NCOCH₃, —CONH₂, —CONHCH₂CH₂CH₂OH, CONHCH₂CH₂N(C$_{(1-4)}$alkyl)₂, —NHCONH₂, —NHCONHCH₂CH₂OH, —NHCOCONH₂, —NR_aCH₂CH₂NA¹A², CO₂R^a, pyridyl, —OCOCH₃, or —CH₂OCOCH₃;

A¹ is H or —C_{(1-4)}alkyl;

A² is —C_{(1-4)}alkyl, —CH₂CH₂OR^a, —COR^a, —CH₂CH₂SC_{(1-4)}alkyl, —CH₂CH₂SOC_{(1-4)}alkyl, pyridyl, or —CH₂CH₂SO₂C_{(1-4)}alkyl;

alternatively, A¹ and A² may be taken together with their attached nitrogen to form a heterocyclic ring selected from the following:

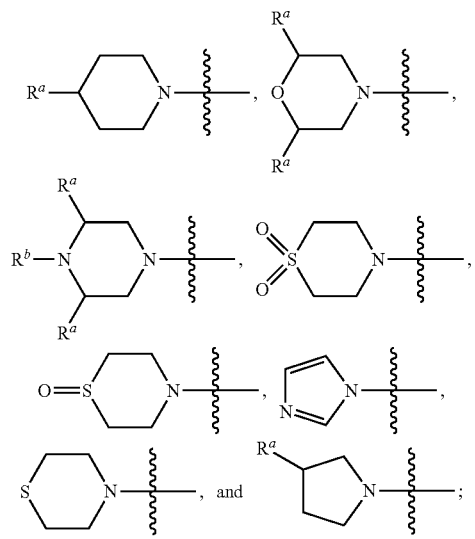

wherein:

R^a is H or C_{(1-4)}alkyl;

R^b is H, —C_{(1-4)}alkyl, alkoxyether, —C(O)C_{(1-4)}alkyl, or —CH₂C(O)—C_{(1-4)}alkyl; and R³ and R^{4a} are independently —CH₂OH, —OCH₃, —CH₂OCH₃, —CO₂H, —CO₂C_{(1-4)}alkyl, OC(O)C_{(1-4)}alkyl, or —OH;

and solvates, hydrates, tautomers and pharmaceutically acceptable salts thereof.

Other preferred compounds of Formula I are those wherein:

W is

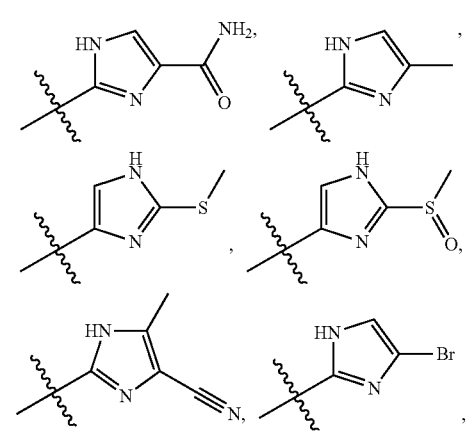

R² is

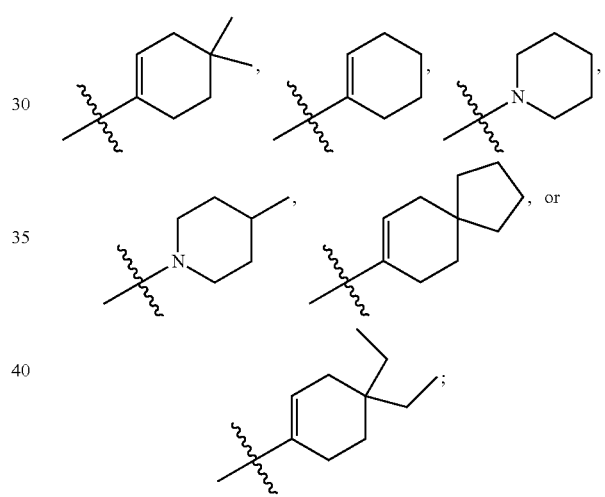

Z is H;

J is CH, or N;

X is —C_{(1-5)}alkylR¹, —CH=CH—CO₂H wherein said CH=CH bond has E stereochemistry, —C_{(1-4)}alkylR³R^{4a}, or propenyl;

wherein:

R¹ is —SO₂NA¹A², —OC_{(1-4)}alkylNA¹A², NA¹A², NHCH₂CH₂NA¹A², NHSO₂CH₃, NCOCH₃, CONH₂, CONHCH₂CH₂CH₂OH, CONHCH₂CH₂N(CH₃)₂, NHCONH₂, NHCONHCH₂CH₂OH, NHCOCONH₂, CO₂R^a, or pyridyl;

A¹ is H or —C_{(1-4)}alkyl;

A² is —C_{(1-4)}alkyl, —CH₂CH₂OR^a, —COCH₃, —CH₂CH₂SC_{(1-4)}alkyl, pyridyl, or —CH₂CH₂SO₂C_{(1-4)}alkyl;

alternatively, A¹ and A² may be taken together with their attached nitrogen to form a heterocyclic ring selected from the following:

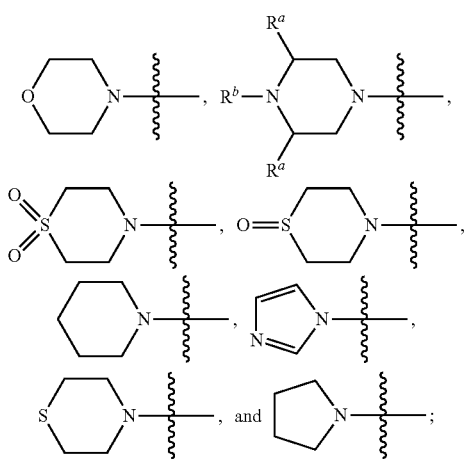

wherein:

$R^a$ is H or $C_{(1-4)}$alkyl;

$R^b$ is H, or —$C_{(1-4)}$alkyl; and $R^3$ and $R^{4a}$ are independently —OCH$_3$, —CH$_2$OCH$_3$, —CO$_2$H, —OC(O)CH$_3$, or —OH;

and solvates, hydrates, tautomers and pharmaceutically acceptable salts thereof.

Other preferred compounds of Formula I are those wherein:

W is

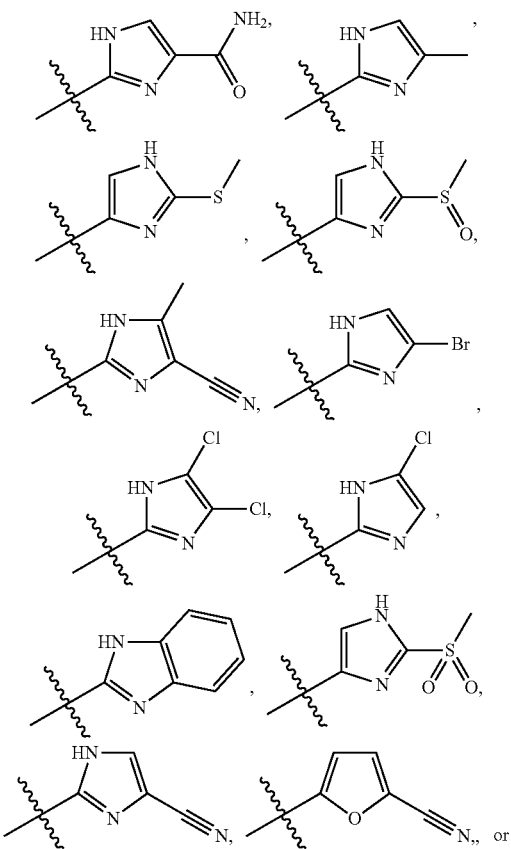

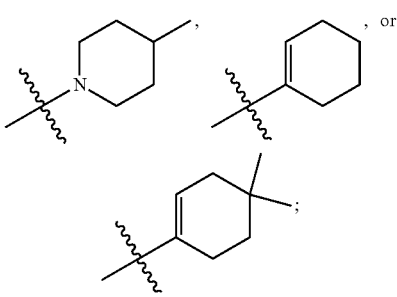

$R^2$ is

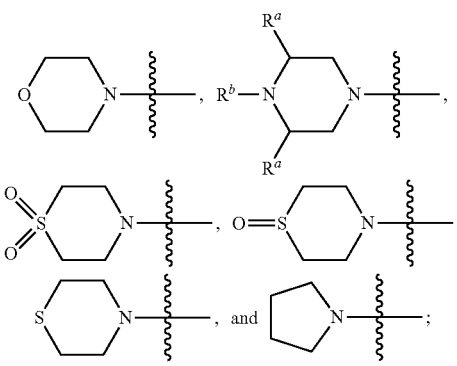

Z is H;

J is CH, or N;

X is —CH$_2$R$^1$, —CH$_2$CH$_2$R$^1$, —C(CH$_3$)$_2$R$^1$, —CH=CH—CO$_2$H wherein said CH=CH bond has E stereochemistry, —C$_{(1-4)}$alkylR$^3$R$^{4a}$, or propenyl;

wherein:

R$^1$ is —SO$_2$NA$^1$A$^2$, —OCH$_2$CH$_2$NA$^1$A$^2$, NA$^1$A$^2$, NHCH$_2$CH$_2$NA$^1$A$^2$, NHSO$_2$CH$_3$, NCOCH$_3$, CONH$_2$, CONHCH$_2$CH$_2$CH$_2$OH, CONHCH$_2$CH$_2$N(CH$_3$)$_2$, NHCONH$_2$, NHCONHCH$_2$CH$_2$OH, NHCOCONH$_2$, or CO$_2$R$^a$;

A$^1$ is H or —C$_{(1-4)}$alkyl;

A$^2$ is —C$_{(1-4)}$alkyl, —CH$_2$CH$_2$OCH$_3$, —CH$_2$CH$_2$SCH$_3$, or —CH$_2$CH$_2$SO$_2$CH$_3$;

alternatively, A$^1$ and A$^2$ may be taken together with their attached nitrogen to form a heterocyclic ring selected from the following:

wherein:

$R^a$ is H, CH$_3$, or CH$_2$CH$_3$;

$R^b$ is H, or CH$_3$; and $R^3$ and $R^{4a}$ are independently, —OCH$_3$, —CH$_2$OCH$_3$, —CO$_2$H, —OC(O)CH$_3$, or —OH;

and solvates, hydrates, tautomers and pharmaceutically acceptable salts thereof.

Yet another embodiment is the compounds of Examples 1 to 122, solvates, hydrates, tautomers and pharmaceutically acceptable salts of these compounds, and any combination thereof.

Another embodiment is compounds of Formula I wherein W is
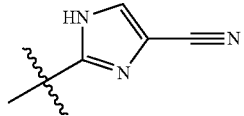 [SMILES: *c1nc(C#N)c[nH]1]
Still another embodiment is compounds selected from the group consisting of:
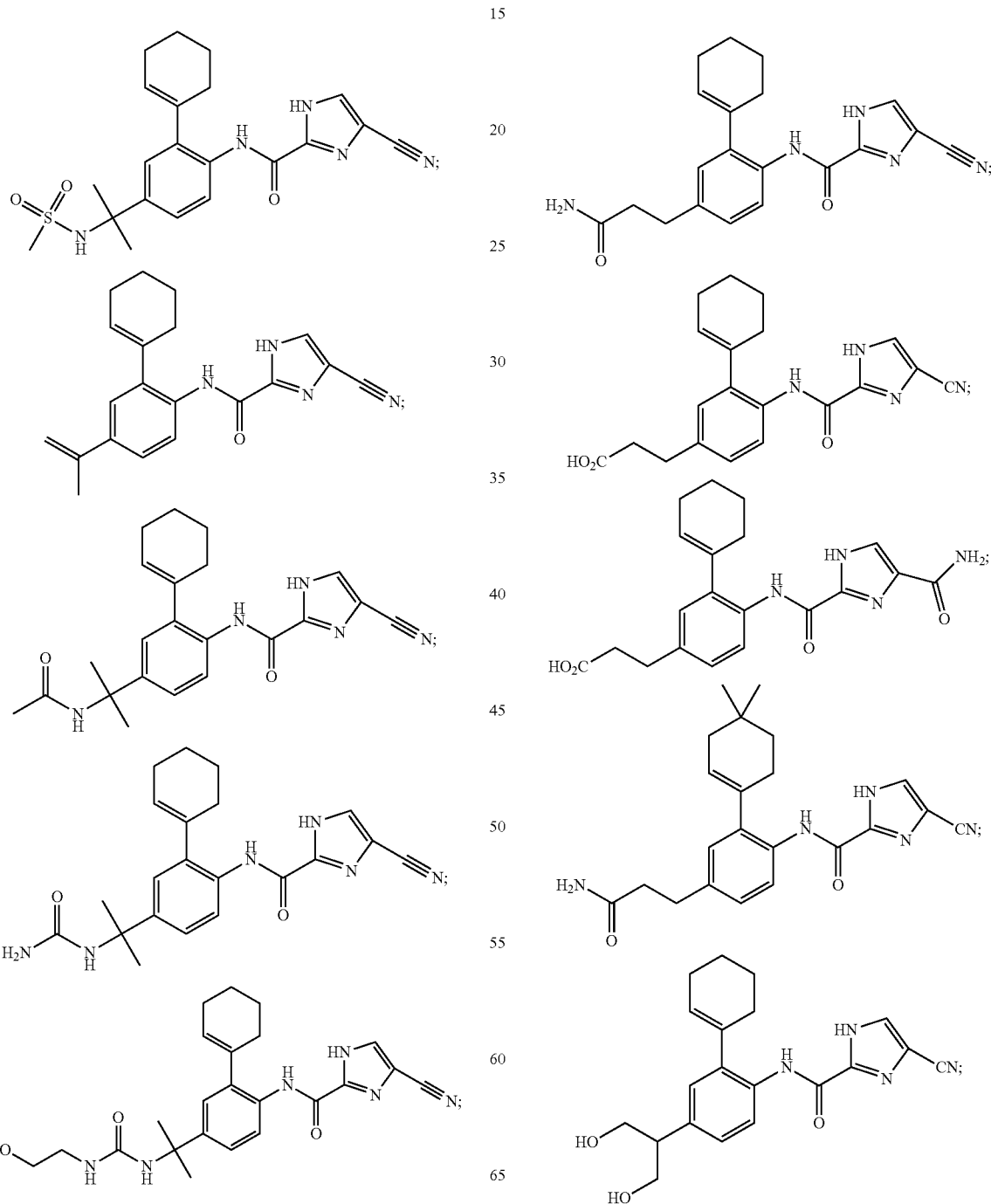
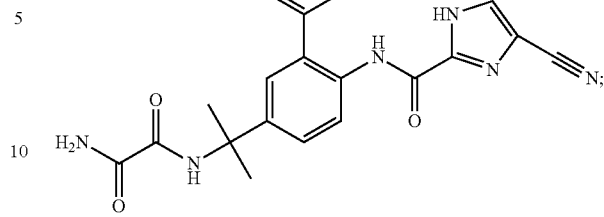

29
-continued
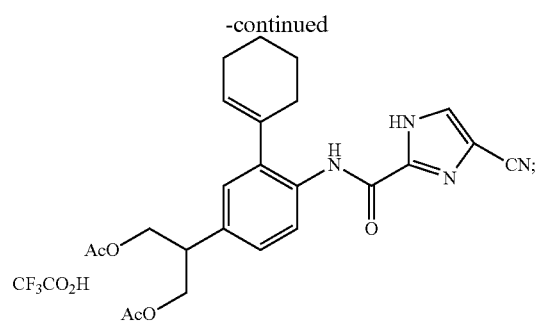
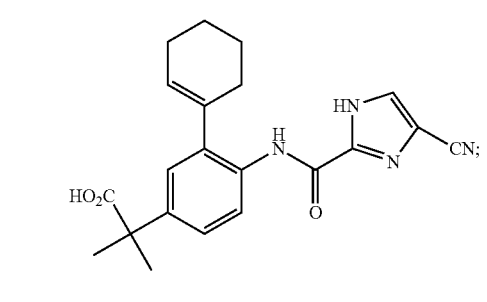
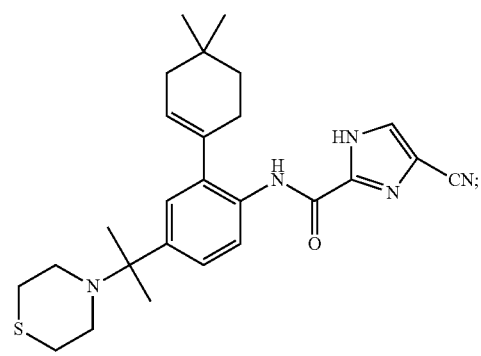
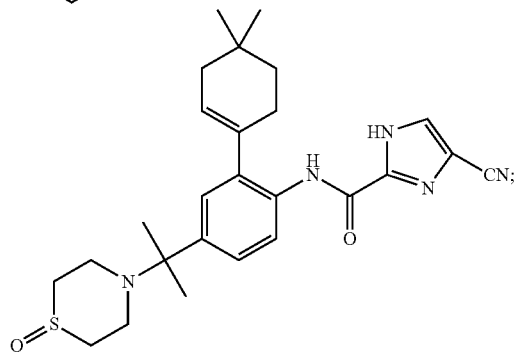
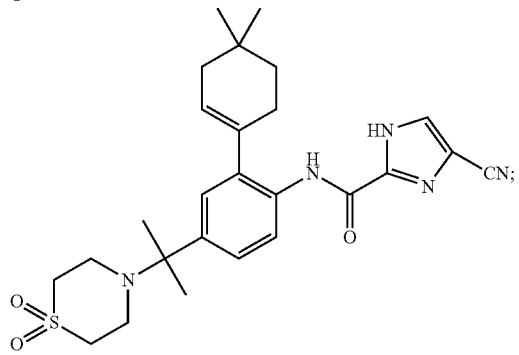
30
-continued
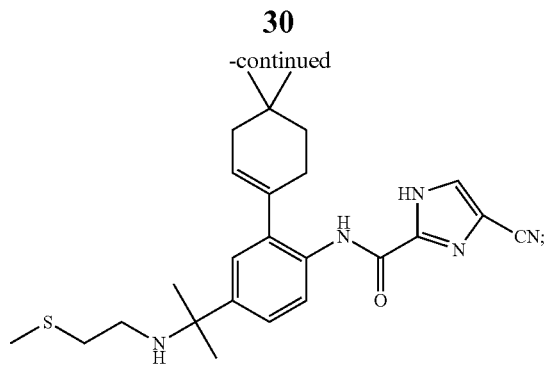
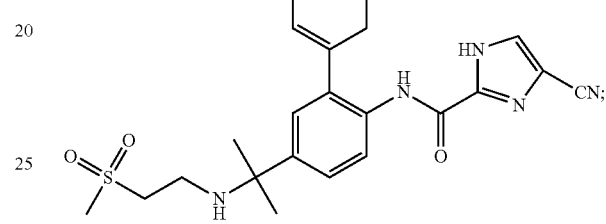
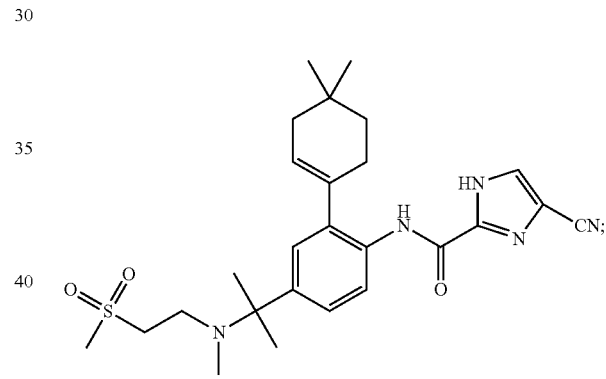
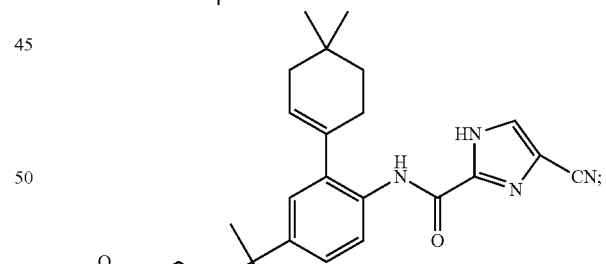
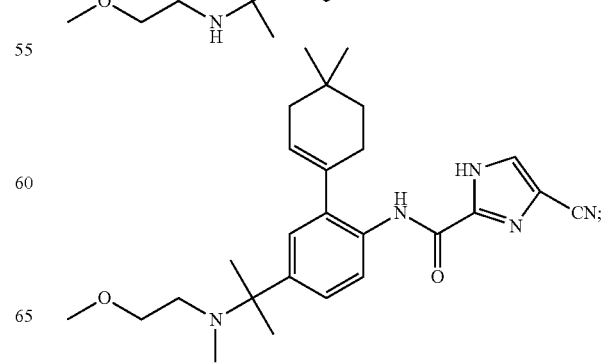

31
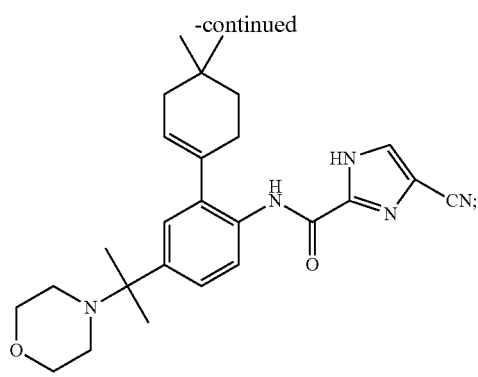
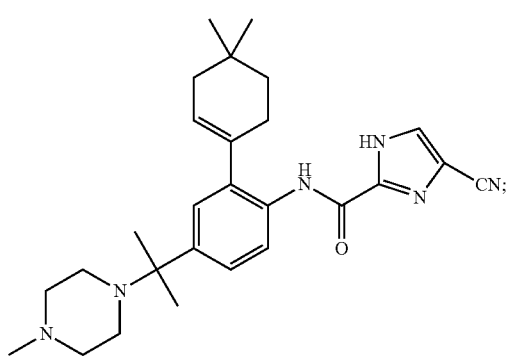
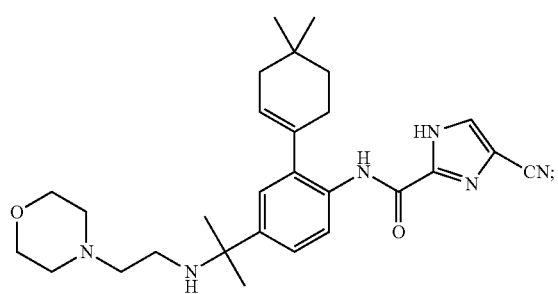
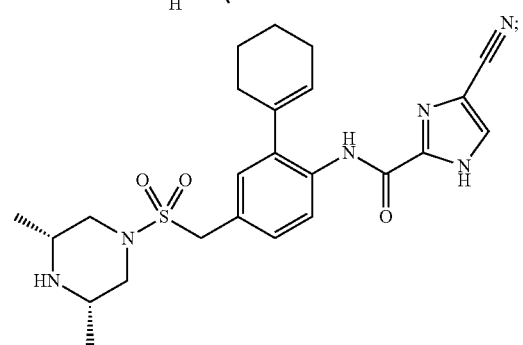
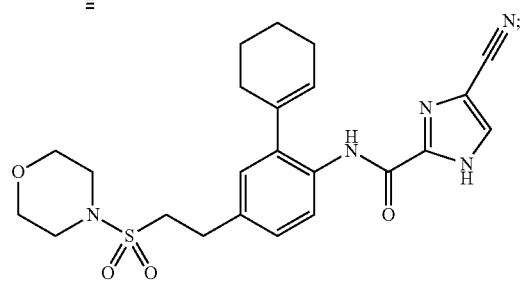
32
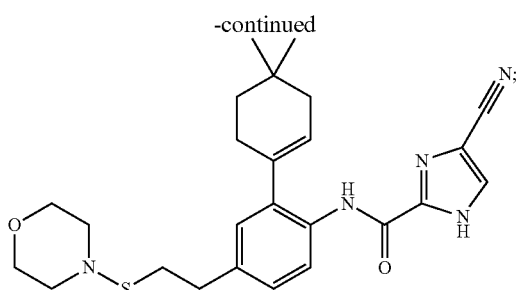
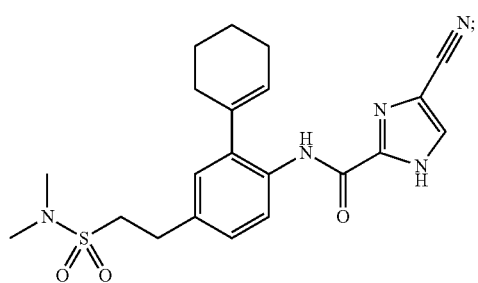
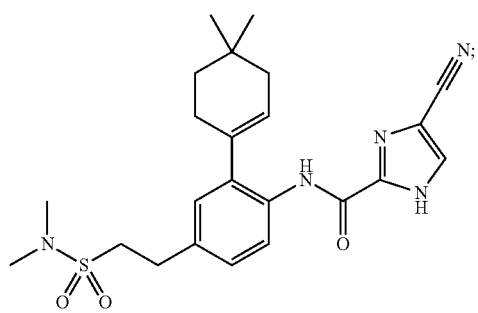
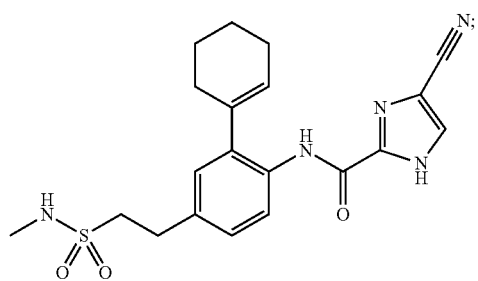
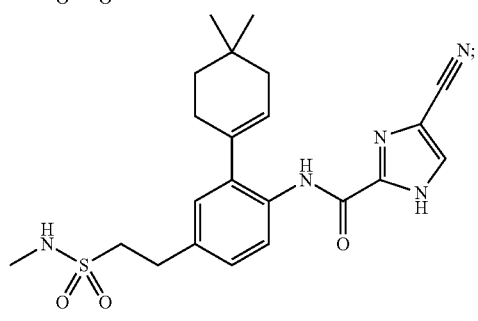

33
-continued
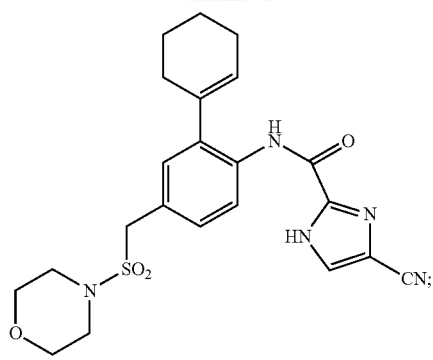
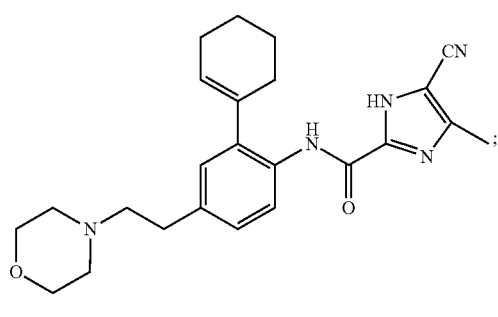
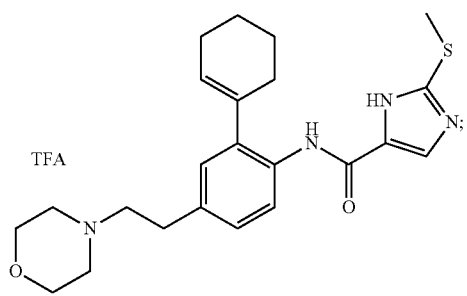
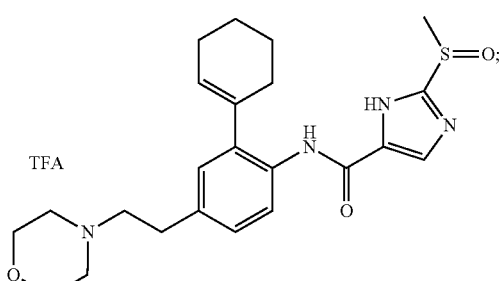
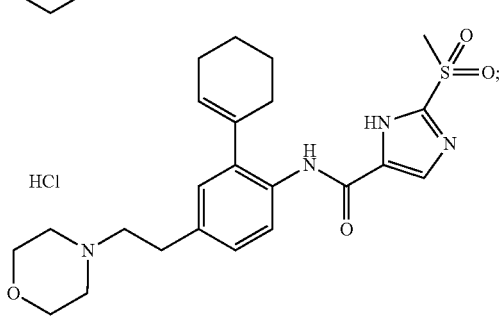
34
-continued
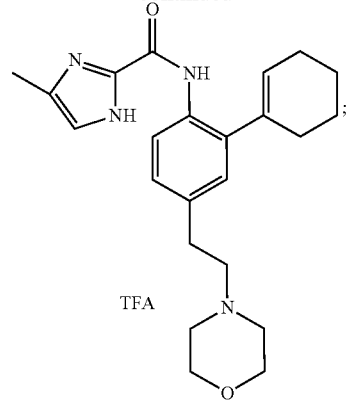
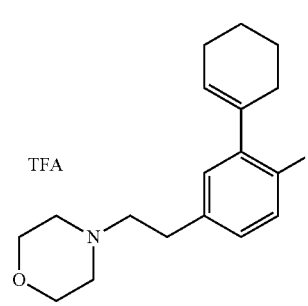
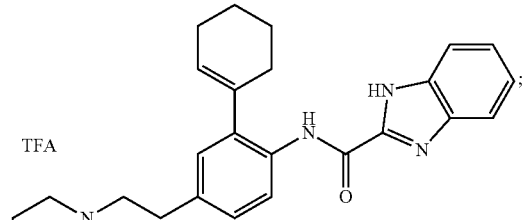
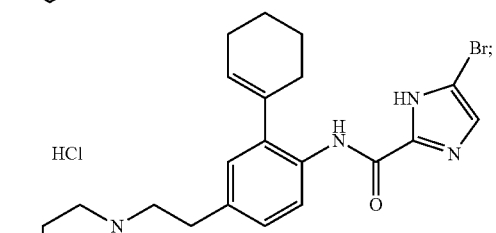
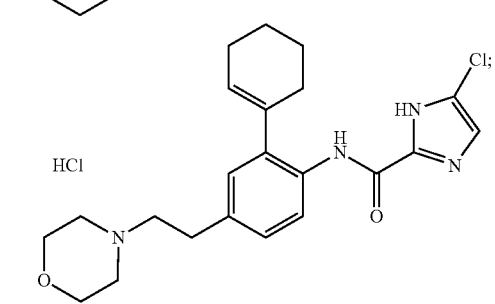

35
-continued
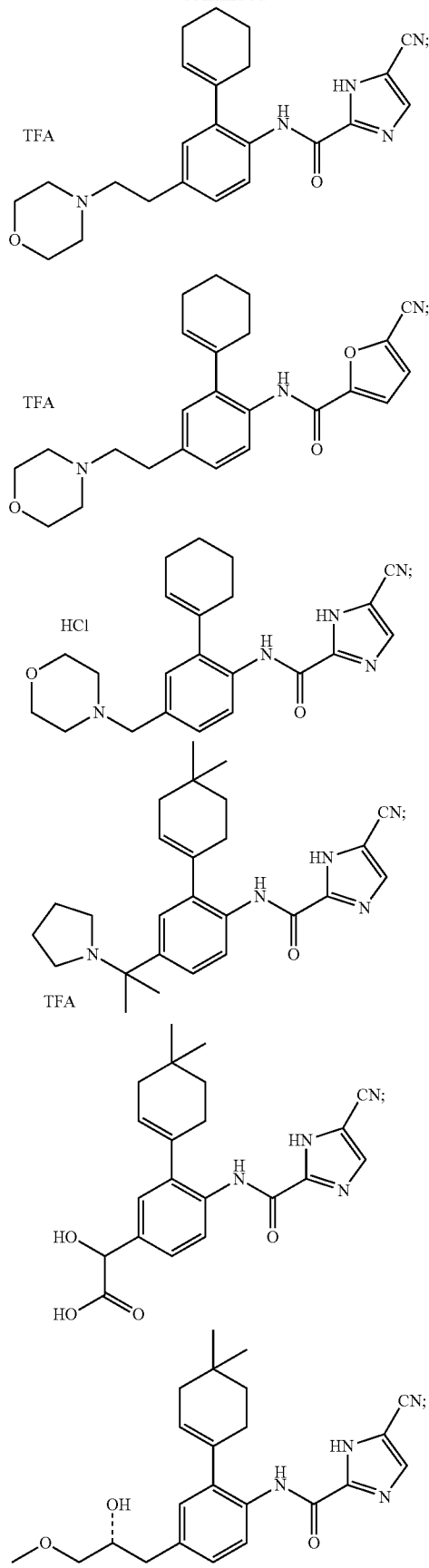
36
-continued
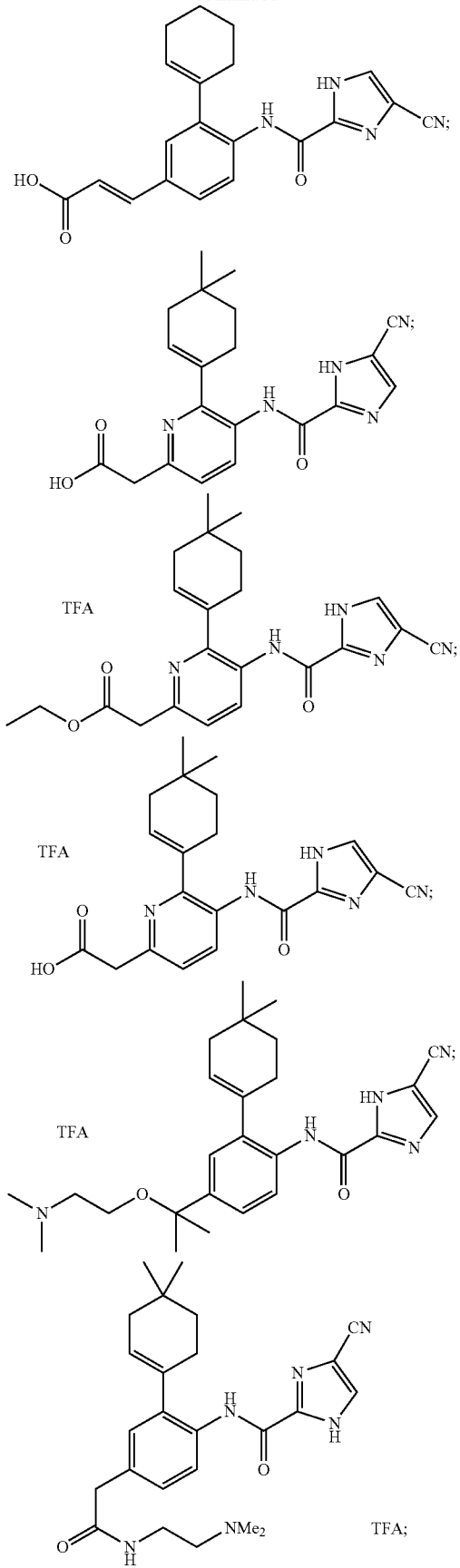

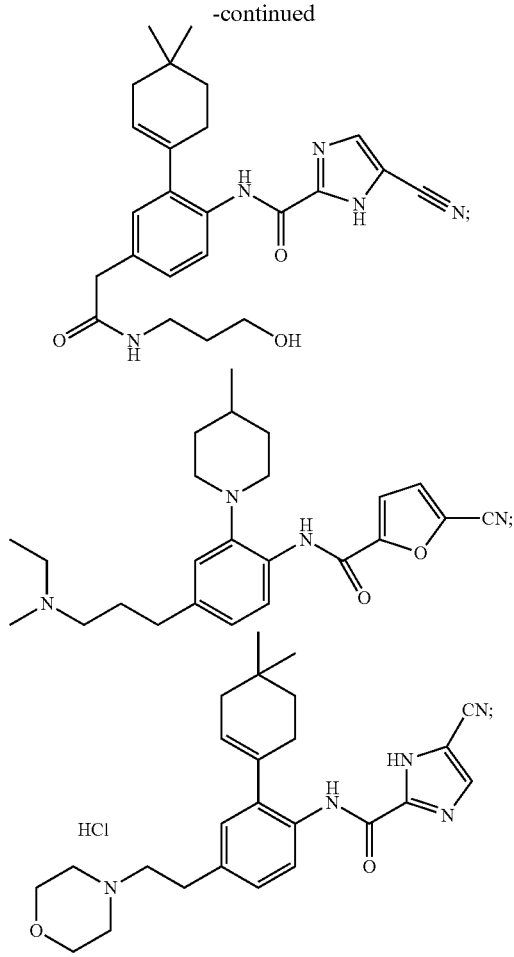
and solvates, hydrates, tautomers and pharmaceutically acceptable salts thereof. The compounds of this embodiment are in Examples 1-55, and 60.
Another embodiment of the invention is a compound selected from the group consisting of:
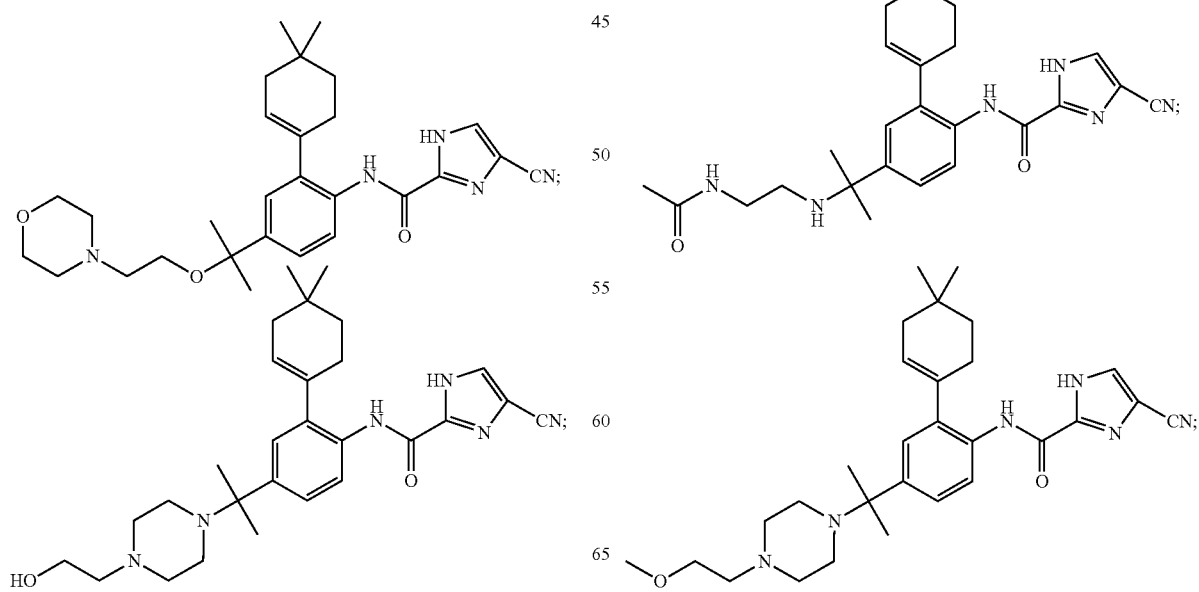

39
-continued
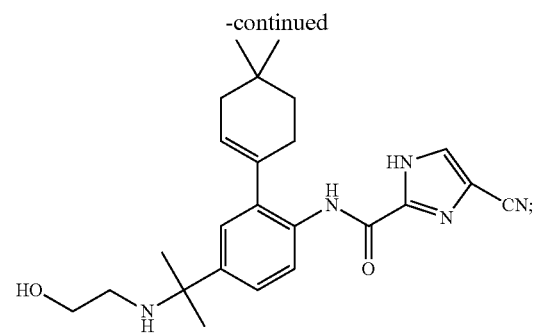
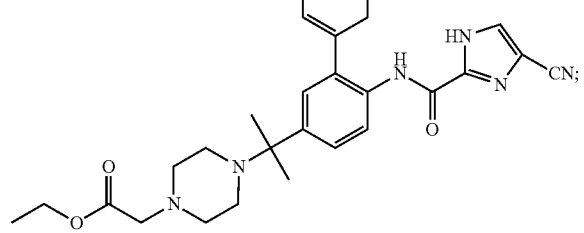
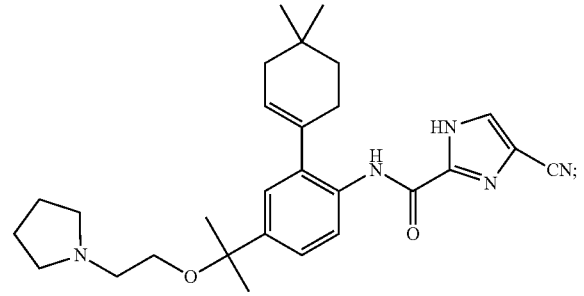
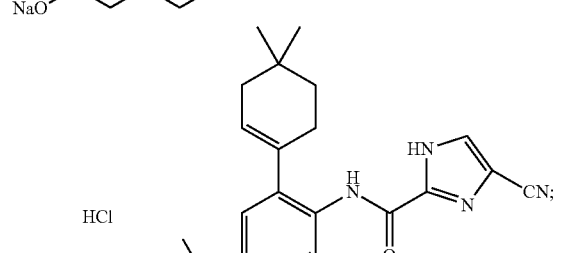
40
-continued
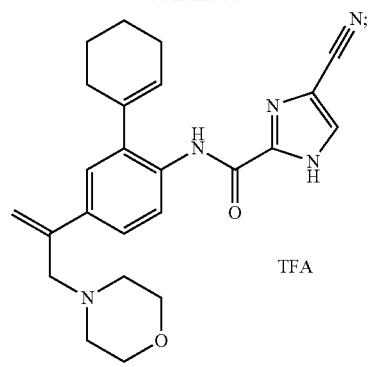
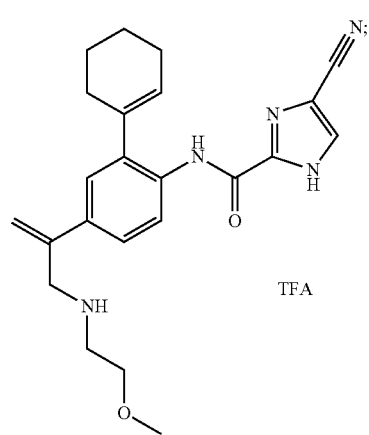
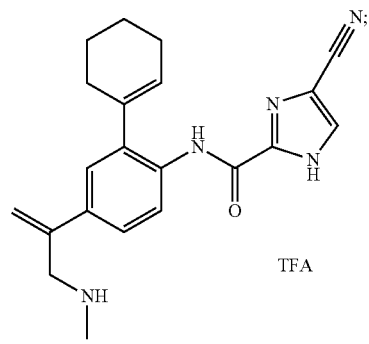
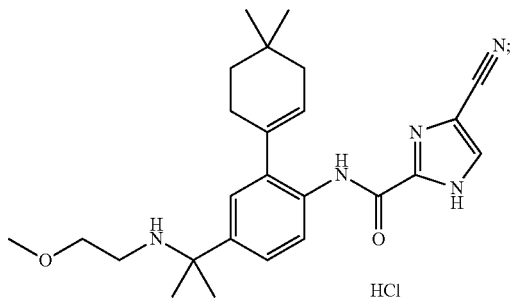

-continued
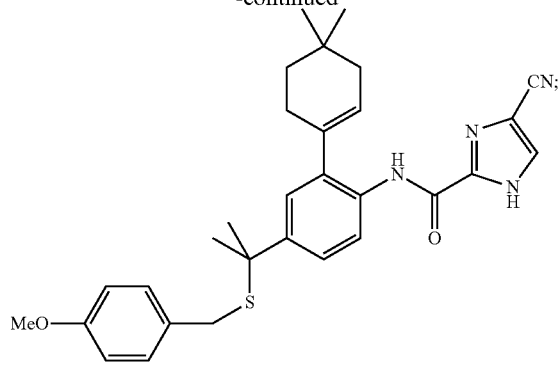
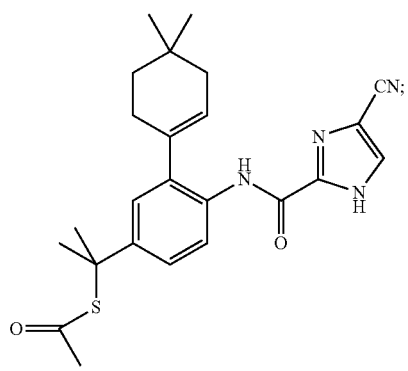
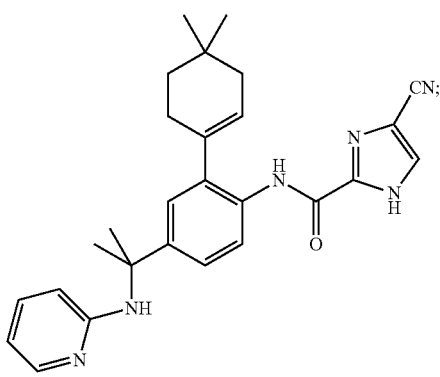
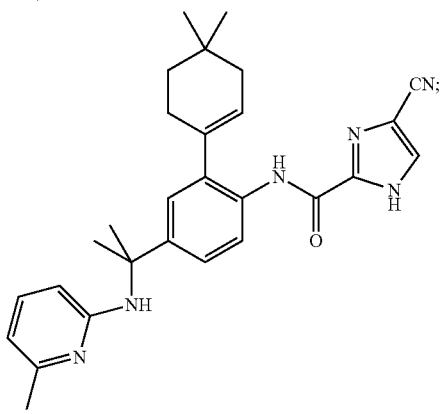
and solvates, hydrates, tautomers and pharmaceutically acceptable salts thereof. The compounds of this embodiment are in Examples 61-80.
Another embodiment is a compound selected from the group consisting of:
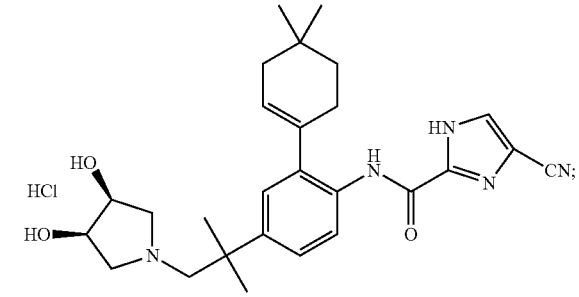
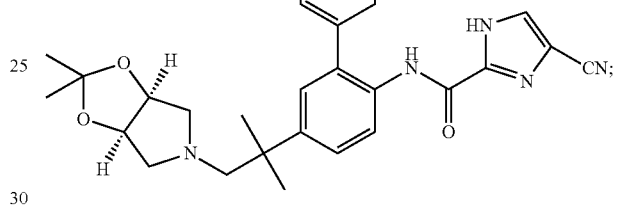
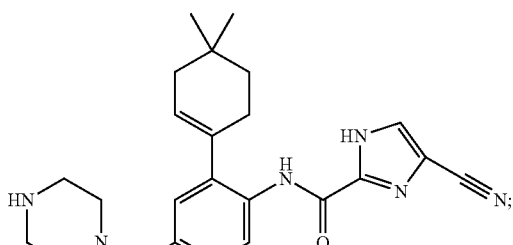
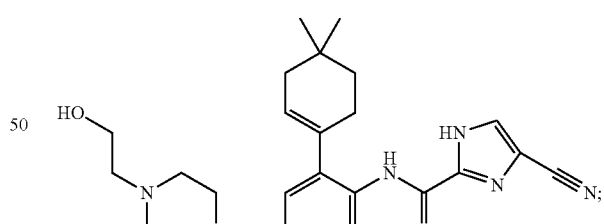
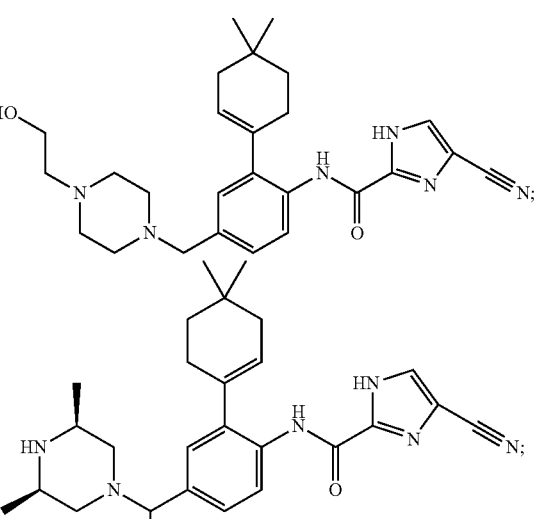

-continued
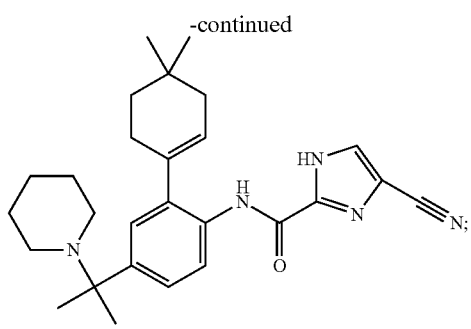
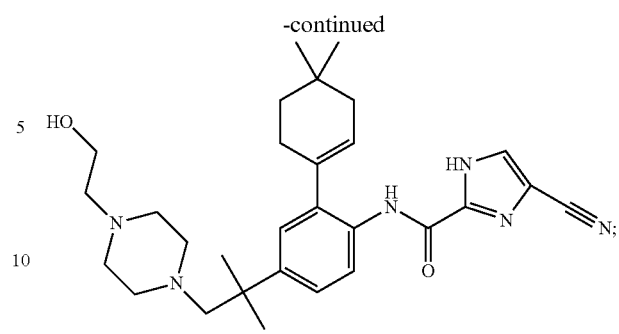
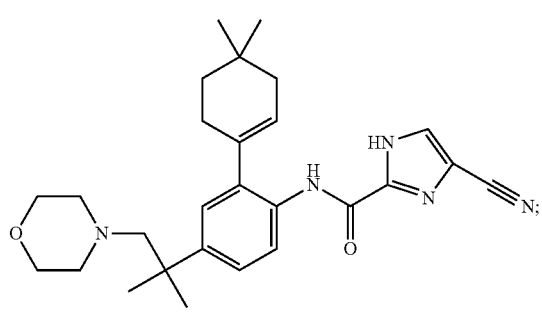
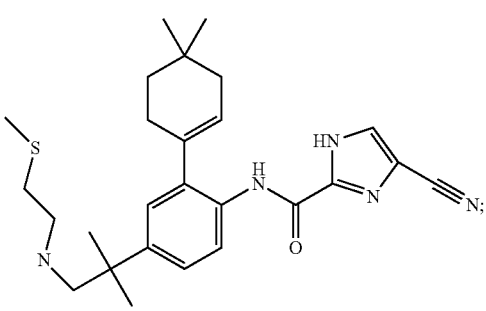
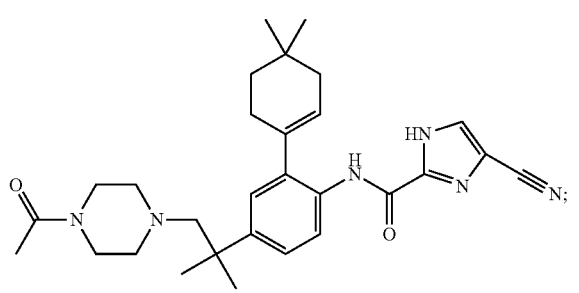
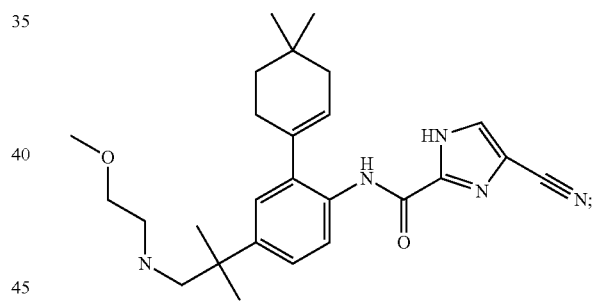
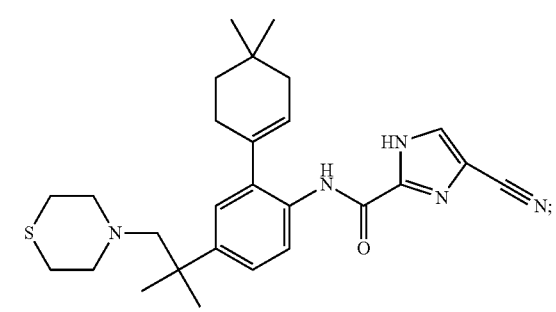
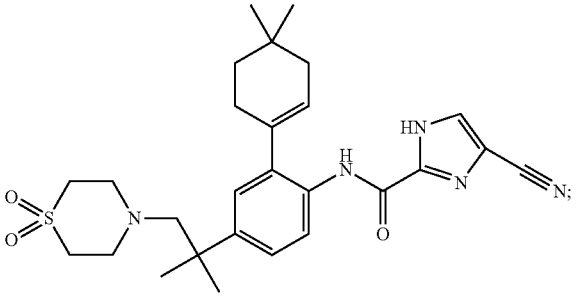
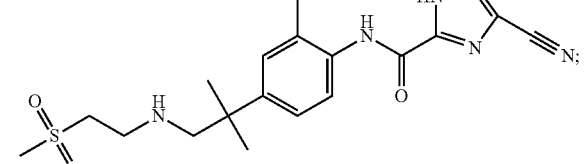
and solvates, hydrates, tautomers and pharmaceutically acceptable salts thereof. There are the compounds of examples 138-151.

Yet another embodiment is a compound selected from the group consisting of:

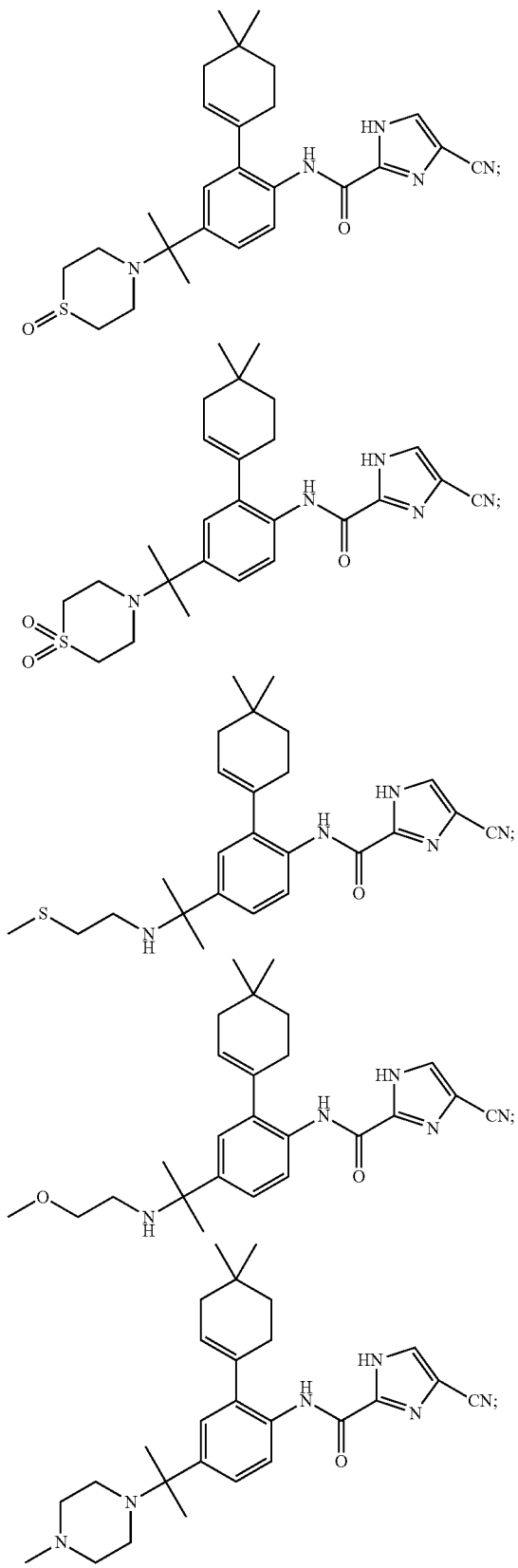
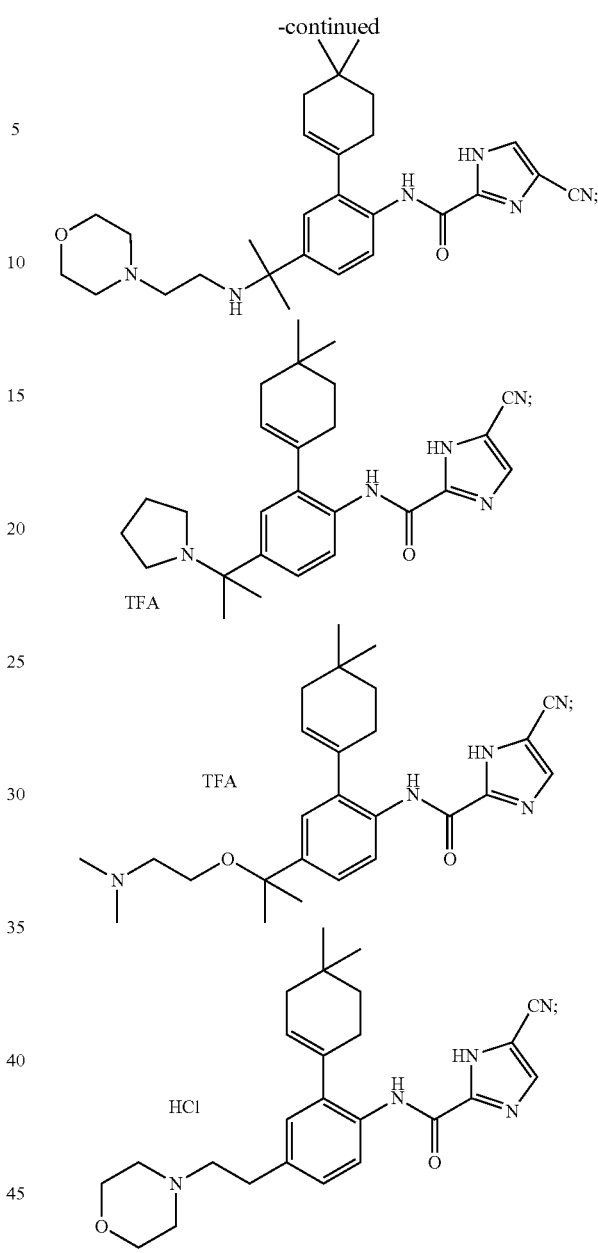

and solvates, hydrates, tautomers and pharmaceutically acceptable salts thereof. These are the compounds of Examples 15, 16, 17, 20, 23, 24, 45, 52, and 60.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

I. DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napthalene.

The term "aralkyl" refers to a $C_{1-6}$ alkyl group containing an aryl substituent. Examples include benzyl, phenylethyl or 2-naphthylmethyl.

The term "sulfonyl" refers to the group —S(O)$_2$R$_a$, where R$_a$ is hydrogen, alkyl, cycloalkyl, haloalkyl, aryl, aralkyl, heteroaryl and heteroaralkyl. A "sulfonylating agent" adds the —S(O)$_2$R$_a$ group to a molecule.

The term "spiro-substituted cycloalkenyl" refers to a pair of cycloalkyl rings that share a single carbon atom and wherein at least one of the rings is partially unsaturated, for example:

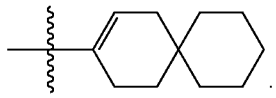 [SMILES: *C1=CCC2(CCCCC2)CC1]

The term "spiro-substituted heterocyclyl" refers to a heterocyclyl and cycloalkyl ring that share a single carbon atom, for example:

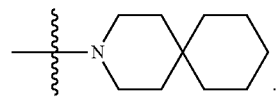

II. THERAPEUTIC USES

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, breast cancer, colon cancer, stomach cancer, hairy cell leukemia and non-small lung carcinoma. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, breast cancer, prostate cancer, lung cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I.

Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Methods of Preparation

Scheme 1

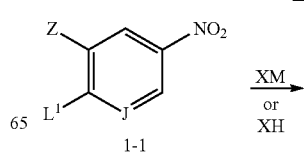

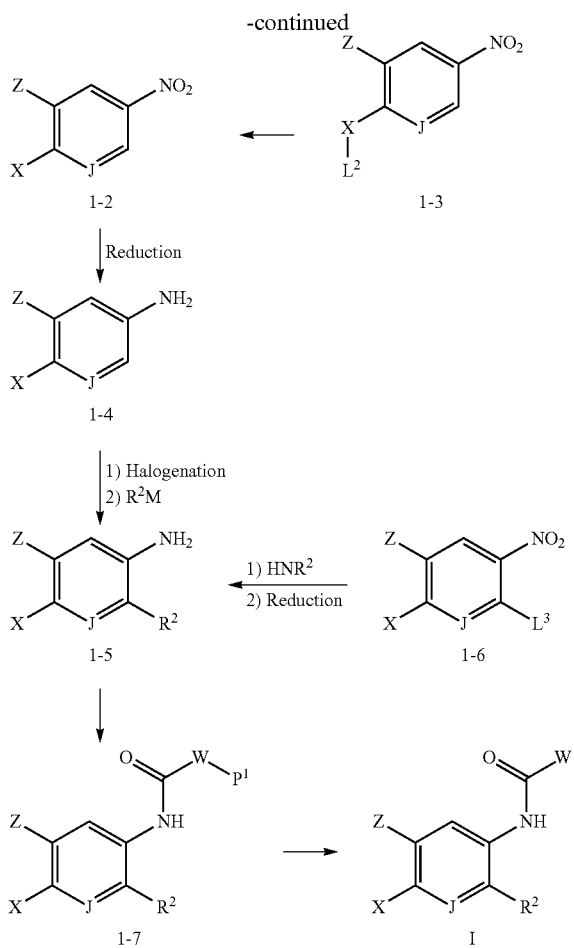

Scheme 1 illustrates general methodology for the preparation of compounds of Formula I where X is neither CO$_2$H, nor —NA$^1$A$^2$ where A$^1$ is H. To illustrate the methodology of this scheme, reagents and conditions for the compounds where J is CH are defined. It is understood that where J is N, minor modifications of the reaction conditions and preferred reagents may be required.

Anilines and aminopyridines of Formula 1-4 may be commercially available or obtained from nitro compounds of Formula 1-2 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol.

In cases where the desired functionality is not present in compounds of Formula 1-2, it can be obtained from compounds of Formula 1-1 by nucleophilic aromatic substitution of leaving groups L$^1$ (preferably fluoro or chloro) that are activated by the nitro group with carbon nucleophiles (for example, malonate esters, where X is CH(CO$_2$C$_{(1-4)}$alkyl)$_2$) in the presence of a suitable base such as NaH. Malonate esters may then be further elaborated by, for example, hydrolysis followed by decarboxylation to acetic acid derivatives, where X is CH$_2$CO$_2$H. Additionally, when the leaving group Cis suitable for metal-catalyzed couplings (preferably bromo, iodo, or trifluoromethane-sulfonyloxy), a number of cross-coupling reactions, such as Heck, Stille, or Suzuki couplings, (for reviews, see N. Miyaura and A. Suzuki, Chem. Rev., 95:2457 (1995); J. K. Stille, Angew. Chem, Int. Ed. Engl., 25: 508-524 (1986); S. Braese and A. de Meijere in Metal-Catalyzed Cross-Coupling Reactions (2nd Edition), p. 217-315, A. de Meijere, F. Diederich, Eds., Wiley-VCH, Weinheim (2004); and A. Suzuki in Metal-Catalyzed Coupling Reactions, F. Deiderich, P. Stang, Eds., Wiley-VCH, Weinheim (1988)) may be performed.

Compounds of Formula 1-2 may also be obtained from compounds of Formula 1-3 where X is a C$_{(1-6)}$alkyl by displacement of L$^2$ (preferably iodo or bromo) with appropriate nucleophiles (for example, HNA$^1$A$^2$) in the presence of a suitable base such as K$_2$CO$_3$, N,N-diisopropylethylamine (DIEA) or NEt$_3$ to obtain compounds of Formula 1-2 where, for example, X is C$_{(1-6)}$alkylNA$^1$A$^2$.

Compounds of Formula 1-5 where R$^2$ is cycloalkyl can be obtained by ortho-halogenation, preferably bromination, of amino compounds of Formula 1-4 followed by metal-catalyzed coupling reactions with boronic acids or boronate esters (Suzuki reactions, where R$^2$M is R$^2$B(OH)$_2$ or a boronic ester) or tin reagents (Stille reactions, where R$^2$M is R$^2$Sn(alkyl)$_3$) (see above for reviews) on the intermediate halo compound. Preferred conditions for the bromination of 1-5 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) (Pd(PPh$_3$)$_4$), an aqueous base such aq. Na$_2$CO$_3$, and a suitable solvent such as toluene, ethanol, 1,4-dioxane, dimethoxyethane (DME), or DMF.

Compounds of Formula 1-5 where R$^2$ is cycloalkylamino (for example, piperidino) can be obtained by nucleophilic aromatic substitution of leaving groups L$^3$ (preferably fluoro or chloro) from compounds of Formula 1-6 that are activated by the nitro group with cycloalkylamines (for example, piperidine) in the presence of a suitable base such as K$_2$CO$_3$, N,N-diisopropylethylamine (DIEA) or NEt$_3$, followed by reduction of the nitro group as described above.

The amino group in compounds of Formula 1-5 can then be coupled with a heterocyclic acid P$^1$—WCOOH (or a corresponding salt thereof P$^1$—WCOOM$^2$, where M$^2$ is Li, Na or K) where P$^1$ is an optional protecting group (for example 2-(trimethylsilyl)ethoxymethyl (SEM) such as when W is imidazole, triazole, pyrrole, or benzimidazole) or where P$^1$ is not present such as when W is furan. (For a list of protecting groups for W, see Theodora W. Greene and Peter G. M. Wuts, Protective Groups in Organic Synthesis, John Wiley and Sons, Inc., NY (1991)). The coupling can be carried out according to standard procedures for amide bond formation (for a review, see: M. Bodansky and A. Bodansky, The Practice of Peptide Synthesis, Springer-Verlag, NY (1984)) or by reaction with acid chlorides P$^1$—WCOCl or activated esters P$^1$—WCO$_2$Rq (where Rq is a leaving group such as pentafluorophenyl or N-succinimide) to form compounds of Formula 1-7. The preferred reaction conditions for coupling with P$^1$—WCOOH or P$^1$—WCOOM$^2$ are: when W is a furan (optional protecting group P$^1$ not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole (optional protecting group P$^1$ not present), 1-(3-dimethylaminopropyl)-3-ethylcarbodiimide hydrochloride (EDCI) and 1-hydroxybenzotriazole (HOBt); and when W is an imidazole, pyrrole or benzimidazole (optional P$^1$ present) the preferred conditions are bromotripyrrolidinophosphonium hexafluorophosphate (PyBroP) and DIEA in a solvent such as DCM or DMF.

When W in compounds of Formula 1-7 contain an optional protecting group P$^1$ as mentioned previously, it can be removed at this point to give compounds of Formula I. For example, when W is imidazole protected on nitrogen with a SEM group, the SEM group can be removed with either acidic reagents such as trifluoroacetic acid (TFA) or fluoride sources such as tetrabutylammonium fluoride (TBAF) (see Greene and Wuts above).

Finally it is understood that compounds of Formula I may be further derivatized. Examples of further derivatization of compounds of I include, but are not limited to: when compounds of Formula I contain a cyano group, this group may be hydrolyzed to amides or acids under acidic or basic conditions; when compounds of Formula I contain an ester, the ester may be hydrolysed to the acid, and the acid may be converted to amides by the methods described above for amide bond formation. Acids may be reduced to alcohols, and alcohols may be oxidized to aldehydes and ketones. The preferred conditions for the reduction of a carboxylic acid in the presence of a cyano group include sodium borohydride and ethyl chloroformate in tetrahydrofuran (THF); and alcohol oxidation can be performed using the Dess-Martin periodinane reagent (*Adv. Syn. Catalysis*, 346, 111-124 (2004)). Aldehydes and ketones may be reacted with primary or secondary amines in the presence of a reducing agent such as sodium triacetoxyborohydride (see *J. Org. Chem.*, 61, 3849-3862, (1996)) to give amines by reductive amination. Olefins, including acrylic acids and acrylate esters (X is CH=CHCO$_2$R$^a$), may be reduced by catalytic hydrogenation or, when R$^2$ contains an alkene, by 1,4-conjugate addition such that the alkene of R$^2$ is not reduced to give alkyls (X is CH$_2$CH$_2$CO$_2$R$^a$) (see Larock, Richard C., *Comprehensive Organic Transformation*; VCH: New York, 1989; p 8-17). When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with NaIO$_4$ (see, for example, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of H$_2$O$_2$ respectively, in the presence of titanium (IV) isopropoxide (see, for example, *J. Chem. Soc., Perkin Trans.* 2, 1039-1051 (2002)).

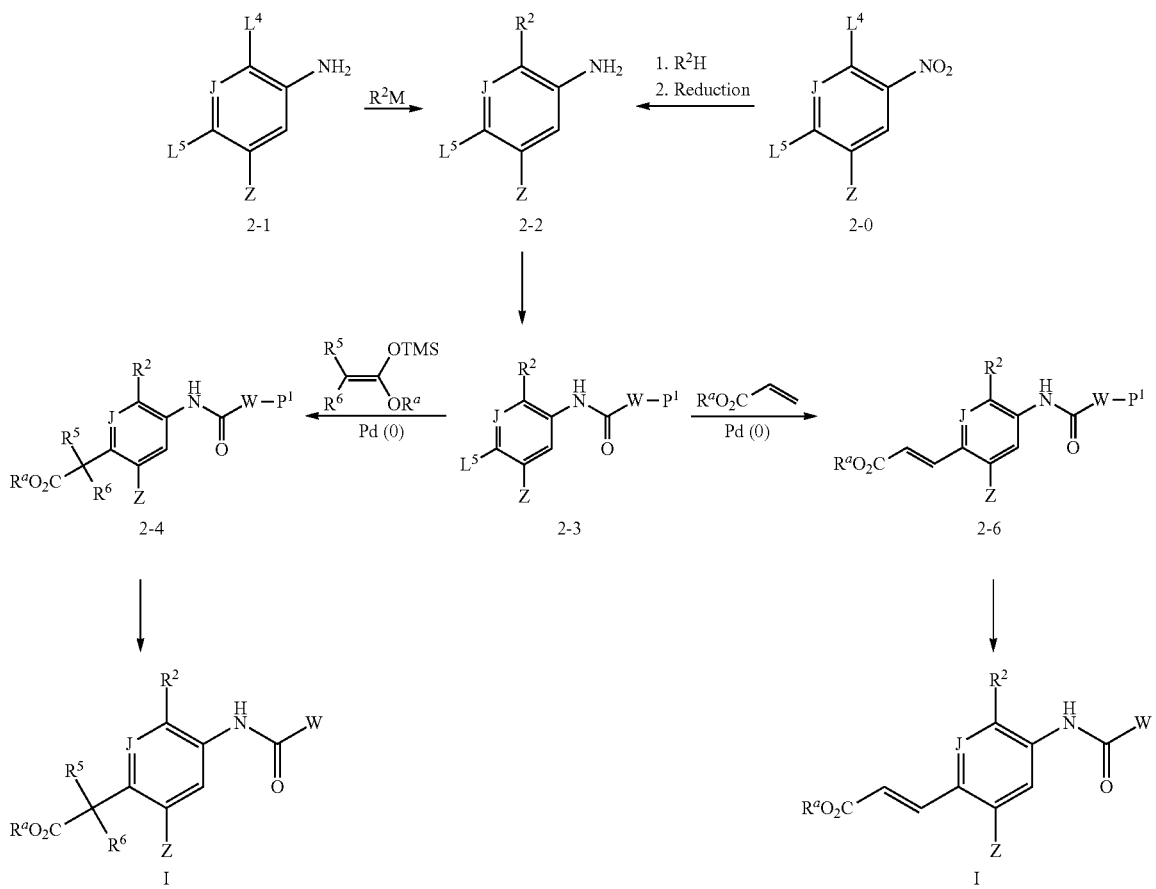

Scheme 2 where R$^a$ is C$_{(1-4)}$alkyl
and TMS is trimethylsilyl

Scheme 2 illustrates general methodology for the preparation of compounds of Formula I where Z is H, X is C($R^5$,$R^6$)$R^1$ or —CH=CH—$R^1$, $R^5$ and $R^6$ are H or Me, and $R^1$ is —$CO_2A^1$.

For the illustration of synthetic strategy in this scheme, reagents and conditions are defined for the substrate where J is CH. As previously mentioned in Scheme 1, it is understood that similar synthetic methods can be utilized with minor modifications when J is N.

When $R^2$ is cycloalkyl (specifically cycloalkenyl), compound 2-2 can be obtained by metal-catalyzed coupling reactions with boronic acids or boronate esters (M is $B(OH)_2$ or a boronic ester) and the starting material 2-1 is a dihaloaniline where $L^4$ is bromo or preferably iodo and where $L^5$ is chloro or preferably bromo. The metal-catalyzed couplings, preferably Suzuki reactions, can be performed according to standard methodology as described in Scheme 1, preferably in the presence of a palladium catalyst such as tetrakis(triphenylphosphine)palladium(0) ($Pd(PPh_3)_4$), an aqueous base such aq. $Na_2CO_3$, and a suitable solvent such as toluene, ethanol, 1,4-dioxane, dimethoxyethane (DME), or DMF.

When $R^2$ is cycloalkylamino (for example, piperidino), compound 2-2 can be obtained from starting material 2-0 by nucleophilic aromatic substitution of leaving group $L^4$ (preferably fluoro or chloro) that is activated by the nitro group with a cycloalkylamine $R^2H$ (for example, piperidine), followed by reduction of the nitro group as described in Scheme 1.

Compound 2-3 can be prepared by reaction of compound 2-2 with carboxylic acids $P^1$—WCOOH where $P^1$ is an optional protecting group according to the procedures for amide bond formation as described in Scheme 1 for the preparation of 1-7.

Compound 2-4 can be obtained from compound 2-3 by palladium-mediated cross-coupling reaction (see, for example, *J. Am. Chem. Soc.* 2004, 126, 5182) with silylketene acetals in the presence of a palladium catalyst such as tris(dibenzylideneacetone)-dipalladium(0) ($Pd_2$(dba)$_3$) or preferably bis(dibenzylideneacetone) palladium (0) ($Pd(dba)_2$), an appropriate ligand such as tri-tert-butylphosphine (P(t-Bu)$_3$), a suitable additive such as $ZnF_2$ and an appropriate solvent such as DMF.

The optional protecting group $P^1$ in compound 2-4 can be removed as described in Scheme 1 to give compound I. For example, when W is imidazole, a SEM group can be removed by either fluoride sources, such as tetrabutylammonium fluoride (TBAF) or preferably by acidic reagents such as trifluoroacetic acid (TFA).

The ester I (where $R^a$ is $C_{(1-4)}$alkyl) can be hydrolyzed by an appropriate metal hydroxide reagent such as sodium hydroxide to give acid I (where $R^a$ is H).

Compound 2-6 can be obtained from compound 2-3 by a palladium-mediated Heck reaction (for reviews, see I. Beletskaya, A. Cheprakov, *Chem. Rev.*, 100:3009 (2000)) with an alkyl acrylate in the presence of an appropriate palladium catalyst such as bis(tri-tert-butylphosphine)palladium (0) (Pd(t-Bu$_3$P)$_2$), a suitable base such as $Cs_2CO_3$ and an appropriate solvent such as 1,4-dioxane.

In compound 2-6, the optional protecting group $P^1$ can be removed by methods described in Scheme 1 and the ester group ($R^a$ is $C_{(1-4)}$alkyl) can be hydrolyzed by base such as sodium hydroxide to afford the acid I ($R^a$ is H). In the case of a tert-butyl ester, both the tert-butyl group and the optional protecting group can be removed to afford I ($R^a$ is H) by acidic reagents such as hydrochloric acid or preferably trifluoroacetic acid (TFA).

It is understood that functional groups in I, especially X, can be further derivatized as outlined in Scheme 1.

Scheme 3

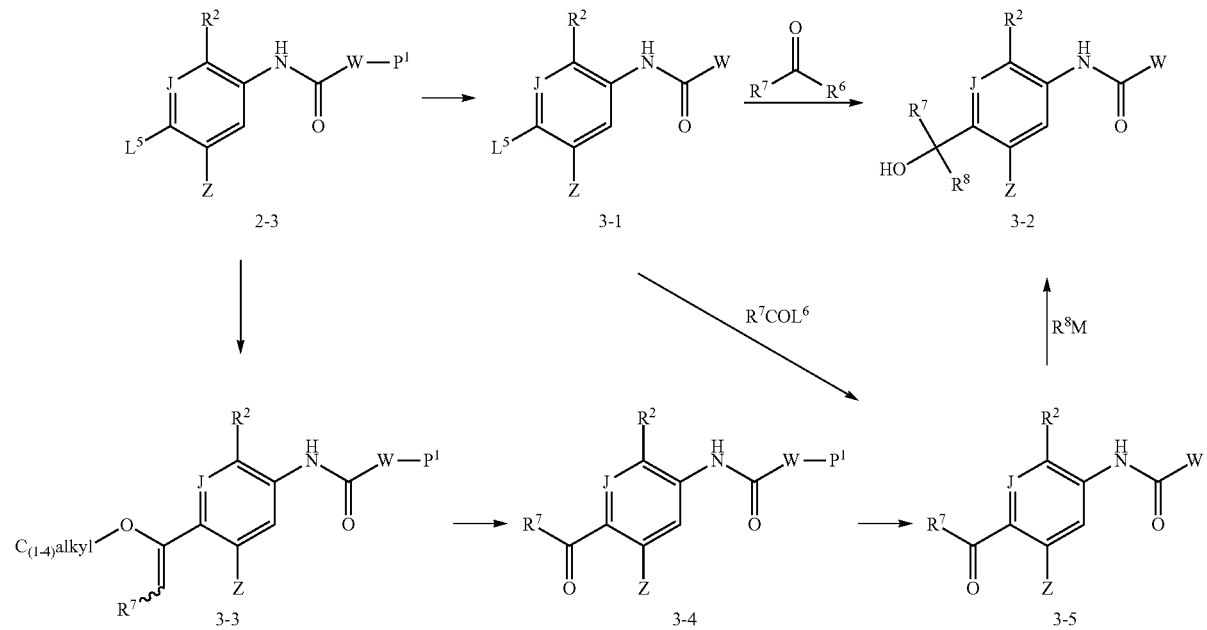

Scheme 3 illustrates two general syntheses for the preparation of the key intermediate compound 3-2, which will be used as a building block in Scheme 4.

For the illustration of synthetic strategy in this scheme, reagents and conditions are defined for the substrate where J is CH. As previously mentioned in Scheme 1, it is understood that similar synthetic methods can be utilized with minor modifications when J is N.

The starting material, compound 2-3, is obtained as described in Scheme 2. Its optional protecting group P¹ can be removed at this point as described in Scheme 1 to give compound 3-1.

The halo compound 3-1 can be converted to alcohol 3-2 by initial deprotonation with a suitable base, such as iso-propylmagnesium chloride (i-PrMgCl) followed by lithium-halogen exchange with an appropriate lithium reagent such as n-butyllithium or preferably tert-butyllithium, and then trapping of the organo-lithium intermediate with a ketone or aldehyde R⁷R⁸CO, where R⁷ and R⁸ are independently H, or C$_{(1-4)}$alkyl.

An alternative method to prepare compound 3-2 begins with material 3-3, which is obtained by Stille coupling of an alkoxyvinyltin reagent (see, for example, J. Org. Chem., 48: 1559-60 (1983)) with compound 2-3. The vinyl alkyl ether group (C$_{(1-4)}$alkylOC=CH(R⁷)—) in compound 3-3 can be hydrolyzed by acidic reagents, such as trifluoroacetic acid or acetic acid, to afford the ketone 3-4.

The optional protecting group P¹ in compound 3-4 can be removed at this point as described for the conversion of 2-3 to 3-1 to give compound 3-5.

The ketone in compound 3-5 can be reacted with an appropriate organometallic reagent R⁸M such as a Grignard reagent (M is MgBr or MgCl), or a suitable reducing reagent, such as NaBH₄ (where R⁸ is H, and M is NaBH₃), to form the alcohol compound 3-2.

Alternatively, 3-5 can be obtained directly from 3-1 by reaction of the organo-lithium intermediate as described for the conversion of 3-1 to 3-2 with an appropriate electrophile R⁷COL⁶ such as an acid chloride (where R⁷ is alkyl, and L⁶ is Cl, see, for example, *J. Med. Chem.*, 48(11): 3930-34 (2005)) or a Weinreb amide (L⁶ is N(OMe)Me, see, for example, *Bioorg. Med. Chem. Lett.*, 14(2): 455-8 (2004)).

It should be noted that the organo-lithium intermediate as described for the conversion of 3-1 to 3-2 and 3-1 to 3-5 is a versatile reagent that can react with various electrophiles.

It is understood that functional groups of compounds in this scheme can be further derivatized as outlined in Scheme 1.

Scheme 4

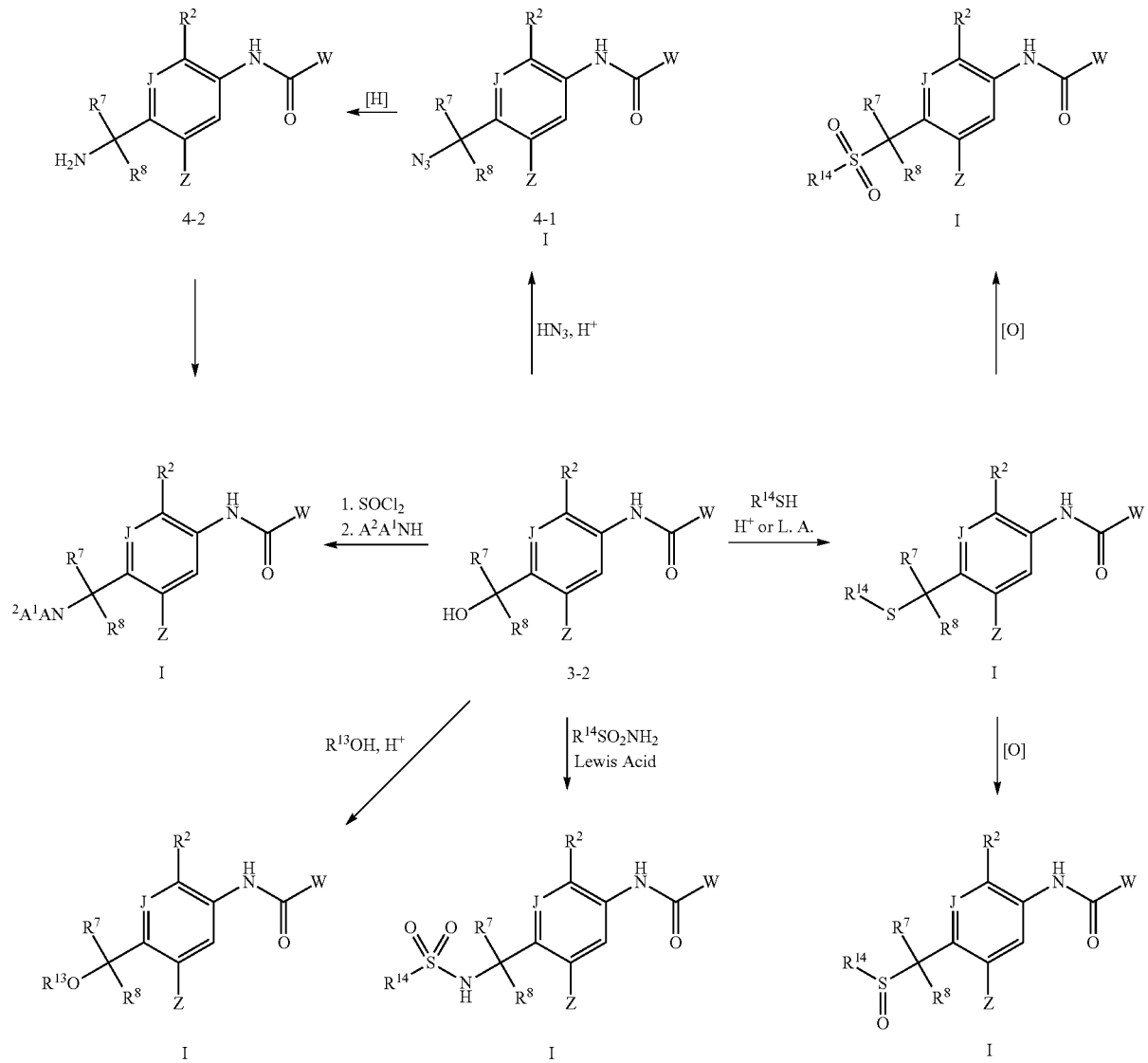

Scheme 4 describes the use of the key intermediate 3-2, as prepared in Scheme 3, to synthesize compounds of Formula I, where X is —C(C$_{(1-4)}$alkyl)$_2$R$^1$ and —CHC$_{(1-4)}$alkylR$^1$ and where R$^1$ is as defined in Formula I.

For the illustration of synthetic strategy in this scheme, reagents and conditions are defined for the substrate where J is CH. As previously mentioned in Scheme 1, it is understood that similar synthetic methods can be utilized with minor modifications when J is N.

The azido compound 4-1 can be obtained from compound 3-2 by treatment with an azide reagent such as sodium azide or preferably hydrazoic acid (HN$_3$), and an appropriate acidic reagent such as TFA in a suitable solvent such as THF.

The azide group in compound 4-1 can be reduced to an amino group to form compound 4-2, preferably by a reducing agent which will not reduce an olefin when R$^2$ is alkenyl such as iron powder in the presence of NH$_4$Cl, or preferably zinc powder in the presence of acetic acid.

The tertiary hydroxyl group in compound 3-2 can also be converted to an amino group in compound I by activating 3-2 with a reagent such as thionyl chloride (SOCl$_2$) and trapping of the resulting intermediate(s) with a primary or secondary amine.

Compounds of Formula I where R$^1$ is alkoxy can be obtained from the hydroxyl compound 3-2 by treatment with acidic reagents such as sulfuric acid or preferably trifluoroacetic acid (TFA) and then trapping of the resulting tertiary cation with an alcohol R$^{13}$OH (where R$^{13}$ is CH$_2$CH$_2$NA$^1$A$^2$ or CH$_2$CH$_2$OR$^a$).

The hydroxyl compound 3-2 can also be reacted with a sulfonamide R$^{14}$SO$_2$NRH in the presence of a Lewis acid (L. A.) such as boron trifluoride diethyl etherate (BF$_3$·OEt$_2$) in a suitable solvent, such as THF to afford compound I (where R$^{14}$ is CH$_2$CH$_2$NA$^1$A$^2$ or R$^a$).

Compounds of Formula I where R$^1$ is a sulfide can be obtained from compound 3-2 by treatment with acidic reagents such as TFA or Lewis acids such as BF$_3$·OEt$_2$ and then trapping of the resulting tertiary cation with a thiol R$^{14}$SH (where R$^{14}$ is CH$_2$CH$_2$NA$^1$A$^2$ or R$^a$).

Compounds of Formula I where R$^1$ is a sulfide can be further oxidized to the corresponding sulfoxide or sulfone of Formula I according to the sulfide oxidation procedures as described in Scheme 1.

Compounds of Formula I where R$^1$ is a sulfone can also be obtained directly from compound 3-2 by reaction with a metal sulfinate salt R$^{14}$SO$_2$M (where M is Na, or K) (see, for example, B. Koutek, et al, *Synth. Commun.*, 6 (4), 305-8 (1976)).

It is understood that functional groups in this scheme can be further derivatized as outlined in Scheme 1. For example, the amino group in compound 4-2 can be reacted with various electrophiles. The amino group can be reacted with carboxylic acids according to standard procedures for amide bond formation or by reaction with acid chlorides or activated esters to form amide compounds as described in Scheme 1. It can be also reacted with an appropriate carbonylation agent, such as phosgene, carbonyldiimidazole or preferably triphosgene, in the presence of a base, such as pyridine or DIEA. The intermediate thus formed can be trapped with a primary or secondary amine, to afford the corresponding urea compound. Similarly, the amino group in compound 4-2 can be reacted with an appropriate oxalylation agent, such as oxalyl chloride, in the presence of a base, such as pyridine or DIEA and the intermediate thus formed can be trapped with a primary or secondary amine to afford oxalamide compounds. Furthermore, the amino group can be reacted with appropriate aldehydes or ketones in the presence of suitable reducing reagents such as NaBH$_4$ or NaBH$_3$CN, or preferably NaBH(OAc)$_3$ according to standard procedures for reductive amination as described in Scheme 1, to form compounds of Formula I where R$^1$ is —NA$^1$A$^2$.

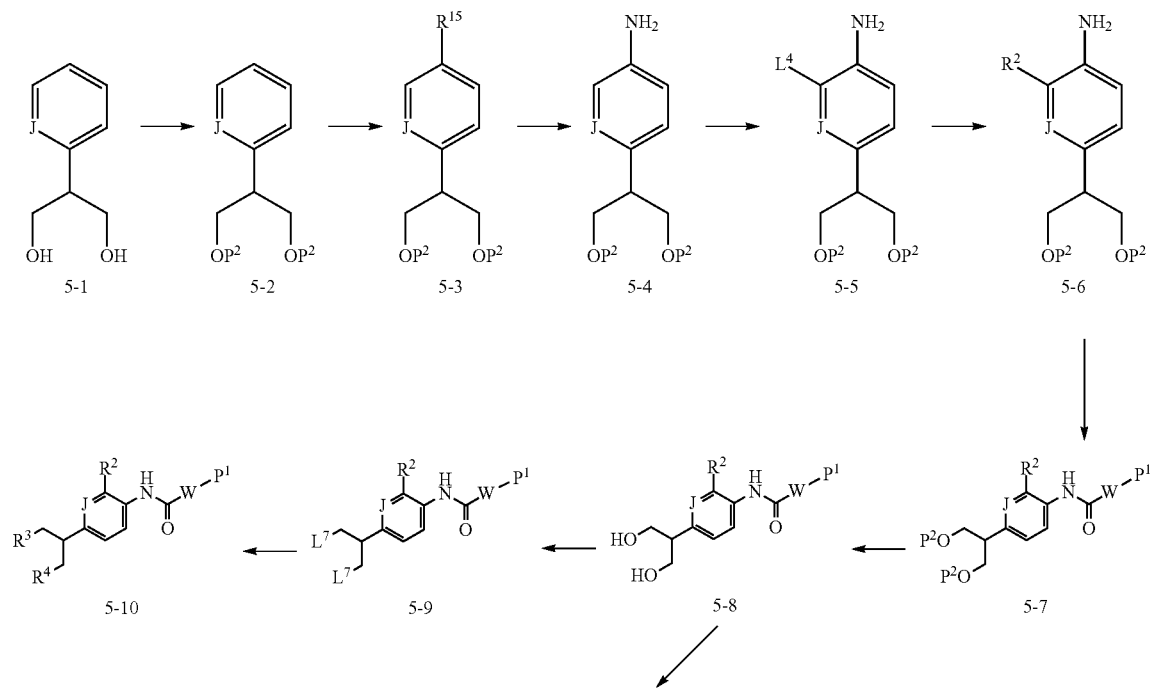

Scheme 5

-continued

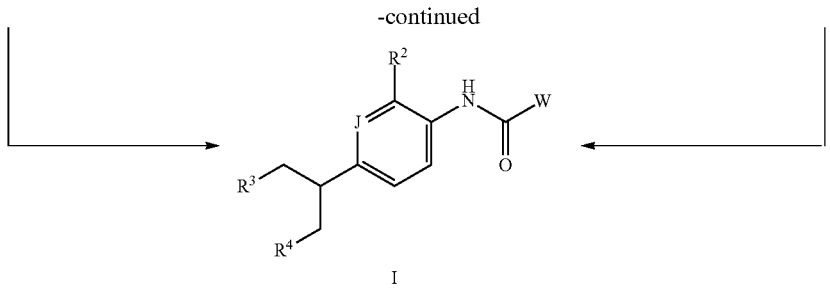

I

Scheme 5 describes the synthesis of compounds of Formula 1 where X is $C_{1-4}$ alkyl$R^3R^{4a}$ and Z is H. To illustrate the methodology of this scheme, reagents and conditions for the substrate where J is CH are defined using commercially available 2-phenylpropane-1,2-diol as starting material 5-1. It is understood that when (2-pyridyl)propane diol (*Tetrahedron: Asymmetry* 8(13), 2175-2187, (1997)) where J is N, is employed as starting material 5-1, minor modifications of the reaction conditions and preferred reagents may be required.

The $P^2$-protected 2-phenylpropane-1,2-diol 5-2 can be employed in this synthetic protocol. The examples of suitable O-protecting groups can be found in "Protective Groups in Organic Synthesis," by Theodora W. Greene and Peter G. M. Wuts, John Wiley & Sons. Inc, NY, (1999). The preferred protections of the hydroxyls include the conversion of diol 5-1 to corresponding diacetate 5-2 where $P^2$ is $CH_3CO$ (*Tetrahedron*, 46 (20), 7081, (1990)).

The conversion of intermediate 5-2 to 5-4 can be accomplished via either halogenation, preferably bromination, of intermediate 5-2 to obtain intermediate 5-3 (where $R^{15}$ is Br) followed by metal-catalyzed amination of halo intermediate 5-3 (for reviews, see: S. L. Buchwald, et al, *Top. Curr. Chem.*, 219:131-209 (2001) and J. F. Hartwig in "*Organopalladium Chemistry for Organic Synthesis*," Wiley Interscience, NY (2002).) or by nitration of intermediate 5-2 to obtain nitro intermediate 5-3 (where $R^{15}$ is $NO_2$) followed by reduction of the nitro group (for references see; *The Nitro Group in Organic Synthesis*" by Noboru Ono, John Wiley & Sons. Inc,). The preferred method for this transformation is the nitration of intermediate 5-2 with conc. $HNO_3$ to obtain nitro compound 5-3, followed by reduction of the nitro group, preferably by catalytic hydrogenation to obtain the corresponding amine 5-4.

The compounds of formula 5-6 can be obtained by ortho-halogenation, preferably bromination, of aniline substrate 5-4 to obtain intermediate 5-5 ($L^4$ is a halogen), followed by a metal-catalyzed coupling reaction with a suitable partner as previously described in Scheme 1 to introduce $R^2$. The preferred conditions for bromination of intermediate 5-4 are NBS in a suitable solvent such as DMF, DCM or acetonitrile. The metal-catalyzed couplings, preferably Suzuki reactions, can be performed according to standard methodology, preferably in the presence of palladium (0) catalyst such as tris(dibenzylideneacetone)dipalladium ($Pd_2(dba)_3$) in the presence of a non-aqueous base such as $K_3PO_4$ and a phosphine ligand such as 2-dicyclohexylphosphino-2',6'-dimethoxy-1,1'-biphenyl (S-Phos) in suitable solvents such as toluene, DME or dioxane.

The amino group in compound 5-6 can then be coupled with a heterocyclic acid $P^1$—WCOOH (or a corresponding salt thereof $P^1$—WCOOM$^2$, M$^2$ is Li, Na or K), according to procedures for amide bond formation as described in Scheme 1 to form amide 5-7.

When $P^2$ is a group present in the final compound, and W in compound 5-7 contains an optional protecting group $P^1$, $P^1$ is removed at this point. For example, when W is imidazole optionally protected with SEM, the SEM group can be removed with either acidic reagents such as TFA or fluoride sources such as tetrabutylammonium fluoride (TBAF) to obtain the final product I (where $R^3$ and $R^{4a}$ are $OP^2$). The preferred method of deprotection is the treatment of compound 5-7 with TFA.

When $P^2$ is not in the final product and is used only as a protecting group, $P^2$ in intermediate 5-7 can be removed at this point by standard methodology (see Green and Wuts reference above) to unmask the diol function while retaining protecting group $P^1$ when it is present. The preferred method of deprotection when, for example, $P^2$ is $CH_3CO$, involves the saponification of diacetate 5-7 with an inorganic base such as KOH in a suitable solvent such as EtOH to provide 5-8.

When the hydroxyl groups are present in the final compound, and W in compound 5-8 contains an optional protecting group $P^1$, $P^1$ can be removed at this point as described previously to obtain the final product I (where $R^3$ and $R^{4a}$ are OH).

The hydroxyl groups of diol 5-8 can also be converted to leaving groups $L^7$ to obtain intermediate 5-9 using known literature methods for further functionalizations. Examples of suitable leaving groups $L^7$ are mesylates, tosylates, triflates and halogens such as Br or I. The preferable leaving group is mesylate which can be prepared by the reaction of diol 5-8 with $CH_3SO_2Cl$ and a tertiary amine bases such as $Et_3N$ in DCM.

It is clear to those who are skilled in the art that the intermediate 5-9 can be subjected to various substitution reactions under appropriate reaction conditions with nucleophiles such as amines, alcohols and thiols to introduce $R^3$ and $R^{4a}$ (where $R^3$ is $R^{4a}$) in intermediate 5-10. When W in compound 5-10 contains an optional protecting group $P^1$, it can be removed at this point to obtain the final product I as described previously.

It is understood that $R^3$ and $R^{4a}$ in intermediates 5-10 and I may be further functionalized as described in Scheme 1.

Scheme 6

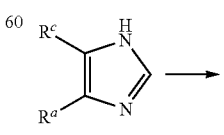

6-1

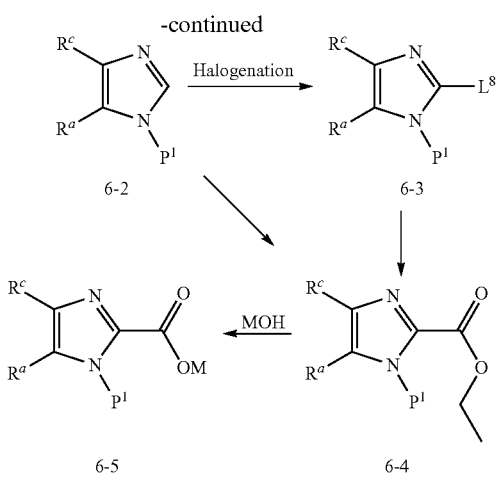

Scheme 6 illustrates a route to the preparation of 2-imidazolecarboxylates of Formula 6-5 where $R^a$ is H or $C_{(1-4)}$ alkyl, and $R^c$ is H, alkyl, —CN, or —CONH$_2$ that are used as intermediates in the synthesis of compounds of Formula I where W is imidazole.

Imidazoles of Formula 6-1 where $R^a$ is H or $C_{(1-4)}$alkyl, and $R^c$ is H, $C_{(1-4)}$alkyl or —CN are either commercially available or, in the case of $R^c$ is —CN, are readily available from commercially available aldehydes (6-1 where $R^c$ is CHO) by reaction with hydroxylamines followed by dehydration with a suitable reagent such as phosphorus oxychloride or acetic anhydride (*Synthesis*, 677, 2003). Imidazoles of Formula 6-1 are protected with a suitable group ($P^1$) such as a methoxymethylamine (MOM), or preferably a SEM group to give compounds of Formula 6-2 (see Theodora W. Greene and Peter G. M. Wuts, Protective Groups in Organic Synthesis, John Wiley and Sons, Inc., NY (1991)).

Imidazoles of Formula 6-2, where $R^c$ is —CN, are halogenated with a suitable reagent such as N-bromosuccinimide or N-iodosuccinimide under either electrophilic conditions in a solvent such as DCM or CH$_3$CN or under radical conditions in the presence of an initiator such as azobis (isobutyronitrile) (AIBN) in a solvent such as CCl$_4$ to give compounds of Formula 6-3 where $L^8$ is a leaving group (preferably bromo or iodo). Halogen-magnesium exchange on compounds of Formula 6-3 provides the organomagnesium species, which is then reacted with a suitable electrophile to provide compounds of Formula 6-4. The preferred conditions for halogen-magnesium exchange are using an alkyl-magnesium reagent, preferably isopropylmagnesium chloride in a suitable solvent such as THF at temperatures between −78° C.-to 0° C. The preferred electrophiles are ethyl chloroformate or ethyl cyanoformate. For examples of halogen-magnesium exchange on cyanoimidazoles see *J. Org. Chem.* 65, 4618, (2000).

For imidazoles of Formula 6-2, where $R^c$ is not —CN, these may be converted directly to imidazoles of Formula 6-4 by deprotonation with a suitable base such as an alkyl-lithium followed by reaction with an electrophile as described above for the organomagnesium species. The preferred conditions are treating the imidazole with n-butyllithium in THF at −78° C. and quenching the resulting organolithium species with ethyl chloroformate (for examples, see *Tetrahedron Lett.*, 29, 3411-3414, (1988)).

The esters of Formula 6-4 may then be hydrolyzed to carboxylic acids (M is H) or carboxylate salts (M is Li, Na, or K,) of Formula 6-5 using one equivalent of an aqueous metal hydroxide (MOH) solution, preferably potassium hydroxide in a suitable solvent such as ethanol or methanol. Synthesis of compounds of Formula 6-5 where $R^c$ is —CONH$_2$ is accomplished by first treating compounds of Formula 6-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

Scheme 7

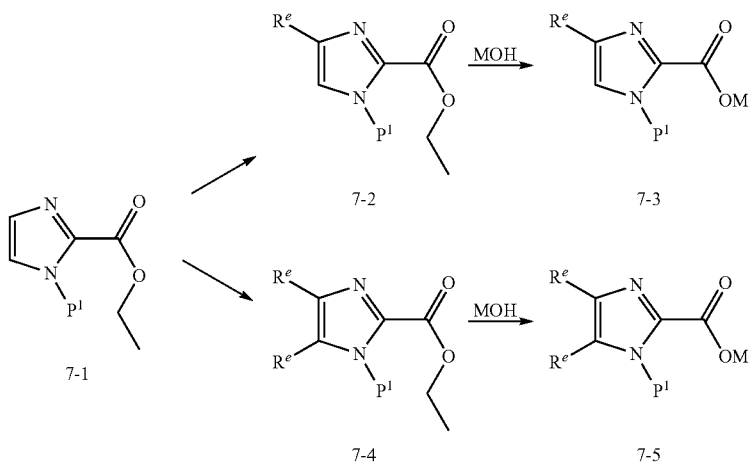

Scheme 7 illustrates a route to 2-imidazolecarboxylates of Formula 7-3 or 7-5 where $R^e$ is chloro or bromo, and M is H, Li, K, or Na that are used as intermediates in the synthesis of compounds of Formula I where W is imidazole.

Compounds of Formula 7-1 are first prepared by protection of commercially available ethyl imidazolecarboxylate according to the methods outlined in Scheme 6, preferably with a SEM group.

Compounds of Formula 7-2 are prepared by reaction of compounds of Formula 7-1 with one equivalent of an appropriate halogenating reagent, such as NBS or N-chlorosuccinimide (NCS) in a suitable solvent such as CH$_3$CN, DCM or DMF at 25° C. Compounds of Formula 7-4 are prepared by reaction of compounds of Formula 7-1 with two equivalents of an appropriate halogenating reagent, such as NBS or NCS in a suitable solvent such as CH₃CN or DMF at temperatures between 30° C. to 80° C. Imidazoles of Formula 7-3 and 7-5 are then obtained from the respective esters by hydrolysis as described in Scheme 6.

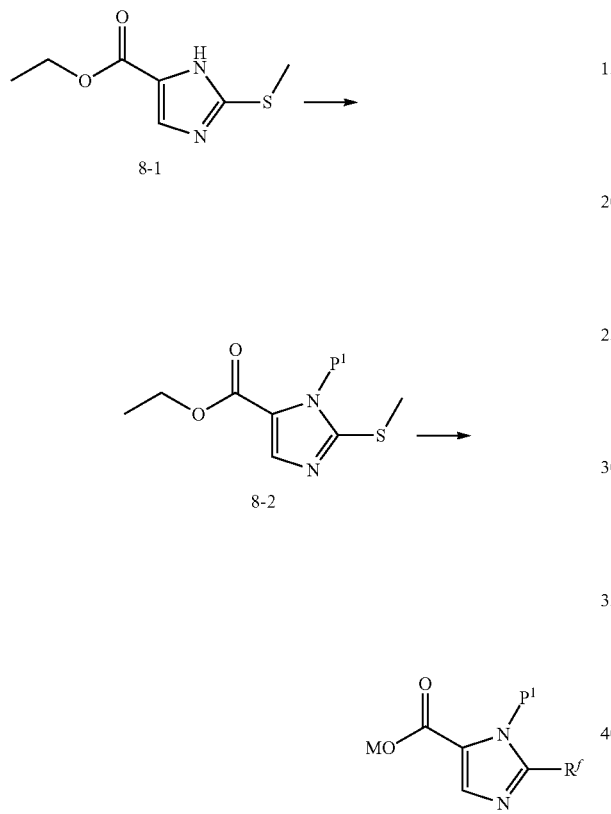

Scheme 8 illustrates a method for the preparation of imidazoles of Formula 8-3 where $R^f$ is —SCH₃, —SOCH₃, or —SO₂CH₃, and M is H, Li, K, or Na that are used as intermediates in the synthesis of compounds of Formula I where W is imidazole.

Imidazole 8-1 (WO 1996011932) is protected according to the methods described in Scheme 6, preferably with a SEM protecting group to give compounds of Formula 8-2. Ester hydrolysis according to the procedure in Scheme 6 gives compounds of Formula 8-3 where $R^f$ is —SCH₃. Oxidation of 2-methylthioimidazoles of Formula 8-2 with one equivalent of an appropriate oxidant, followed by ester hydrolysis according to the procedure in Scheme 6 gives compounds of Formula 8-3 where $R^f$ is —SOCH₃. Oxidation with two equivalents of an appropriate oxidant, followed by ester hydrolysis according to the procedure in Scheme 6 gives compounds of Formula 8-3 where $R^f$ is —SO₂CH₃. The preferred reagent for oxidation is MCPBA in DCM. References for the conversion of sulfides to sulfoxides and sulfones are given in Scheme 1.

The following examples are for exemplary purposes only and are in no way meant to limit the invention.

EXAMPLES

Example 1 and Example 2

4-Cyano-1H-imidazole-2-carboxylic acid [2-cyclohex-1-enyl-4-(1-methanesulfonylamino-1-methylethyl)-phenyl]-amide (1) and 4-Cyano-1H-imidazole-2-carboxylic acid (2-cyclohex-1-enyl-4-isopropenyl-phenyl)-amide (2)

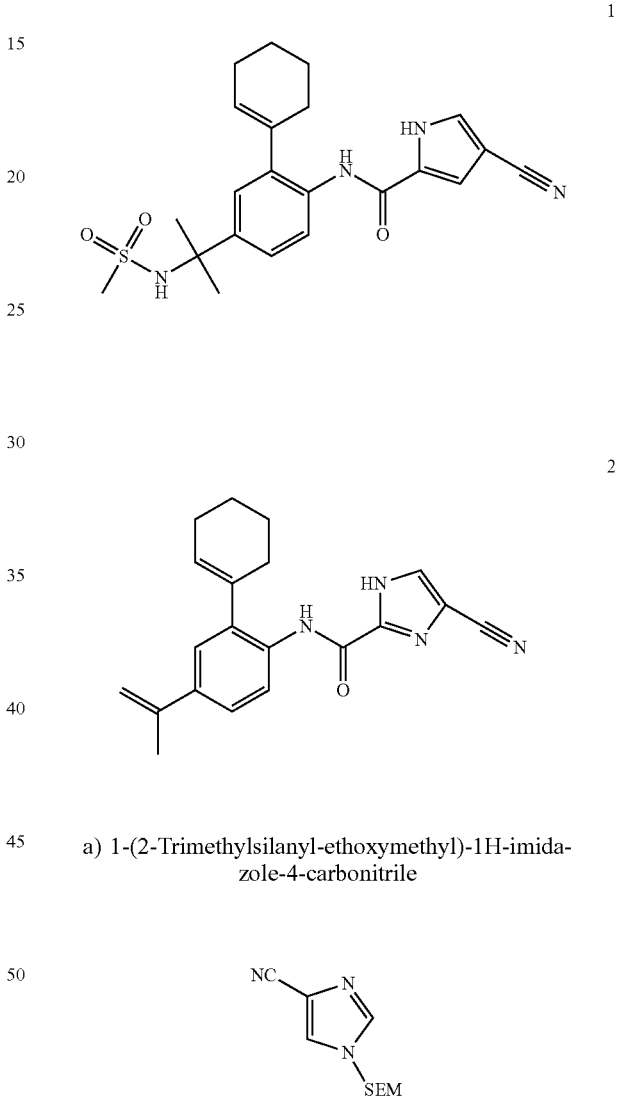

a) 1-(2-Trimethylsilanyl-ethoxymethyl)-1H-imidazole-4-carbonitrile

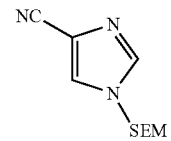 [SMILES: C[Si](C)(C)CCOCn1cnc(C#N)c1]

A flask charged with imidazole-4-carbonitrile (0.50 g, 5.2 mmol) (*Synthesis*, 677, 2003), 2-(trimethylsilyl)ethoxymethyl chloride (SEMCl) (0.95 mL, 5.3 mmol), K₂CO₃ (1.40 g, 10.4 mmol), and acetone (5 mL) was stirred for 10 h at RT. The mixture was diluted with ethyl acetate (EtOAc) (20 mL) and washed with water (20 mL) and brine (20 mL) and the organic layer was dried over MgSO₄. The crude product was eluted from a 20-g SPE cartridge (silica) with 30% EtOAc/hexane to give 0.80 g (70%) of the title compound as a colorless oil. Mass spectrum (CI (CH₄), m/z) Calcd. for C₁₀H₁₇N₃OSi, 224.1 (M+H). found 224.1.

b) 2-Bromo-1-(2-trimethylsilanyl-ethoxymethyl)-1H-imidazole-4-carbonitrile

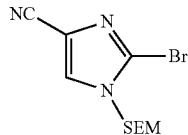 [SMILES: C[Si](C)(C)CCOCn1cc(C#N)nc1Br]

To a solution of 1-(2-trimethylsilanyl-ethoxymethyl)-1H-imidazole-4-carbonitrile (0.70 g, 3.1 mmol) (as prepared in the previous step) in $CCl_4$ (10 mL) was added N-bromosuccinimide (NBS) (0.61 g, 3.4 mmol) and azobis(isobutyronitrile) (AIBN) (cat), and the mixture was heated at 60° C. for 4 h. The reaction was diluted with EtOAc (30 mL), washed with $NaHCO_3$ (2×30 mL), brine (30 mL), the organic layer was dried over $Na_2SO_4$ and then concentrated. The title compound was eluted from a 20-g SPE cartridge (silica) with 30% EtOAc/hexane to give 0.73 g (77%) of a yellow solid. Mass spectrum (CI ($CH_4$), m/z) Calcd. for $C_{10}H_{16}BrN_3OSi$, 302.0/304.0 (M+H). found 302.1/304.1.

c) 4-Cyano-1-(2-trimethylsilanyl-ethoxymethyl)-1H-imidazole-2-carboxylic acid ethyl ester

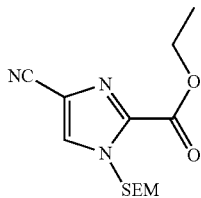 [SMILES: CCOC(=O)c1nc(C#N)cn1COCC[Si](C)(C)C]

To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added dropwise a solution of 2 M i-PrMgCl in THF (1 mL). The reaction was allowed to stir for 10 min at −40° C. and then cooled to −78° C., and ethyl cyanoformate (0.30 g, 3.0 mmol) was added. The reaction was allowed to attain RT and stirred for 1 h. The reaction was quenched with satd aq $NH_4Cl$, diluted with EtOAc (20 mL), washed with brine (2×20 mL). The organic layer was dried over $Na_2SO_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for $C_{13}H_{21}N_3O_3Si$, 296.1 (M+H). found 296.1.

d) 4-Cyano-1-(2-trimethylsilanyl-ethoxymethyl)-1H-imidazole-2-carboxylate potassium salt

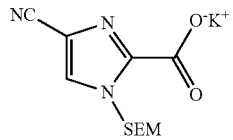

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.2 mL, 1.2 mmol) and the reaction was stirred for 10 min and then concentrated to give 0.40 g (100%) of the title compound as a yellow solid. $^1$H-NMR ($CD_3OD$; 400 MHz) δ 7.98 (s, 1H), 5.92 (s, 2H), 3.62 (m, 2H), 0.94 (m, 2H), 0.00 (s, 9H). Mass spectrum (ESI-neg, m/z): Calcd. for $C_{11}H_{16}KN_3O_3Si$, 266.1 (M-K). found 266.0.

e) 4-Bromo-2-cyclohex-1-enyl-phenylamine

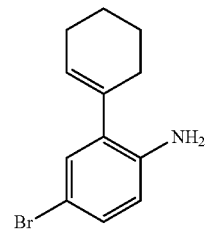 [SMILES: Nc1ccc(Br)cc1C1=CCCCC1]

To a mixture of 4-bromo-2-iodo-phenylamine (2.00 g, 6.71 mmol), 2-cyclohex-1-enyl-4,4,5,5-tetramethyl-[1,3,2]dioxaborolane (1.40 g, 6.71 mmol) and $Pd(PPh_3)_4$ (388 mg, 0.336 mmol) in 40 mL of 1,4-dioxane was added 2.0 M aq $Na_2CO_3$ solution (26.8 mL, 53.7 mmol). After stirring at 80° C. for 5 h under Ar, the reaction was cooled to room temperature (RT). The mixture was treated with EtOAc (100 mL), washed with $H_2O$ (3×30 mL) and brine (20 mL). The organic layer was dried ($Na_2SO_4$) and concentrated in vacuo. The residue was purified by flash chromatography on silica gel (10-20% EtOAc/hexane) to give 1.47 g (87%) of the title compound as a light brown oil. Mass spectrum (ESI, m/z): Calcd. for $C_{12}H_{14}BrN$, 252.0 (M+H). found 252.0.

f) 4-Cyano-1-(2-trimethylsilanyl-ethoxymethyl)-1H-imidazole-2-carboxylic acid (4-bromo-2-cyclohex-1-enyl-phenyl)-amide

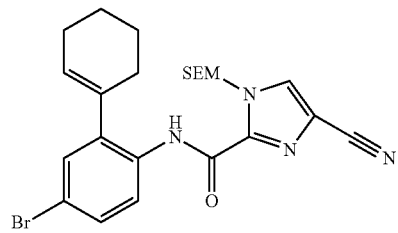 [SMILES: C[Si](C)(C)CCOCn1cc(C#N)nc1C(=O)Nc1ccc(Br)cc1C1=CCCCC1]

To a mixture of 4-bromo-2-cyclohex-1-enyl-phenylamine (as prepared in the previous step, 1.23 g, 4.88 mmol), potassium 4-cyano-1-(2-trimethylsilanyl-ethoxymethyl)-1H-imidazole-2-carboxylate (as prepared in Example 1, step (d), 1.49 g, 4.88 mmol) and bromotripyrrolidinophosphonium hexafluorophosphate (PyBroP) (2.27 g, 4.88 mmol) in 25 mL of DMF was added N,N-diisopropylethylamine (DIEA) (2.55 mL, 14.6 mmol). After stirring at RT for 16 h, the mixture was treated with 100 mL of EtOAc and washed with $H_2O$ (2×30 mL), brine (30 mL) and dried ($Na_2SO_4$). The organic solvent was evaporated and the residue was purified by flash chromatography on silica gel (5-10%

EtOAc/hexane) to give 2.21 g (90%) of the title compound as a white solid. ¹H-NMR (CDCl₃; 400 MHz): δ 9.70 (s, 1H), 8.26 (d, 1H, J=8.6 Hz), 7.78 (s, 1H), 7.36 (dd, 1H, J=8.6, 2.3 Hz), 7.31 (d, 1H, J=2.3 Hz), 5.94 (s, 2H), 5.86 (m, 1H), 3.66 (t, 2H, J=8.3 Hz), 2.19-2.33 (m, 4H), 1.75-1.88 (m, 4H), 0.97 (t, 2H, J=8.3 Hz), 0.00 (s, 9H).

g) 4-Cyano-1H-imidazole-2-carboxylic acid (4-bromo-2-cyclohex-1-enyl-phenyl)-amide

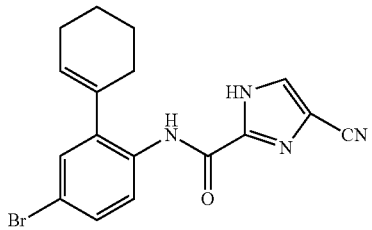 [SMILES: N#Cc1c[nH]c(C(=O)Nc2ccc(Br)cc2C2=CCCCC2)n1]

To a solution of 4-cyano-1-(2-trimethylsilanyl-ethoxymethyl)-1H-imidazole-2-carboxylic acid (4-bromo-2-cyclohex-1-enyl-phenyl)-amide (as prepared in the previous step, 1.20 g, 2.39 mmol) in 10 mL of DCM (CH₂Cl₂) was added 0.30 mL of EtOH followed by 5.0 mL of TFA. After stirring at RT for 3 h, the mixture was treated with 20 mL of n-propanol and concentrated in vacuo. The residue was triturated with DCM to afford 853 mg (96%) of the title compound as a white solid. ¹H-NMR (dimethylsulfoxide (DMSO)-d₆; 400 MHz): δ 9.80 (s, 1H), 8.30 (s, 1H), 7.94 (d, 1H, J=8.6 Hz), 7.50 (dd, 1H, J=8.6, 2.3 Hz), 7.39 (d, 1H, J=2.3 Hz), 5.80 (m, 1H), 2.12-2.25 (m, 4H), 1.61-1.77 (m, 4H). Mass spectrum (ESI, m/z): Calcd. for C₁₇H₁₅BrN₄O, 371.0 (M+H). found 371.0.

h) 4-Cyano-1H-imidazole-2-carboxylic acid [2-cyclohex-1-enyl-4-(1-hydroxy-1-methyl-ethyl)phenyl]-amide

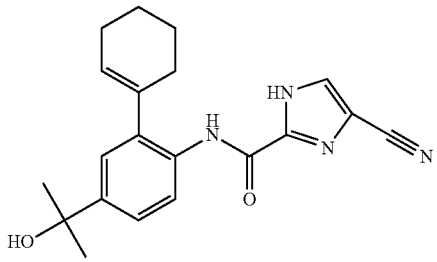 [SMILES: CC(C)(O)c1ccc(NC(=O)c2nc(C#N)c[nH]2)c(C2=CCCCC2)c1]

To a solution of 4-cyano-1H-imidazole-2-carboxylic acid (4-bromo-2-cyclohex-1-enyl-phenyl)-amide (as prepared in the previous step, 50.0 mg, 0.135 mmol) in 2 mL of THF at −78° C. under Ar was added isopropyl magnesium chloride (71 μL, 0.14 mmol, 2.0 M in THF). The resulting mixture was warmed to RT and stirred for 15 min, cooled to −78° C. again. To the mixture was added tert-butyllithium (240 μL, 0.405 mmol, 1.7 M in pentane) and the resulting mixture was stirred at −78° C. for 5 min and then acetone (0.40 mL, 0.68 mmol) was added. The reaction was warmed to RT and stirred for 1 h under Ar. The mixture was treated with 1 mL of saturated NH₄Cl followed by 40 mL of EtOAc and washed with H₂O (10 mL), brine (5 mL) and dried (Na₂SO₄). Removal of the solvent under reduced pressure followed by flash chromatography of the residue on silica gel (1-2% MeOH/DCM) gave 32.1 mg (68%) of the title compound as a white solid. ¹H-NMR (CDCl₃; 400 MHz): δ 11.88 (s, 1H), 9.58 (s, 1H), 8.29 (d, 1H, J=8.6 Hz), 7.74 (s, 1H), 7.42 (dd, 1H, J=8.6, 2.2 Hz), 7.35 (d, 1H, J=2.2 Hz), 5.87 (m, 1H), 2.23-2.34 (m, 4H), 1.73-1.90 (m, 4H), 1.79 (s, 1H, OH), 1.61 (s, 6H). Mass spectrum (ESI, m/z): Calcd. for C₂₀H₂₂N₄O₂, 351.2 (M+H). found 351.0.

i) 4-Cyano-1H-imidazole-2-carboxylic acid [2-cyclohex-1-enyl-4-(1-methanesulfonylamino-1-methyl-ethyl)-phenyl]-amide (1) and 4-Cyano-1H-imidazole-2-carboxylic acid (2-cyclohex-1-enyl-4-isopropenyl-phenyl)-amide (2)

To a solution of 4-cyano-1H-imidazole-2-carboxylic acid [2-cyclohex-1-enyl-4-(1-hydroxy-1-methyl-ethyl)-phenyl]-amide (as prepared in the previous step, 30.0 mg, 0.0856 mmol) and methanesulfonamide (40.7 mg, 0.428 mmol) in 1 mL of THF at −78° C. was added BF₃.OEt₂ (16.0 μL, 0.128 mmol) under Ar. The resulting mixture was warmed to −10° C. and stirred for 2 h and then at RT for 16 h under Ar. The reaction was treated with 2 mL of saturated aqueous NaHCO₃ and 10 ml of brine and then extracted with EtOAc (2×20 mL). The combined organic layers were concentrated under reduced pressure and the residue was purified by flash chromatography on silica gel (10-20% EtOAc/DCM) to give the title compound 1 (24.3 mg, 66%) as a white solid and the title compound 2 (9.3 mg, 33%) as a white solid. 1: ¹H-NMR (CDCl₃; 400 MHz): δ 11.89 (s, 1H), 9.55 (s, 1H), 8.30 (d, 1H, J=8.6 Hz), 7.72 (d, 1H, J=2.3 Hz), 7.59 (dd, 1H, J=8.6, 2.3 Hz), 7.29 (d, 1H, J=2.3 Hz), 5.84 (m, 1H), 5.64 (s, 1H), 2.82 (s, 3H), 2.18-2.34 (m, 4H), 1.74-1.88 (m, 4H), 1.80 (s, 6H). Mass spectrum (ESI, m/z): Calcd. for C₂₁H₂₅N₅O₃S, 428.2 (M+H). found 428.0. 2: ¹H-NMR (CDCl₃; 400 MHz): δ 12.56 (s, 1H), 9.65 (s, 1H), 8.30 (d, 1H, J=8.6 Hz), 7.77 (s, 1H), 7.43 (dd, 1H, J=8.6, 2.3 Hz), 7.31 (d, 1H, J=2.3 Hz), 5.88 (m, 1H), 5.40 (br s, 1H), 5.11 (m, 1H), 2.24-2.36 (m, 4H), 2.17 (s, 3H), 1.76-1.91 (m, 4H). Mass spectrum (ESI, m/z): Calcd. for C₂₀H₂₀N₄O₄, 333.2 (M+H). found 333.1.

Example 3

4-Cyano-1H-imidazole-2-carboxylic acid [4-(1-acetylamino-1-methyl-ethyl)-2-cyclohex-1-enyl-phenyl]-amide

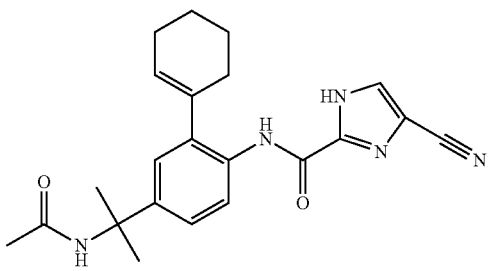 [SMILES: CC(=O)NC(C)(C)c1ccc(NC(=O)c2nc(C#N)c[nH]2)c(C2=CCCCC2)c1]

a) 4-Cyano-1H-imidazole-2-carboxylic acid [4-(1-azido-1-methyl-ethyl)-2-cyclohex-1-enyl-phenyl]-amide

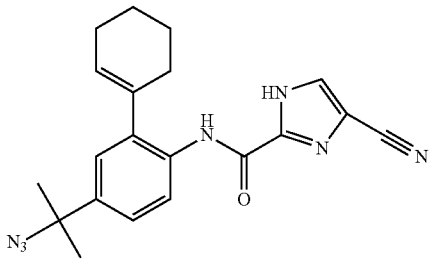 [SMILES: CC(C)(N=[N+]=[N-])c1ccc(NC(=O)c2nc(C#N)c[nH]2)c(C2=CCCCC2)c1]

To a mixture of 4-cyano-1H-imidazole-2-carboxylic acid [2-cyclohex-1-enyl-4-(1-hydroxy-1-methyl-ethyl)-phenyl]-amide (as prepared in example 1, step (h), 15.0 mg, 0.0428 mmol) and NaN$_3$ (27.8 mg, 0.428 mmol) in 1 mL of chloroform at 0° C. under Ar was added TFA (49 μL, 0.64 mmol). The resulting mixture was stirred at 0° C. for 1 h under Ar. Treated with 30 mL of EtOAc, the mixture was washed with saturated aqueous NaHCO$_3$ (10 mL), brine (10 mL) and dried (Na$_2$SO$_4$). Removal of the solvent under reduced pressure followed by flash chromatography of the residue on silica gel (0-5% EtOAc/DCM) gave 13.6 mg (84%) of the title compound as a white solid. Mass spectrum (ESI, m/z): Calcd. for C$_{20}$H$_{21}$N$_7$O, 376.2 (M+H). found 376.0.

b) 4-Cyano-1H-imidazole-2-carboxylic acid [4-(1-amino-1-methyl-ethyl)-2-cyclohex-1-enyl-phenyl]-amide acetic acid salt

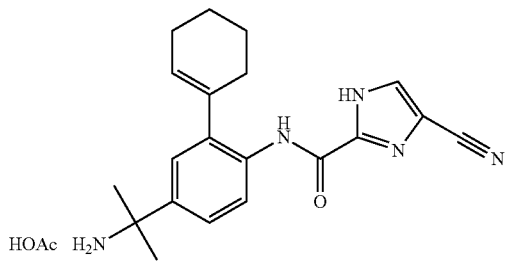 [SMILES: CC(C)(N)c1ccc(NC(=O)c2nc(C#N)c[nH]2)c(C2=CCCCC2)c1 ; "HOAc"]

To a mixture of 4-cyano-1H-imidazole-2-carboxylic acid [4-(1-azido-1-methyl-ethyl)-2-cyclohex-1-enyl-phenyl]-amide (as prepared in the previous step, 13.6 mg, 0.0362 mmol) and zinc (9.5 mg, 0.15 mmol) in 1 mL of THF was added acetic acid (0.20 mL). The resulting mixture was stirred at RT for 3 h under Ar. The solid was removed by filtration on Celite and the filtrate was concentrated in vacuo to give a light brown oil. The mixture was triturated with DCM (2×4 mL). The solvent was removed by filtration and the solid was dried in vacuo to give 13.5 mg (91%) of the title compound as a white solid. $^1$H-NMR (CD$_3$OD; 400 MHz): δ 8.27 (s, 1H), 7.70 (s, 1H), 7.43 (d, 1H, J=7.3 Hz), 7.29 (s, 1H), 5.81 (m, 1H), 2.11-2.37 (m, 4H), 1.91 (s, 3H), 1.59-1.84 (m, 4H), 1.71 (s, 6H).

c) 4-Cyano-1H-imidazole-2-carboxylic acid [4-(1-acetylamino-1-methyl-ethyl)-2-cyclohex-1-enyl-phenyl]-amide A mixture of 4-cyano-1H-imidazole-2-carboxylic acid [4-(1-amino-1-methyl-ethyl)-2-cyclohex-1-enyl-phenyl]-amide acetic acid salt (as prepared in the previous step, 50.0 mg, 0.122 mmol) and DIEA (85.0 μL, 0.488 mmol) in 2 mL of CHCl$_3$ was stirred at RT for 5 min before dimethylaminopyridine (DMAP) (4.1 mg, 0.037 mmol) was added. The mixture was cooled to 0° C. and a solution of acetyl chloride (10 μL, 0.15 mmol) in 2 mL of CHCl$_3$ was added dropwise. The reaction was warmed to RT and stirred for 18 h under Ar. The mixture was treated with EtOAc (40 mL), washed with saturated aqueous NaHCO$_3$ (5 mL), brine (10 mL) and dried over Na$_2$SO$_4$. Removal of the solvent under reduced pressure followed by flash chromatography of the residue on silica gel (1-2% MeOH/DCM) gave 7.6 mg (16%) of the title compound as a white solid. $^1$H-NMR (CD$_3$OD; 400 MHz): δ 8.17 (s, 1H), 8.10 (d, 1H, J=8.6 Hz), 7.99 (s, 1H), 7.27 (dd, 1H, J=8.6, 2.3 Hz), 7.16 (d, 1H, J=2.3 Hz), 5.80 (m, 1H), 2.20-2.32 (m, 4H), 1.94 (s, 3H), 1.74-1.88 (m, 4H), 1.62 (s, 6H). Mass spectrum (ESI, m/z): Calcd. for C$_{22}$H$_{25}$N$_5$O$_2$, 392.2 (M+H). found 391.8.

Example 4

4-Cyano-1H-imidazole-2-carboxylic acid [2-cyclohex-1-enyl-4-(1-methyl-1-ureido-ethyl)-phenyl]-amide

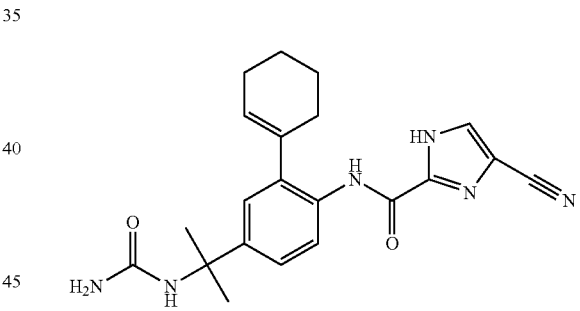

To a solution of triphosgene (7.2 mg, 0.024 mmol) in 2 mL of THF at 0° C. was added a solution of 4-cyano-1H-imidazole-2-carboxylic acid [4-(1-amino-1-methyl-ethyl)-2-cyclohex-1-enyl-phenyl]-amide acetic acid salt (as prepared in Example 3, step (b), 25.0 mg, 0.0611 mmol) and DIEA (32 μL, 0.18 mmol) in 2 mL of THF under Ar. The resulting mixture was stirred at RT for 20 min and cooled to 0° C. NH$_3$ (g) was bubbled into the mixture for ca. 4 min and the reaction was then sealed and stirred at RT for 0.5 h. The mixture was treated with brine (10 mL) and extracted with EtOAc (2×25 mL). The combined organic layers were concentrated in vacuo and the residue was purified by flash chromatography on silica gel (3-6% MeOH/DCM) to afford 7.2 mg (30%) of the title compound as a white solid. $^1$H-NMR (CD$_3$OD; 400 MHz): δ 8.11 (d, 1H, J=8.6 Hz), 7.98 (s, 1H), 7.32 (dd, 1H, J=8.6, 2.1 Hz), 7.22 (d, 1H, J=2.1 Hz), 5.80 (m, 1H), 2.20-2.34 (m, 4H), 1.73-1.89 (m, 4H), 1.61 (s, 6H). Mass spectrum (ESI, m/z): Calcd. for C$_{21}$H$_{24}$N$_6$O$_2$, 393.2 (M+H). found 393.0.

Example 5

4-Cyano-1H-imidazole-2-carboxylic acid (2-cyclohex-1-enyl-4-{1-[3-(2-hydroxy-ethyl)-ureido]-1-methyl-ethyl}-phenyl)-amide

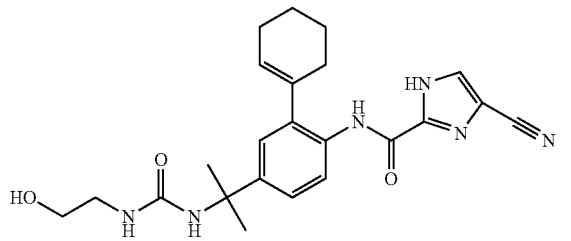 [SMILES: CC(C)(NC(=O)NCCO)c1ccc(NC(=O)c2nc(C#N)c[nH]2)c(C2=CCCCC2)c1]

To a solution of triphosgene (11.9 mg, 0.0400 mmol) in 2 mL of THF at 0° C. was added a solution of 4-cyano-1H-imidazole-2-carboxylic acid [4-(1-amino-1-methyl-ethyl)-2-cyclohex-1-enyl-phenyl]-amide acetic acid salt (as prepared in Example 3, step (b), 41.0 mg, 0.100 mmol) and DIEA (52 μL, 0.30 mmol) in 2 mL of THF under Ar. The resulting mixture was stirred at RT for 10 min and cooled to 0° C. 2-Amino-ethanol (60.0 μL, 1.00 mmol) was added into the mixture and the reaction was stirred at RT for 2 h. The mixture was treated with brine (10 mL) and extracted with EtOAc (2×25 mL). The combined organic layers were concentrated in vacuo and the residue was purified by flash chromatography on silica gel (2-8% MeOH/DCM) to give 15.1 mg (35%) of the title compound as a light yellow oil. $^1$H-NMR (CD$_3$OD; 400 MHz): δ 8.11 (d, 1H, J=8.4 Hz), 7.99 (s, 1H), 7.31 (dd, 1H, J=8.4, 2.4 Hz), 7.21 (d, 1H, J=2.4 Hz), 6.48 (s, 1H), 5.80 (m, 1H), 3.52 (t, 2H, J=5.6 Hz), 3.16 (t, 2H, J=5.6 Hz), 2.20-2.33 (m, 4H), 1.73-1.88 (m, 4H), 1.60 (s, 6H). Mass spectrum (ESI, m/z): Calcd. for C$_{23}$H$_{28}$N$_6$O$_3$, 437.2 (M+H). found 437.1.

Example 6

N-(1-{4-[(4-Cyano-1H-imidazole-2-carbonyl)-amino]-3-cyclohex-1-enyl-phenyl}-1-methyl-ethyl)-oxalamide

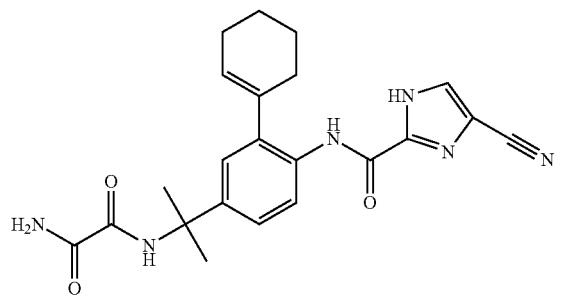 [SMILES: CC(C)(NC(=O)C(N)=O)c1ccc(NC(=O)c2nc(C#N)c[nH]2)c(C2=CCCCC2)c1]

The procedure of Example 4 was followed using 4-cyano-1H-imidazole-2-carboxylic acid [4-(1-amino-1-methyl-ethyl)-2-cyclohex-1-enyl-phenyl]-amide acetic acid salt (as prepared in Example 3, step (b), 28.0 mg, 0.0684 mmol), oxalyl chloride (51 μL, 0.10 mmol, 2.0 M in DCM) and DIEA (36 μL, 0.21 mmol). Flash chromatography on silica gel (1-2% MeOH/DCM) afforded 9.2 mg (34%) of the title compound as a white solid. $^1$H-NMR (CD$_3$OD; 400 MHz): δ 8.14 (d, 1H, J=8.4 Hz), 7.99 (s, 1H), 7.31 (dd, 1H, J=8.4, 2.3 Hz), 7.20 (d, 1H, J=2.3 Hz), 5.81 (m, 1H), 2.22-2.31 (m, 4H), 1.74-1.89 (m, 4H), 1.71 (s, 6H). Mass spectrum (ESI, m/z): Calcd. for C$_{22}$H$_{24}$N$_6$O$_3$, 421.2 (M+H). found 421.0.

Example 7

4-Cyano-1H-imidazole-2-carboxylic acid [4-(2-carbamoyl-ethyl)-2-cyclohex-1-enyl-phenyl]-amide

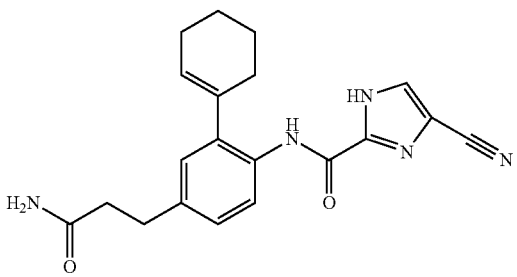 [SMILES: N#Cc1c[nH]c(C(=O)Nc2ccc(CCC(N)=O)cc2C2=CCCCC2)n1]

a) 3-(4-Amino-phenyl)-propionic acid methyl ester sulfuric acid salt

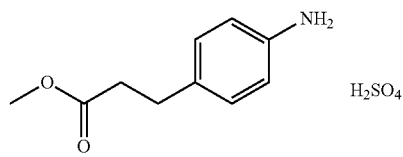

To a mixture of 3-(4-amino-phenyl)-propionic acid (1.00 g, 6.05 mmol) in 10 mL of methyl alcohol (MeOH) was added 0.80 mL of conc H$_2$SO$_4$. The resulting mixture was refluxed for 2 h, concentrated down to ca. half volume by distillation and then cooled to 45° C. Methyl tert-butyl ether (MTBE, 15 mL) was added. The mixture was allowed to cool to 0° C. and stirred for 0.5 h. The solid was collected by filtration and washed with 1:4 MeOH/MTBE (2×10 mL), MTBE (3×10 mL) and dried under reduced pressure. The title compound (1.43 g, 85%) was obtained as a white solid. $^1$H-NMR (DMSO-d$_6$; 400 MHz): δ 8.40-11.0 (br s, 4H), 7.34 (d, 2H, J=8.2 Hz), 7.23 (d, 2H, J=8.2 Hz), 3.57 (s, 3H), 2.86 (t, 2H, J=7.4 Hz), 2.64 (t, 2H, J=7.4 Hz).

b) 3-(4-Amino-phenyl)-propionamide

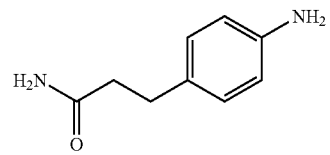 [SMILES: NC(=O)CCc1ccc(N)cc1]

To a suspension of 3-(4-amino-phenyl)-propionic acid methyl ester sulfuric acid salt (as prepared in the previous step, 277 mg, 1.00 mmol) in 8 mL of conc NH$_4$OH was added 0.75 g of NaCl in 3 mL of H$_2$O. After stirring at RT for 16 h, the resulting mixture was treated with 10 mL of brine and extracted with EtOAc (5×25 mL). The combined organic layers were dried (Na₂SO₄) and concentrated to give 133 mg (81%) of the title compound as a white solid. Mass spectrum (ESI, m/z): Calcd. for $C_9H_{12}N_2O$, 165.1 (M+H). found 165.0.

c) 3-(4-Amino-3-bromo-phenyl)-propionamide

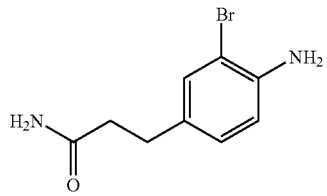 [SMILES: NC(=O)CCc1ccc(N)c(Br)c1]

To a mixture of 3-(4-amino-phenyl)-propionamide (as prepared in the previous step, 123 mg, 0.749 mmol) in 10 mL of 1:1 DCM/CH₃CN at 0° C. was added N-bromosuccinimide (NBS) (133 mg, 0.749 mmol) in 4 mL of 1:1 DCM/CH₃CN. The mixture was warmed to RT and stirred for 1 h under Ar. Treated with 20 mL of brine, the mixture was extracted with EtOAc (3×20 mL). The combined organic layers were concentrated in vacuo and the residue was purified by flash chromatography on silica gel (1-4% MeOH/DCM) giving 133 mg (81%) of the title compound as a white solid. Mass spectrum (ESI, m/z): Calcd. for $C_9H_{11}BrN_2O$, 243.0 (M+H). found 242.9.

d) 3-(4-Amino-3-cyclohex-1-enyl-phenyl)-propionamide

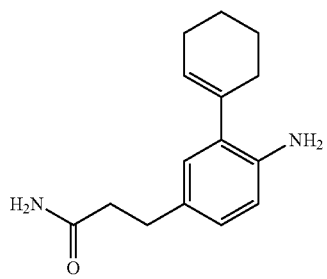 [SMILES: NC(=O)CCc1ccc(N)c(C2=CCCCC2)c1]

To a mixture of 3-(4-amino-3-bromo-phenyl)-propionamide (as prepared in the previous step, 100 mg, 0.411 mmol), 2-cyclohex-1-enyl-4,4,5,5-tetramethyl-[1,3,2]dioxaborolane (94.1 mg, 0.452 mmol) and Pd(PPh₃)₄ (47.5 mg, 0.0411 mmol) in 3 mL of 1,4-dioxane was added 2.0 M aq Na₂CO₃ solution (1.64 mL, 3.29 mmol). After stirring at 80° C. for 16 h under Ar, the reaction was cooled to RT and treated with 15 mL of brine. The mixture was extracted with EtOAc (2×30 mL) and the combined organic layers were dried (Na₂SO₄) and concentrated in vacuo. The residue was purified by flash chromatography on silica gel (1-3% MeOH/DCM) giving 88.1 mg (88%) of the title compound as a colorless oil. Mass spectrum (ESI, m/z): Calcd. for $C_{15}H_{20}N_2O$, 245.2 (M+H). found 245.1.

e) 4-Cyano-1-(2-trimethylsilanyl-ethoxymethyl)-1H-imidazole-2-carboxylic acid [4-(2-carbamoyl-ethyl)-2-cyclohex-1-enyl-phenyl]-amide

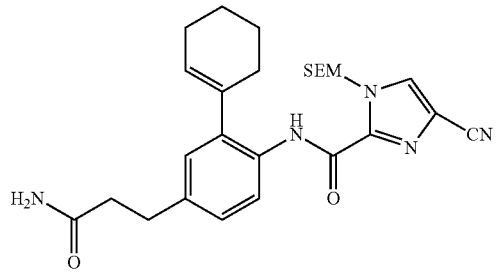 [SMILES: C[Si](C)(C)CCOCn1cc(C#N)nc1C(=O)Nc1ccc(CCC(N)=O)cc1C1=CCCCC1]

To a mixture of 3-(4-amino-3-cyclohex-1-enyl-phenyl)-propionamide (as prepared in the previous step, 85.0 mg, 0.378 mmol), potassium 4-cyano-1-(2-trimethylsilanyl-ethoxymethyl)-1H-imidazole-2-carboxylate (as prepared in Example 1, step (d), 117 mg, 0.383 mmol) and PyBroP (179 mg, 0.383 mmol) in 2.5 mL of DMF was added DIEA (182 μL, 1.04 mmol). After stirring at RT for 16 h, the mixture was treated with 30 mL of EtOAc and washed with H₂O (2×10 mL), brine (10 mL) and dried (Na₂SO₄). The organic solvent was evaporated in vacuo and the residue was purified by flash chromatography on silica gel (0-2% MeOH/DCM) to give 156 mg (91%) of the title compound as a white solid. Mass spectrum (ESI, m/z): Calcd. for $C_{26}H_{35}N_5O_3Si$, 494.3 (M+H). found 494.0.

f) 4-Cyano-1H-imidazole-2-carboxylic acid [4-(2-carbamoyl-ethyl)-2-cyclohex-1-enyl-phenyl]-amide To a solution of 4-cyano-1-(2-trimethylsilanyl-ethoxymethyl)-1H-imidazole-2-carboxylic acid [4-(2-carbamoyl-ethyl)-2-cyclohex-1-enyl-phenyl]-amide (as prepared in the previous step, 150 mg, 0.304 mmol) in 2 mL of DCM was added 60 μL of EtOH followed by 1 mL of TFA. The resulting solution was stirred at RT for 3 h. The reaction was treated with 20 mL of n-propanol and concentrated in vacuo. The residue was purified by flash chromatography on silica gel (2-5% MeOH/DCM) to afford 86.1 mg (78%) of the title compound as a white solid. ¹H-NMR (CD₃OD; 400 MHz): δ 8.08 (d, 1H, J=8.3 Hz), 8.00 (s, 1H), 7.14 (dd, 1H, J=8.3, 2.2 Hz), 7.06 (d, 1H, J=2.2 Hz), 5.79 (m, 1H), 2.89 (t, 2H, J=7.7 Hz), 2.50 (t, 2H, J=7.7 Hz), 2.20-2.30 (m, 4H), 1.72-1.88 (m, 4H). Mass spectrum (ESI, m/z): Calcd. for $C_{20}H_{21}N_5O_2$, 364.2 (M+H). found 364.1.

Examples 8 and 9

3-{4-[(4-Cyano-1H-imidazole-2-carbonyl)-amino]-3-cyclohex-1-enyl-pheny}-propionic acid (8) and 3-{4-[(4-Carbamoyl-1H-imidazole-2-carbonyl)-amino]-3-cyclohex-1-enyl-pheny}-propionic acid (9)

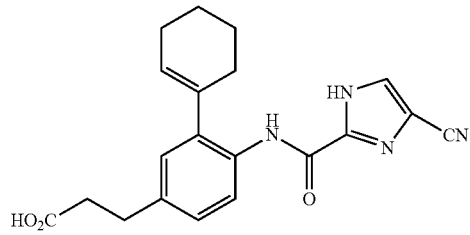

8

77

-continued

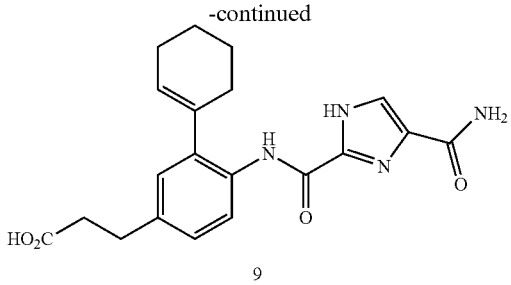

9

To a solution of 4-cyano-1H-imidazole-2-carboxylic acid [4-(2-carbamoyl-ethyl)-2-cyclohex-1-enyl-phenyl]-amide (as prepared in Example 7, step (f), 30.0 mg, 0.0826 mmol) in 1 mL of 1:1 MeOH/THF was added 6 N NaOH (138 μL, 0.826 mmol). The resulting mixture was stirred at RT for 2 h and at reflux for 5 h. After cooling to RT, the mixture was treated with 10 mL of H$_2$O, neutralized to a pH of 6 with 15% aqueous citric acid and extracted with EtOAc (2×20 mL). The combined organic layers were dried (Na$_2$SO$_4$) and concentrated in vacuo. The residue was purified by flash chromatography on silica gel with 1-5% MeOH/DCM to afford 13.8 mg (46%) of the title compound 8 as a white solid and 11.3 mg (36%) of the title compound 9 as a white solid. 8: $^1$H-NMR (CD$_3$OD; 400 MHz): δ 8.07 (d, 1H, J=8.3 Hz), 8.00 (s, 1H), 7.15 (dd, 1H, J=8.3, 2.2 Hz), 7.06 (d, 1H, J=2.2 Hz), 5.80 (m, 1H), 2.90 (t, 2H, J=7.6 Hz), 2.60 (t, 2H, J=7.6 Hz), 2.26 (m, 4H), 1.74-1.88 (m, 4H). Mass spectrum (ESI, m/z): Calcd. for C$_{20}$H$_{20}$N$_4$O$_3$, 365.2 (M+H). found 365.2. 9: $^1$H-NMR (CD$_3$OD; 400 MHz): δ 8.01 (d, 1H, J=8.3 Hz), 7.81 (s, 1H), 7.16 (dd, 1H, J=8.3, 2.0 Hz), 7.08 (d, 1H, J=2.0 Hz), 5.82 (m, 1H), 2.90 (t, 2H, J=7.6 Hz), 2.60 (t, 2H, J=7.6 Hz), 2.22-2.31 (m, 4H), 1.77-1.88 (m, 4H). Mass spectrum (ESI, m/z): Calcd. for C$_{20}$H$_{22}$N$_4$O$_4$, 383.2 (M+H). found 383.2.

Example 10

4-Cyano-1H-imidazole-2-carboxylic acid [4-(2-carbamoyl-ethyl)-2-(4,4-dimethyl-cyclohex-1-enyl)-phenyl]-amide

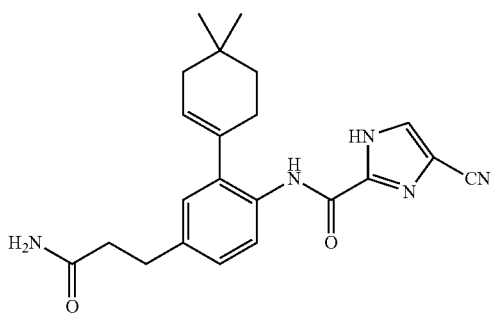 [SMILES: CC1(C)CC=C(c2cc(CCC(N)=O)ccc2NC(=O)c2nc(C#N)c[nH]2)CC1]

78 a) 3-[4-Amino-3-(4,4-dimethyl-cyclohex-1-enyl)-phenyl]-propionamide

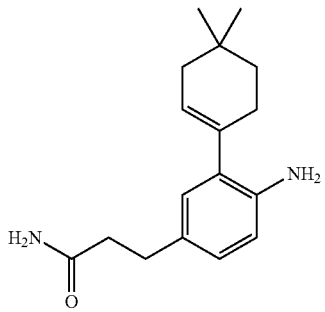 [SMILES: CC1(C)CC=C(c2cc(CCC(N)=O)ccc2N)CC1]

The title compound was prepared by the Suzuki coupling procedure of Example 7, step (d) using 3-(4-amino-3-bromo-phenyl)-propionamide (as prepared in Example 7, step (c), 76.0 mg, 0.351 mmol), and 4,4-dimethylcyclohexen-1-yl boronic acid (59.5 mg, 0.387 mmol). Silica gel chromatography (0-2% MeOH/DCM) afforded the title compound (79 mg, 92%) as a light brown oil. Mass spectrum (ESI, m/z): Calcd. for C$_{17}$H$_{24}$N$_2$O, 273.2 (M+H). found 273.2.

b) 4-Cyano-1-(2-trimethylsilanyl-ethoxymethyl)-1H-imidazole-2-carboxylic acid [4-(2-carbamoyl-ethyl)-2-(4,4-dimethyl-cyclohex-1-enyl)-phenyl]-amide

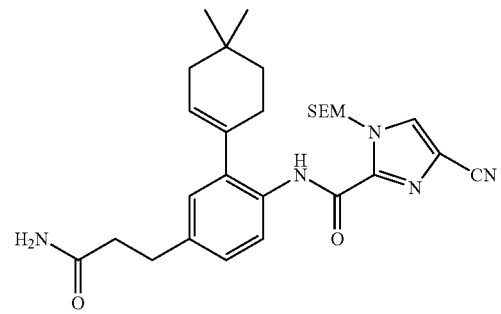 [SMILES: CC1(C)CC=C(c2cc(CCC(N)=O)ccc2NC(=O)c2nc(C#N)cn2COCC[Si](C)(C)C)CC1]

The title compound was prepared by the coupling procedure of Example 7, step (e) using 3-[4-amino-3-(4,4-dimethyl-cyclohex-1-enyl)-phenyl]-propionamide (as prepared in the previous step, 75.0 mg, 0.307 mmol), and potassium 4-cyano-1-(2-trimethylsilanyl-ethoxymethyl)-1H-imidazole-2-carboxylate (as prepared in Example 1, step (d), 103 mg, 0.338 mmol). Silica gel chromatography (0-2% MeOH/DCM) afforded the title compound (124 mg, 82%) as a white solid. Mass spectrum (ESI, m/z): Calcd. for C$_{28}$H$_{39}$N$_5$O$_3$Si, 522.3 (M+H). found 522.1.

c) 4-Cyano-1H-imidazole-2-carboxylic acid [4-(2-carbamoyl-ethyl)-2-(4,4-dimethyl-cyclohex-1-enyl)-phenyl]-amide A solution of 4-cyano-1-(2-trimethylsilanyl-ethoxymethyl)-1H-imidazole-2-carboxylic acid [4-(2-carbamoyl-ethyl)-2-(4,4-dimethyl-cyclohex-1-enyl)-phenyl]-amide (as prepared in the previous step, 160 mg, 0.307 mmol) and tetrabutylammonium fluoride (357 μL, 0.357 mmol, 1.0 M in THF) in 4.5 mL of THF was stirred at reflux for 1.5 h under Ar. After cooling to RT, the mixture was treated with EtOAc (40 mL), washed with saturated aq NaHCO$_3$ (5 mL), brine (10 mL) and dried (Na$_2$SO$_4$). The organic layer was concentrated in vacuo and the residue was purified by flash chromatography on silica gel (5% MeOH/DCM) to give 29.2 mg (24%) of the title compound as a white solid. $^1$H-NMR (CD$_3$OD; 400 MHz): δ 8.09 (d, 1H, J=8.3 Hz), 7.98 (s, 1H), 7.14 (dd, 1H, J=8.3, 2.1 Hz), 7.07 (d, 1H, J=2.1 Hz), 5.71 (m, 1H), 2.89 (t, 2H, J=7.7 Hz), 2.50 (t, 2H, J=7.7 Hz), 2.29 (m, 2H), 2.06 (m, 2H), 1.57 (t, 2H, J=6.3 Hz), 1.07 (s, 6H). Mass spectrum (ESI, m/z): Calcd. for C$_{22}$H$_{25}$N$_5$O$_2$, 392.2 (M+H). found 392.2.

Example 11

4-Cyano-1H-imidazole-2-carboxylic acid [2-cyclohex-1-enyl-4-(2-hydroxy-1-hydroxymethyl-ethyl)-phenyl]-amide

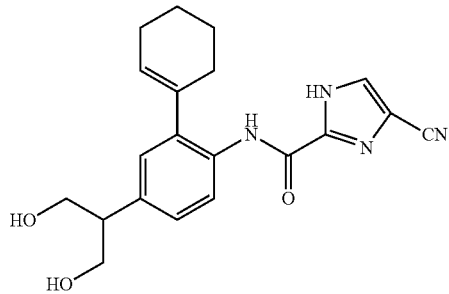 [SMILES: N#Cc1c[nH]c(C(=O)Nc2ccc(C(CO)CO)cc2C2=CCCCC2)n1]

a) 2-(3-Bromo-4-nitro-phenyl)-malonic acid dimethyl ester

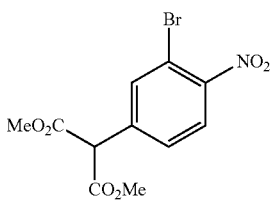 [SMILES: COC(=O)C(C(=O)OC)c1ccc([N+](=O)[O-])c(Br)c1]

To a suspension of NaH (364 mg, 9.08 mmol) in 10 mL of DMF at 0° C. was added malonic acid dimethyl ester (519 μL, 4.54 mmol). The resulting mixture was warmed to RT and stirred for 0.5 h under Ar. 2-Bromo-4-fluoro-1-nitrobenzene (500 mg, 2.27 mmol) was added to the mixture and the reaction was stirred at RT for 16 h under Ar. The mixture was then treated with 2 mL of satd aq NH$_4$Cl followed by 10 mL of H$_2$O and extracted with DCM (3×10 mL). The combined extracts were washed with water (10 mL), brine (5 mL) and dried (Na$_2$SO$_4$). Removal of the solvent in vacuo followed by flash chromatography of the residue on silica gel (1:4 hexane-DCM) gave 604 mg (80%) of a yellow-green oil containing the pure title compound as a mixture of di-ester (A) and its enol tautomer (B): $^1$H-NMR (CDCl$_3$; 400 MHz): A: δ 8.48 (d, 1H, J=2.5 Hz), 8.21 (dd, 1H, J=8.8, 2.5 Hz), 7.85 (d, 1H, J=8.8 Hz), 5.34 (s, 1H), 3.81 (s, 6H). B: δ 7.85 (d, 1H, J=8.4 Hz), 7.82 (d, 1H, J=1.9 Hz), 7.54 (dd, 1H, J=8.4, 1.9 Hz), 4.68 (s, 1H), 3.80 (s, 6H).

b) 2-(3-Cyclohex-1-enyl-4-nitro-phenyl)-malonic acid dimethyl ester

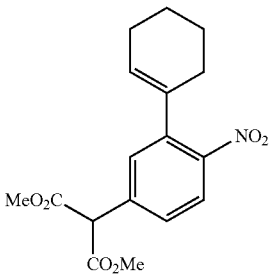

To a mixture of 2-(3-bromo-4-nitro-phenyl)-malonic acid dimethyl ester (as prepared in the previous step, 300 mg, 0.903 mmol), cyclohex-1-enyl boronic acid (125 mg, 0.994 mmol) and dichloro[1,1'-bis(diphenylphosphino)ferrocene] palladium (II) dichloromethane adduct (Pd(dppf)Cl$_2$) (66.0 mg, 0.0903 mmol) in 5 mL of DMF was added K$_3$PO$_4$ (765 mg, 3.61 mmol). The resulting mixture was stirred at 60° C. for 9 h under Ar. After cooling to RT, the mixture was treated with 50 mL of EtOAc, washed with H$_2$O (3×10 mL) and brine (10 mL). The organic layer was dried (Na$_2$SO$_4$) and concentrated in vacuo. The residue was purified by flash chromatography on silica gel with 10% EtOAc-hexane to afford 210 mg (70%) of the title compound as a yellow oil: Mass spectrum (ESI, m/z): Calcd. for C$_{17}$H$_{19}$NO$_6$, 334.1 (M+H). found 334.0.

c) 2-(4-Amino-3-cyclohex-1-enyl-phenyl)-malonic acid dimethyl ester

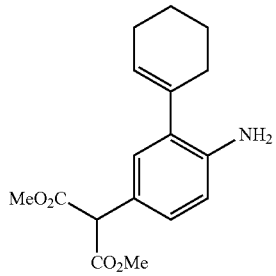 [SMILES: COC(=O)C(C(=O)OC)c1ccc([N+](=O)[O-])c(C2=CCCCC2)c1]

A mixture of 2-(3-cyclohex-1-enyl-4-nitro-phenyl)-malonic acid dimethyl ester (as prepared in the previous step, 200 mg, 0.600 mmol), iron powder (168 mg, 3.00 mmol) and NH$_4$Cl (321 mg, 6.00 mmol) in 6 mL of ethanol was stirred at 80° C. for 16 h. After cooling to RT, the mixture was treated with 30 mL of H$_2$O and extracted with EtOAc (3×20 mL). The combined organic layers were dried (Na$_2$SO$_4$) and concentrated in vacuo. The residue was purified by flash chromatography on silica gel (30% EtOAc-hexane) to give 129 mg (71%) of the title compound as a faint yellow oil: Mass spectrum (ESI, m/z): Calcd. for C$_{17}$H$_{21}$NO$_4$, 304.2 (M+H). found 304.1.

d) 2-(4-{[4-Cyano-1-(2-trimethylsilanyl-ethoxymethyl)-1H-imidazole-2-carbonyl]-amino}-3-cyclohex-1-enyl-phenyl)-malonic acid dimethyl ester

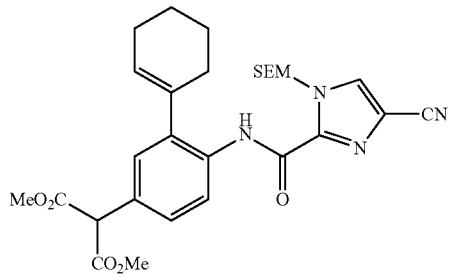 [SMILES: COC(=O)C(C(=O)OC)c1ccc(NC(=O)c2nc(C#N)cn2COCC[Si](C)(C)C)c(C2=CCCCC2)c1]

To a mixture of 2-(4-amino-3-cyclohex-1-enyl-phenyl)-malonic acid dimethyl ester (as prepared in the previous step, 100 mg, 0.330 mmol), potassium 4-cyano-1-(2-trimethylsilanyl-ethoxymethyl)-1H-imidazole-2-carboxylate (as prepared in Example 1, step (d), 106 mg, 0.346 mmol) and bromotripyrrolidinophosphonium hexafluorophosphate (PyBroP) (154 mg, 0.330 mmol) in 3 mL of DMF was added DIEA (0.172 mL, 0.990 mmol). After stirring at RT for 16 h, the mixture was treated with 50 mL of EtOAc and washed with $H_2O$ (2×15 mL), brine (15 mL) and dried ($Na_2SO_4$). The organic solvent was evaporated and the residue was purified by flash chromatography on silica gel (5-10% EtOAc-hexane) to give 118 mg (85%) of the title compound as a colorless oil: Mass spectrum (ESI, m/z): Calcd. for $C_{28}H_{36}N_4O_6Si$, 553.2 (M+H). found 552.6.

e) 2-{4-[(4-Cyano-1H-imidazole-2-carbonyl)-amino]-3-cyclohex-1-enyl-pheny}-malonic acid dimethyl ester

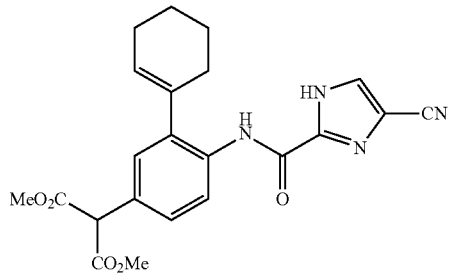 [SMILES: COC(=O)C(C(=O)OC)c1ccc(NC(=O)c2nc(C#N)c[nH]2)c(C2=CCCCC2)c1]

To a solution of 2-(4-{[4-cyano-1-(2-trimethylsilanyl-ethoxymethyl)-1H-imidazole-2-carbonyl]-amino}-3-cyclohex-1-enyl-phenyl)-malonic acid dimethyl ester (as prepared in the previous step, 145 mg, 0.262 mmol) in 1.0 mL of DCM ($CH_2Cl_2$) was added 1.0 mL of TFA. After stirring at RT for 4 h, the mixture was concentrated in vacuo. The residue was purified by flash chromatography on silica gel (20-30% EtOAc-hexane) to give 93 mg (84%) of the title compound as a white solid: Mass spectrum (ESI, m/z): Calcd. for $C_{22}H_{22}N_4O_5$, 423.1 (M+H). found 422.8.

f) 4-Cyano-1H-imidazole-2-carboxylic acid [2-cyclohex-1-enyl-4-(2-hydroxy-1-hydroxymethyl-ethyl)-phenyl]-amide To a mixture of 2-{4-[(4-cyano-1H-imidazole-2-carbonyl)-amino]-3-cyclohex-1-enyl-phenyl}-malonic acid dimethyl ester (as prepared in the previous step, 30.0 mg, 0.0710 mmol) and $NaBH_4$ (13.4 mg, 0.355 mmol) in 1 mL of tert-butyl alcohol (t-BuOH) at 80° C. was added MeOH (50 μL) over 5 min. The resulting mixture was stirred at 80° C. for 16 h under Ar. After cooling to RT, the mixture was treated with 10% aq citric acid to a pH of 7. The mixture was then treated with 30 mL of EtOAc, washed with $H_2O$ (5 mL) and brine (10 mL). The organic layer was dried ($Na_2SO_4$) and concentrated in vacuo. The residue was purified by flash chromatography on silica gel with 1-5% MeOH-DCM to afford 14.1 mg (61%) of the title compound as a white solid: $^1$H-NMR ($CD_3OD$; 400 MHz): δ 8.00 (s, 1H), 7.54 (dd, 1H, J=8.2, 2.3 Hz), 7.46 (d, 1H, J=2.3 Hz), 7.27 (d, 1H, J=8.2 Hz), 5.59 (m, 1H), 3.71-3.84 (m, 4H), 3.29 (m, 1H), 2.15-2.29 (m, 4H), 1.67-1.84 (m, 4H). Mass spectrum (ESI, m/z): Calcd. for $C_{20}H_{22}N_4O_3$, 367.2 (M+H). found 366.8.

Example 12

Acetic acid 3-acetoxy-2-{4-[(4-cyano-1H-imidazole-2-carbonyl)-amino]-3-cyclohex-1-enyl-pheny}-propylester trifloroacetic acid salt a) Acetic acid 3-acetoxy-2-(4-amino-3-cyclohex-1-enyl-phenyl)-propyl ester To a solution of acetic acid 3-acetoxy-2-(4-amino-phenyl)-propyl ester (Tetrahedron, 46(20), 7081, (1990), 1.2 g, 5.0 mmol) in DCM (50 mL), NBS (903 mg, 5.07 mol) was added at 0° C. The resulting mixture was stirred at RT for 2 h and subjected to the usual work up to obtain acetic acid 3-acetoxy-2-(4-amino-3-bromo-phenyl)-propyl ester (1.4 g, 89%) which was directly used in the next step.

The title compound was prepared according to the Suzuki coupling procedure of Example 1, step (e) using acetic acid 3-acetoxy-2-(4-amino-3-bromo-phenyl)-propyl ester (as prepared above) and cyclohex-1-enyl boronic acid: Mass spectrum, (ESI, m/z): Calcd. for $C_{19}H_{25}NO_4$, 332.1 (M+H). found 332.1.

b) Acetic acid 3-acetoxy-2-(4-{[4-cyano-1-(2-trimethylsilanyl-ethoxymethyl)-1H-imidazole-2-carbonyl]-amino}-3-cyclohex-1-enyl-phenyl)-propyl ester

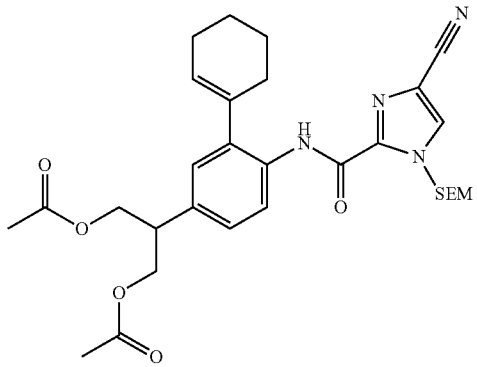 [SMILES: CC(=O)OCC(COC(C)=O)c1ccc(NC(=O)c2nc(C#N)cn2COCC[Si](C)(C)C)c(C2=CCCCC2)c1]

Acetic acid 3-acetoxy-2-(4-amino-3-cyclohex-1-enyl-phenyl)-propyl ester (as prepared in the previous step) was coupled to 4-cyano-1-(2-trimethylsilanyl-ethoxymethyl)-1H-imidazole-2-carboxylic acid, potassium salt (as prepared in Example 1, step (d)) as described in Example 1, step (f) to obtain the title compound: Mass spectrum (ESI, m/z): Calcd. for $C_{30}H_{40}N_4O_6Si$, 581.2 (M+H). found 581.0.

c) Acetic acid 3-acetoxy-2-{4-[(4-cyano-1H-imidazole-2-carbonyl)-amino]-3-cyclohex-1-enyl-phenyl}-propylester trifluoroacetic acid salt A solution of acetic acid 3-acetoxy-2-(4-{[4-cyano-1-(2-trimethylsilanyl-ethoxymethyl)-1H-imidazole-2-carbonyl]-amino}-3-cyclohex-1-enyl-phenyl)-propyl ester (as prepared in the previous step, 102 mg, 0.175 mmol) in DCM (2 mL) was treated with ethyl alcohol (EtOH) (60 μl) and TFA (0.6 mL) at RT for 2 h and concentrated in vacuo. The reaction mixture was dissolved in DCM (10 mL) and poured into satd aq NaHCO₃. The organic layer was separated, dried (Na₂SO₄) and concentrated. The solid obtained was suspended in 1:1 ether/hexane, sonicated and concentrated in vacuo. The resulting residue was dried in vacuo to obtain the title compound (57 mg, 57%): ¹H-NMR (CDCl₃; 400 MHz): δ 12.90 (br s, 1H), 9.75 (s, 1H), 8.32 (d, 1H, J=8.4 Hz), 7.78 (s, 1H), 7.24 (dd, 1H, J=8.4, 2.0 Hz), 7.06 (d, 1H, J=2.0 Hz), 5.82 (br s, 1H), 4.38 (m, 4H), 3.35 (m, 1H), 2.23-2.35 (m, 4H), 2.10 (s, 6H), 1.75-1.92 (m, 4H): Mass spectrum, (ESI, m/z): Calcd. for $C_{24}H_{26}N_4O_5$, 451.2 (M+H). found 451.0.

Example 13

2-{4-[(4-Cyano-1H-imidazole-2-carbonyl)-amino]-3-cyclohex-1-enyl-phenyl}-2-methyl-propionic acid

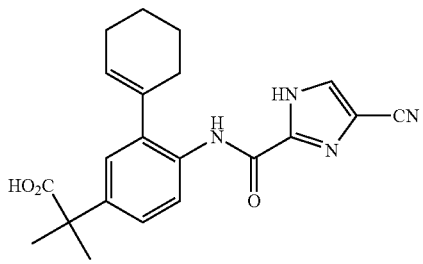 [SMILES: CC(C)(C(=O)O)c1ccc(NC(=O)c2nc(C#N)c[nH]2)c(C2=CCCCC2)c1]

a) 2-(4-{[4-Cyano-1-(2-trimethylsilanyl-ethoxymethyl)-1H-imidazole-2-carbonyl]-amino}-3-cyclohex-1-enyl-phenyl)-2-methyl-propionic acid methyl ester

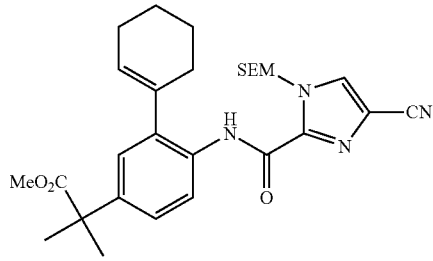 [SMILES: COC(=O)C(C)(C)c1ccc(NC(=O)c2nc(C#N)cn2COCC[Si](C)(C)C)c(C2=CCCCC2)c1]

A mixture of 4-cyano-1-(2-trimethylsilanyl-ethoxymethyl)-1H-imidazole-2-carboxylic acid (4-bromo-2-cyclohex-1-enyl-phenyl)-amide (as prepared in Example 1, step (f), 100 mg, 0.200 mmol), (1-methoxy-2-methyl-propenyloxy)-trimethyl-silane (61 μL, 0.30 mmol), Pd(t-Bu₃P)₂ (10.2 mg, 0.0200 mmol) and ZnF₂ (10.3 mg, 0.100 mmol) in 2 mL of DMF was stirred at 80° C. for 2 d under Ar. After cooling to RT, the mixture was treated with H₂O (20 mL) and extracted with EtOAc (2×20 mL). The combined organic layers were washed with H₂O (10 mL) and brine (10 mL). After drying over Na₂SO₄ and concentrating in vacuo, the residue was purified by silica gel chromatography (DCM) to afford the title compound (48 mg, 46%) as a colorless oil. LC-MS (ESI, m/z): Calcd. for $C_{28}H_{38}N_4O_4Si$, 523.3 (M+H). found 523.0.

b) 2-{4-[(4-Cyano-1H-imidazole-2-carbonyl)-amino]-3-cyclohex-1-enyl-phenyl}-2-methyl-propionic acid methyl ester

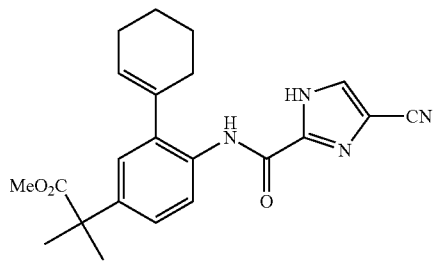 [SMILES: COC(=O)C(C)(C)c1ccc(NC(=O)c2nc(C#N)c[nH]2)c(C2=CCCCC2)c1]

The title compound was prepared by the procedure of Example 1, step (g) using 2-(4-{[4-cyano-1-(2-trimethylsilanyl-ethoxymethyl)-1H-imidazole-2-carbonyl]-amino}-3-cyclohex-1-enyl-phenyl)-2-methyl-propionic acid methyl ester (as prepared in the previous step, 80.0 mg, 0.153 mmol). The title compound (60 mg, 100%) is a white solid. Mass spectrum (ESI, m/z): Calcd. for $C_{22}H_{24}N_4O_3$, 393.2 (M+H). found 393.1.

c) 2-{4-[(4-Cyano-1H-imidazole-2-carbonyl)-amino]-3-cyclohex-1-enyl-phenyl}-2-methyl-propionic acid To a solution of 2-{4-[(4-cyano-1H-imidazole-2-carbonyl)-amino]-3-cyclohex-1-enyl-phenyl}-2-methyl-propionic acid methyl ester (as prepared in the previous step, 60.0 mg, 0.153 mmol) in 1 mL of 1:1 THF/MeOH was added 6 N NaOH (250 μL, 1.50 mmol). After stirring at RT for 18 h, the mixture was treated with 10 mL of H$_2$O and washed with EtOAc (3×10 mL). The aqueous layer was acidified to a pH of 6 with 1 N aqueous HCl and extracted with 10:1 EtOAc-MeOH (3×10 mL). The combined organic layers were washed with H$_2$O (10 mL), brine (10 mL) and dried (Na$_2$SO$_4$). The organic solvent was evaporated in vacuo to give the title compound (48 mg, 83%) as a white solid. $^1$H-NMR (CD$_3$OD; 400 MHz): δ 8.19 (m, 1H), 7.90 (s, 1H), 7.31 (m, 1H), 7.20 (s, 1H), 5.84 (m, 1H), 2.17-2.40 (m, 4H), 1.76-1.92 (m, 4H), 1.57 (s, 6H). Mass spectrum (ESI, m/z): Calcd. for C$_{21}$H$_{22}$N$_4$O$_3$, 379.2 (M+H). found 379.2.

Example 14

4-Cyano-1H-imidazole-2-carboxylic acid [2-(4,4-dimethyl-cyclohex-1-enyl)-4-(1-methyl-1-thiomorpholin-4-yl-ethyl)-phenyl]-amide

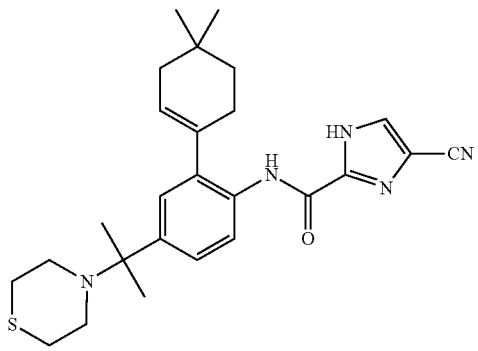 [SMILES: CC1(C)CC=C(c2cc(C(C)(C)N3CCSCC3)ccc2NC(=O)c2nc(C#N)c[nH]2)CC1]

a) 4-Bromo-2-(4,4-dimethyl-cyclohex-1-enyl)-phenylamine

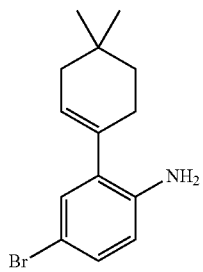 [SMILES: CC1(C)CC=C(c2cc(Br)ccc2N)CC1]

A mixture of 4-bromo-2-iodo-phenylamine (873 mg, 2.93 mmol), 4,4-dimethylcyclohexen-1-ylboronic acid (496 mg, 3.22 mmol), Pd(PPh$_3$)$_4$ (169 mg, 0.147 mmol) and 2.0 M aq Na$_2$CO$_3$ (11.7 mL, 23.4 mmol) in 20 mL of 1,4-dioxane was stirred at 80° C. for 12 h under Ar. After cooling to RT, the reaction was treated with EtOAc (50 mL) and washed with H$_2$O (25 mL) and brine (20 mL). The organic layer was dried (Na$_2$SO$_4$) and concentrated in vacuo. The residue was purified by flash chromatography on silica gel (5% EtOAc/hexane) to afford 770 mg (91%) of the title compound as a colorless oil. Mass spectrum (ESI, m/z): Calcd. for C$_{14}$H$_{18}$BrN, 280.1 (M+H). found 280.1.

b) 4-Cyano-1-(2-trimethylsilanyl-ethoxymethyl)-1H-imidazole-2-carboxylic acid [4-bromo-2-(4,4-dimethyl-cyclohex-1-enyl)-phenyl]-amide

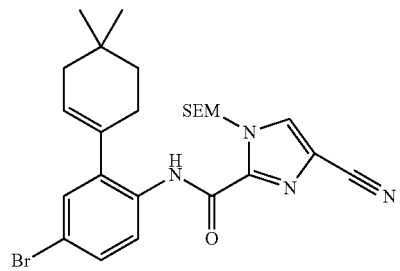 [SMILES: CC1(C)CC=C(c2cc(Br)ccc2NC(=O)c2nc(C#N)cn2COCC[Si](C)(C)C)CC1]

To a mixture of 4-bromo-2-(4,4-dimethyl-cyclohex-1-enyl)-phenylamine (as prepared in the previous step, 770 mg, 2.75 mmol), potassium 4-cyano-1-(2-trimethylsilanyl-ethoxymethyl)-1H-imidazole-2-carboxylate (as prepared in Example 1, step (d), 840 mg, 2.75 mmol) and PyBroP (1.28 g, 2.75 mmol) in 20 mL of DMF was added DIEA (1.44 mL, 8.25 mmol). The resulting mixture was stirred at RT for 16 h under Ar. Treated with 80 mL of EtOAc, the mixture was washed with H$_2$O (2×20 mL), brine (20 mL) and dried (Na$_2$SO$_4$). Removal of the solvent under reduced pressure followed by flash chromatography of the residue on silica gel (5-10% EtOAc/hexane) gave 1.28 g (88%) of the title compound as a white solid. Mass spectrum (ESI, m/z): Calcd. for C$_{25}$H$_{33}$BrN$_4$O$_2$Si, 529.2 (M+H). found 528.9.

c) 4-Cyano-1H-imidazole-2-carboxylic acid [4-bromo-2-(4,4-dimethyl-cyclohex-1-enyl)-phenyl]-amide

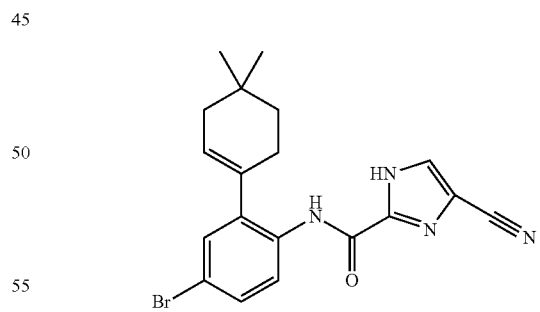

The title compound was prepared by the procedure of Example 1, step (g) using 4-cyano-1-(2-trimethylsilanyl-ethoxymethyl)-1H-imidazole-2-carboxylic acid [4-bromo-2-(4,4-dimethyl-cyclohex-1-enyl)-phenyl]-amide (as prepared in the previous step, 350 mg, 0.661 mmol). The title compound (253 mg, 96%) was obtained as a white solid. $^1$H-NMR (CDCl$_3$; 400 MHz): δ 8.19 (d, 2H, J=8.8 Hz), 7.50 (d, 2H, J=8.8 Hz), 6.23 (m, 1H), 4.12 (m, 2H), 3.66 (m, 2H), 2.54 (m, 2H), 1.49 (s, 9H). Mass spectrum (ESI, m/z): Calcd. for C$_{19}$H$_{19}$BrN$_4$O, 399.1 (M+H). found 399.1.

d) 4-Cyano-1H-imidazole-2-carboxylic acid [2-(4,4-dimethyl-cyclohex-1-enyl)-4-(1-hydroxy-1-methyl-ethyl)phenyl]-amide

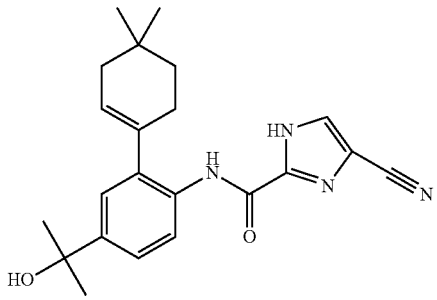 [SMILES: CC1(C)CC=C(c2cc(C(C)(C)O)ccc2NC(=O)c2nc(C#N)c[nH]2)CC1]

To a solution of 4-cyano-1H-imidazole-2-carboxylic acid [4-bromo-2-(4,4-dimethyl-cyclohex-1-enyl)-phenyl]-amide (as prepared in the previous step, 200 mg, 0.501 mmol) in 8 mL of THF at −78° C. under Ar was added isopropylmagnesium chloride (275 µL, 0.551 mmol, 2.0 M in THF). The resulting mixture was warmed to RT and stirred for 5 min, cooled to −78° C. again. To the mixture was added tert-butyllithium (884 µL, 1.50 mmol, 1.7 M in pentane) and the resulting mixture was stirred at −78° C. for 10 min. Acetone (736 µL, 10.0 mmol) was then added, and the reaction was warmed to RT and stirred for 0.5 h under Ar. The mixture was treated with 5 mL of saturated NH$_4$Cl followed by 40 mL of EtOAc, washed with brine (10 mL) and dried (Na$_2$SO$_4$). Removal of the solvent under reduced pressure followed by flash chromatography of the residue on silica gel (1-4% MeOH/DCM) gave 101 mg (53%) of the title compound as a white solid. $^1$H-NMR (CDCl$_3$; 400 MHz): δ 12.52 (s, 1H), 9.68 (s, 1H), 8.29 (d, 1H, J=8.6 Hz), 7.72 (d, 1H, J=2.3 Hz), 7.42 (dd, 1H, J=8.6, 2.3 Hz), 7.35 (d, 1H, J=2.3 Hz), 5.78 (m, 1H), 2.64 (s, 1H, OH), 2.30 (m, 2H), 2.11 (m, 2H), 1.62 (s, 6H), 1.59 (t, 2H, J=6.5 Hz), 1.11 (s, 6H). Mass spectrum (ESI, m/z): Calcd. for C$_{22}$H$_{26}$N$_4$O$_2$, 379.2 (M+H). found 379.3.

e) 4-Cyano-1H-imidazole-2-carboxylic acid [2-(4,4-dimethyl-cyclohex-1-enyl)-4-(1-methyl-1-thiomorpholin-4-yl-ethyl)-phenyl]-amide To a suspension of 4-cyano-1H-imidazole-2-carboxylic acid [2-(4,4-dimethyl-cyclohex-1-enyl)-4-(1-hydroxy-1-methyl-ethyl)-phenyl]-amide (as prepared in the previous step, 65 mg, 0.17 mmol) in 1.5 mL of DCM at 0° C. was added SOCl$_2$ (38 µL, 0.52 mmol) under Ar. After stirring at RT for 1 h, the mixture was cooled back to 0° C. To the reaction was added thiomorpholine (172 µL, 1.72 mmol) and the resulting mixture was stirred at 0° C. for 1 h. After warming to RT, the mixture was treated with EtOAc (30 mL) and washed with H$_2$O (2×10 mL) and brine (10 mL). The organic layer was dried over Na$_2$SO$_4$ and concentrated in vacuo. The residue was purified by silica gel chromatography (5% EtOAc/DCM then 1-2% MeOH/DCM) to afford the title compound (70 mg, 88%) as a white solid. $^1$H-NMR (CDCl$_3$; 400 MHz): δ 11.90 (s, 1H), 9.65 (s, 1H), 8.28 (d, 1H, J=8.6 Hz), 7.74 (s, 1H), 7.45 (dd, 1H, J=8.6, 2.3 Hz), 7.33 (d, 1H, J=2.3 Hz), 5.78 (m, 1H), 2.77 (m, 4H), 2.65 (m, 4H), 2.29 (m, 2H), 2.12 (m, 2H), 1.60 (t, 2H, J=6.3 Hz), 1.33 (s, 6H), 1.12 (s, 6H). Mass spectrum (ESI-neg, m/z): Calcd. for C$_{26}$H$_{33}$N$_5$OS, 462.2 (M−H). found 462.4.

Example 15

4-Cyano-1H-imidazole-2-carboxylic acid {2-(4,4-dimethyl-cyclohex-1-enyl)-4-[1-methyl-1-(1-oxo-1λ$^4$-thiomorpholin-4-yl)-ethyl]-pheny}-amide

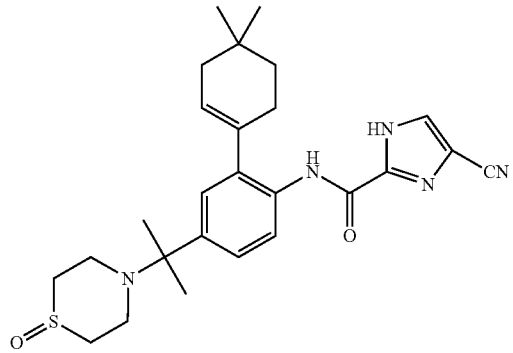 [SMILES: CC1(C)CC=C(c2cc(C(C)(C)N3CCS(=O)CC3)ccc2NC(=O)c2nc(C#N)c[nH]2)CC1]

To a solution of 4-cyano-1H-imidazole-2-carboxylic acid [2-(4,4-dimethyl-cyclohex-1-enyl)-4-(1-methyl-1-thiomorpholin-4-yl-ethyl)-phenyl]-amide (as prepared in Example 14, step (e), 30.0 mg, 0.0647 mmol) in 0.5 mL of DCM at RT was added titanium (IV) isopropoxide (19 µL, 0.065 mmol). The mixture was cooled to 0° C. and H$_2$O$_2$ (13 µL, 0.13 mmol, 30 wt % in H$_2$O) was added. After stirring at 0° C. for 4 h, the mixture was treated with EtOAc (50 mL) and washed with H$_2$O (2×10 mL) and brine (10 mL). The organic layer was dried over Na$_2$SO$_4$ and concentrated in vacuo, the residue was purified by silica gel chromatography (1-4% MeOH/DCM) to afford the title compound (30 mg, 95%) as a colorless oil. $^1$H-NMR (CDCl$_3$; 400 MHz): δ 13.06 (s, 1H), 9.63 (s, 1H), 8.34 (d, 1H, J=8.6 Hz), 7.71 (s, 1H), 7.51 (dd, 1H, J=8.6, 2.0 Hz), 7.27 (d, 1H, J=2.0 Hz), 5.78 (m, 1H), 3.17 (m, 2H), 2.84-3.08 (m, 4H), 2.71 (m, 2H), 2.28 (m, 2H), 2.11 (m, 2H), 1.60 (t, 2H, J=6.3 Hz), 1.40 (s, 6H), 1.11 (s, 6H). Mass spectrum (ESI-neg, m/z): Calcd. for C$_{26}$H$_{33}$N$_5$O$_2$S, 478.2 (M−H). found 478.3.

Example 16

4-Cyano-1H-imidazole-2-carboxylic acid {2-(4,4-dimethyl-cyclohex-1-enyl)-4-[1-methyl-1-(2-methyl-sulfanyl-ethylamino)-ethyl]-pheny}-amide

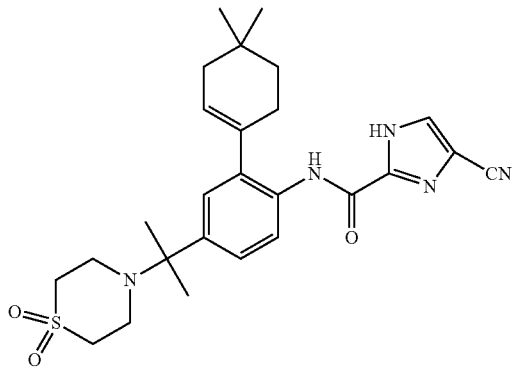 [SMILES: CC1(C)CC=C(c2cc(C(C)(C)N3CCS(=O)(=O)CC3)ccc2NC(=O)c2nc(C#N)c[nH]2)CC1]

To a solution of 4-cyano-1H-imidazole-2-carboxylic acid [2-(4,4-dimethyl-cyclohex-1-enyl)-4-(1-methyl-1-thiomorpholin-4-yl-ethyl)-phenyl]-amide (as prepared in Example 14, step (e), 38.0 mg, 0.0820 mmol) in 0.5 mL of DCM at RT was added titanium (IV) isopropoxide (24.0 μL, 0.0820 mmol). The mixture was cooled to 0° C. and H$_2$O$_2$ (18 μL, 0.16 mmol, 30 wt % in H$_2$O) was added. After stirring at 0° C. for 0.5 h and at −20° C. for 16 h, the mixture was treated with EtOAc (50 mL) and washed with H$_2$O (2×10 mL) and brine (10 mL). The organic layer was dried over Na$_2$SO$_4$ and concentrated in vacuo. The residue was purified by silica gel chromatography (15-25% EtOAc/DCM) to afford the title compound (33 mg, 80%) as a white solid. $^1$H-NMR (CD$_3$OD; 400 MHz): δ 8.16 (d, 1H, J=8.6 Hz), 7.99 (s, 1H), 7.49 (dd, 1H, J=8.6, 2.3 Hz), 7.37 (d, 1H, J=2.3 Hz), 5.74 (m, 1H), 2.91-3.07 (m, 8H), 2.31 (m, 2H), 2.08 (m, 2H), 1.60 (t, 2H, J=6.3 Hz), 1.42 (s, 6H), 1.09 (s, 6H). Mass spectrum (ESI-neg, m/z): Calcd. for C$_{26}$H$_{33}$N$_5$O$_3$S, 494.2 (M−H). found 494.2.

Example 17

4-Cyano-1H-imidazole-2-carboxylic acid {2-(4,4-dimethyl-cyclohex-1-enyl)-4-[1-methyl-1-(2-methylsulfanyl-ethylamino)-ethyl]-pheny}-amide

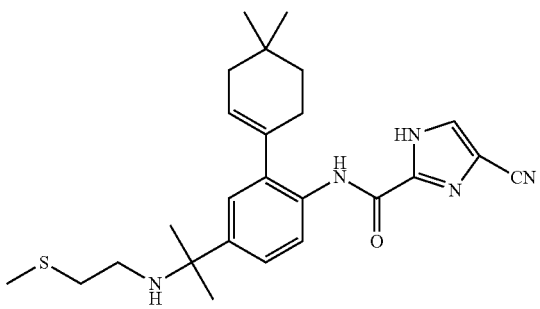 [SMILES: CSCCNC(C)(C)c1ccc(NC(=O)c2nc(C#N)c[nH]2)c(C2=CCC(C)(C)CC2)c1]

The title compound was prepared by the procedure of Example 14, step (e) using 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d), 120 mg, 0.317 mmol) and 2-methylsulfanyl-ethylamine (69.0 μL, 0.951 mmol). Silica gel chromatography (1-4% MeOH/DCM) afforded the title compound (72 mg, 50%) as a white solid. $^1$H-NMR (CD$_3$OD; 400 MHz): δ 8.26 (d, 1H, J=8.6 Hz), 7.94 (s, 1H), 7.39 (dd, 1H, J=8.6, 2.3 Hz), 7.32 (d, 1H, J=2.3 Hz), 5.75 (m, 1H), 2.51-2.61 (m, 4H), 2.29-2.36 (m, 2H), 2.05-2.12 (m, 2H), 1.91 (s, 3H), 1.60 (t, 2H, J=6.3 Hz), 1.54 (s, 6H), 1.09 (s, 6H). Mass spectrum (ESI-neg, m/z): Calcd. for C$_{25}$H$_{33}$N$_5$OS, 450.4 (M−H). found 450.2.

Example 18

4-Cyano-1H-imidazole-2-carboxylic acid {2-(4,4-dimethyl-cyclohex-1-enyl)-4-[1-(2-methanesulfonyl-ethylamino)-1-methyl-ethyl]-pheny}-amide

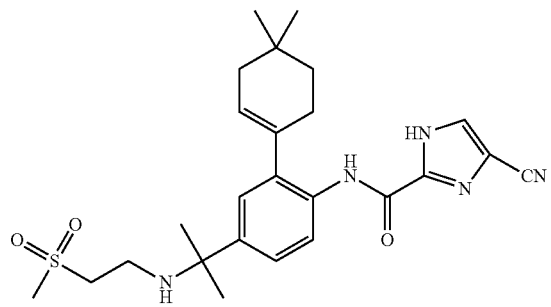 [SMILES: CC1(C)CC=C(c2cc(C(C)(C)NCCS(C)(=O)=O)ccc2NC(=O)c2nc(C#N)c[nH]2)CC1]

The title compound was prepared by the procedure of Example 16 using 4-cyano-1H-imidazole-2-carboxylic acid {2-(4,4-dimethyl-cyclohex-1-enyl)-4-[1-methyl-1-(2-methylsulfanyl-ethylamino)-ethyl]-phenyl}-amide (as prepared in Example 17, 63.0 mg, 0.140 mmol). Silica gel chromatography (1-3% MeOH/DCM) afforded the title compound (47 mg, 70%) as a white solid. $^1$H-NMR (CDCl$_3$; 400 MHz): δ 9.67 (s, 1H), 8.31 (d, 1H, J=8.6 Hz), 7.75 (s, 1H), 7.40 (dd, 1H, J=8.6, 2.3 Hz), 7.25 (d, 1H, J=2.3 Hz), 5.78 (m, 1H), 4.23-6.25 (br s, 2H), 3.14 (t, 2H, J=6.0 Hz), 2.98 (s, 3H), 2.89 (t, 2H, J=6.0 Hz), 2.30 (m, 2H), 2.11 (m, 2H), 1.60 (t, 2H, J=6.3 Hz), 1.49 (s, 6H), 1.11 (s, 6H). Mass spectrum (ESI-neg, m/z): Calcd. for C$_{25}$H$_{33}$N$_5$O$_3$S, 482.2 (M−H). found 482.4.

Example 19

4-Cyano-1H-imidazole-2-carboxylic acid (2-(4,4-dimethyl-cyclohex-1-enyl)-4-{1-[(2-methanesulfonyl-ethyl)-methyl-amino]-1-methyl-ethyl}-phenyl)-amide

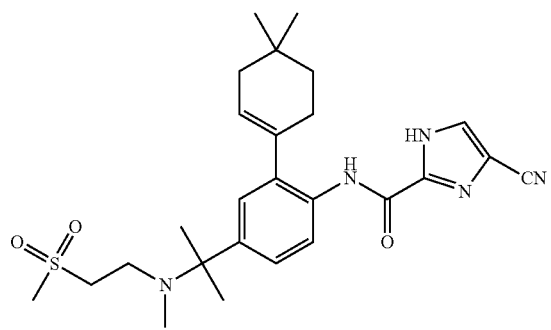 [SMILES: CN(CCS(C)(=O)=O)C(C)(C)c1ccc(NC(=O)c2nc(C#N)c[nH]2)c(C2=CCC(C)(C)CC2)c1]

A mixture of 4-cyano-1H-imidazole-2-carboxylic acid {2-(4,4-dimethyl-cyclohex-1-enyl)-4-[1-(2-methanesulfonyl-ethylamino)-1-methyl-ethyl]-phenyl}-amide (as prepared in Example 18, 8.0 mg, 0.017 mmol), iodomethane (25 μL, 0.40 mmol) and solid NaHCO$_3$ (25 mg, 0.30 mmol) in 1.0 mL of THF was stirred at RT for 6 h. The solvent was removed by evaporation and the residue was purified by silica gel chromatography (0-2% MeOH/DCM) to afford the title compound (5.0 mg, 61%) as a colorless oil. $^1$H-NMR (CDCl$_3$; 400 MHz): δ 11.90 (s, 1H), 9.63 (s, 1H), 8.31 (d, 1H, J=8.6 Hz), 7.75 (s, 1H), 7.41 (dd, 1H, J=8.6, 2.3 Hz), 7.28 (d, 1H, J=2.3 Hz), 5.77 (m, 1H), 3.11 (t, 2H, J=7.1 Hz), 2.87 (s, 3H), 2.84 (t, 2H, J=6.0 Hz), 2.29 (m, 2H), 2.24 (s, 3H), 2.11 (m, 2H), 1.60 (t, 2H, J=6.3 Hz), 1.40 (s, 6H), 1.11 (s, 6H). Mass spectrum (ESI-neg, m/z): Calcd. for C$_{26}$H$_{35}$N$_5$O$_3$S, 496.3 (M−H). found 496.1.

The following compounds were prepared according to the examples as indicated:

| Example | Name | Structure | Procedure | Mass Spectrum (ESI-neg, m/z) |
| --- | --- | --- | --- | --- |
| 20 | 4-Cyano-1H-imidazole-2-carboxylic acid {2-(4,4-dimethyl-cyclohex-1-enyl)-4-[1-(2-methoxy-ethylamino)-1-methyl-ethyl]-phenyl}-amide | 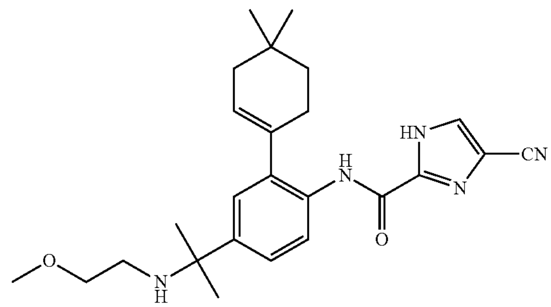 [SMILES: COCCNC(C)(C)c1ccc(NC(=O)c2nc(C#N)c[nH]2)c(C2=CCC(C)(C)CC2)c1] | Ex. 14, step (e) | Calcd. for C$_{25}$H$_{33}$N$_5$O$_2$, 434.3 (M − H), found 434.4. |
| 21 | 4-Cyano-1H-imidazole-2-carboxylic acid (2-(4,4-dimethyl-cyclohex-1-enyl)-4-{1-[(2-methoxy-ethyl)-methyl-amino]-1-methyl-ethyl}phenyl)-amide | 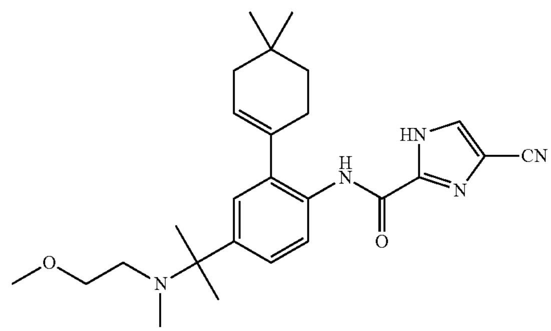 [SMILES: COCCN(C)C(C)(C)c1ccc(NC(=O)c2nc(C#N)c[nH]2)c(C2=CCC(C)(C)CC2)c1] | Ex. 14, step (e) | Calcd. for C$_{26}$H$_{35}$N$_5$O$_2$, 448.3 (M − H), found 448.5. |
| 22 | 4-Cyano-1H-imidazole-2-carboxylic acid [2-(4,4-dimethyl-cyclohex-1-enyl)-4-(1-methyl-1-morpholin-4-yl-ethyl)-phenyl]-amide | 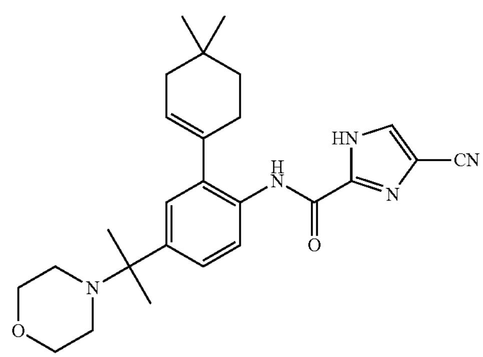 [SMILES: CC1(C)CC=C(c2cc(C(C)(C)N3CCOCC3)ccc2NC(=O)c2nc(C#N)c[nH]2)CC1] | Ex. 14, step (e) | Calcd. for C$_{26}$H$_{33}$N$_5$O$_2$, 446.3 (M − H), found 446.4. |
| 23 | 4-Cyano-1H-imidazole-2-carboxylic acid {2-(4,4-dimethyl-cyclohex-1-enyl)-4-[1-methyl-1-(4-methyl-piperazin-1-yl)-ethyl]-phenyl}-amide | 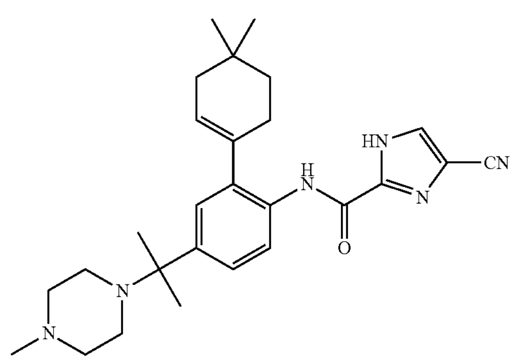 [SMILES: CN1CCN(C(C)(C)c2ccc(NC(=O)c3nc(C#N)c[nH]3)c(C3=CCC(C)(C)CC3)c2)CC1] | Ex. 14, step (e) | Calcd. for C$_{27}$H$_{36}$N$_6$O, 459.3 (M − H), found 459.5. |

| Example | Name | Structure | Procedure | Mass Spectrum (ESI-neg, m/z) |
|---|---|---|---|---|
| 24 | 4-Cyano-1H-imidazole-2-carboxylic acid {2-(4,4-dimethyl-cyclohex-1-enyl)-4-[1-methyl-1-(2-morpholin-4-yl-ethylamino)-ethyl]-phenyl}-amide | 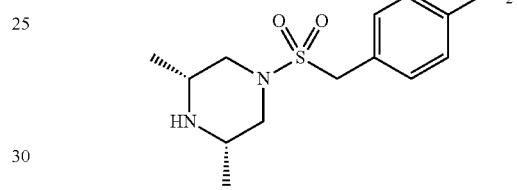 | Ex. 14, step (e) | Calcd. for $C_{28}H_{38}N_6O_2$, 489.3 (M − H), found 489.5. |

Example 25

4-Cyano-1H-imidazole-2-carboxylic acid [2-cyclohex-1-enyl-4-(3,5-cis-dimethyl-piperazine-1-sulfonylmethyl)-phenyl]-amide

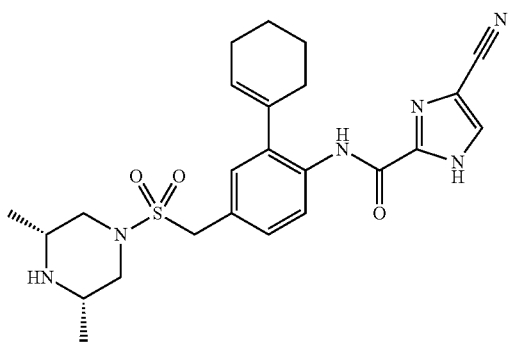 [SMILES: C[C@@H]1CN(S(=O)(=O)Cc2ccc(NC(=O)c3nc(C#N)c[nH]3)c(C3=CCCCC3)c2)C[C@H](C)N1]

a) Cis-3,5-dimethyl-1-(4-nitro-phenylmethanesulfonyl)-piperazine

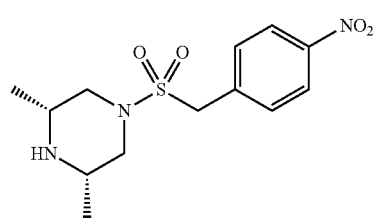 [SMILES: C[C@@H]1CN(S(=O)(=O)Cc2ccc([N+](=O)[O-])cc2)C[C@H](C)N1]

A solution of 250 mg (1.06 mmol) of 4-nitrophenylmethanesulfonyl chloride and 133 mg (1.17 mmol) of cis-2,6-dimethylpiperazine in $CH_2Cl_2$ (10 mL) was treated with 325 µL (2.33 mmol) of triethylamine at RT for 20 min. The mixture was diluted with $CH_2Cl_2$ (15 mL) and washed with water (1×15 mL). The organic layer was dried ($MgSO_4$) and concentrated in vacuo to afford 298 mg (90%) of the title compound as an off-white solid: $^1$H-NMR ($CDCl_3$; 400 MHz): δ 8.25 (d, 2H, J=8.8 Hz), 7.87 (d, 2H, J=8.8 Hz), 4.24 (s, 1H), 3.59-3.53 (m, 2H), 2.92-2.82 (m, 2H), 2.30-2.23 (m, 2H), 1.04 (d, 6H, J=6.0 Hz). Mass spectrum (ESI, m/z): Calcd. for $C_{13}H_{19}N_3O_4S$, 314.1 (M+H). found 314.1.

b) 4-(Cis-3,5-dimethyl-piperazine-1-sulfonylmethyl)-phenylamine

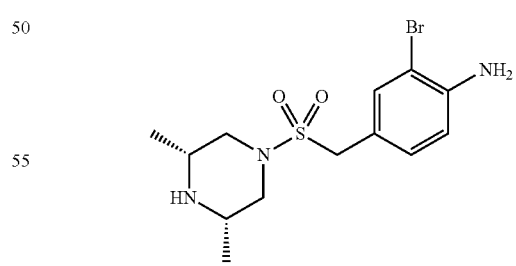

A solution of 298 mg (0.951 mmol) of cis-3,5-dimethyl-1-(4-nitro-phenylmethanesulfonyl)-piperazine (as prepared in the previous step) in MeOH (15 mL) was treated with 20 mg of 10% Pd/C (Degussa type E101-NE/W, Aldrich, 50% by weight water) and $H_2$ (1 atm) at RT for 18 h. The mixture was filtered through Celite, and the filter cake was washed with MeOH. The solvent was removed in vacuo to afford 283 mg (100%) the title compound as an off-white solid: $^1$H-NMR ($CDCl_3$; 400 MHz): δ 7.14 (d, 2H, J=8.4 Hz), 6.66 (d, 2H, J=8.4 Hz), 4.08 (s, 2H), 3.75 (br s, 2H), 3.52-3.50 (m, 1H), 3.48 (s, 4H), 2.88-2.76 (m, 2H), 2.23-2.15 (m, 2H).

c) 2-Bromo-4-(cis-3,5-dimethyl-piperazine-1-sulfonylmethyl)-phenylamine

A solution of 283 mg (0.999 mmol) of 4-(cis-3,5-dimethyl-piperazine-1-sulfonylmethyl)-phenyl amine (as prepared in the previous step) in $CH_2Cl_2$ (15 mL) was cooled to −78° C. and treated portionwise with 176 mg (0.989 mmol) of NBS. The mixture was stirred at −78° C. for 1 h and at RT for 2 h. The mixture was diluted with $CH_2Cl_2$ (15 mL) and washed with saturated aqueous $NaHCO_3$ (1×20 mL) and brine (1×20 mL). The organic layer was dried (MgSO$_4$) and concentrated in vacuo to afford 356 mg (98%) of the title compound as a tan solid: Mass spectrum (ESI, m/z): Calcd. for C$_{13}$H$_{20}$H$_3$O$_2$SBr, 362.0/364.0 (M+H). found 361.8/363.3.

d) 2-Cyclohex-1-enyl-4-(cis-3,5-dimethyl-piperazine-1-sulfonylmethyl)-phenylamine

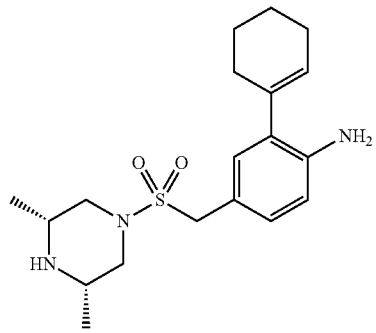 [SMILES: C[C@@H]1CN(S(=O)(=O)Cc2ccc(N)c(C3=CCCCC3)c2)C[C@H](C)N1]

A solution of 356 mg (0.983 mmol) of 2-bromo-4-(cis-3,5-dimethyl-piperazine-1-sulfonylmethyl)-phenylamine (as prepared in the previous step) in toluene (8 mL) and EtOH (4 mL) was treated with 3.93 mL (7.86 mmol) of 2.0 M aqueous Na$_2$CO$_3$ and 186 mg (1.47 mmol) of cyclohex-1-enylboronic acid. The mixture was degassed via sonication, placed under Ar, treated with 170 mg (0.147 mmol) of Pd(PPh$_3$)$_4$, and heated to 80° C. for 4.3 h. The mixture was cooled to RT, diluted with EtOAc (10 mL), and washed with saturated aqueous NaHCO$_3$ (1×10 mL) and brine (1×10 mL). The organic layer was dried (MgSO$_4$) and concentrated in vacuo. Silica gel chromatography of the residue with 0-4% MeOH—CH$_2$Cl$_2$ afforded 307 mg (86%) of the title compound as a white solid: $^1$H-NMR (CDCl$_3$; 400 MHz): δ 7.01 (dd, 1H, J=8.0, 2.0 Hz), 6.99 (d, 1H, J=2.0 Hz), 6.57 (d, 1H, J=8.0 Hz), 5.77-5.72 (m, 1H), 4.07 (s, 2H), 3.85 (br s, 2H), 3.55-3.47 (m, 2H), 2.88-2.77 (m, 2H), 2.26-2.13 (m, 6H), 1.81-1.73 (m, 2H), 1.72-1.64 (m, 2H), 0.99 (d, 6H, J=6.0 Hz).

e) 4-Cyano-1-(2-trimethylsilanyl-ethoxymethyl)-1H-imidazole-2-carboxylic acid [2-cyclohex-1-enyl-4-(cis-3,5-dimethyl-piperazine-1-sulfonylmethyl)-phenyl]-amide

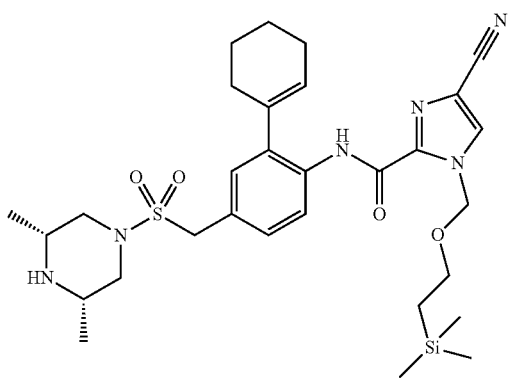 [SMILES: C[C@@H]1CN(S(=O)(=O)Cc2ccc(NC(=O)c3nc(C#N)cn3COCC[Si](C)(C)C)c(C3=CCCCC3)c2)C[C@H](C)N1]

A solution of 153 mg (0.422 mmol) of 2-cyclohex-1-enyl-4-(cis-3,5-dimethyl-piperazine-1-sulfonylmethyl)-phenylamine (as prepared in the previous step) in CH$_2$Cl$_2$ (10 mL) was treated with 295 mg (0.633 mmol) of PyBroP and 142 mg (0.464 mmol) of 4-cyano-1-(2-trimethylsilanyl-ethoxymethyl)-1H-imidazole-2-carboxylate potassium salt (as prepared in Example 1, step (d)) to form a slurry, which was cooled to 0° C., treated with 184 μL (1.06 mmol) of DIEA, and warmed to RT for 6.5 h. The mixture was diluted with CH$_2$Cl$_2$ (15 mL) and washed with saturated aqueous NaHCO$_3$ (1×15 mL) and brine (1×15 mL). The organic layer was dried (MgSO$_4$) and concentrated in vacuo to afford 163 mg (63%) of the title compound as a white solid: Mass spectrum (ESI, m/z): Calcd. for C$_{30}$H$_{44}$N$_6$O$_4$SSi, 613.3 (M+H). found 612.9.

f) 4-Cyano-1H-imidazole-2-carboxylic acid [2-cyclohex-1-enyl-4-(cis-3,5-dimethyl-piperazine-1-sulfonylmethyl)-phenyl]-amide A solution of 163 mg (0.266 mmol) of 4-cyano-1-(2-trimethylsilanyl-ethoxymethyl)-1H-imidazole-2-carboxylic acid [2-cyclohex-1-enyl-4-(cis-3,5-dimethyl-piperazine-1-sulfonylmethyl)-phenyl]-amide (as prepared in the previous step) in CH$_2$Cl$_2$ (15 mL) was treated with EtOH (300 μL) and TFA (4.5 mL), and stirred at RT for 4 h. Solvents were evaporated in vacuo, and the residue was purified by reverse phase high pressure liquid chromatography (RP-HPLC) (C18) with 10-80% CH$_3$CN in 0.1% TFA/H$_2$O over 30 min to afford 8.8 mg (7%) of the title compound as a white solid: $^1$H-NMR (CD$_3$OD; 400 MHz): δ 8.31 (d, 1H, J=8.4 Hz), 8.04 (s, 1H), 7.39 (dd, 1H, J=8.4, 2.0 Hz), 7.33 (d, 1H, J=2.0 Hz), 5.91-5.87 (m, 1H), 4.47 (s, 2H), 3.87-3.79 (m, 2H), 3.31-3.25 (m, 2H), 2.76-2.67 (m, 2H), 2.36-2.27 (m, 4H), 1.94-1.79 (m, 4H), 1.29 (d, 6H, J=6.4 Hz). Mass spectrum (ESI, m/z): Calcd. for C$_{24}$H$_{30}$N$_6$O$_3$S, 483.2 (M+H). found 482.9.

Example 26

4-Cyano-1H-imidazole-2-carboxylic acid {2-cyclohex-1-enyl-4-[2-(morpholine-4-sulfonyl)-ethyl]phenyl}-amide

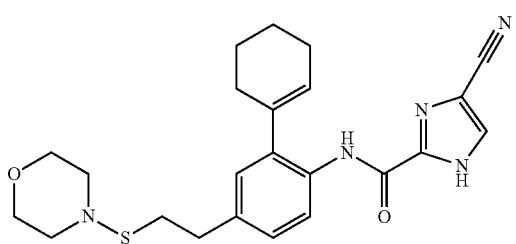

a) Thioacetic acid S-[2-(4-nitro-phenyl)-ethyl]ester

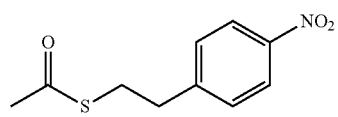

A solution of 2.00 g (8.69 mmol) of 1-(2-bromo-ethyl)-4-nitro-benzene in DMSO (10 mL) was treated with 1.99 g (17.4 mmol) of potassium thioacetate and stirred at RT for 5 h. The mixture was diluted with EtOAc (100 mL) and washed with water (6×60 mL). The organic layer was dried (MgSO$_4$) and concentrated in vacuo to afford 1.48 g (76%) of the title compound as a brown oil: $^1$H-NMR (CD$_3$OD; 400 MHz): δ 8.23-8.15 (m, 2H), 7.60-7.53 (m, 2H), 3.27-3.10 (m, 4H), 3.03-2.94 (m, 3H).

b) 2-(4-Nitro-phenyl)-ethanesulfonic acid

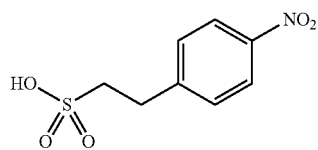

A solution of 1.48 g (6.57 mmol) of thioacetic acid S-[2-(4-nitro-phenyl)-ethyl]ester (as prepared in the previous step) in acetic acid (30 mL) was treated with 30% aqueous H$_2$O$_2$ (10 mL) and stirred at RT for 18 h. The mixture was diluted with water (50 mL) and solvents were removed in vacuo at <40° C. (caution: hazard). The residue was dried overnight on a high vacuum pump to afford 1.14 g (75%) of the title compound as a pale yellow solid: Mass spectrum (ESI, negative mode, m/z): Calcd. for C$_8$H$_9$NO$_5$S, 230.0 (M−H). found 230.1.

c) 4-[2-(4-Nitro-phenyl)-ethanesulfonyl]-morpholine

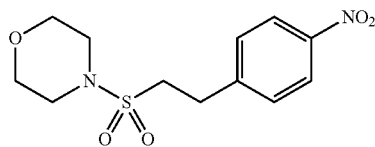 [SMILES: O=[N+]([O-])c1ccc(CCS(=O)(=O)N2CCOCC2)cc1]

A flask was charged with 491 mg (2.12 mmol) of solid 2-(4-nitro-phenyl)-ethanesulfonic acid (as prepared in the previous step), which was treated with 3.10 mL (42.4 mmol) of thionyl chloride and heated to 80° C. for 7 h. The volatile components were removed in vacuo, the residue was taken up in THF (20 mL), and 927 μL (10.6 mmol) of morpholine was added. The mixture was stirred at RT for 16 h, diluted with water (15 mL) and saturated aqueous NaHCO$_3$ (15 mL) and extracted with EtOAc (2×70 mL). The organic layer was dried (MgSO$_4$) and concentrated in vacuo to afford 370 mg (52%) of the title compound as a pale yellow solid: $^1$H-NMR (CDCl$_3$; 400 MHz): δ 8.20 (d, 2H, J=8.8 Hz), 7.40 (d, 2H, J=8.8 Hz), 3.79-3.73 (m, 4H), 3.31-3.23 (m, 6H), 3.21-3.14 (m, 2H).

d) 4-[2-(Morpholine-4-sulfonyl)-ethyl]-phenylamine

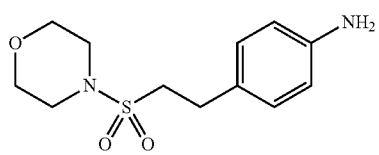

A solution of 370 mg (1.11 mmol) of 4-[2-(4-nitro-phenyl)-ethanesulfonyl]-morpholine (as prepared in the previous step) in MeOH (20 mL) was treated with 10% Pd/C (Degussa type E101-NE/W, Aldrich, 50% by weight water) and H$_2$ (1 atm) at RT for 3 h. The mixture was filtered through Celite, the filter cake was washed with MeOH, and solvents were evaporated in vacuo. Silica gel chromatography of the residue on a 50-g Varian MegaBond Elut SPE column with 50-70% EtOAc-hexane afforded 103 mg (34%) of the title compound as an off-white solid: Mass spectrum (ESI, m/z): Calcd. for C$_{12}$H$_{18}$H$_2$O$_3$S, 271.1 (M+H). found 270.9.

e) 2-Bromo-4-[2-(morpholine-4-sulfonyl)-ethyl]-phenylamine

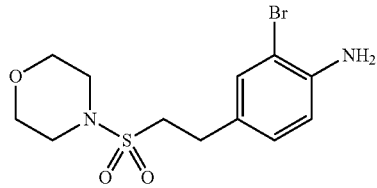 [SMILES: Nc1ccc(CCS(=O)(=O)N2CCOCC2)cc1Br]

A solution of 103 mg (0.381 mmol) of 4-[2-(morpholine-4-sulfonyl)-ethyl]-phenylamine (as prepared in the previous step) in CH$_2$Cl$_2$ (15 mL) was cooled to 0° C. and treated portionwise with 67.8 mg (0.381 mmol) of solid NBS. The mixture was stirred at 0° C. for 15 min, diluted with CH$_2$Cl$_2$ (30 mL) and washed with saturated aqueous NaHCO$_3$ (1×20 mL). The organic layers were dried (MgSO$_4$) and concentrated in vacuo to afford 133 mg (100%) of the title compound as a tan solid: Mass spectrum (ESI, m/z): Calcd. for C$_{12}$H$_{17}$N$_2$O$_3$SBr, 349.0/351.0 (M+H). found 348.7/350.8.

f) 2-Cyclohex-1-enyl-4-[2-(morpholine-4-sulfonyl)-ethyl]-phenylamine

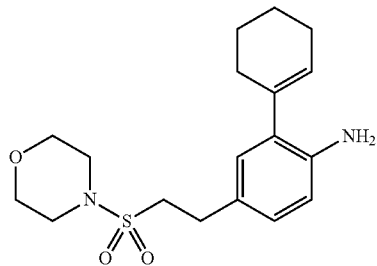 [SMILES: Nc1ccc(CCS(=O)(=O)N2CCOCC2)cc1C1=CCCCC1]

A solution of 133 mg (0.381 mmol) of 2-bromo-4-[2-(morpholine-4-sulfonyl)-ethyl]-phenylamine (as prepared in the previous step) in toluene (6 mL) and EtOH (3 mL) was treated with 1.52 mL (3.05 mmol) of 2.0 M aqueous Na$_2$CO$_3$ and 60.0 mg (0.476 mmol) of cyclohex-1-enylboronic acid. The mixture was degassed via sonication, placed under Ar, treated with 30.8 mg (0.027 mmol) of Pd(PPh$_3$)$_4$, and heated to 80° C. for 2.5 h. The mixture was cooled to RT, diluted with EtOAc (20 mL), and washed with saturated aqueous NaHCO$_3$ (1×15 mL) and brine (1×15 mL). The organic layer was dried (MgSO$_4$) and concentrated in vacuo to afford 132 mg (99%) of the title compound as a tan solid: Mass spectrum (ESI, m/z): Calcd. for C$_{18}$H$_{26}$N$_2$O$_3$S, 351.2 (M+H). found 351.1.

g) 4-Cyano-1-(2-trimethylsilanyl-ethoxymethyl)-1H-imidazole-2-carboxylic acid {2-cyclohex-1-enyl-4-[2-(morpholine-4-sulfonyl)-ethyl]-pheny}-amide

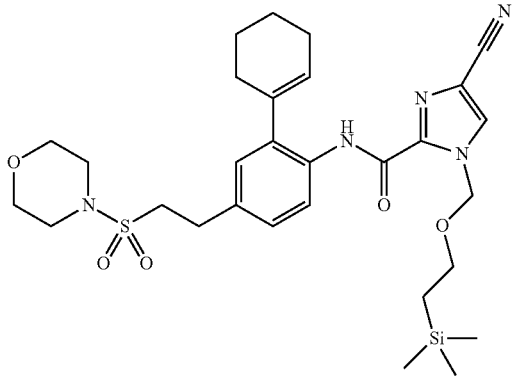 [SMILES: C[Si](C)(C)CCOCn1cc(C#N)nc1C(=O)Nc1ccc(CCS(=O)(=O)N2CCOCC2)cc1C1=CCCCC1]

A solution of 132 mg (0.377 mmol) of 2-cyclohex-1-enyl-4-[2-(mopholine-4-sulfonyl)-ethyl]-phenylamine (as prepared in the previous step) in $CH_2Cl_2$ (15 mL) was treated with 126 mg (0.414 mmol) of 4-cyano-1-(2-trimethylsilanyl-ethoxymethyl)-1H-imidazole-2-carboxylate potassium salt (as prepared in Example 1, step (d)), and 93.9 mg (0.565 mmol) of PyBroP to form a slurry, which was treated with 197 µL (1.13 mmol) of DIEA. The mixture was stirred at RT for 3.5 h, diluted with $CH_2Cl_2$ (15 mL), and washed with saturated aqueous $NaHCO_3$ (1×20 mL). The organic layer was dried ($MgSO_4$) and concentrated in vacuo to afford 221 mg (98%) of the title compound as an off-white solid: Mass spectrum (ESI, m/z): Calcd. for $C_{29}H_{41}N_5O_5SSi$, 600.3 (M+H). found 599.8.

h) 4-Cyano-1H-imidazole-2-carboxylic acid {2-cyclohex-1-enyl-4-[2-(morpholine-4-sulfonyl)-ethyl]-phenyl}-amide A solution of 221 mg (0.367 mmol) of 4-cyano-1-(2-trimethylsilanyl-ethoxymethyl)-1H-imidazole-2-carboxylic acid {2-cyclohex-1-enyl-4-[2-(morpholine-4-sulfonyl)-ethyl]-phenyl}-amide (as prepared in the previous step) in $CH_2Cl_2$ (20 mL) was treated with EtOH (3 drops) and TFA (1.8 mL) and stirred at RT for 2 h. Solvents were evaporated in vacuo, and the resulting residue was chromatographed on a 25-g Varian MegaBond Elut SPE column with 50-70% EtOAc-hexane to afford 6.6 mg (4%) of the title compound as a white solid: $^1$H-NMR ($CD_3OD$; 400 MHz): δ 8.15 (d, 1H, J=8.0 Hz), 7.96 (s, 1H), 7.20 (dd, 1H, J=8.0, 2.0 Hz), 7.12 (s, 1H, J=2.0 Hz), 5.83-5.78 (m, 1H), 3.72-3.66 (m, 4H), 3.48-3.46 (m, 1H), 3.26-3.20 (m, 4H), 3.14-3.11 (m, 1H), 3.10-3.03 (m, 2H), 2.32-2.23 (m, 4H), 1.90-1.73 (m, 4H). Mass spectrum (ESI, m/z): Calcd. for $C_{23}H_{27}N_5O_4S$, 470.2 (M+H). found 469.9.

Example 27

4-Cyano-1H-imidazole-2-carboxylic acid {2-(4,4-dimethyl-cyclohex-1-enyl)-4-[2-(morpholine-4-sulfonyl)-ethyl]-pheny}-amide

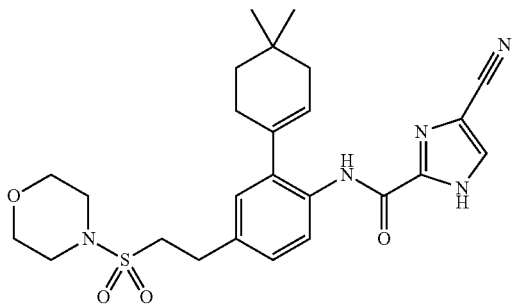 [SMILES: CC1(C)CC=C(c2cc(CCS(=O)(=O)N3CCOCC3)ccc2NC(=O)c2nc(C#N)c[nH]2)CC1]

a) 2-(4,4-Dimethyl-cyclohex-1-enyl)-4-[2-(morpholine-4-sulfonyl)-ethyl]-phenylamine

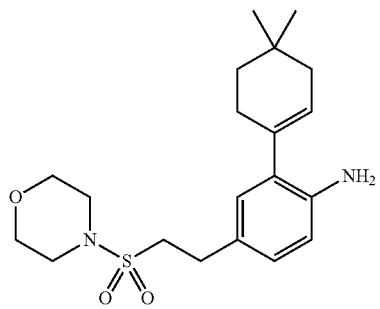 [SMILES: CC1(C)CC=C(c2cc(CCS(=O)(=O)N3CCOCC3)ccc2N)CC1]

A solution of 40.0 mg (0.114 mmol) of 2-bromo-4-[2-(morpholine-4-sulfonyl)-ethyl]-phenylamine (as prepared Example 26, step (e)) in toluene (4 mL) and EtOH (2 mL) was treated with 458 µL (0.229 mmol) of 2.0 M aqueous $Na_2CO_3$ and 29.8 mg (0.226 mmol) of 4,4-dimethyl-cyclohex-1-enylboronic acid. The mixture was degassed via sonication, placed under Ar, treated with 13.2 mg (0.0110 mmol) of $Pd(PPh_3)_4$, and heated to 80° C. for 5 h. The mixture was cooled to RT, diluted with EtOAc (10 mL), and washed with saturated aqueous $NaHCO_3$ (1×10 mL) and brine (1×10 mL). The organic layer was dried ($MgSO_4$) and concentrated in vacuo to afford 60.0 mg of the title compound as a tan solid: Mass spectrum (ESI, m/z): Calcd. for $C_{20}H_{30}N_2O_3S$, 379.2 (M+H). found 379.1.

b) 4-Cyano-1-(2-trimethylsilanyl-ethoxymethyl)-1H-imidazole-2-carboxylic acid {2-(4,4-dimethyl-cyclohex-1-enyl)-4-[2-(morpholine-4-sulfonyl)-ethyl]-pheny}-amide

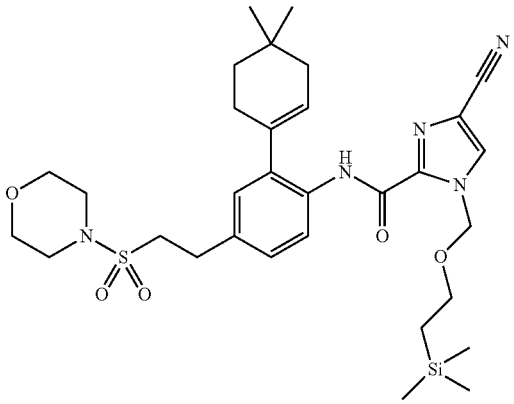 [SMILES: CC1(C)CC=C(c2cc(CCS(=O)(=O)N3CCOCC3)ccc2NC(=O)c2nc(C#N)cn2COCC[Si](C)(C)C)CC1]

A solution of 60.0 mg of crude 2-(4,4-dimethyl-cyclohex-1-enyl)-4-[2-(mopholine-4-sulfonyl)-ethyl]-phenylamine (as prepared in the previous step) in $CH_2Cl_2$ (5 mL) was treated with 53.3 mg (0.174 mmol) of 4-cyano-1-(2-trimethylsilanyl-ethoxymethyl)-1H-imidazole-2-carboxylate potassium salt (as prepared in Example 1, step (d)), and 111 mg (0.238 mmol) of PyBroP to form a slurry, which was treated with 82.8 µL (0.476 mmol) of DIEA. The mixture was stirred at RT for 4 h, diluted with $CH_2Cl_2$ (10 mL) and washed with saturated aqueous $NaHCO_3$ (1×10 mL). The organic layer was dried ($MgSO_4$) and concentrated in vacuo to afford 60.3 mg (crude) of the title compound as an off-white solid: Mass spectrum (ESI, m/z): Calcd. for $C_{31}H_{41}N_5O_5SSi$, 628.3 (M+H). found 628.0.

c) 4-Cyano-1H-imidazole-2-carboxylic acid {2-(4,4-dimethyl-cyclohex-1-enyl)-4-[2-(morpholine-4-sulfonyl)-ethyl]-pheny}-amide A solution of 60.3 mg of crude 4-cyano-1-(2-trimethylsilanyl-ethoxymethyl)-1H-imidazole-2-carboxylic acid {2-(4,4-dimethyl-cyclohex-1-enyl)-4-[2-(morpholine-4-sulfonyl)-ethyl]-phenyl}-amide (as prepared in the previous step) in CH$_2$Cl$_2$ (5 mL) was treated with EtOH (2 drops) and TFA (1 mL) and stirred at RT for 1.5 h. Solvents were evaporated in vacuo, and the residue was purified by RP-HPLC (C18) with 20-100% CH$_3$CN in 0.1% TFA/H$_2$O over 30 min to afford 11.2 mg (20% over three steps) of the title compound as a white solid: $^1$H-NMR (CD$_3$OD; 400 MHz): δ 8.16 (d, 1H, J=8.4 Hz), 7.91 (s, 1H), 7.21 (dd, 1H, J=8.4, 2.4 Hz), 5.76-5.71 (m, 1H), 3.71-3.65 (m, 4H), 3.50-3.46 (m, 1H), 3.26-3.20 (m, 4H), 3.14-3.11 (m, 1H), 3.10-3.04 (m, 2H), 3.35-2.27 (m, 2H), 2.10-2.05 (m, 2H), 1.59 (t, 2H, J=6.4 Hz), 1.08 (s, 6H). Mass spectrum (ESI, m/z): Calcd. for C$_{25}$H$_{31}$N$_5$O$_4$S, 498.2 (M+H). found 498.0.

Example 28

4-Cyano-1H-imidazole-2-carboxylic acid [2-cyclohex-1-enyl-4-(2-dimethylsulfamoyl-ethyl)phenyl]-amide

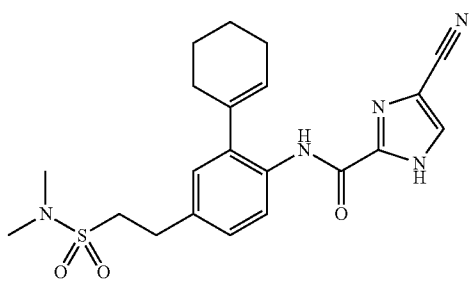 [SMILES: CN(C)S(=O)(=O)CCc1ccc(NC(=O)c2nc(C#N)c[nH]2)c(C2=CCCCC2)c1]

a) 2-(4-Nitro-phenyl)-ethanesulfonic acid dimethylamide

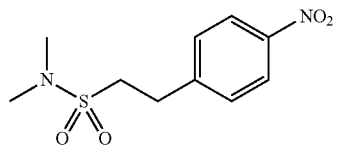

A flask was charged with 4.60 g (19.9 mmol) of solid 2-(4-nitro-phenyl)-ethanesulfonic acid (as prepared in Example 26, step (b)), which was treated with 29.0 mL (398 mmol) of thionyl chloride and heated to 80° C. for 6 h. Solvents were evaporated in vacuo, and the resulting solid was dried overnight under high vacuum. A solution of 2.12 g (8.49 mmol) of this solid sulfonyl chloride in 40 mL CH$_2$Cl$_2$ was treated with 15.0 mL (127 mmol) of 40% w/v aqueous dimethylamine and stirred at RT for 16 h then warmed to 40° C. for 3 h. The mixture was diluted with CH$_2$Cl$_2$ (100 mL) and washed with water (2×50 mL). The aqueous layer was extracted with CH$_2$Cl$_2$ (50 mL). The combined organic layers were dried (MgSO$_4$) and concentrated in vacuo. Silica gel chromatography of the residue on a 50-g Varian MegaBond Elut SPE column with 50% EtOAc-hexane afforded 912 mg (41%) of the title compound as an off-white solid: $^1$H-NMR (CD$_3$OD; 400 MHz): δ 8.20 (d, 2H, J=8.8 Hz), 7.41 (d, 2H, J=8.8 Hz), 3.29-3.14 (m, 4H), 2.89 (s, 6H).

b) 2-(4-Amino-phenyl)-ethanesulfonic acid dimethylamide

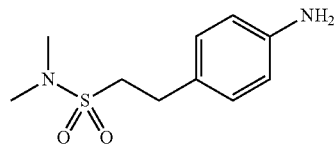 [SMILES: CN(C)S(=O)(=O)CCc1ccc([N+](=O)[O-])cc1]

A suspension of 912 mg (3.53 mmol) of 2-(4-nitro-phenyl)-ethanesulfonic acid dimethylamide (as prepared in the previous step) in MeOH (30 mL) was hydrogenated with 10% Pd/C (Degussa type E101-NE/W, Aldrich, 50% by weight water) at 20 psi H$_2$ at RT for 2 days. The mixture was filtered through Celite, the filter cake was washed with MeOH, and the solvents were evaporated in vacuo. Silica gel chromatography of the residue on a 25-g Varian MegaBond Elut SPE column with 50% EtOAc-hexane afforded 737 mg (91%) of the title compound as a white solid: $^1$H-NMR (CD$_3$CN; 400 MHz): δ 7.01 (d, 2H, J=8.4 Hz), 6.61 (d, 2H, J=8.4 Hz), 4.06 (br s, 2H), 3.19-3.13 (m, 2H), 2.95-2.88 (m, 2H), 2.84 (s, 6H).

c) 2-(4-Amino-3-bromo-phenyl)-ethanesulfonic acid dimethylamide

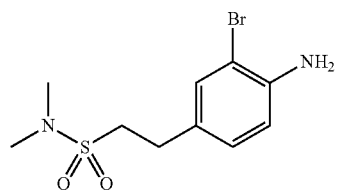 [SMILES: CN(C)S(=O)(=O)CCc1ccc(N)c(Br)c1]

A solution of 737 mg (3.23 mmol) of 2-(4-amino-phenyl)-ethanesulfonic acid dimethylamide (as prepared in the previous step) in CH$_2$Cl$_2$ (20 mL) was cooled to 0° C. and treated with 574 mg (3.23 mmol) of NBS. The ice bath was removed and the mixture stirred at RT for 25 min. The mixture was diluted with CH$_2$Cl$_2$ (40 mL) and washed with saturated aqueous NaHCO$_3$ (2×30 mL). The aqueous layer was extracted with CH$_2$Cl$_2$ (1×30 mL) the combined organic layers were dried (MgSO$_4$) and concentrated in vacuo to afford 955 mg (96%) of the title compound as a white solid: $^1$H-NMR (CD$_3$OD; 400 MHz): δ 7.35 (d, 1H, J=2.0 Hz), 7.04 (dd, 1H, J=8.0, 2.0 Hz), 4.44 (br s, 2H), 3.21-3.14 (m, 2H), 2.96-2.89 (m, 2H), 2.84 (s, 6H). Mass spectrum (ESI, m/z): Calcd. for C$_{10}$H$_{15}$N$_2$OSBr, 307.0/309.0 (M+H). found 307.0/309.0.

d) 2-(4-Amino-3-cyclohex-1-enyl-phenyl)-ethanesulfonic acid dimethylamide

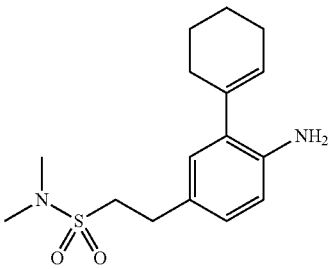 [SMILES: CN(C)S(=O)(=O)CCc1ccc(N)c(C2=CCCCC2)c1]

A solution of 477 mg (1.55 mmol) of 2-(4-amino-3-bromo-phenyl)-ethanesulfonic acid dimethylamide (as prepared in the previous step) in toluene (13 mL) and EtOH (6.5 mL) was treated with 215 mg (1.71 mg) of cyclohex-1-enylboronic acid and 6.21 mL (12.4 mmol) of 2.0 M aqueous $Na_2CO_3$. The mixture was degassed via sonication, placed under Ar, treated with 179 mg (0.155 mmol) of $Pd(PPh_3)_4$, and heated to 80° C. for 17.5 h. The mixture was cooled to RT, diluted with EtOAc (50 mL), and washed with water (2×25 mL). The aqueous layer was extracted with EtOAc (30 mL). The combined organic layers were dried ($MgSO_4$) and concentrated in vacuo. Silica gel chromatography of the residue on a 50-g Varian MegaBond Elut SPE column with 50% EtOAc-hexane afforded 365 mg (76%) of the title compound as a white solid: $^1$H-NMR ($CD_3CN$; 400 MHz): δ 6.90 (dd, 1H, J=8.4, 2.4 Hz), 6.84 (d, 1H, J=2.4 Hz), 6.62 (d, 1H, J=8.4 Hz), 5.70-5.66 (m, 1H), 4.03 (br s, 2H), 3.20-3.13 (m, 2H), 2.93-2.87 (m, 2H), 2.83 (s, 6H), 2.24-2.17 (m, 4H), 1.82-1.74 (m, 2H), 1.74-1.66 (m, 2H). Mass spectrum (ESI, m/z): Calcd. for $C_{16}H_{24}N_2O_2S$, 309.2 (M+H). found 309.1.

e) 4-Cyano-1-(2-trimethylsilanyl-ethoxymethyl)-1H-imidazole-2-carboxylic acid [2-cyclohex-1-enyl-4-(2-dimethylsulfamoyl-ethyl)-phenyl]-amide

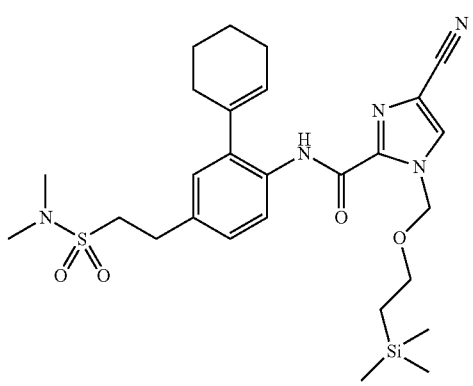 [SMILES: CN(C)S(=O)(=O)CCc1ccc(NC(=O)c2nc(C#N)cn2COCC[Si](C)(C)C)c(C2=CCCCC2)c1]

A solution of 365 mg (1.18 mmol) of 2-(4-amino-3-cyclohex-1-enyl-phenyl)-ethanesulfonic acid dimethylamide (as prepared in the previous step) in $CH_2Cl_2$ (10 mL) was treated with 827 mg (1.78 mmol) of PyBroP, 398 mg (1.30 mmol) of 4-cyano-1-(2-trimethylsilanyl-ethoxymethyl)-1H-imidazole-2-carboxylate potassium salt (as prepared in Example 1, step (d)), and 618 μL (3.55 mmol) of DIEA at RT for 16.5 h. The mixture was diluted with $CH_2Cl_2$ (20 mL) and washed with water (1×20 mL). The aqueous layer was extracted with $CH_2Cl_2$ (1×20 mL) and the combined organic layers dried ($MgSO_4$) and concentrated in vacuo. Silica gel chromatography of the residue on a 50-g Varian MegaBond Elut SPE column with 25-40% EtOAc-hexane afforded 660 mg (100%) of the title compound as a white solid: Mass spectrum (ESI, m/z): Calcd. for $C_{27}H_{39}N_5O_4SSi$, 558.2 (M+H). found 557.9.

f) 4-Cyano-1H-imidazole-2-carboxylic acid [2-cyclohex-1-enyl-4-(2-dimethylsulfamoyl-ethyl)phenyl]-amide A solution of 660 mg (1.19 mmol) of 4-cyano-1-(2-trimethylsilanyl-ethoxymethyl)-1H-imidazole-2-carboxylic acid [2-cyclohex-1-enyl-4-(2-dimethylsulfamoyl-ethyl)-phenyl]-amide (as prepared in the previous step) in $CH_2Cl_2$ (30 mL) was treated with EtOH (600 μL) and TFA (3 mL) and stirred at RT for 24 h. MeOH (20 mL) was added, and the solvents were evaporated in vacuo. The solid was triturated with acetonitrile to afford 342 mg (67% of the title compound as a white solid: $^1$H-NMR ($CD_3CN$; 400 MHz): δ 8.20-8.09 (m, 1H), 7.92 (s, 1H), 7.24-7.16 (m, 1H), 7.13 (s, 1H), 5.84-5.75 (m, 1H), 3.30-3.19 (m, 4H), 3.08-2.96 (m, 2H), 2.82 (s, 6H), 2.29-2.17 (m, 4H), 1.85-1.68 (m, 4H). Mass spectrum (ESI, m/z): Calcd. for $C_{21}H_{25}N_5O_3S$, 428.2 (M+H). found 428.1.

Example 29

4-Cyano-1H-imidazole-2-carboxylic acid [2-(4,4-dimethyl-cyclohex-1-enyl)-4-(2-dimethylsulfamoyl-ethyl)-phenyl]-amide

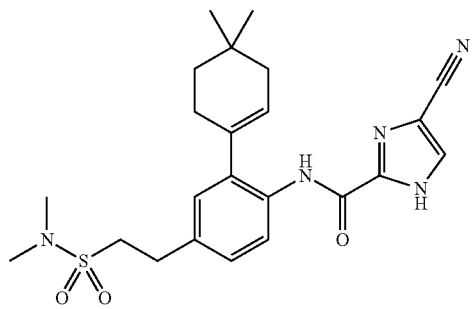 [SMILES: CN(C)S(=O)(=O)CCc1ccc(NC(=O)c2nc(C#N)c[nH]2)c(C2=CCC(C)(C)CC2)c1]

a) 2-[4-Amino-3-(4,4-dimethyl-cyclohex-1-enyl)-phenyl]-ethanesulfonic acid dimethylamide

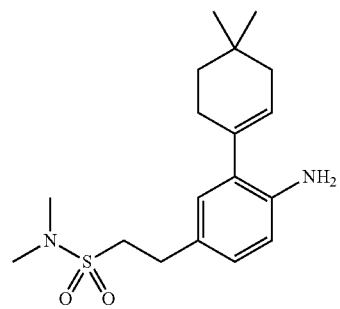 [SMILES: CN(C)S(=O)(=O)CCc1ccc(N)c(C2=CCC(C)(C)CC2)c1]

A solution of 477 mg (1.55 mmol) of 2-(4-amino-3-bromo-phenyl)-ethanesulfonic acid dimethylamide (as prepared in Example 28, step (c)) in toluene (13 mL) and EtOH (6.5 mL) was treated with 6.21 mL (12.4 mmol) of 2.0 M aqueous Na$_2$CO$_3$ and 403 mg (1.71 mmol) of 2-(4,4-dimethyl-cyclohex-1-enyl)-4,4,5,5-tetramethyl-[1,3,2]dioxaborolane. The mixture was degassed via sonication, placed under Ar, treated with 179 mg (0.155 mmol) of Pd(PPh$_3$)$_4$ and heated to 80° C. for 18 h. The mixture was cooled to RT, diluted with EtOAc (50 mL) and washed with water (1×50 mL). The aqueous layer was extracted with EtOAc (1×50 mL). The combined organic layers were dried (MgSO$_4$) and concentrated in vacuo. Silica gel chromatography of the residue on a 50-g Varian MegaBond Elut SPE column with 50% EtOAc-hexane afforded 215 mg (41%) of the title compound as a white solid: Mass spectrum (ESI, m/z): Calcd. for C$_{18}$H$_{28}$N$_2$O$_2$S, 337.2 (M+H). found 337.1.

b) 4-Cyano-1-(2-trimethylsilanyl-ethoxymethyl)-1H-imidazole-2-carboxylic acid [2-(4,4-dimethyl-cyclohex-1-enyl)-4-(2-dimethylsulfamoyl-ethyl)-phenyl]-amide

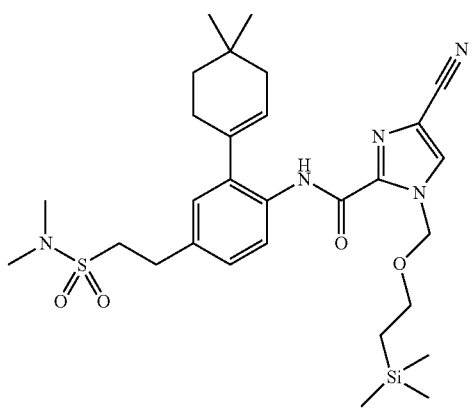 [SMILES: CN(C)S(=O)(=O)CCc1ccc(NC(=O)c2nc(C#N)cn2COCC[Si](C)(C)C)c(C2=CCC(C)(C)CC2)c1]

A solution of 215 mg (0.638 mmol) of 2-[4-amino-3-(4,4-dimethyl-cyclohex-1-enyl)-phenyl]-ethanesulfonic acid dimethylamide (as prepared in the previous step) in CH$_2$Cl$_2$ (10 mL) was treated with 446 mg (0.957 mmol) of PyBroP, 214 mg (0.701 mmol) of 4-cyano-1-(2-trimethylsilanyl-ethoxymethyl)-1H-imidazole-2-carboxylate potassium salt (as prepared in Example 1, step (d)) and 333 µL (1.91 mmol) of DIEA and stirred at RT for 18 h. The mixture was diluted with CH$_2$Cl$_2$ (20 mL) and washed with water (1×20 mL). The aqueous layer was extracted with CH$_2$Cl$_2$ (1×20 mL). The combined organic layers were dried (MgSO$_4$) and concentrated in vacuo. Silica gel chromatography of the residue on a 50-g Varian MegaBond Elut SPE column with 25% EtOAc-hexane afforded 355 mg (95%) of the title compound as a white solid: Mass spectrum (ESI, m/z): Calcd. for C$_{29}$H$_{43}$N$_5$O$_4$SSi, 586.3 (M+H). found 585.9.

c) 4-Cyano-1H-imidazole-2-carboxylic acid [2-(4,4-dimethyl-cyclohex-1-enyl)-4-(2-dimethylsulfamoyl-ethyl)-phenyl]-amide A solution of 355 mg (0.606 mmol) of 4-cyano-1-(2-trimethylsilanyl-ethoxymethyl)-1H-imidazole-2-carboxylic acid [2-(4,4-dimethyl-cyclohex-1-enyl)-4-(2-dimethylsulfamoyl-ethyl)-phenyl]-amide (as prepared in the previous step) in CH$_2$Cl$_2$ (15 mL) was treated with EtOH (300 µL) and TFA (1.5 mL) at RT for 24 h. MeOH (20 mL) was added, and the solvents were evaporated in vacuo. The solid was triturated with acetonitrile to afford 169 mg (61%) of the title compound as a white solid: $^1$H-NMR (CD$_3$CN; 400 MHz): δ 9.41 (s, 1H), 8.23 (d, 1H, J=8.0 Hz), 7.91 (s, 1H), 7.22 (d, 1H, J=8.0 Hz), 7.18 (s, 1H), 5.80-5.71 (m, 1H), 3.31-3.21 (m, 2H), 3.10-3.00 (m, 2H), 2.85 (s, 6H), 2.37-2.27 (m, 2H), 2.10-2.04 (m, 2H), 1.64-1.55 (m, 2H), 1.10 (s, 6H). Mass spectrum (ESI, m/z): Calcd. for C$_{23}$H$_{29}$N$_5$O$_3$S, 456.2 (M+H). found 456.1.

Example 30

4-Cyano-1H-imidazole-2-carboxylic acid [2-cyclohex-1-enyl-4-(2-methylsulfamoyl-ethyl)-phenyl]-amide

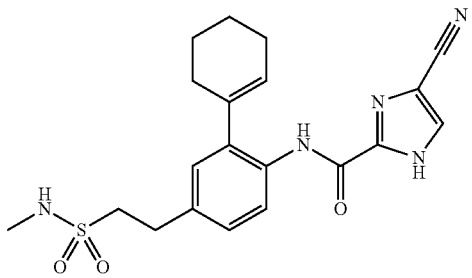 [SMILES: CNS(=O)(=O)CCc1ccc(NC(=O)c2nc(C#N)c[nH]2)c(C2=CCCCC2)c1]

a) 2-(4-Nitro-phenyl)-ethanesulfonic acid methylamide

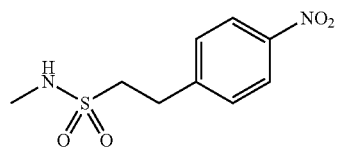

A suspension of 2.12 g (8.49 mmol) of 2-(4-nitro-phenyl)-ethanesulfonyl chloride (as prepared in Example 26, step (c)) in MeOH (40 mL) was cooled to 0° C. and treated with 21.2 mL (42.4 mmol) of methylamine (2.0 M in MeOH). The mixture was slowly warmed to RT, stirred for 16 h, and warmed to 40° C. for 3 days. Solvents were evaporated in vacuo. Silica gel chromatography of the residue on a 50-g Varian MegaBond Elut SPE column with 50% EtOAc-hexane afforded 402 mg (19%) of the title compound as a white solid: $^1$H-NMR (CD$_3$CN; 400 MHz): δ 8.19 (d, 2H, J=8.8 Hz), 7.54 (d, 2H, J=8.8 Hz), 5.15-5.05 (br s, 1H), 3.39-3.32 (m, 2H), 3.22-3.15 (m, 2H), 2.70 (d, 3H, J=5.2 Hz).

b) 2-(4-Aminophenyl)-ethanesulfonic acid methylamide

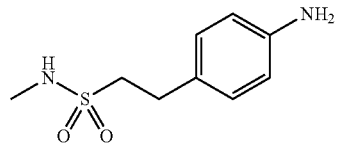 [SMILES: CNS(=O)(=O)CCc1ccc([N+](=O)[O-])cc1]

A solution of 402 mg (1.65 mmol) of 2-(4-nitro-phenyl)-ethanesulfonic acid methylamide (as prepared in the previous step) in MeOH (30 mL) was hydrogenated over 10% Pd/C (Degussa type E101-NE/W, Aldrich, 50% by weight water) at 20 psi of $H_2$ for 19 h. The reaction mixture was filtered through Celite, and the filter cake was washed with MeOH. Solvents were evaporated in vacuo. Silica gel chromatography of the residue on a 25-g Varian MegaBond Elut SPE column with 50% EtOAc-hexane afforded 318 mg (90%) of the title compound as a white solid: $^1$H-NMR ($CD_3CN$; 400 MHz): δ 7.01 (d, 2H, J=8.4 Hz), 6.61 (d, 2H, J=8.4 Hz), 5.00-4.92 (br s, 1H), 4.12-4.02 (br s, 2H), 3.24-3.17 (m, 2H), 2.92-2.86 (m, 2H), 2.67 (s, 3H, J=5.2 Hz).

c) 2-(4-Amino-3-bromo-phenyl)-ethanesulfonic acid methylamide

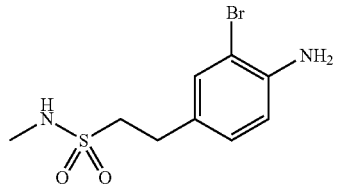

A solution of 318 mg (1.48 mmol) of 2-(4-aminophenyl)-ethanesulfonic acid methylamide (as prepared in the previous step) in $CH_2Cl_2$ (20 mL) was cooled to 0° C. and treated with 251 mg (1.41 mmol) of NBS at that temperature for 1 h. The mixture was diluted with $CH_2Cl_2$ (30 mL) and washed with saturated aqueous $NaHCO_3$ (1×30 mL). The organic layer was dried ($MgSO_4$) and concentrated in vacuo. Silica gel chromatography of the residue on a 25-g Varian MegaBond Elut SPE column with 50% EtOAc-hexane afforded 354 mg (81%) of the title compound as a white solid: $^1$H-NMR ($CD_3CN$; 400 MHz): δ 7.34 (d, 1H, J=2.0 Hz), 7.03 (dd, 1H, J=8.0, 2.0 Hz), 6.77 (d, 1H, J=8.0 Hz), 5.06-4.97 (m, 1H), 4.48-4.40 (br s, 2H), 3.25-3.18 (m, 2H), 2.93-2.86 (m, 2H), 2.67 (d, 3H, J=5.2 Hz). Mass spectrum (ESI, m/z): Calcd. for $C_9H_{13}N_2O_2SBr$, 293.0/295.0 (M+H). found 293.0/295.0.

d) 2-(4-Amino-3-cyclohex-1-enyl-phenyl)-ethanesulfonic acid methylamide

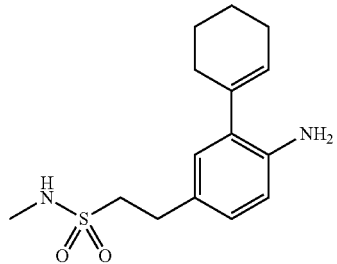 [SMILES: CNS(=O)(=O)CCc1ccc(N)c(C2=CCCCC2)c1]

A solution of 177 mg (0.604 mmol) of 2-(4-amino-3-bromo-phenyl)-ethanesulfonic acid methylamide (as prepared in the previous step) in toluene (5 mL) and EtOH (2.5 mL) was treated with 83.7 mg (0.664 mmol) of cyclohex-1-enylboronic acid and 2.40 mL (4.83 mmol) of 2.0 M aqueous $Na_2CO_3$. The mixture was degassed via sonication, placed under Ar, treated with 67.3 mg (0.0604 mmol) of $Pd(PPh_3)_4$, and heated to 80° C. for 19 h. The mixture was diluted with EtOAc (15 mL) and washed with water (1×10 mL). The aqueous layer was extracted with EtOAc (1×10 mL), and the combined organic layers were dried ($MgSO_4$) and concentrated in vacuo. Silica gel chromatography of the residue on a 25-g Varian MegaBond Elut SPE column with 50% EtOAc-hexane afforded 123 mg (69%) of the title compound as a white solid: $^1$H-NMR ($CD_3CN$; 400 MHz): δ 6.90 (dd, 1H, J=8.0, 2.0 Hz), 6.83 (d, 1H, J=2.0 Hz), 6.32 (d, 1H, J=8.0 Hz), 5.70-5.66 (m, 1H), 4.97-4.90 (m, 2H), 4.08-3.99 (br s, 2H), 3.24-3.17 (m, 2H), 2.91-2.84 (m, 2H), 2.66 (d, 3H, J=5.2 Hz), 2.24-2.15 (m, 4H), 1.82-1.74 (m, 2H), 1.74-1.66 (m, 2H).

e) 4-Cyano-1-(2-trimethylsilanyl-ethoxymethyl)-1H-imidazole-2-carboxylic acid [2-cyclohex-1-enyl-4-(2-methylsulfamoyl-ethyl)-phenyl]-amide

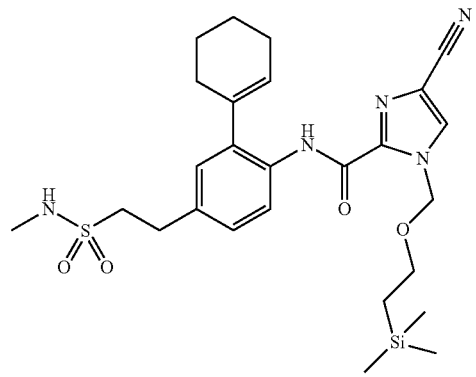 [SMILES: CNS(=O)(=O)CCc1ccc(NC(=O)c2nc(C#N)cn2COCC[Si](C)(C)C)c(C2=CCCCC2)c1]

A solution of 123 mg (0.418 mmol) of 2-(4-amino-3-cyclohex-1-enyl-phenyl)-ethanesulfonic acid methylamide (as prepared in the previous step) in $CH_2Cl_2$ (10 mL) was treated with 292 mg (0.627 mmol) of PyBroP, 140 mg (0.460 mmol) of 4-cyano-1-(2-trimethylsilanyl-ethoxymethyl)-1H-imidazole-2-carboxylate potassium salt (as prepared in Example 1, step (d)), and 218 µL (1.25 mmol) of DIEA. The mixture was stirred at RT for 2 h, diluted with $CH_2Cl_2$ (20 mL) and washed with saturated aqueous $NaHCO_3$ (1×20 mL). The organic layer was dried ($MgSO_4$) and concentrated in vacuo. Silica gel chromatography of the residue on a 50-g Varian MegaBond Elut SPE column with 50% EtOAc-hexane afforded 177 (71%) of the title compound as a white solid: Mass spectrum (ESI, m/z): Calcd. for $C_{26}H_{37}N_5O_4SSi$, 544.2 (M+H). found 543.9.

f) 4-Cyano-1H-imidazole-2-carboxylic acid [2-cyclohex-1-enyl-4-(2-methylsulfamoyl-ethyl)-phenyl]-amide A solution of 177 mg (0.326 mmol) of 4-cyano-1-(2-trimethylsilanyl-ethoxymethyl)-1H-imidazole-2-carboxylic acid [2-cyclohex-1-enyl-4-(2-methylsulfamoyl-ethyl)-phenyl]-amide (as prepared in the previous step) in $CH_2Cl_2$ (10 mL) was treated with MeOH (300 µL) and TFA (3 mL) at RT for 45 min. MeOH (10 mL) was added, and solvents were evaporated in vacuo. The solid residue was triturated with a minimum amount of acetonitrile with sonication, but further purification was needed. Silica gel chromatography of the solid with 50% EtOAc-hexane also afforded impure material. The solid was purified by RP-HPLC (C18) with 40-100% CH$_3$CN in 0.1% TFA/H$_2$O over 30 min to afford 14.9 mg (11%) of the title compound as a white solid: $^1$H-NMR (CD$_3$CN; 400 MHz): δ 9.38 (s, 1H), 8.27-8.20 (m, 1H), 7.93 (s, 1H), 7.27-7.20 (m, 1H), 7.18-7.14 (m, 1H), 5.89-5.82 (m, 1H), 5.09-5.01 (m, 1H), 3.36-3.26 (m, 2H), 3.08-3.00 (m, 2H), 2.70 (d, 3H, J=5.2 Hz), 2.32-2.25 (m, 4H), 1.90-1.74 (m, 4H). Mass spectrum (ESI, m/z): Calcd. for C$_{20}$H$_{23}$N$_5$O$_3$S, 414.1 (M+H). found 414.1.

Example 31

4-Cyano-1H-imidazole-2-carboxylic acid [2-(4,4-dimethyl-cyclohex-1-enyl)-4-(2-methylsulfamoyl-ethyl)-phenyl]-amide

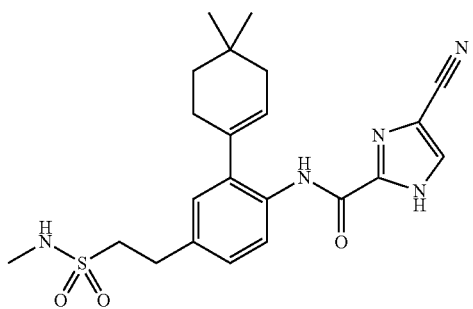 [SMILES: CNS(=O)(=O)CCc1ccc(NC(=O)c2nc(C#N)c[nH]2)c(C2=CCC(C)(C)CC2)c1]

a) 2-[4-Amino-3-(4,4-dimethyl-cyclohex-1-enyl)-phenyl]-ethanesulfonic acid methylamide

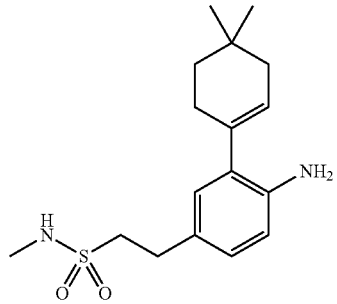 [SMILES: CNS(=O)(=O)CCc1ccc(N)c(C2=CCC(C)(C)CC2)c1]

A solution of 177 mg (0.604) of 2-(4-amino-3-bromo-phenyl)-ethanesulfonic acid methylamide (as prepared in Example 30, step (c)) in toluene (5 mL) and EtOH (2.5 mL) was treated with 157 mg (0.664 mmol) of 2-(4,4-dimethyl-cyclohex-1-enyl)-4,4,5,5-tetramethyl-[1,3,2]dioxaborolane and 2.40 mL (4.83 mmol) of 2.0 M aqueous Na$_2$CO$_3$. The mixture was degassed via sonication, placed under Ar, treated with 70.0 mg (0.0604 mmol) of Pd(PPh$_3$)$_4$, and heated to 80° C. for 17 h. The mixture was diluted with EtOAc (15 mL) and washed with water (1×10 mL). The aqueous layer was extracted with EtOAc (1×10 mL), and the combined organic layers were dried (MgSO$_4$) and concentrated in vacuo. Silica gel chromatography of the residue on a 50-g Varian MegaBond Elut SPE column with 50% EtOAc-hexane afforded 65.0 mg (33%) of the title compound as a white solid: $^1$H-NMR (CD$_3$CN; 400 MHz): δ 6.90 (dd, 1H, J=8.0, 2.0 Hz), 6.85 (d, 1H, J=2.0 Hz), 6.63 (d, 1H, J=8.0 Hz), 5.65-5.59 (m, 1H), 5.00-4.91 (m, 1H), 4.06-3.97 (br s, 2H), 3.26-3.18 (m, 2H), 2.93-2.85 (m, 2H), 2.67 (d, 3H, J=5.2 Hz), 2.29-2.21 (m, 2H), 2.18 (s, 2H), 2.02-1.96 (m, 2H), 1.58-1.50 (m, 2H), 1.02 (s, 6H).

b) 4-Cyano-1-(2-trimethylsilanyl-ethoxymethyl)-1H-imidazole-2-carboxylic acid [2-(4,4-dimethyl-cyclohex-1-enyl)-4-(2-methylsulfamoyl-ethyl)-phenyl]-amide

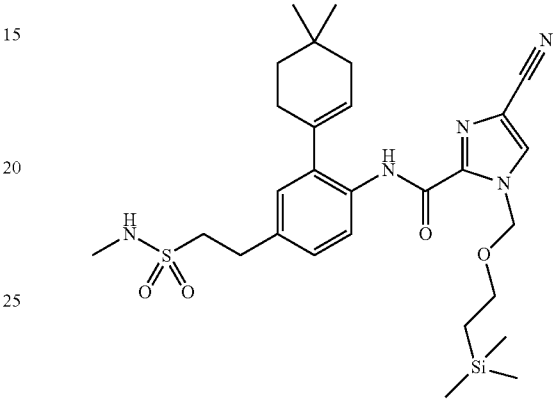

A solution of 65.0 mg (0.202 mmol) of 2-[4-amino-3-(4,4-dimethyl-cyclohex-1-enyl)-phenyl]-ethanesulfonic acid methylamide (as prepared in the previous step) in CH$_2$Cl$_2$ (5 mL) was treated with 141 mg (0.303 mmol) of PyBroP, 67.7 mg (0.222 mmol) of 4-cyano-1-(2-trimethylsilanyl-ethoxymethyl)-1H-imidazole-2-carboxylate potassium salt (as prepared in Example 1, step (d)), and 105 μL (0.605 mmol) of DIEA at RT for 2 h. The mixture was diluted with CH$_2$Cl$_2$ (10 mL) and washed with saturated aqueous NaHCO$_3$ (1×10 mL). The organic layer was dried (MgSO$_4$) and concentrated in vacuo. Silica gel chromatography of the residue on a 50-g Varian MegaBond Elut SPE column with 50% EtOAc-hexane afforded 96.0 mg (83%) of the title compound as a white solid: Mass spectrum (ESI, m/z): Calcd. for C$_{28}$H$_{41}$N$_5$O$_4$SSi, 572.3 (M+H). found 572.0.

c) 4-Cyano-1H-imidazole-2-carboxylic acid [2-(4,4-dimethyl-cyclohex-1-enyl)-4-(2-methylsulfamoyl-ethyl)-phenyl]-amide A solution of 97.0 mg (0.170 mmol) of 4-cyano-1-(2-trimethylsilanyl-ethoxymethyl)-1H-imidazole-2-carboxylic acid [2-(4,4-dimethyl-cyclohex-1-enyl)-4-(2-methylsulfamoyl-ethyl)-phenyl]-amide (as prepared in the previous step) in CH$_2$Cl$_2$ (30 mL) was treated with MeOH (1 mL) and TFA (10 mL) at RT for 1 h. MeOH (10 mL) was added and the solvents were removed in vacuo. The residue was purified by RP-HPLC (C18) with 40-100% CH$_3$CN in 0.1% TFA/H$_2$O over 30 min to afford 19.8 mg (26%) of the title compound as a white solid: $^1$H-NMR (CD$_3$CN; 400 MHz): δ 9.41 (s, 1H), 8.24 (d, 1H, J=8.0 Hz), 7.91 (s, 1H), 7.22 (dd, 1H, J=8.0, 2.0 Hz), 5.79-5.74 (m, 1H), 5.08-5.00 (m, 1H), 3.34-3.27 (m, 2H), 3.06-2.99 (m, 2H), 2.70 (d, 3H, J=5.2 Hz), 2.35-2.28 (m, 2H), 2.10-2.05 (m, 2H), 1.59 (t, 2H, J=6.4 Hz), 1.10 (s, 6H). Mass spectrum (ESI, m/z): Calcd. for C$_{22}$H$_{27}$N$_5$O$_3$S, 442.2 (M+H). found 442.1.

Example 32

4-Cyano-1H-imidazole-2-carboxylic acid [2-cyclohex-1-enyl-4-(morpholine-4-sulfonylmethyl)-phenyl]-amide

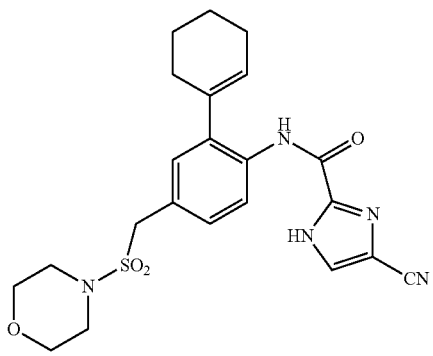 [SMILES: N#Cc1c[nH]c(C(=O)Nc2ccc(CS(=O)(=O)N3CCOCC3)cc2C2=CCCCC2)n1]

a) 2-Bromo-4-(morpholine-4-sulfonylmethyl)-phenylamine

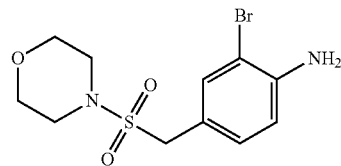 [SMILES: Nc1ccc(CS(=O)(=O)N2CCOCC2)cc1Br]

To a solution of 4-(morpholine-4-sulfonylmethyl)-phenylamine (437 mg, 1.70 mmol, WO 9720822) in DCM (10 mL) was added NBS (304 mg, 1.70 mmol) at 0° C. The solution was allowed to stir at RT for 15 min. Satd aq NaHCO$_3$ (20 mL) was then added and the organic layer was separated, dried (Na$_2$SO$_4$) and concentrated to afford the title compound (564 mg, 98%). $^1$H-NMR (CDCl$_3$; 400 MHz): δ 7.47 (d, 1H, J=1.9 Hz), 7.15 (dd, 1H, J=8.2, 1.9 Hz), 6.77 (d, 1H, J=8.2 Hz), 4.23 (br s, 2H), 4.12 (s, 2H), 3.65-3.68 (m, 4H), 3.14-3.17 (m, 4H).

b) 2-Cyclohex-1-enyl-4-(morpholine-4-sulfonylmethyl)-phenylamine

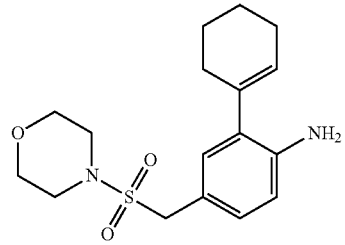 [SMILES: Nc1ccc(CS(=O)(=O)N2CCOCC2)cc1C1=CCCCC1]

The title compound was prepared according to the Suzuki coupling procedure of the Example 1, step (e) using cyclohex-1-enyl boronic acid (157 mg, 1.25 mmol) and 2-bromo-4-(morpholine-4-sulfonylmethyl)-phenylamine (as prepared in the previous step, 335 mg, 1.00 mmol) and purified on silica (20% EtOAc/hexanes) (276 mg, 82%). $^1$H-NMR (CDCl$_3$; 400 MHz): δ 7.05 (dd, 1H, J=8.2, 1.9 Hz), 6.95 (d, 1H, J=1.9 Hz) 6.67 (d, 1H, J=8.2 Hz), 5.76 (br s, 1H), 4.12 (s, 2H), 3.90 (br s, 2H), 3.60-3.62 (m, 4H), 3.09-3.12 (m, 4H), 2.19-2.23 (m, 4H), 1.24-1.62 (m, 4H).

c) 4-Cyano-1-(2-trimethylsilanyl-ethoxymethyl)-1H-imidazole-2-carboxylic acid [2-cyclohex-1-enyl-4-(morpholine-4-sulfonylmethyl)-phenyl]-amide

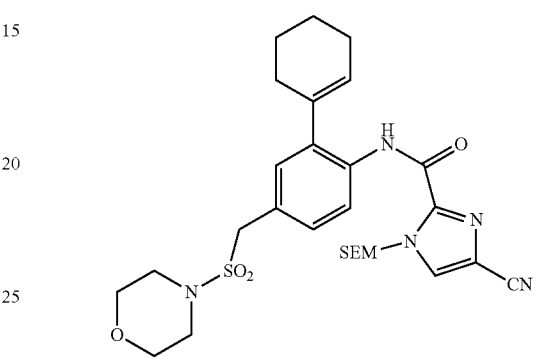

A mixture of 4-cyano-1-(2-trimethylsilanyl-ethoxymethyl)-1H-imidazole-2-carboxylic acid, potassium salt (as prepared in the Example 1, step (d), 33.6 mg, 0.110 mmol), DIEA (34 µL, 0.20 mmol), 2-cyclohex-1-enyl-4-(morpholine-4-sulfonylmethyl)-phenylamine (as prepared in the previous step, 33.6 mg, 0.110 mmol) and PyBroP (69.9 mg, 0.150 mmol) in DCM (2 mL) was stirred at RT for 12 h. The reaction mixture was diluted with DCM (10 mL) and washed with satd aq NaHCO$_3$ (10 mL) and water (10 mL). The organic layer was separated, dried (Na$_2$SO$_4$) and concentrated in vacuo. The residue was purified on silica (20-40% EtOAc/hexane) to afford 4-cyano-1-(2-trimethylsilanyl-ethoxymethyl)-1H-imidazole-2-carboxylic acid [2-cyclohex-1-enyl-4-(morpholine-4-sulfonylmethyl)-phenyl]-amide (56 mg, 95%). Mass spectrum (ESI, m/z): Calcd. for $C_{28}H_{39}N_5O_5SSi$, 586.2 (M+H). found 586.1.

d) 4-Cyano-1H-imidazole-2-carboxylic acid [2-cyclohex-1-enyl-4-(morpholine-4-sulfonylmethyl)-phenyl]-amide To a solution of 4-cyano-1-(2-trimethylsilanyl-ethoxymethyl)-1H-imidazole-2-carboxylic acid [2-cyclohex-1-enyl-4-(morpholine-4-sulfonylmethyl)-phenyl]-amide (as prepared in the previous step, 33.7 mg, 0.057 mmol) in DCM (0.5 mL) and EtOH (10 µL), TFA (0.10 mL) was added. The resulting solution was stirred at RT for 6 h and concentrated in vacuo. The residue obtained was dried and purified on silica (30% EtOAc/hexane) to obtain the title compound (11 mg, 95%): $^1$H-NMR (CDCl$_3$; 400 MHz): δ 9.63 (s, 1H), 8.43 (d, 1H, J=8.4 Hz), 7.73 (s, 1H), 7.36 (dd, 1H, J=8.4, 1.9 Hz), 7.25 (d, 1H, J=1.9 Hz), 5.85 (br s, 1H), 4.12 (s, 2H), 3.66-3.68 (m, 4H), 3.17-3.19 (m, 4H), 2.19-2.23 (m, 4H), 1.62-1.85 (m, 4H). Mass spectrum (ESI, m/z): Calcd. for $C_{22}H_{25}N_5O_4S$, 456.2 (M+H). found 455.9.

Example 33

5-Cyano-4-methyl-1H-imidazole-2-carboxylic acid [2-cyclohex-1-enyl-4-(2-morpholin-4-yl-ethyl)-phenyl]-amide hydrochloride

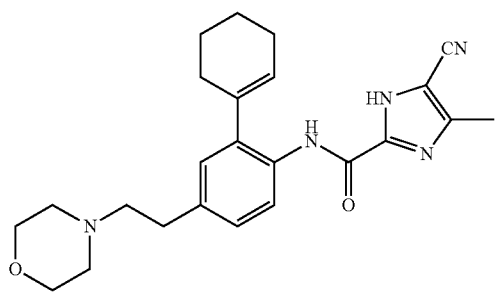 [SMILES: Cc1nc(C(=O)Nc2ccc(CCN3CCOCC3)cc2C2=CCCCC2)[nH]c1C#N]

a) 4-[2-(4-Nitro-phenyl)-ethyl]-morpholine

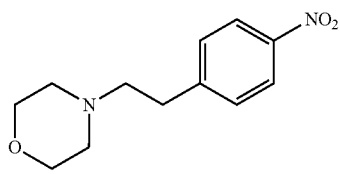 [SMILES: O=[N+]([O-])c1ccc(CCN2CCOCC2)cc1]

A mixture of 1-(2-bromo-ethyl)-4-nitro-benzene (0.740 g, 3.22 mmol), morpholine (0.840 mL, 9.65 mmol), and sodium iodide (0.480 g, 3.22 mmol) in N,N-dimethylacetamide (3 mL) was heated at 80° C. for 10 min. The mixture was diluted with 30 mL EtOAc and washed with $H_2O$ (2×30 mL) and brine (30 mL) and dried over $Na_2SO_4$ to give the title compound as a yellow oil of sufficient purity to use in the next step. Mass spectrum (ESI, m/z): Calcd. for $C_{12}H_{16}N_2O_3$, 237.1 (M+H). found 237.2.

b) 2-Bromo-4-(2-morpholin-4-yl-ethyl)-phenylamine

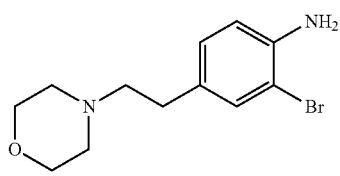 [SMILES: Nc1ccc(CCN2CCOCC2)cc1Br]

To a solution 4-[2-(4-nitro-phenyl)-ethyl]-morpholine (0.70 g, 2.97 mmol) (as prepared in the previous step) in 15 mL of MeOH was added 10% Pd/C (30 mg) and the mixture hydrogenated under 20 psi of $H_2$ for 2 h. The mixture was filtered though Celite and concentrated. The residue was dissolved in DCM (20 mL) and NBS (0.53 g, 2.97 mmol) was added and the reaction stirred for 20 min at RT. The reaction was diluted with DCM (20 mL) and washed with $NaHCO_3$ (2×40 mL) and the organic layer dried over $Na_2SO_4$ and concentrated. The title compound was eluted from a 20-g SPE with 100% EtOAc to give 0.49 g (58%) of a light yellow oil. Mass spectrum (ESI, m/z): Calcd. for $C_{12}H_{17}BrN_2O$, 285.0 (M+H). found 285.0.

c) 2-Cyclohex-1-enyl-4-(2-morpholin-4-yl-ethyl)-phenylamine

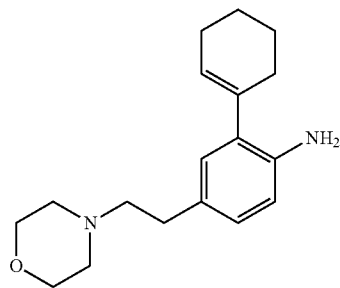 [SMILES: Nc1ccc(CCN2CCOCC2)cc1C1=CCCCC1]

This compound is prepared by Suzuki coupling of 2-bromo-4-(2-morpholin-4-yl-ethyl)-phenylamine (as prepared in the previous step) and 1-cyclohexen-1-yl-boronic acid according to the procedure in Example 1, step(e). Mass spectrum (ESI, m/z): Calcd. for $C_{18}H_{26}N_2O$, 287.2 (M+H). found 287.0.

d) 5-Methyl-1H-imidazole-4-carbonitrile

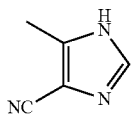

To a suspension of 5-methyl-1H-imidazole-4-carbaldehyde (9.0 g, 82 mmol) in 24 mL of pyridine was added hydroxylamine hydrochloride (6.3 g, 91 mmol) and the mixture was stirred for 1 hour at RT and then heated to 85° C. Acetic anhydride (15 mL, 159 mmol) was added over 10 min and then the mixture heated to 110° C. for 30 min. The mixture was cooled to RT, concentrated and the residue dissolved in EtOAc (100 mL) and neutralized with aqueous $NaHCO_3$. The aqueous layer was extracted with EtOAc (4×200 mL), then the combined organic fractions were dried ($Na_2SO_4$) and concentrated to give 8.7 g (99%) of a white solid. $^1$H-NMR (400 MHz, DMSO-$d_6$): δ 12.80 (s, 1H), 7.76 (s, 1H), 2.32 (s, 3H).

e) 5-Cyano-4-methyl-1-(2-trimethylsilanyl-ethoxymethyl)-1H-imidazole-2-carboxylate potassium salt

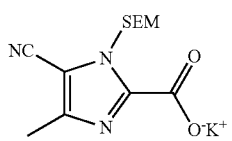

This compound was prepared from 5-methyl-1H-imidazole-4-carbonitrile (as prepared in the previous step) according to the procedures in Example 1, steps (a), (b), (c), and (d). Mass spectrum (ESI, m/z): Calcd. for $C_{12}H_{18}KN_3O_3Si$, 282.1 (M-K+2H). found 281.6.

f) 5-Cyano-4-methyl-1H-imidazole-2-carboxylic acid [2-cyclohex-1-enyl-4-(2-morpholin-4-yl-ethyl)-phenyl]-amide hydrochloride The title compound was prepared by coupling 5-cyano-4-methyl-1-(2-trimethylsilanyl-ethoxymethyl)-1H-imidazole-2-carboxylate potassium salt (as prepared in the previous step) and 2-cyclohex-1-enyl-4-(2-morpholin-4-yl-ethyl)-phenylamine (prepared in step (c)) according to the procedure in Example 34, step (c), followed by SEM deprotection according to the procedure in Example 34, step (d). The hydrochloride salt was then obtained by ion-exchange of the trifluoroacetic acid salt using a BioRad AG-2X8 resin, Cl⁻ ion form. $^1$H-NMR (400 MHz, DMSO-d$_6$): δ 14.05 (s, 1H), 10.78 (s, 1H), 9.64 (s, 1H), 8.92 (d, J=8.3 Hz, 1H), 7.20 (m, 1H), 7.08 (m, 1H), 5.78 (m, 1H), 4.05-3.70 (m, 4H), 3.52-3.46 (m, 2H), 3.18-2.98 (m, 4H), 2.40 (s, 3H), 2.22-2.16 (m, 4H), 1.80-1.65 (m, 4H). Mass spectrum (ESI, m/z): Calcd. for $C_{24}H_{29}N_5O_2$, 420.2 (M+H). found 420.2.

Example 34

2-Methylsulfanyl-3H-imidazole-4-carboxylic acid [2-cyclohex-1-enyl-4-(2-morpholin-4-yl-ethyl)-phenyl]-amide trifluoroacetic acid salt

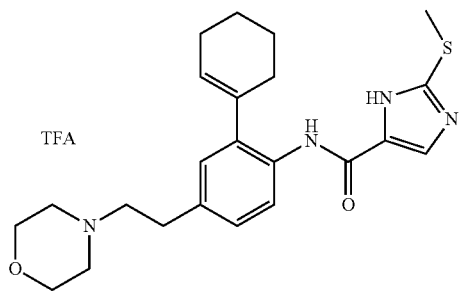 [SMILES: CSc1ncc(C(=O)Nc2ccc(CCN3CCOCC3)cc2C2=CCCCC2)[nH]1]

a) 2-Methylsulfanyl-3-(2-trimethylsilanyl-ethoxymethyl)-3H-imidazole-4-carboxylic acid ethyl ester

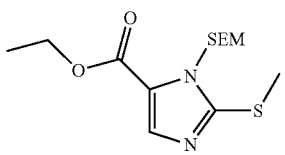 [SMILES: CCOC(=O)c1cnc(SC)n1COCC[Si](C)(C)C]

To a solution of 2-mercapto-3H-imidazole-4-carboxylic acid ethyl ester (1.0 g, 5.8 mmol) in 15 ml, of DCM was added triethylamine (NEt$_3$) (1.0 mL, 7.2 mmol) and iodomethane (0.4 mL, 6.4 mmol) and the mixture stirred for 3 h at RT. The mixture was cooled in an ice bath, NEt$_3$ (1.0 mL, 7.2 mmol) and SEM-Cl (1.2 mL, 6.4 mmol) was added, the mixture stirred for 3 hours at RT and then an additional portion of NEt$_3$ (0.5 mL, 3.6 mmol) and SEM-Cl (0.6 mL, 3.2 mmol) was added and the mixture stirred for 8 h at RT. The mixture was diluted with 50 mL of DCM and washed with NaHCO$_3$ (2×60 mL) and brine (60 mL) and dried over Na$_2$SO$_4$. Flash chromatography of the residue on Si gel with 30% EtOAc/hexanes gave the title compound as a colorless oil (1.0 g, 55%). Mass spectrum (ESI, m/z): Calcd. for $C_{13}H_{24}N_2O_3SSi$, 317.1 (M+H). found 316.7.

b) 2-Methylsulfanyl-3-(2-trimethylsilanyl-ethoxymethyl)-3H-imidazole-4-carboxylate potassium salt

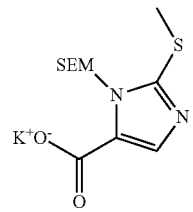

To a solution of 2-methylsulfanyl-3-(2-trimethylsilanyl-ethoxymethyl)-3H-imidazole-4-carboxylic acid ethyl ester (99 mg, 0.31 mmol) (as prepared in the previous step) was added 2 N KOH (0.16 mL, 0.32 mmol) and the mixture heated to 60° C. for 3 h. The mixture was concentrated and dried under vacuum to give the title compound as a white solid. Mass spectrum (ESI, m/z): Calcd. for $C_{11}H_{19}KN_2O_3SSi$, 289.1 (M-K+2H). found 288.7.

c) 2-Methylsulfanyl-3-(2-trimethylsilanyl-ethoxymethyl)-3H-imidazole-4-carboxylic acid [2-cyclohex-1-enyl-4-(2-morpholin-4-yl-ethyl)-phenyl]-amide

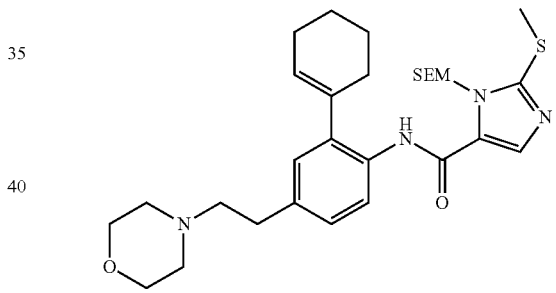

A mixture of 2-methylsulfanyl-3-(2-trimethylsilanyl-ethoxymethyl)-3H-imidazole-4-carboxylate potassium salt (90 mg, 0.28 mmol) (as prepared in the previous step), 2-cyclohex-1-enyl-4-(2-morpholin-4-yl-ethyl)-phenylamine (81 mg, 0.28 mmol) (as prepared in Example 33, step(c)), PyBrOP (170 mg, 0.37 mmol), and DIEA (0.10 mL, 0.57 mmol) in 1.5 mL of DCM was stirred for 8 h at RT. The mixture was diluted with 20 mL of DCM and washed with NaHCO$_3$ (2×30 mL) and brine (30 mL) and dried over Na$_2$SO$_4$. Flash chromatography of the residue on Si gel with 100% EtOAc gave the title compound as a white solid (107 mg, 70%). Mass spectrum (ESI, m/z): Calcd. for $C_{29}H_{44}N_4O_3SSi$, 557.3 (M+H). found 556.8.

d) 2-Methylsulfanyl-3H-imidazole-4-carboxylic acid [2-cyclohex-1-enyl-4-(2-morpholin-4-yl-ethyl)-phenyl]-amide trifluoroacetic acid salt To a solution of 2-methylsulfanyl-3-(2-trimethylsilanyl-ethoxymethyl)-3H-imidazole-4-carboxylic acid [2-cyclohex-1-enyl-4-(2-morpholin-4-yl-ethyl)-phenyl]-amide (100 mg, 0.18 mmol) (as prepared in the previous step) in 1 mL of DCM was added 1 mL of TFA and the mixture stirred at RT for 6 h. The mixture was concentrated and the title compound purified by RP-HPLC on a C18 column eluting with a linear gradient of 35-55% CH$_3$CN in 0.1% TFA/H$_2$O over 8 min to give 35 mg (36%) of a white solid. $^1$H-NMR (400 MHz, CD$_3$OD): δ 8.22 (d, J=8.4 Hz, 1H), 7.71 (s, 1H), 7.20 (dd, J=8.4, 2.2 Hz, 1H), 7.12 (d, J=2.2 Hz, 1H), 5.79 (m, 1H), 4.07 (m 2H), 3.82 (m, 2H), 3.57 (m, 2H), 3.40 (m, 2H), 3.20 (m, 2H), 3.15 (m, 2H), 2.65 (s, 3H), 2.30-2.22 (m, 4H), 1.88-1.72 (m, 4H). Mass spectrum (ESI, m/z): Calcd. for C$_{23}$H$_{30}$N$_4$O$_2$S, 427.2 (M+H). found 427.1.

Example 35

2-Methanesulfinyl-3H-imidazole-4-carboxylic acid [2-cyclohex-1-enyl-4-(2-morpholin-4-yl-ethyl)-phenyl]-amide trifluoroacetic acid salt

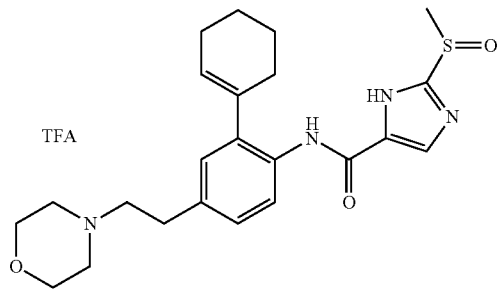 [SMILES: CS(=O)c1ncc(C(=O)Nc2ccc(CCN3CCOCC3)cc2C2=CCCCC2)[nH]1]

To a solution of 2-methylsulfanyl-3-(2-trimethylsilanyl-ethoxymethyl)-3H-imidazole-4-carboxylic acid [2-cyclohex-1-enyl-4-(2-morpholin-4-yl-ethyl)-phenyl]-amide (85 mg, 0.15 mmol) (as prepared in Example 34) in 1.4 mL of DCM was added MCPBA (77%, 34 mg, 0.15 mmol) and the mixture stirred at RT for 10 min. The mixture was diluted with 20 mL of DCM and washed with NaHCO$_3$ (2×30 mL) and brine (30 mL) and dried over Na$_2$SO$_4$. The residue was dissolved in 2 mL of DCM, 1 mL of TFA was added and the mixture stirred at RT for 1 h. The mixture was concentrated and the title compound purified by RP-HPLC on a C18 column eluting with a linear gradient of 30-50% CH$_3$CN in 0.1% TFA/H$_2$O over 9 min to give 55 mg (65%) of a white solid. $^1$H-NMR (400 MHz, DMSO-d$_6$): δ 12.82 (s, 1H), 9.41 (s, 1H), 8.34 (d, J=8.3 Hz, 1H), 7.79 (s, 1H), 7.18 (dd, J=8.3, 2.1 Hz, 1H), 7.11 (d, J=2.1 Hz, 1H), 5.76 (m, 1H), 4.05-3.86 (m, 6H), 3.78-3.68 (m, 4H), 3.14-3.05 (m, 2H), 2.60 (s, 3H), 2.22-2.16 (m, 4H), 1.80-1.65 (m, 4H). Mass spectrum (ESI, m/z): Calcd. for C$_{23}$H$_{30}$N$_4$O$_3$S, 443.2 (M+H). found 443.0.

Example 36

2-Methanesulfonyl-3H-imidazole-4-carboxylic acid [2-cyclohex-1-enyl-4-(2-morpholin-4-yl-ethyl)-phenyl]-amide hydrochloride

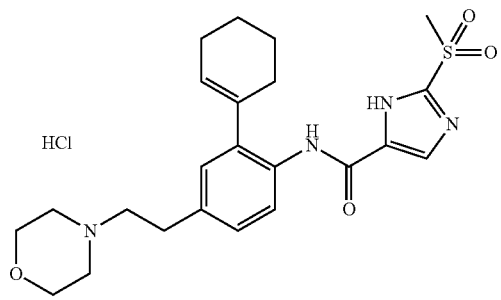 [SMILES: CS(=O)(=O)c1ncc(C(=O)Nc2ccc(CCN3CCOCC3)cc2C2=CCCCC2)[nH]1 ; Cl]

The title compound was prepared according to the procedure in Example 35 using 2 eq of MCPBA. The hydrochloride salt was then obtained by ion-exchange of the trifluoroacetic acid salt using a BioRad AG-2X8 resin, Cl$^-$ ion form. $^1$H-NMR (400 MHz, DMSO-d$_6$): δ 14.10 (s, 1H), 12.38 (s, 1H), 9.44 (s, 1H), 8.32 (d, J=8.3 Hz, 1H), 8.08 (s, 1H), 7.24 (m, 1H), 7.18 (m, 1H), 5.80 (m, 1H), 4.05-3.86 (m, 6H), 3.80-3.64 (m, 4H), 3.18-3.05 (m, 2H), 3.02 (s, 3H), 2.22-2.16 (m, 4H), 1.80-1.65 (m, 4H). Mass spectrum (ESI, m/z): Calcd. for C$_{23}$H$_{30}$N$_4$O$_4$S, 459.2 (M+H). found 459.0.

Example 37

4-Methyl-1H-imidazole-2-carboxylic acid [2-cyclohex-1-enyl-4-(2-morpholin-4-yl-ethyl)-phenyl]-amide trifluoroacetic acid salt

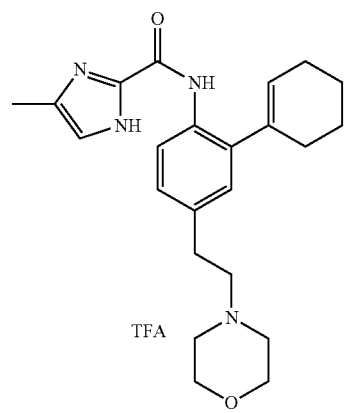 [SMILES: Cc1c[nH]c(C(=O)Nc2ccc(CCN3CCOCC3)cc2C2=CCCCC2)n1]

a) 5-Methyl-1-(2-trimethylsilanyl-ethoxymethyl)-1H-imidazole

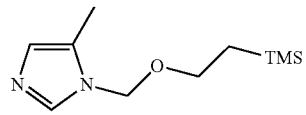

To a solution of 4-methylimidazole (2.70 g, 33.0 mmol) in 10 mL of acetonitrile at 0° C. was added NEt$_3$ (4.00 g, 39.6 mmol) and acetyl chloride (2.80 g, 36.3 mmol). The mixture was allowed to attain RT then filtered to remove the ppt and the filtrate was concentrated to give 1-(4-methyl-imidazol-1-yl)-ethanone, which was used without further purification in the next step. To a solution of 1-(4-methyl-imidazol-1-yl)-ethanone (4.10 g, 33.0 mmol) in 15 mL acetonitrile was added SEM-Cl (5.80 g, 35.0 mmol) and the solution was stirred at 25° C. for 10 h. The solvents were removed by evaporation and to the residue was added 100 mL of 2.5 M NaOH and the mixture was stirred at 25° C. for 1 h. The reaction mixture was then extracted with ether (3×100 mL), dried over Na$_2$SO$_4$ and concentrated. The title compound was purified by chromatography on Silica gel eluting with 75% EtOAc/hexanes to give 4.30 g (61%) of a colorless oil: Mass spectrum (ESI, m/z): Calcd. for C$_{10}$H$_{20}$N$_2$O$_4$Si, 213.1 (M+H). found 213.1.

b) 5-Methyl-1-(2-trimethylsilanyl-ethoxymethyl)-1H-imidazole-2-carboxylic acid ethyl ester

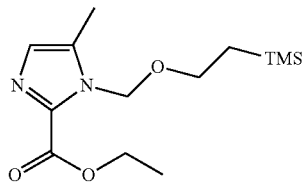 [SMILES: CCOC(=O)c1ncc(C)n1COCC[Si](C)(C)C]

To a solution of 5-methyl-1-(2-trimethylsilanyl-ethoxymethyl)-1H-imidazole (0.320 g, 1.50 mmol) in 5 mL of THF at −78° C. was added n-BuLi (0.80 mL, 1.60 mmol, 2 M in cyclohexane) and the mixture was allowed to attain RT and stirred for 30 min. The mixture was cooled to −78° C. and ethyl cyanoformate (0.160 g, 1.65 mmol) was added and the mixture allowed to stir for 10 h at RT. The reaction was diluted with 15 mL of EtOAc and washed with NaHCO$_3$ (2×15 mL) and brine (15 mL). The title compound was eluted from a 20-g SPE with 50% EtOAc/hexanes to give 0.160 g (38%) of a light brown oil: Mass spectrum (ESI, m/z): Calcd. for $C_{13}H_{24}N_2O_3Si$, 285.2 (M+H). found 284.9.

c) 4-Methyl-1H-imidazole-2-carboxylic acid [2-cyclohex-1-enyl-4-(2-morpholin-4-yl-ethyl)-phenyl]-amide trifluoroacetic acid salt To a solution of 5-methyl-1-(2-trimethylsilanyl-ethoxymethyl)-1H-imidazole-2-carboxylic acid ethyl ester (0.090 g, 0.32 mmol) in 2 mL of EtOH at RT was added 0.16 mL of 2N KOH and the mixture stirred for 1 h and then concentrated and dried under vacuum. DCM (3 mL) was added followed by 2-cyclohex-1-enyl-4-(2-morpholin-4-yl-ethyl)-phenylamine (0.090 g, 0.31 mmol) (Example 33, step (c)), DIEA (0.11 mL, 0.64 mmol), and PyBroP (0.16 g, 0.34 mmol) and the mixture stirred for 10 h at RT. The reaction was diluted with 15 mL of DCM and washed with NaHCO$_3$ (2×15 mL) and brine (15 mL), dried over Na$_2$SO$_4$ and concentrated. The residue was dissolved in 1.0 mL of DCM and 0.040 mL of EtOH and 1.0 mL of TFA were added and the reaction stirred at RT for 3 h and then concentrated. The title compound was purified by RP-HPLC, eluting with a linear gradient of 30% to 50% acetonitrile in 0.1% TFA/H$_2$O over 9 min on a C18 column giving 0.015 g (10%) of a light yellow solid. $^1$H-NMR (400 MHz, CD$_3$OD): δ 7.69 (d, J=8.2 Hz, 1H), 7.27 (s, 1H), 7.24 (dd, J=2.1, 8.2 Hz, 1H), 7.19 (d, J=2.1 Hz, 1H), 5.73 (s, 1H), 4.10 (m, 2H), 3.78 (m, 2H), 3.58 (m, 2H), 3.42 (m, 2H), 3.19 (m, 2H), 3.08 (m, 2H), 2.40 (s, 3H), 2.24 (m, 2H), 2.15 (m, 2H), 1.80-1.60 (m, 4H). Mass spectrum (ESI): Calcd. for $C_{23}H_{30}N_4O_2$ 395.2, (M+H). found 395.2.

Example 38

4,5-Dichloro-1H-imidazole-2-carboxylic acid [2-cyclohex-1-enyl-4-(2-morpholin-4-yl-ethyl)-phenyl]-amide trifluoroacetic acid salt

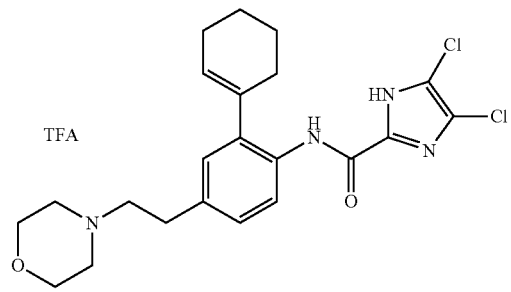 [SMILES: O=C(Nc1ccc(CCN2CCOCC2)cc1C1=CCCCC1)c1nc(Cl)c(Cl)[nH]1]

The title compound was prepared by coupling 4,5-dichloro-1H-imidazole-2-carboxylic acid (*J. Heterocyclic Chem*, 17, 409, (1980)) and 2-cyclohex-1-enyl-4-(2-morpholin-4-yl-ethyl)-phenylamine (as prepared in Example 33, step (c)) according to the procedure in Example 34, step (c). $^1$H-NMR (400 MHz, CD$_3$OD) δ 8.19 (d, J=8.3 Hz, 1H), 7.23 (dd, J=8.3, 2.1 Hz, 1H), 7.16 (d, J=2.1 Hz, 1H), 5.83 (m, 1H), 4.14 (m, 2H), 3.80 (m, 2H), 3.60 (m, 2H), 3.42 (m, 2H), 3.22 (m, 2H), 3.07 (m, 2H), 2.34-2.23 (m, 4H), 1.90-1.75 (m, 4H). Mass spectrum (ESI, m/z): Calcd. for $C_{22}H_{26}Cl_2N_4O_2$ 449.1 (M+H). found 449.0.

Example 39

1H-Benzoimidazole-2-carboxylic acid [2-cyclohex-1-enyl-4-(2-morpholin-4-yl-ethyl)-phenyl]-amide trifluoroacetic acid salt

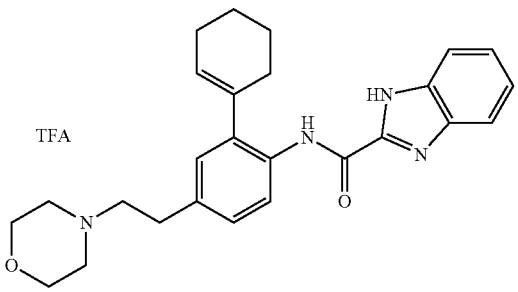 [SMILES: O=C(Nc1ccc(CCN2CCOCC2)cc1C1=CCCCC1)c1nc2ccccc2[nH]1]

The title compound was prepared by coupling 1H-benzoimidazole-2-carboxylic acid and 2-cyclohex-1-enyl-4-(2-morpholin-4-yl-ethyl)-phenylamine (as prepared in Example 33, step (c)) according to the procedure in Example 34, step (c). $^1$H-NMR (400 MHz, CD$_3$OD): δ 8.27 (d, J=8.3 Hz, 1H), 7.69 (dd, J=6.2, 3.2 Hz, 1H), 7.41-7.35 (m, 1H), 7.28 (dd, J=8.4, 2.1 Hz, 1H), 7.21 (d, J=2.0 Hz, 1H), 5.89 (s, 1H), 4.16 (m, 2H), 3.82 (m, 2H), 3.62 (m, 2H), 3.48 (m, 2H), 3.22 (m, 2H), 3.09 (m, 2H), 2.40-2.33 (m, 4H), 1.96-1.80 (m, 4H). Mass spectrum (ESI, m/z): Calcd. for $C_{26}H_{30}N_4O_2$, 431.2 (M+H). found 431.2.

Example 40

5-Bromo-1H-imidazole-2-carboxylic acid [2-cyclohex-1-enyl-4-(2-morpholin-4-yl-ethyl)-phenyl]-amide hydrochloride

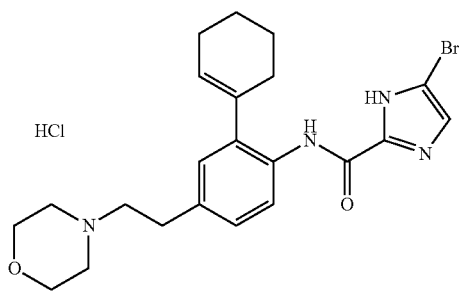 [SMILES: O=C(Nc1ccc(CCN2CCOCC2)cc1C1=CCCCC1)c1ncc(Br)[nH]1 ; Cl]

a) 1-(2-Trimethylsilanyl-ethoxymethyl)-1H-imidazole-2-carboxylic acid ethyl ester

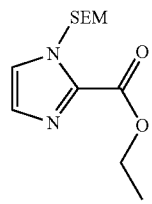 [SMILES: CCOC(=O)c1nccn1COCC[Si](C)(C)C]

A flask charged with 1H-imidazole-2-carboxylic acid ethyl ester (1.03 g, 7.36 mmol), $K_2CO_3$ (2.00 g, 14.5 mmol), SEM-Cl (1.56 mL, 8.89 mmol), and 20 mL of acetone was stirred for 10 h at RT. The reaction was diluted with EtOAc (100 mL), washed with $NaHCO_3$ (2×100 mL), brine (100 mL), and the organic layer dried over $Na_2SO_4$ and concentrated. The title compound was eluted from a 20-g SPE with 50% EtOAc/hexanes to give 1.50 g (76%) of a colorless oil. Mass spectrum (ESI, m/z): Calcd. for $C_{12}H_{22}N_3O_3Si$, 271.1 (M+H). found 271.1.

b) 4-Bromo-1-(2-trimethylsilanyl-ethoxymethyl)-1H-imidazole-2-carboxylic acid ethyl ester

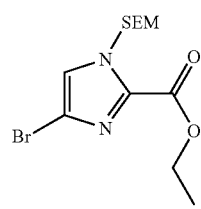 [SMILES: CCOC(=O)c1nc(Cl)cn1COCC[Si](C)(C)C]

To a solution of 1-(2-trimethylsilanyl-ethoxymethyl)-1H-imidazole-2-carboxylic acid ethyl ester (0.20 g, 0.74 mmol) (as prepared in the previous step) in 2 mL of $CH_3CN$ was added NBS (0.13 g, 0.74 mmol) and the mixture heated to 60° C. for 2 h. The mixture was concentrated and the title compound purified by elution from a 20-g SPE column with 20% EtOAc/hexanes to give 0.1 g (39%) of a colorless oil. Mass spectrum (ESI, m/z): Calcd. for $C_{12}H_{21}BrN_2O_3Si$, 349.0 (M+H). found 348.7.

c) 4-Bromo-1-(2-trimethylsilanyl-ethoxymethyl)-1H-imidazole-2-carboxylate potassium salt

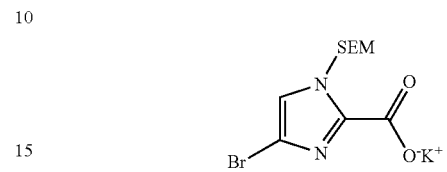

The title compound was prepared from 4-bromo-1-(2-trimethylsilanyl-ethoxymethyl)-1H-imidazole-2-carboxylic acid ethyl ester (as prepared in the previous step) according to the procedure in Example 1, step (d). Mass spectrum (ESI, m/z): Calcd. for $C_{10}H_{16}BrKN_2O_3Si$, 321.0/323.0 (M-K+2H). found 320.6/322.6.

d) 5-Bromo-1H-imidazole-2-carboxylic acid [2-cyclohex-1-enyl-4-(2-morpholin-4-yl-ethyl)phenyl]-amide hydrochloride The title compound was prepared by coupling 4-bromo-1-(2-trimethylsilanyl-ethoxymethyl)-1H-imidazole-2-carboxylate potassium salt (as prepared in the previous step) and 2-cyclohex-1-enyl-4-(2-morpholin-4-yl-ethyl)-phenylamine (as prepared in Example 33, step (c)) according to the procedure in Example 34, step(c), followed by SEM deprotection according to the procedure in Example 34, step (d). The hydrochloride salt was prepared from the trifluoroacetic acid salt using a BioRad AG2-X8 resin, Cl⁻ ion form. ¹H-NMR (400 MHz, $CD_3OD$) δ 8.18 (d, J=8.3 Hz, 1H), 7.33 (s, 1H), 7.23 (dd, J=8.3, 2.1 Hz, 1H), 7.16 (d, J=2.1 Hz, 1H), 5.83 (m, 1H), 4.08 (m, 2H), 3.81 (m, 2H), 3.60 (m, 2H), 3.42 (m, 2H), 3.22 (m, 2H), 3.08 (m, 2H), 2.34-2.23 (m, 4H), 1.91-1.76 (m, 4H). Mass spectrum (ESI, m/z): Calcd. for $C_{22}H_{27}BrN_4O_2$, 459.1/461.1 (M+H). found 459.0/461.0.

Example 41

5-Chloro-1H-imidazole-2-carboxylic acid [2-cyclohex-1-enyl-4-(2-morpholin-4-yl-ethyl)-phenyl]-amide hydrochloride

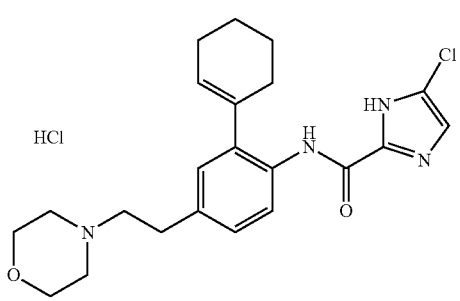

a) 4-Chloro-1-(2-trimethylsilanyl-ethoxymethyl)-1H-imidazole-2-carboxylic acid ethyl ester

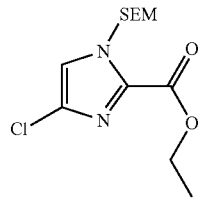

This was prepared according to the procedure in Example 40, step (b) substituting N-chlorosuccinimide for NBS. Mass spectrum (ESI, m/z): Calcd. for $C_{12}H_{21}Cl\ N_2O_3Si$, 305.1 (M+H). found 304.7.

b) 4-Chloro-1-(2-trimethylsilanyl-ethoxymethyl)-1H-imidazole-2-carboxylate potassium salt

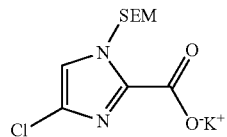

This compound was prepared from 4-chloro-1-(2-trimethylsilanyl-ethoxymethyl)-1H-imidazole-2-carboxylic acid ethyl ester (as prepared in the previous step) according to the procedure in Example 1, step(d). Mass spectrum (ESI, m/z): Calcd. for $C_{10}H_{16}Cl\ KN_2O_3Si$, 277.1 (M-K+2H). found 276.7.

c) 5-Chloro-1H-imidazole-2-carboxylic acid [2-cyclohex-1-enyl-4-(2-morpholin-4-yl-ethyl)-phenyl]-amide hydrochloride The title compound was prepared by coupling 4-chloro-1-(2-trimethylsilanyl-ethoxymethyl)-1H-imidazole-2-carboxylate potassium salt and (as prepared in the previous step) and 2-cyclohex-1-enyl-4-(2-morpholin-4-yl-ethyl)-phenylamine (as prepared in Example 33, step (c)) according to the procedure in Example 34, step (c), followed by SEM deprotection according to the procedure in Example 34, step (d). The hydrochloride salt was prepared from the trifluoroacetic acid salt using a BioRad AG2-X8 resin, Cl⁻ ion form. $^1$H-NMR (400 MHz, DMSO-$d_6$): δ 13.73 (s, 1H), 10.52 (s, 1H), 9.58 (s, 1H), 8.00 (d, J=8.1 Hz, 1H), 7.53 (s, 1H), 7.20 (dd, J=8.1, 2.1 Hz, 1H), 7.14 (d, J=2.1 Hz, 1H), 5.77 (m, 1H), 4.00 (m, 2H), 3.74 (m, 2H), 3.57-3.41 (m, 4H), 3.19-2.93 (m, 4H), 2.27-2.13 (m, 4H), 1.79-1.65 (m, 4H). Mass spectrum (ESI, m/z): Calcd. for $C_{22}H_{27}Cl\ N_4O_2$, 415.2 (M+H). found 415.1.

Example 42

5-Cyano-1H-imidazole-2-carboxylic acid [2-cyclohex-1-enyl-4-(2-morpholin-4-yl-ethyl)-phenyl]-amide trifluoroacetic acid salt

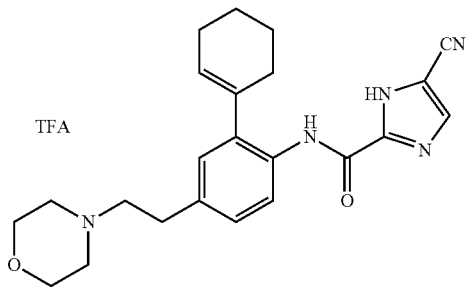 [SMILES: N#Cc1cnc(C(=O)Nc2ccc(CCN3CCOCC3)cc2C2=CCCCC2)[nH]1 ; "TFA"]

The title compound was prepared by coupling 4-cyano-1-(2-trimethylsilanyl-ethoxymethyl)-1H-imidazole-2-carboxylate potassium salt (as prepared in Example 1, step (d)) and 2-cyclohex-1-enyl-4-(2-morpholin-4-yl-ethyl)-phenylamine (as prepared in Example 33, step (c)) according to the procedure in Example 34, step (c), followed by SEM deprotection according to the procedure in Example 34, step (d). $^1$H-NMR (400 MHz, CD$_3$OD) δ 8.19 (d, J=8.3 Hz, 1H), 8.02 (s, 1H), 7.23 (dd, J=8.3, 2.1 Hz, 1H), 7.17 (d, J=2.1 Hz, 1H), 5.83 (m, 1H), 4.17-4.01 (m, 2H), 3.89-3.76 (m, 2H), 3.66-3.50 (m, 2H), 3.47-3.36 (m, 2H), 3.28-3.15 (m, 2H), 3.12-3.03 (m, 2H), 2.35-2.22 (m, 4H), 1.90-1.75 (m, 4H). Mass spectrum (ESI, m/z): Calcd. for $C_{23}H_{27}N_5O_2$, 406.2 (M+H). found 406.2.

Example 43

5-Cyano-furan-2-carboxylic acid [2-cyclohex-1-enyl-4-(2-morpholin-4-yl-ethyl)-phenyl]-amide trifluoroacetic acid salt

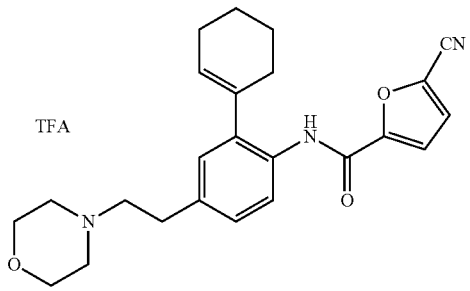 [SMILES: N#Cc1ccc(C(=O)Nc2ccc(CCN3CCOCC3)cc2C2=CCCCC2)o1 ; "TFA"]

The title compound was prepared by coupling 5-cyano-furan-2-carboxylic acid (WO2004096795) and 2-cyclohex-1-enyl-4-(2-morpholin-4-yl-ethyl)-phenylamine (as prepared in Example 33, step (c)) according to the procedure in Example 34, step (c). $^1$H-NMR (400 MHz, CD$_3$OD): δ 7.81 (d, J=8.2 Hz, 1H), 7.50 (d, J=3.8 Hz, 1H), 7.34 (d, J=3.8 Hz, 1H), 7.26 (dd, J=8.2, 2.1 Hz, 1H), 7.22 (d, J=2.1 Hz, 1H), 5.81 (m, 1H), 4.18-4.05 (m, 2H), 3.84-3.73 (m, 2H), 3.63-3.53 (m, 2H), 3.48-3.39 (m, 2H), 3.29-3.17 (m, 2H), 3.14-3.04 (m, 2H), 2.35-2.17 (m, 4H), 1.86-1.68 (m, 4H). Mass spectrum (ESI, m/z): Calcd. for $C_{24}H_{27}N_3O_3$, 406.2 (M+H). found 406.2.

Example 44

5-Cyano-1H-imidazole-2-carboxylic acid (2-cyclohex-1-enyl-4-morpholin-4-ylmethyl-phenyl)-amide hydrochloride

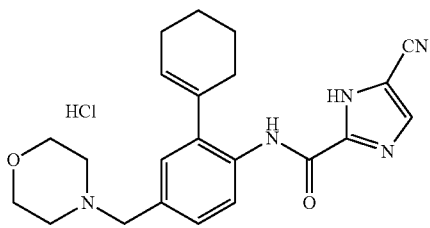 [SMILES: N#Cc1cnc(C(=O)Nc2ccc(CN3CCOCC3)cc2C2=CCCCC2)[nH]1 ; Cl]

a) 2-Cyclohex-1-enyl-4-morpholin-4-ylmethyl-phenylamine

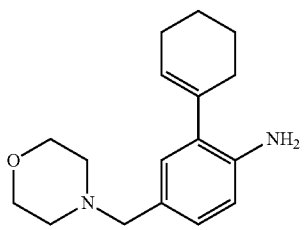 [SMILES: Nc1ccc(CN2CCOCC2)cc1C1=CCCCC1]

This compound was prepared from 4-morpholin-4-ylmethyl-phenylamine by brominating according to the procedure in Example 33, step (b), followed by Suzuki coupling to 1-cyclohexen-1-yl-boronic acid according to the procedure in Example 1, step (e). Mass spectrum (ESI, m/z): Calcd. for $C_{17}H_{24}N_2O$, 273.2 (M+H). found 272.7.

b) 5-Cyano-1H-imidazole-2-carboxylic acid (2-cyclohex-1-enyl-4-morpholin-4-ylmethyl-phenyl)-amide hydrochloride The title compound was prepared by coupling 4-cyano-1-(2-trimethylsilanyl-ethoxymethyl)-1H-imidazole-2-carboxylate potassium salt (as prepared in Example 1, step (d)) and 2-cyclohex-1-enyl-4-morpholin-4-ylmethyl-phenylamine (as prepared in the previous step) according to the procedure in Example 34, step (c), followed by SEM deprotection according to the procedure in Example 34, step (d). The hydrochloride salt was prepared from the trifluoroacetic acid salt using a BioRad AG2-X8 resin, Cl⁻ ion form. $^1$H-NMR (400 MHz, DMSO-$d_6$): δ 14.34 (br s, 1H), 10.45 (br s, 1H), 9.85 (s, 1H), 8.37 (s, 1H), 8.09 (d, J=8.4 Hz, 1H), 7.48 (dd, J=8.4, 1.9 Hz, 1H), 7.44 (d, J=1.9 Hz, 1H), 5.84 (m, 1H), 4.32 (s, 2H), 4.01-3.92 (m, 2H), 3.77-3.65 (m, 2H), 3.31-3.23 (m, 2H), 3.15-3.03 (m, 2H), 2.29-2.15 (m, 4H), 1.80-1.64 (m, 4H). Mass spectrum (ESI, m/z): Calcd. for $C_{22}H_{25}N_5O_2$, 392.2 (M+H). found 391.9.

Example 45

5-Cyano-1H-imidazole-2-carboxylic acid [2-(dimethyl-cyclohex-1-enyl)-4-(1-methyl-1-pyrrolidin-1-yl-ethyl)-phenyl]-amide trifluoroacetic acid salt

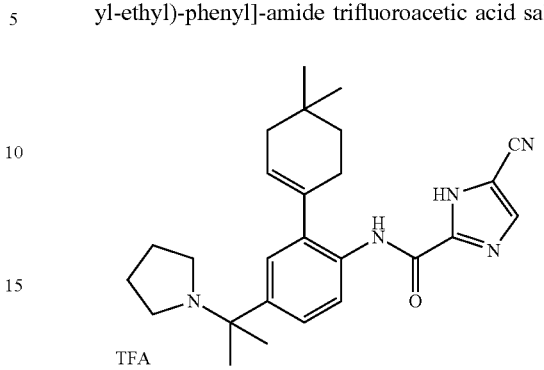

The title compound was prepared according to the procedure in Example 46 step (a) using N-isopropylidenepyrrolidinium perchlorate, (J. Org. Chem., 28, 3021, (1963)) as the electrophile. $^1$H-NMR (400 MHz, CD$_3$OD): δ 8.43 (d, J=8.7 Hz, 1H), 8.04 (s, 1H), 7.61 (dd, J=8.7, 2.5 Hz, 1H), 7.52 (d, J=2.5 Hz, 1H), 5.84 (m, 1H), 3.30-3.22 (m, 4H), 2.36 (m, 2H), 2.13 (m, 2H), 2.08-1.93 (m, 4H), 1.86 (s, 6H), 1.64 (t, J=6.3 Hz, 2H), 1.13 (s, 6H). Mass spectrum (ESI, m/z): Calcd. for $C_{26}H_{33}N_5O$, 432.3 (M+H). found 431.9.

Example 46

[4-[(5-Cyano-1H-imidazole-2-carbonyl)-amino]-3-(4,4-dimethyl-cyclohex-1-enyl)-phenyl]-hydroxy-acetic acid

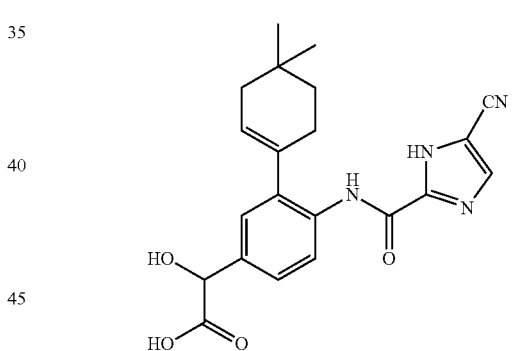

a) [4-[(5-Cyano-1H-imidazole-2-carbonyl)-amino]-3-(4,4-dimethyl-cyclohex-1-enyl)-phenyl]-hydroxy-acetic acid ethyl ester

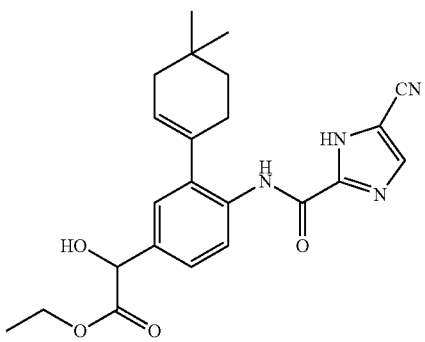 [SMILES: CCOC(=O)C(O)c1ccc(NC(=O)c2ncc(C#N)[nH]2)c(C2=CCC(C)(C)CC2)c1]

To a suspension of 4-cyano-1H-imidazole-2-carboxylic acid [4-bromo-2-(4,4-dimethyl-cyclohex-1-enyl)-phenyl]-amide (71 mg, 0.18 mmol) (as prepared in Example 14, step(c)) in 3 mL THF at −40° C. was added a 2M solution of isopropylmagnesium chloride (i-PrMgCl) in THF (0.23 mL, 0.46 mmol) and the solution was then warmed to 0° C. and stirred for 10 min. The solution was then cooled to −78° C. and a 1.7 M solution of t-BuLi in pentane (0.28 mL, 0.48 mmol) was added dropwise and then a 40% solution of ethyl glyoxalate in toluene (0.23 mL, 0.90 mmol) was added immediately thereafter. After 5 min at −78° C. the reaction was quenched with satd $NH_4Cl$ (10 mL) and extracted with EtOAc (3×10 mL) and dried over $Na_2SO_4$ and concentrated in vacuo. The title compound was purified by flash chromatography (silica gel) eluting with 50-100% EtOAc/hexanes to give 37 mg (50%) of the title compound as a white solid. Mass spectrum (ESI, m/z): Calcd. for $C_{23}H_{26}N_4O_2$, 423.2 (M+H). found 423.1.

b) [4-[(5-Cyano-1H-imidazole-2-carbonyl)-amino]-3-(4,4-dimethyl-cyclohex-1-enyl)-phenyl]-hydroxy-acetic acid To a solution of [4-[(5-cyano-1H-imidazole-2-carbonyl)-amino]-3-(4,4-dimethyl-cyclohex-1-enyl)-phenyl]-hydroxy-acetic acid ethyl ester (as prepared in the previous step) (30.0 mg, 71 µmol) in 0.2 mL of EtOH at RT was added a 2N KOH solution (71 uL, 14.2 µmol) and the reaction stirred for 2 h. The pH was then adjusted to 2 with a 2 M TFA solution and the title compound was purified by RP-HPLC, eluting with a linear gradient of 20% to 50% $CH_3CN$ in 0.1% $TFA/H_2O$ over 10 min to give 20 mg (71%) of a white solid. $^1$H-NMR (400 MHz, $CD_3OD$): δ 8.24 (d, J=8.4 Hz, 1H), 8.00 (s, 1H), 7.40 (dd, J=8.4, 2.1 Hz, 1H), 7.33 (d, J=2.1 Hz, 1H), 5.78 (m, 1H), 5.15 (s, 1H), 2.33 (m, 2H), 2.10 (m, 2H), 1.62 (t, J=6.3, 6.3 Hz, 2H), 1.11 (s, 6H). Mass spectrum (ESI, m/z): Calcd. for $C_{21}H_{22}N_4O_2$, 395.2 (M+H). found 395.1.

Example 47

5-Cyano-1H-imidazole-2-carboxylic acid [2-(4,4-dimethyl-cyclohex-1-enyl)-4-((R)-2-hydroxy-3-methoxy-propyl)-phenyl]-amide

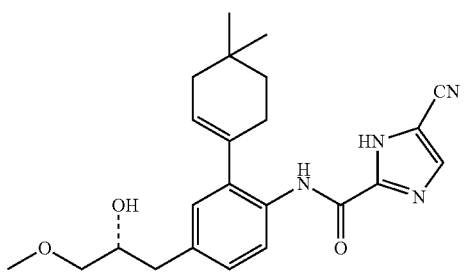 [SMILES: COC[C@H](O)Cc1ccc(NC(=O)c2ncc(C#N)[nH]2)c(C2=CCC(C)(C)CC2)c1]

This compound was prepared from 4-cyano-1H-imidazole-2-carboxylic acid [4-bromo-2-(4,4-dimethyl-cyclohex-1-enyl)-phenyl]-amide (as prepared in Example 14, step(c)) according to the procedure in Example 46 step (a) using (S)-glycidyl methyl ether as the electrophile. $^1$H-NMR (400 MHz, $CD_3OD$): δ 8.10 (d, J=8.3 Hz, 1H), 7.98 (s, 1H), 7.15 (dd, J=8.3, 2.1 Hz, 1H), 7.07 (d, J=2.1 Hz, 1H), 5.73 (m, 1H), 3.91 (m, 1H), 3.36 (s, 3H), 2.80 (dd, J=13.7, 5.7 Hz, 1H), 2.69 (dd, J=13.7, 7.5 Hz, 1H), 2.31 (m, 2H), 2.07 (m, 2H), 1.58 (t, J=6.3 Hz, 2H), 1.07 (s, 6H). Mass spectrum (ESI, m/z): Calcd. for $C_{23}H_{28}N_4O_3$, 409.2 (M+H). found 409.1.

Example 48

3-{4-[(4-Cyano-1H-imidazole-2-carbonyl)-amino]-3-cyclohex-1-enyl-pheny}-acrylic acid

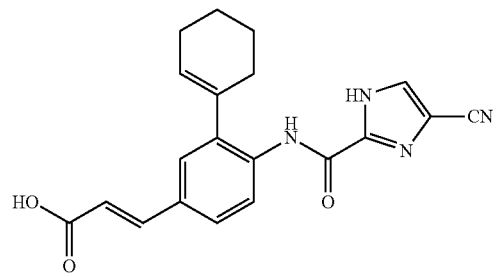 [SMILES: N#Cc1c[nH]c(C(=O)Nc2ccc(/C=C/C(=O)O)cc2C2=CCCCC2)n1]

a) 3-(4-{[4-Cyano-1-(2-trimethylsilanyl-ethoxymethyl)-1H-imidazole-2-carbonyl]-amino}-3-cyclohex-1-enyl-phenyl)-acrylic acid tert-butyl ester

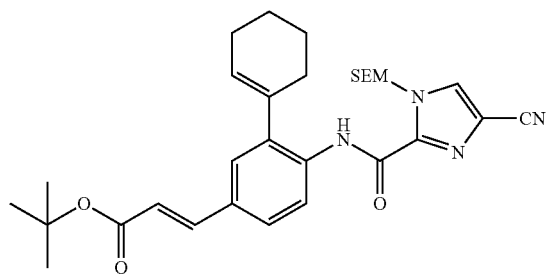 [SMILES: CC(C)(C)OC(=O)/C=C/c1ccc(NC(=O)c2nc(C#N)cn2COCC[Si](C)(C)C)c(C2=CCCCC2)c1]

A flask was charged with 4-cyano-1-(2-trimethylsilanyl-ethoxymethyl)-1H-imidazole-2-carboxylic acid (4-bromo-2-cyclohex-1-enyl-phenyl)-amide (79 mg, 0.16 mmol) (as prepared in Example 1, step (f)), t-butyl acrylate (41 mg, 0.32 mmol), cesium carbonate (57 mg, 0.18 mmol), $(t-Bu_3P)_2$ Pd(0) (8.2 mg, 0.016 mmol), and 1 mL of dioxane and heated in a microwave reactor for 30 min at 135° C. The crude reaction mixture was loaded on a 10-g SPE column and the title compound was eluted with 10% EtOAc/hexanes to give 30 mg (34%) of a white solid. Mass spectrum (ESI, m/z): Calcd. for $C_{30}H_{40}N_4O_4Si$, 549.2 (M+H). found 548.9.

b) 3-{4-[(4-Cyano-1H-imidazole-2-carbonyl)-amino]-3-cyclohex-1-enyl-pheny}-acrylic acid To a solution of 3-(4-{[4-cyano-1-(2-trimethylsilanyl-ethoxymethyl)-1H-imidazole-2-carbonyl]-amino}-3-cyclohex-1-enyl-phenyl)-acrylic acid tert-butyl ester (30 mg, 0.055 mmol) (as prepared in the previous step) in 1.0 mL of DCM was added 0.30 mL of TFA, 0.026 mL of EtOH and stirred at RT for 2 h. The mixture was concentrated and the residue triturated with MeOH to give 19 mg (95%) of the title compound as a white solid. $^1$H-NMR (400 MHz, DMSO-$d_6$): δ 14.39 (br s, 1H), 9.83 (s, 1H), 8.38 (d, J=2.5 Hz, 1H), 8.15 (d, J=8.5 Hz, 1H), 7.65 (dd, J=8.5, 1.9 Hz, 1H), 7.57 (d, J=1.9 Hz, 1H), 7.56 (d, J=16.0 Hz, 1H), 6.53 (d, J=16.0 Hz, 1H), 5.83 (m, 1H), 2.31-2.14 (m, 4H), 1.81-1.65 (m, 4H). Mass spectrum (ESI, m/z): Calcd. for $C_{20}H_{18}N_4O_3$, 363.1 (M+H). found 363.0.

Example 49

[5-[(5-Cyano-1H-imidazole-2-carbonyl)-amino]-6-(4,4-dimethyl-cyclohex-1-enyl)-pyridin-2-yl]-acetic acid

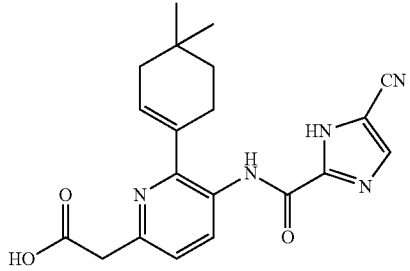 [SMILES: CC1(C)CC=C(c2nc(CC(=O)O)ccc2NC(=O)c2ncc(C#N)[nH]2)CC1]

a) (5-Nitro-pyridin-2-yl)-acetic acid ethyl ester

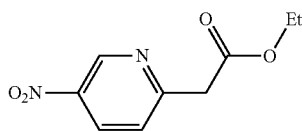 [SMILES: CCOC(=O)Cc1ccc([N+](=O)[O-])cn1]

To a suspension of NaH (60% dispersion, 0.900 g, 22.5 mmol) in 40 mL of THF was added malonic acid tert-butyl ester ethyl ester (4.00 mL, 21.1 mmol) and the mixture stirred for 15 min at RT. To this mixture was then added 2-chloro-5-nitro-pyridine (2.56 g, 16.0 mmol) and the reaction stirred for 10 h at RT. The mixture was diluted with 100 mL of EtOAc and washed with NH$_4$Cl (2×100 mL) and brine (100 mL) and dried over Na$_2$SO$_4$ and concentrated in vacuo. The residue was dissolved in DCM (20 mL), TFA (10 mL) was added and the mixture stirred for 2 h at RT. The mixture was concentrated, the residue dissolved in 100 mL of EtOAc and washed with NaHCO$_3$ (2×100 mL) and brine (100 mL) and again dried over Na$_2$SO$_4$ and concentrated in vacuo. The title compound was purified by flash chromatography eluting with 30% EtOAc/hexanes to give 2.35 g (70%) of a light yellow solid. $^1$H-NMR (CDCl$_3$, 400 MHz): δ 9.38 (d, J=2.6 Hz, 1H), 8.46 (dd, J=8.6, 2.6 Hz, 1H), 7.55 (d, J=8.6 Hz, 1H), 4.22 (q, J=7.1 Hz, 2H), 3.99 (s, 2H), 1.28 (t, J=7.1 Hz, 3H).

b) [5-Amino-6-(4,4-dimethyl-cyclohex-1-enyl)-pyridin-2-yl]-acetic acid ethyl ester

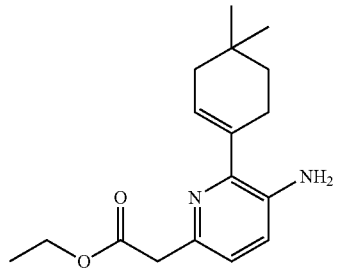 [SMILES: CCOC(=O)Cc1ccc(N)c(C2=CCC(C)(C)CC2)n1]

This compound was prepared from (5-nitro-pyridin-2-yl)-acetic acid ethyl ester (as prepared in the previous step) according to the procedure for nitro reduction and bromination in Example 33, step (b), followed by Suzuki coupling to 4,4-dimethyl-1-cyclohexen-1-ylboronic acid according to the procedure in Example 1, step (e). Mass spectrum (APCI, m/z): Calcd. for $C_{17}H_{24}N_2O_2$, 289.2 (M+H). found 289.2.

c) [5-[(5-Cyano-1H-imidazole-2-carbonyl)-amino]-6-(4,4-dimethyl-cyclohex-1-enyl)-pyridin-2-yl]-acetic acid ethyl ester

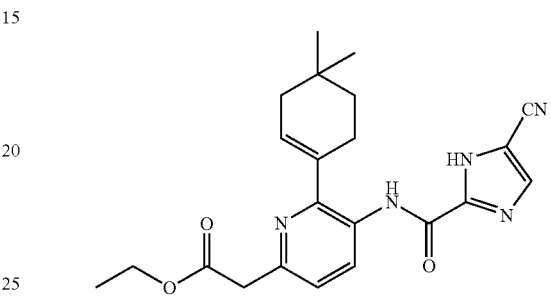

The title compound was prepared by coupling 4-cyano-1-(2-trimethylsilanyl-ethoxymethyl)-1H-imidazole-2-carboxylate potassium salt (as prepared in Example 1, step (d)) and [5-amino-6-(4,4-dimethyl-cyclohex-1-enyl)-pyridin-2-yl]-acetic acid ethyl ester (as prepared in the previous step) according to the procedure in Example 34, step (c), followed by SEM deprotection according to the procedure in Example 34, step (d). Mass spectrum (ESI, m/z): Calcd. for $C_{22}H_{25}ClN_5O_3$, 408.2 (M+H). found 408.2.

d) [5-[(5-Cyano-1H-imidazole-2-carbonyl)-amino]-6-(4,4-dimethyl-cyclohex-1-enyl)-pyridin-2-yl]-acetic acid

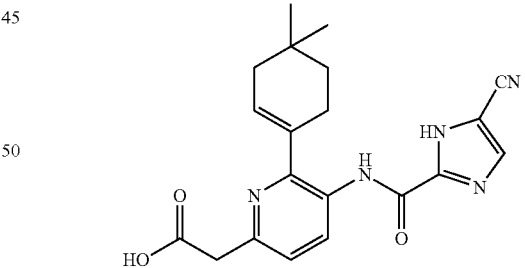

The title compound was prepared from [5-[(5-cyano-1H-imidazole-2-carbonyl)-amino]-6-(4,4-dimethyl-cyclohex-1-enyl)-pyridin-2-yl]-acetic acid ethyl ester (as prepared in the previous step) by hydrolysis of the ethyl ester according to the procedure in Example 46, step (b). $^1$H-NMR (400 MHz, DMSO-d$_6$): δ 14.28 (s, 1H), 12.47 (s, 1H), 10.08 (s, 1H), 8.34 (d, J=2.4 Hz, 1H), 8.12 (d, J=8.2 Hz, 1H), 7.28 (d, J=8.2 Hz, 1H), 5.87 (m, 1H), 3.74 (s, 2H), 2.39 (m, 2H), 1.91 (m, 2H), 1.47 (t, J=6.3 Hz, 2H), 0.97 (s, 6H). Mass spectrum (ESI, m/z): Calcd. for $C_{20}H_{21}N_5O_3$, 380.2 (M+H). found 380.2.

Example 50

[5-[(4-Cyano-1H-pyrrole-2-carbonyl)-amino]-6-(4,4-dimethyl-cyclohex-1-enyl)-pyridin-2-yl]-acetic acid ethyl ester trifluoroacetic acid salt

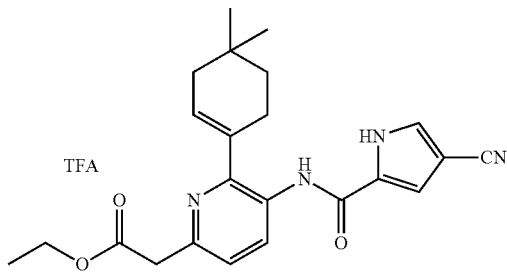 [SMILES: CCOC(=O)Cc1ccc(NC(=O)c2cc(C#N)c[nH]2)c(C2=CCC(C)(C)CC2)n1]

The title compound was prepared by coupling 4-cyano-1H-pyrrole-2-carboxylic acid (Can. J. Chem., 59(17), 2673-6, (1981)) and [5-amino-6-(4,4-dimethyl-cyclohex-1-enyl)-pyridin-2-yl]-acetic acid ethyl ester (as prepared in Example 49, step (b)) according to the procedure in Example 34, step (c). $^1$H-NMR (400 MHz, DMSO-$d_6$) δ 12.48 (s, 1H), 9.51 (s, 1H), 7.57 (m, 2H), 7.09 (d, J=8.2 Hz, 1H), 7.07 (m, 1H), 5.65 (m, 1H), 3.93 (q, J=7.1 Hz, 2H), 3.66 (s, 2H), 2.19 (m, 2H), 1.64 (m, 2H), 1.22 (t, J=6.4 Hz, 2H), 1.01 (t, J=7.1 Hz, 3H), 0.70 (s, 6H). Mass spectrum (ESI, m/z): Calcd. for $C_{23}H_{26}N_4O_3$, 407.2 (M+H). found 407.2.

Example 51

[5-[(4-Cyano-1H-pyrrole-2-carbonyl)-amino]-6-(4,4-dimethyl-cyclohex-1-enyl)-pyridin-2-yl]-acetic acid trifluoroacetic acid salt

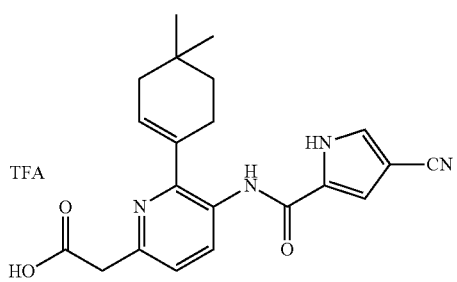 [SMILES: CC1(C)CC=C(c2nc(CC(=O)O)ccc2NC(=O)c2cc(C#N)c[nH]2)CC1]

The title compound was prepared from [5-[(4-cyano-1H-pyrrole-2-carbonyl)-amino]-6-(4,4-dimethyl-cyclohex-1-enyl)-pyridin-2-yl]-acetic acid ethyl ester (as prepared in the previous step) by hydrolysis of the ethyl ester according to the procedure in Example 46, step (b). $^1$H-NMR (400 MHz, DMSO-$d_6$): δ 12.70 (br s, 1H), 9.74 (s, 1H), 7.81 (d, J=8.0 Hz, 1H), 7.78 (dd, J=3.2, 1.5 Hz, 1H), 7.33 (d, J=8.0 Hz, 1H), 7.29 (m, 1H), 5.87 (m, 1H), 3.80 (s, 2H), 2.40 (m, 2H), 1.86 (m, 2H), 1.43 (t, J=6.4 Hz, 2H), 0.92 (s, 6H). Mass spectrum (ESI, m/z): Calcd. for $C_{21}H_{22}N_4O_3$, 379.2 (M+H). found 379.2.

Example 52

5-Cyano-1H-imidazole-2-carboxylic acid [4-[1-(2-dimethylamino-ethoxy)-1-methyl-ethyl]-2-(4,4-dimethyl-cyclohex-1-enyl)-phenyl]-amide trifluoroacetic acid salt

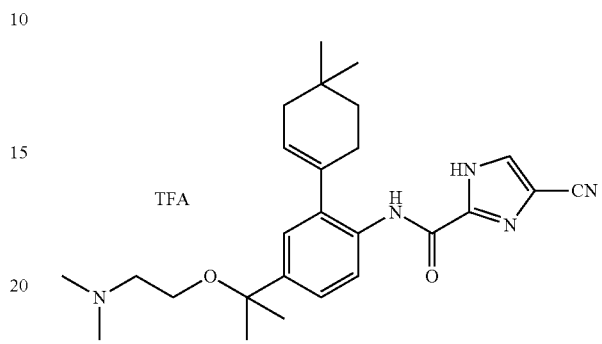

To a suspension of 5-cyano-1H-imidazole-2-carboxylic acid [2-(4,4-dimethyl-cyclohex-1-enyl)-4-(1-hydroxy-1-methyl-ethyl)-phenyl]-amide (60 mg, 0.16 mmol) (as prepared in Example 14, step (d)) in 1 mL of DCM was added 2-dimethylamino-ethanol (0.32 mL, 3.20 mmol), TFA (0.37 mL, 4.80 mmol), and the mixture heated to 60° C. for 6 h. The mixture was concentrated and the title compound purified by RP-HPLC on a C18 column eluting with a linear gradient of 30-55% $CH_3CN$ in 0.1% TFA/$H_2O$ over 9 min to give 10 mg (11%) of a white solid. $^1$H-NMR (400 MHz, $CD_3OD$): δ 8.26 (d, J=8.5 Hz, 1H), 8.09 (s, 1H), 7.44 (dd, J=8.5, 2.2 Hz, 1H), 7.30 (d, J=2.2 Hz, 1H), 5.77 (m, 1H), 3.52 (m, 2H), 3.30 (m, 2H), 2.91 (s, 6H), 2.34 (m, 2H), 2.11 (m, 2H), 1.64 (s, 6H), 1.60 (m, 2H), 1.12 (s, 6H). Mass spectrum (ESI, m/z): Calcd. for $C_{26}H_{35}N_5O_2$, 450.3 (M+H). found 450.0.

Example 53

4-Cyano-1H-imidazole-2-carboxylic acid [4-[(2-dimethylamino-ethylcarbamoyl)-methyl]-2-(4,4-dimethyl-cyclohex-1-enyl)-phenyl]-amide trifluoroacetic acid salt

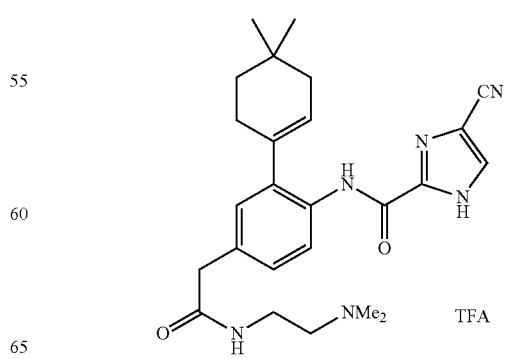

a) 2-(4-Amino-3-bromo-phenyl)-N-(2-dimethyl-amino-ethyl)-acetamide

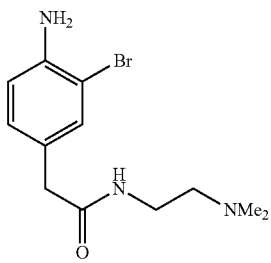 [SMILES: CN(C)CCNC(=O)Cc1ccc(N)c(Br)c1]

To a solution of (4-amino-phenyl)-acetic acid (320 mg, 2.10 mmol) in CH$_3$CN (4 mL) and AcOH (2 mL) at 0° C. was added NBS (373 mg, 2.10 mmol) in CH$_3$CN (3 mL). The reaction was allowed to warm to room temperature over 1 h and then concentrated in vacuo to give a mixture of (4-amino-3-bromo-phenyl)-acetic acid and starting material which was used without further purification. The crude (4-amino-3-bromo-phenyl)-acetic acid (490 mg, 2.12 mmol), EDCI (487 mg, 2.54 mmol), HOBt (343 mg, 2.54 mmol), and N$^1$,N$^1$-dimethyl-ethane-1,2-diamine (281 mg, 3.19 mmol) were slurried in DCM (10 mL), treated with NEt$_3$ (910 µL, 6.36 mmol) and stirred overnight. The reaction was diluted with DCM (50 mL), washed with water (2×50 mL), dried (Na$_2$SO$_4$) and concentrated in vacuo. The crude residue was purified by preparative TLC (10% MeOH—CHCl$_3$) to afford 70 mg (11%) of the title compound. $^1$H-NMR (CDCl$_3$; 400 MHz) δ 7.25 (s, 1H, J=2.0 Hz), 6.93 (dd, 1H, J=8.1, 2.0 Hz), 6.65 (d, 1H, J=8.1 Hz), 6.04 (br s, 1H), 4.03 (br s, 2H), 3.32 (s, 2H), 3.24-3.19 (m, 2H), 2.30-2.27 (m, 2H), 2.11 (s, 6H).

b) 2-[4-Amino-3-(4,4-dimethyl-cyclohex-1-enyl)-phenyl]-N-(2-dimethylamino-ethyl)-acetamide

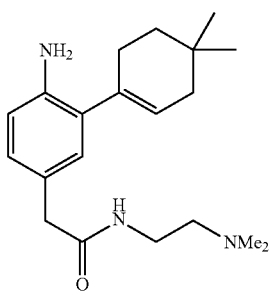 [SMILES: CN(C)CCNC(=O)Cc1ccc(N)c(C2=CCC(C)(C)CC2)c1]

To a flask containing 2-(4-amino-3-bromo-phenyl)-N-(2-dimethylamino-ethyl)-acetamide (as prepared in the previous step, 83 mg, 0.27 mmol), tris(dibenzylideneacetone)dipalladium (0) (4.0 mg, 0.0080 mmol), 2-(dicyclohexylphosphino)-2',6'-dimethoxy-1,1'-biphenyl (5.6 mg, 0.010 mmol) and K$_3$PO$_4$ (0.17 g, 0.82 mmol) was charged dioxane (3 mL) and the reaction was heated to 100° C. for 48 h. At this time the reaction was diluted with EtOAc (25 mL) and washed with water (25 mL). The organic layer was dried (Na$_2$SO$_4$) and concentrated in vacuo. The crude residue was purified by preparative TLC (10% MeOH—CHCl$_3$) to afford 26 mg (28%) of the title compound as a tan solid. $^1$H-NMR (CDCl$_3$; 400 MHz): δ 6.85 (dd, 1H, J=8.0, 2.1 Hz), 6.79 (d, 1H, J=2.1 Hz), 6.59 (d, 1H, J=8.0 Hz), 6.01 (br s, 1H), 5.60 (m, 1H), 3.66 (br s, 2H), 3.35 (s, 2H), 3.23-3.18 (m, 2H), 2.27 (t, 1H, J=6.1 Hz), 2.20-2.14 (m, 2H), 2.09 (s, 6H), 1.90-1.88 (m, 2H), 1.44 (t, 2H, J=6.3 Hz), 0.92 (s, 6H).

c) 4-Cyano-1-(2-trimethylsilanyl-ethoxymethyl)-1H-imidazole-2-carboxylic acid [4-[(2-dimethylamino-ethylcarbamoyl)-methyl]-2-(4,4-dimethyl-cyclohex-1-enyl)-phenyl]-amide

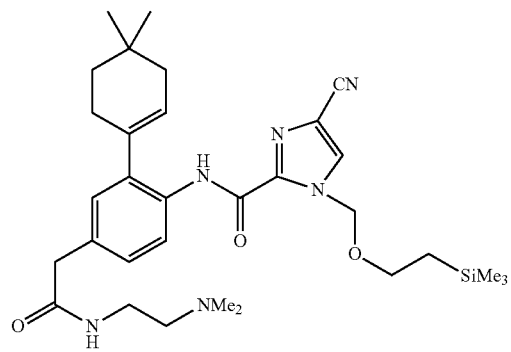 [SMILES: CN(C)CCNC(=O)Cc1ccc(NC(=O)c2nc(C#N)cn2COCC[Si](C)(C)C)c(C2=CCC(C)(C)CC2)c1]

The title compound was prepared from 2-[4-amino-3-(4,4-dimethyl-cyclohex-1-enyl)-phenyl]-N-(2-dimethylamino-ethyl)-acetamide (as prepared in the previous step) and potassium 4-cyano-1-(2-trimethylsilanyl-ethoxymethyl)-1H-imidazole-2-carboxylate (as prepared in Example 1, step (d)) according to the procedure in Example 1, step (f). Mass spectrum (ESI, m/z): Calcd. for C$_{31}$H$_{46}$N$_6$O$_3$Si, 579.3 (M+H). found 579.3.

d) 4-Cyano-1H-imidazole-2-carboxylic acid [4-[(2-dimethylamino-ethylcarbamoyl)-methyl]-2-(4,4-dimethyl-cyclohex-1-enyl)-phenyl]-amide trifluoroacetic acid salt The title compound was prepared from 4-cyano-1-(2-trimethylsilanyl-ethoxymethyl)-1H-imidazole-2-carboxylic acid [4-[(2-dimethylamino-ethylcarbamoyl)-methyl]-2-(4,4-dimethyl-cyclohex-1-enyl)-phenyl]-amide (as prepared in the previous step) according to the procedure in Example 1, step (g). $^1$H-NMR (CD$_3$OD; 400 MHz): δ 8.17 (d, 1H, J=8.3 Hz), 7.99 (s, 1H), 7.22 (dd, 1H, J=8.3, 2.0 Hz), 7.15 (1H, d, J=2.0 Hz), 5.74 (m, 1H), 3.57-3.54 (m, 4H), 3.25 (t, 2H, J=5.9 Hz), 2.92 (s, 6H), 2.32-2.28 (m, 2H), 2.07-2.06 (m, 2H), 1.58 (t, 2H, J=6.3 Hz), 1.08 (s, 6H). Mass spectrum (ESI, m/z): Calcd. for C$_{25}$H$_{32}$N$_6$O$_2$, 449.2 (M+H). found 449.3.

Example 54

5-Cyano-1H-imidazole-2-carboxylic acid {2-(4,4-dimethyl-cyclohex-1-enyl)-4-[(3-hydroxy-propylcarbamoyl)-methyl]-pheny}-amide

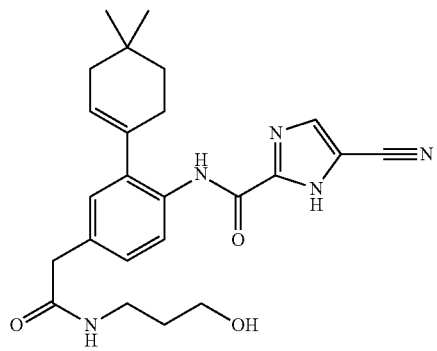 [SMILES: CC1(C)CC=C(c2cc(CC(=O)NCCCO)ccc2NC(=O)c2ncc(C#N)[nH]2)CC1]

a) N-(3-Hydroxy-propyl)-2-(4-nitro-phenyl)-acetamide

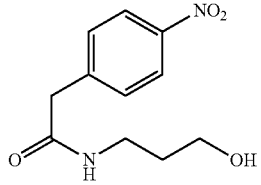 [SMILES: O=C(Cc1ccc([N+](=O)[O-])cc1)NCCCO]

To a stirred solution of 3-hydroxypropylamine (507 mg, 6.76 mmol) and triethylamine (1.88 mL, 0.013 mol) in DCM (10 mL) at 0° C. was added (4-nitro-phenyl)-acetyl chloride (1.35 g, 6.76 mmol) in DCM (10 mL) dropwise. The dark red solution was allowed to warm to room temperature and then poured into water (50 mL). The layers were separated and the organic layer was dried ($Na_2SO_4$) and concentrated in vacuo. The crude material was purified by preparative thin layer chromatography (TLC) (5%-MeOH—$CHCl_3$) to afford 183 mg (11%) of the title compound as a solid. $^1$H-NMR ($CDCl_3$; 400 MHz): δ 8.12 (d, 2H, J=8.7 Hz), 7.39 (d, 1H, J=8.7 Hz), 6.09 (br s, 1H), 3.58 (s, 2H), 3.57-3.54 (m, 2H), 3.40 (br s, 1H), 3.36-3.31 (m, 2H), 1.63-1.57 (m, 2H).

b) 2-(4-Amino-phenyl)-N-(3-hydroxy-propyl)-acetamide

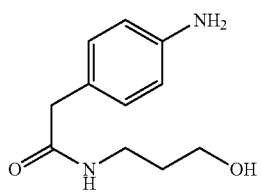 [SMILES: Nc1ccc(CC(=O)NCCCO)cc1]

A slurry of N-(3-hydroxy-propyl)-2-(4-nitro-phenyl)-acetamide (as prepared in the previous step, 183 mg, 0.768 mmol) and 5% Pd—C (130 mg) in EtOH-EtOAc (5 mL, 4:1 v/v) was stirred under 1 atm $H_2$ for 2 h. The reaction was filtered and concentrated to afford 152 mg (95%) of the title compound. $^1$H-NMR (DMSO-$d_6$; 400 MHz): δ 7.78 (br s, 1H), 6.88 (d, 2H, J=8.3 Hz), 6.47 (d, 2H, J=8.3 Hz), 4.88 (br s, 2H), 4.39 (t, 1H, J=5.2 Hz), 3.43-3.34 (m, 2H), 3.16 (s, 2H), 3.08-3.03 (m, 2H), 1.55-1.48 (m, 2H).

c) 2-(4-Amino-3-bromo-phenyl)-N-(3-hydroxy-propyl)-acetamide

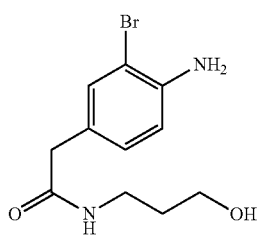 [SMILES: Nc1ccc(CC(=O)NCCCO)cc1Br]

The title compound was prepared from 2-(4-amino-phenyl)-N-(3-hydroxy-propyl)-acetamide (as prepared in the previous step) and NBS according to the procedure in Example 7, step (c). Mass spectrum (ESI, m/z): Calcd. for $C_{11}H_{15}BrN_2O_2$, 287.0 (M+H). found 287.0.

d) 2-[4-Amino-3-(4,4-dimethyl-cyclohex-1-enyl)-phenyl]-N-(3-hydroxy-propyl)-acetamide

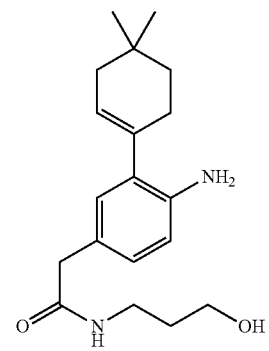 [SMILES: CC1(C)CC=C(c2cc(CC(=O)NCCCO)ccc2N)CC1]

The title compound was prepared from 2-(4-amino-3-bromo-phenyl)-N-(3-hydroxy-propyl)-acetamide (as prepared in the previous step), 4,4-dimethylcyclohexen-1-yl boronic acid and $Pd(PPh_3)_4$ according to the procedure in Example 1, step (e). Mass Spectrum (ESI, m/z): Calcd. for $C_{19}H_{28}N_2O_2$, 317.2 (M+H). found 317.1.

e) 4-Cyano-1-(2-trimethylsilanyl-ethoxymethyl)-1H-imidazole-2-carboxylic acid {2-(4,4-dimethyl-cyclohex-1-enyl)-4-[(3-hydroxy-propylcarbamoyl)-methyl]-pheny}-amide

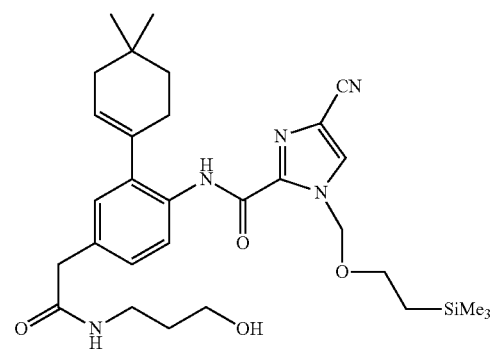 [SMILES: CC1(C)CC=C(c2cc(CC(=O)NCCCO)ccc2NC(=O)c2nc(C#N)cn2COCC[Si](C)(C)C)CC1]

The title compound was prepared from 2-[4-amino-3-(4,4-dimethyl-cyclohex-1-enyl)-phenyl]-N-(3-hydroxy-propyl)-acetamide (as prepared in the previous step), potassium 4-cyano-1-(2-trimethylsilanyl-ethoxymethyl)-1H-imidazole-2-carboxylate (as prepared in Example 1, step (d)), PyBroP and DIEA according to the procedure in Example 1, step (f). $^1$H-NMR ($CDCl_3$; 400 MHz): δ 9.74 (s, 1H), 8.31 (d, 1H, J=8.3 Hz), 7.78 (s, 1H), 7.20 (dd. 1H, J=8.4, 1.9 Hz), 7.11 (d, 1H, J=1.9 Hz), 7.03 (br s, 1H), 5.94 (s, 2H), 5.75 (s, 1H), 4.22 (t, 1H, J=6.1 Hz), 3.67-3.63 (m, 2H), 3.61-3.56 (m, 2H), 3.52 (s, 2H), 3.38-3.33 (m, 2H), 2.27-2.23 (m, 2H), 2.08-2.07 (m, 2H), 1.67-1.61 (m, 2H), 1.57 (t, 2H, J=6.2 Hz), 1.09 (s, 6H), 0.98-0.94 (m, 2H), 0.00 (s, 9H).

f) 5-Cyano-1H-imidazole-2-carboxylic acid {2-(4,4-dimethyl-cyclohex-1-enyl)-4-[(3-hydroxy-propylcarbamoyl)-methyl]-pheny}-amide

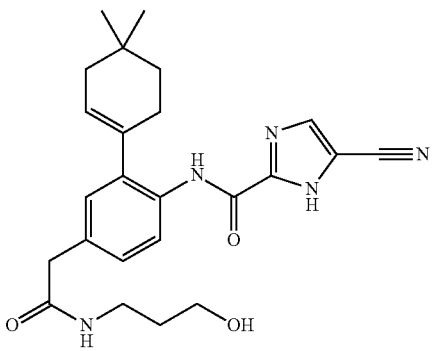 [SMILES: CC1(C)CC=C(c2cc(CC(=O)NCCCO)ccc2NC(=O)c2ncc(C#N)[nH]2)CC1]

The title compound was prepared from 4-cyano-1-(2-trimethylsilanyl-ethoxymethyl)-1H-imidazole-2-carboxylic acid {2-(4,4-dimethyl-cyclohex-1-enyl)-4-[(3-hydroxy-propylcarbamoyl)-methyl]-phenyl}-amide (as prepared in the previous step) according to the procedure in Example 1, step (g). $^1$H NMR (CD$_3$OD; 400 MHz): δ 8.05 (d, 1H, J=7.9 Hz), 7.87 (s, 1H), 7.11 (dd, 1H, J=8.2, 1.8 Hz), 7.04 (d, 1H, J=1.9 Hz), 5.64 (m, 1H), 3.45 (t, 2H, J=6.3 Hz), 3.37 (s, 2H), 3.20 (m, 2H), 2.21-2.18 (m, 2H), 1.97-1.96 (m, 1H), 1.60 (m, 2H), 1.48 (t, 2H, J=6.2 Hz), 0.97 (s, 6H). Mass spectrum (ESI, m/z): Calcd. for C$_{24}$H$_{29}$N$_5$O$_3$, 436.2 (M+H). found 436.2.

Example 55

5-Cyano-furan-2-carboxylic acid [4-[3-(ethyl-methyl-amino)-propyl]-2-(4-methyl-piperidin-1-yl)-phenyl]-amide

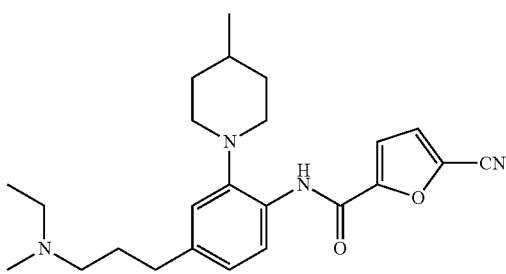 [SMILES: CCN(C)CCCc1ccc(NC(=O)c2ccc(C#N)o2)c(N2CCC(C)CC2)c1]

a) 1-(5-Bromo-2-nitro-phenyl)-4-methyl-piperidine

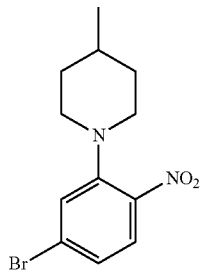

To a round bottom flask containing 4-bromo-2-fluoro-1-nitro-benzene (640 mg, 2.92 mmol) was added 4-methyl piperidine (4 mL) and the reaction was stirred at 40° C. overnight. At this time the dark solution was poured into water (25 mL) and extracted with DCM (2×25 mL). The combined organic layers were washed with water (2×25 mL), dried (Na$_2$SO$_4$) and concentrated in vacuo to afford 556 mg (64%) of 1-(5-bromo-2-nitro-phenyl)-4-methyl-piperidine as an orange oil which was used without further purification.

b) 3-[3-(4-Methyl-piperidin-1-yl)-4-nitro-phenyl]-prop-2-yn-1-ol

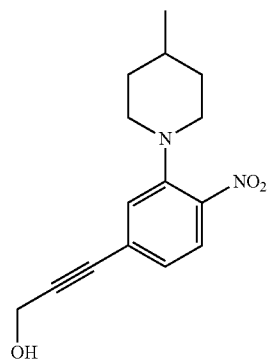 [SMILES: CC1CCN(c2cc(C#CCO)ccc2[N+](=O)[O-])CC1]

To a round bottom flask containing 1-(5-bromo-2-nitro-phenyl)-4-methyl-piperidine (as prepared above, 400 mg, 1.33 mmol) in 8 mL of dioxane was added propargyl alcohol (155 µL, 2.64 mmol), bis-dichloro(triphenylphosphinyl) palladium (II) (56.3 mg, 0.0798 mmol), copper (I) iodide (5.0 mg, 0.02 mmol) and triethylamine (741 µL, 5.32 mmol). The result was heated at 80° C. for 16 h. The reaction was then diluted with EtOAc (50 mL), washed with water (2×50 mL), dried (Na$_2$SO$_4$), and concentrated in vacuo. Purification of the crude material by preparative thin layer chromatography (75% EtOAc-hexanes) afforded 280 mg (77%) of the title compound as a reddish oil. $^1$H-NMR (CDCl$_3$; 400 MHz): δ 7.73 (d, 1H, J=8.6 Hz), 7.17 (d, 1H, J=1.6 Hz), 6.98 (dd, 1H, J=8.6, 1.6 Hz), 3.23-3.26 (m, 2H), 4.53 (s, 2H), 1.73-1.42 (m, 5H), 2.86-2.79 (m, 2H), 1.00 (d, 3H, J=6.4 Hz).

c) Ethyl-methyl-{3-[3-(4-methyl-piperidin-1-yl)-4-nitro-phenyl]-prop-2-ynyl}-amine

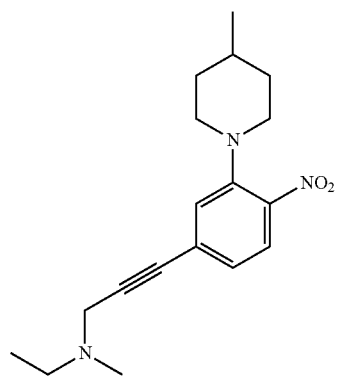 [SMILES: CCN(C)CC#Cc1ccc([N+](=O)[O-])c(N2CCC(C)CC2)c1]

To a stirred solution of 3-[3-(4-methyl-piperidin-1-yl)-4-nitro-phenyl]-prop-2-yn-1-ol (as prepared in the previous step, 47 mg, 0.17 mmol) in 4 mL of DCM at 0° C. was added triethylamine (71 µL, 0.51 mmol) followed by methanesulfonyl chloride (17 µL, 0.22 mmol). The reaction was allowed to stir for 10 min, at which time ethylmethylamine (4 drops) was added. The result was heated at reflux for 20 min. and then poured into water (20 mL). The aqueous layer was extracted with DCM (2×25 mL), the organic layers were dried (Na$_2$SO$_4$) and concentrated in vacuo. The residue was purified by preparative TLC (10%-MeOH—CHCl$_3$) to afford 59 mg (100%) of the title compound as an oil. Mass spectrum (ESI, m/z) Calcd for C$_{18}$H$_{25}$N$_3$O$_2$, 316.1 (M+H). found 316.2.

d) 4-[3-(Ethyl-methyl-amino)-propyl]-2-(4-methyl-piperidin-1-yl)-phenylamine

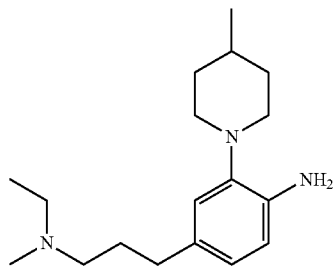 [SMILES: CCN(C)CCCc1ccc(N)c(N2CCC(C)CC2)c1]

The title compound was prepared from ethyl-methyl-{3-[3-(4-methyl-piperidin-1-yl)-4-nitro-phenyl]-prop-2-ynyl}-amine (as prepared in the previous step) according to the procedure in Example 54, step (b). Mass spectrum (ESI, m/z) Calcd for C$_{18}$H$_{31}$N$_3$, 290.2 (M+H). found 290.2.

e) 5-Cyano-furan-2-carboxylic acid [4-[3-(ethyl-methyl-amino) propyl]-2-(4-methyl-piperidin-1-yl)-phenyl]-amide To a mixture of 5-cyano-furan-2-carboxylic acid (WO 2004096795-A2, 23 mg, 0.16 mmol) in DCM (2 mL) at 0° C. was added DMF (10 µL) followed by oxalyl chloride (15 µL, 0.17 mmol) and stirred for 1 h. The reaction was concentrated in vacuo, azeotroped with toluene (2×5 mL) and used immediately without further purification.
To a solution of 4-[3-(ethyl-methyl-amino)-propyl]-2-(4-methyl-piperidin-1-yl)-phenylamine (as prepared in the previous step, 32 mg, 0.11 mmol) in DCM (2 mL) at 0° C. was added DIEA (48 µL, 0.27 mmol) followed by 5-cyano-furan-2-carbonyl chloride (as prepared above, 22 mg, 0.16 mmol). The reaction was allowed to warm to RT overnight, at which time it was diluted with DCM (20 mL), washed with saturated aqueous NaHCO$_3$ (10 mL), dried (Na$_2$SO$_4$) and concentrated in vacuo. Purification by preparative TLC (10% MeOH—CHCl$_3$) afforded 20 mg (45%) of the title compound as an oily amber solid. $^1$H-NMR (CDCl$_3$; 400 MHz): δ 9.69 (s, 1H), 8.38 (d, 1H, J=8.4 Hz), 7.26 (d, 1H, J=3.6 Hz), 7.05 (d, 1H, J=2.0 Hz), 7.00-6.97 (m, 1H), 6.91 (d, 1H, J=4.0 Hz), 3.01-2.98 (m, 2H), 2.78-2.64 (m, 7H), 2.50 (s, 3H), 2.04-1.98 (m, 2H), 1.89-1.85 (m, 2H), 1.63-1.46 (m, 5H), 1.25 (t, 3H, J=4.6 Hz), 1.10 (d, 3H, J=6.4 Hz), 0.93-0.89 (m, 2H). Mass spectrum (ESI, m/z) calcd for C$_{24}$H$_{32}$N$_4$O$_2$, 409.2 (M+H). found 409.3.

Example 56

4-Cyano-1H-imidazole-2-carboxylic acid {2-(4,4-dimethyl-cyclohex-1-enyl)-6-[1-(4-ethyl-piperazin-1-yl)-1-methyl-ethyl]-pyridin-3-yl}-amide

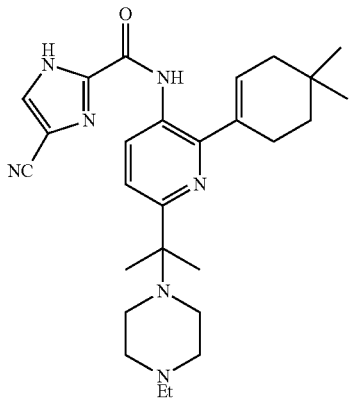

a) 6-Bromo-2-iodo-pyridin-3-ylamine

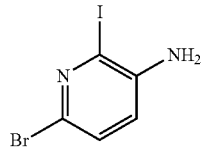

To a stirred solution of 6-bromo-pyridin-3-ylamine (10.2 g, 0.0580 mol) and Ag$_2$SO$_4$ (18.1 g, 0.0580 mol) in EtOH (150 mL) was added I$_2$ (7.59 g, 0.0580 mol) and the reaction was allowed to stir overnight. At this time hexane (200 mL) was added and the resultant mixture was filtered through Celite. The solvent was removed in vacuo, dissolved in CHCl$_3$ (200 mL), washed with aqueous saturated Na$_2$S$_2$O$_3$ (100 mL), water (1×100 mL), and dried (Na$_2$SO$_4$). The solvent was concentrated in vacuo and the residue was dissolved in hot EtOAc (100 mL), filtered and treated with hexanes (100 mL). Filtration gave 11.2 g (65%) of the title compound as a white crystalline material. $^1$H-NMR (CDCl$_3$; 400 MHz): δ 7.10 (d, 1H, J=8.2 Hz), 6.74 (d, 1H, J=8.2 Hz), 4.06 (br s, 2H).

b) 6-Bromo-2-(4,4-dimethyl-cyclohex-1-enyl)-pyridin-3-ylamine

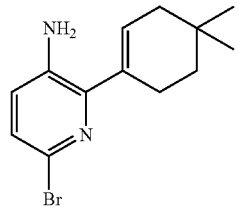 [SMILES: CC1(C)CC=C(c2nc(Br)ccc2N)CC1]

The title compound was prepared from 6-bromo-2-iodo-pyridin-3-ylamine (as prepared in the previous step, 348 mg,

141

1.17 mmol), 4,4-dimethylcyclohexen-1-yl boronic acid (198 mg, 1.28 mmol), Pd(PPh$_3$)$_4$ (135 mg, 0.117 mol) and 2M Na$_2$CO$_3$ (15.2 mL, 30.5 mmol) according to the procedure in Example 34, step (b) (417 mg, 46%). $^1$H-NMR (CDCl$_3$; 400 MHz): δ 7.06 (d, 1H, J=8.3 Hz), 6.85 (d, 1H, J=8.3 Hz), 5.95 (m, 1H), 3.86 (br s, 2H), 2.43-2.39 (m, 2H), 1.99-1.97 (m, 2H), 1.51 (t, 2H, J=6.4 Hz), 0.99 (s, 6H).

c) 4-Cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide

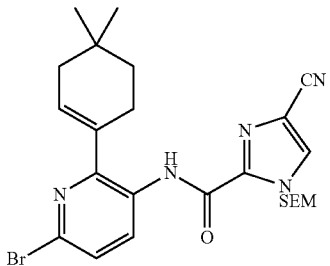 [SMILES: CC1(C)CC=C(c2nc(Br)ccc2NC(=O)c2nc(C#N)cn2COCC[Si](C)(C)C)CC1]

The title compound was prepared from 6-bromo-2-(4,4-dimethyl-cyclohex-1-enyl)-pyridin-3-ylamine (as prepared in the previous step, 60 mg, 0.21 mmol), potassium 4-cyano-1-(2-trimethylsilanyl-ethoxymethyl)-1H-imidazole-2-carboxylate (as prepared in Example 1, step (d), 91.0 mg, 0.290 mmol), PyBroP (157 mg, 0.330 mmol) and DIEA (91.0 μL, 0.520 mmol) according to the procedure in Example 1, step (f) (84 mg, 78%). $^1$H-NMR (CDCl$_3$; 400 MHz): δ 9.91 (s, 1H), 8.64 (d, 1H, J=8.6 Hz), 7.79 (s, 1H), 7.38 (d, 1H, J=8.6 Hz), 6.00 (m, 1H), 5.92 (s, 2H), 3.67 (m, 2H), 2.46 (m, 2H), 2.14 (m, 2H), 1.62 (t, 2H, J=6.3 Hz), 1.12 (s, 6H), 0.98 (m, 2H).

d) 5-Cyano-1H-imidazole-2-carboxylic acid [6-bromo-2-(4,4-dimethyl-cyclohex-1-enyl)-pyridin-3-yl]-amide

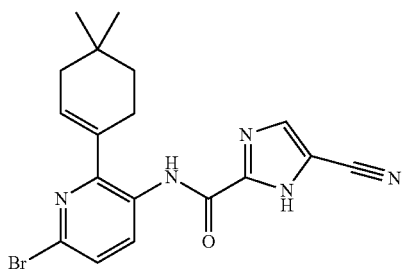 [SMILES: CC1(C)CC=C(c2nc(Br)ccc2NC(=O)c2ncc(C#N)[nH]2)CC1]

The title compound was prepared from 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in the previous step) according to the procedure in Example 1, step (g). Mass spectrum (ESI, m/z): Calcd. for C$_{18}$H$_{18}$BrN$_5$O, 400.0 (M+H). found 400.0.

142 e) 5-Cyano-1H-imidazole-2-carboxylic acid [2-(4,4-dimethyl-cyclohex-1-enyl)-6-(1-hydroxy-1-methyl-ethyl)-pyridin-3-yl]-amide

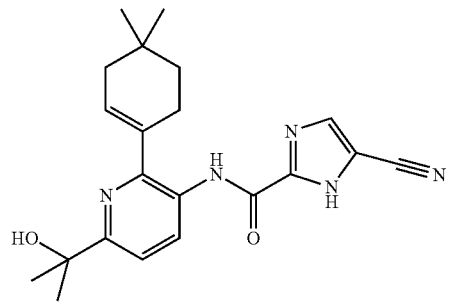 [SMILES: CC1(C)CC=C(c2nc(C(C)(C)O)ccc2NC(=O)c2ncc(C#N)[nH]2)CC1]

The title compound is prepared from 5-cyano-1H-imidazole-2-carboxylic acid [6-bromo-2-(4,4-dimethyl-cyclohex-1-enyl)-pyridin-3-yl]-amide (as prepared in the previous step) according to the procedure in Example 1, step (h).

f) 4-Cyano-1H-imidazole-2-carboxylic acid {2-(4,4-dimethyl-cyclohex-1-enyl)-6-[1-(4-ethyl-piperazin-1-yl)-1-methyl-ethyl]-pyridin-3-yl}-amide The title compound is prepared from 5-cyano-1H-imidazole-2-carboxylic acid [2-(4,4-dimethyl-cyclohex-1-enyl)-6-(1-hydroxy-1-methyl-ethyl)-pyridin-3-yl]-amide (as prepared in the previous step), N-ethylpiperizine, and thionyl chloride in DCM solvent according to the procedure in Example 14, step (e).

Example 57

5-Cyano-1H-imidazole-2-carboxylic acid {2-(4,4-dimethyl-cyclohex-1-enyl)-6-[1-methyl-1-(4-methyl-piperazin-1-yl)-ethyl]-pyridin-3-yl}-amide

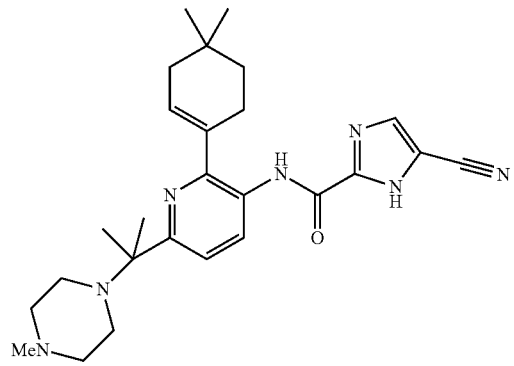 [SMILES: CN1CCN(C(C)(C)c2ccc(NC(=O)c3ncc(C#N)[nH]3)c(C3=CCC(C)(C)CC3)n2)CC1]

a) 5-Cyano-1H-imidazole-2-carboxylic acid {2-(4,4-dimethyl-cyclohex-1-enyl)-6-[1-methyl-1-(4-methyl-piperazin-1-yl)-ethyl]-pyridin-3-yl}-amide The title compound is prepared from 5-cyano-1H-imidazole-2-carboxylic acid [2-(4,4-dimethyl-cyclohex-1-enyl)-6-(1-hydroxy-1-methyl-ethyl)-pyridin-3-yl]-amide (as prepared in Example 56, step (e)), N-methylpiperizine and thionyl chloride in DCM solvent according to the procedure in Example 14, step (e).

Example 58

5-Cyano-1H-imidazole-2-carboxylic acid [2-(4,4-dimethyl-cyclohex-1-enyl)-6-(1-methyl-1-morpholin-4-yl-ethyl)-pyridin-3-yl]-amide

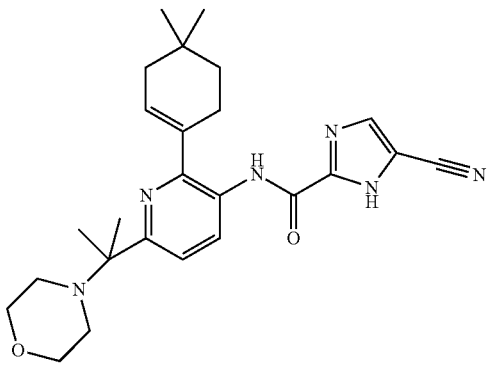 [SMILES: CC1(C)CC=C(c2nc(C(C)(C)N3CCOCC3)ccc2NC(=O)c2ncc(C#N)[nH]2)CC1]

a) 5-Cyano-1H-imidazole-2-carboxylic acid [2-(4,4-dimethyl-cyclohex-1-enyl)-6-(1-methyl-1-morpholin-4-yl-ethyl)-pyridin-3-yl]-amide The title compound is prepared from 5-cyano-1H-imidazole-2-carboxylic acid [2-(4,4-dimethyl-cyclohex-1-enyl)-6-(1-hydroxy-1-methyl-ethyl)-pyridin-3-yl]-amide (as prepared in Example 56, step (e)), morpholine, and thionyl chloride in DCM solvent according to the procedure in Example 14, step (e).

Example 59

5-Cyano-1H-imidazole-2-carboxylic acid {2-(4,4-dimethyl-cyclohex-1-enyl)-6-[1-(2-methoxy-ethyl-amino)-1-methyl-ethyl]-pyridin-3-yl}-amide

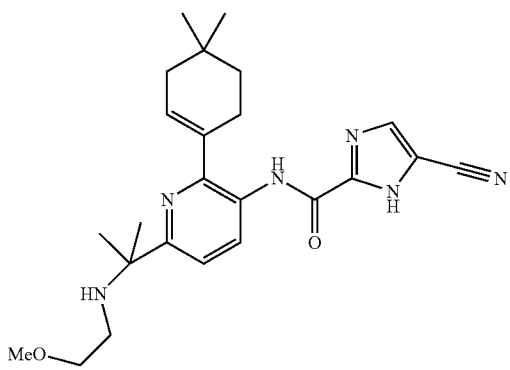 [SMILES: COCCNC(C)(C)c1ccc(NC(=O)c2ncc(C#N)[nH]2)c(C2=CCC(C)(C)CC2)n1]

a) 4-Cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide

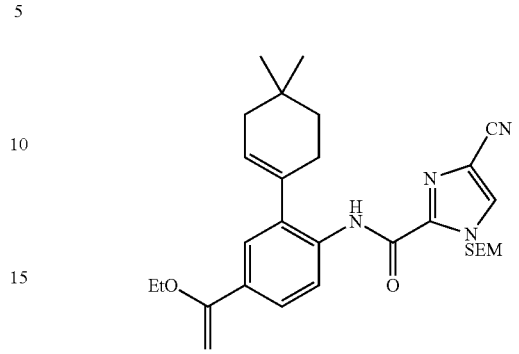

To a round bottom flask containing 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in Example 56, step (c), 32 mg, 0.060 mmol), Pd(PPh$_3$)$_4$ (7 mg, 0.006 mmol), and tributyl-(1-ethoxy-vinyl)-stannane (30 mg, 0.080 mmol) was added DMF (0.7 mL) and the resultant solution was allowed to stir at 100° C. overnight. The reaction was diluted with EtOAc (25 mL), washed with water (2×25 mL), dried (Na$_2$SO$_4$) and concentrated in vacuo. Purification of the residue by preparative TLC (20% EtOAc-hexanes) afforded 12 mg (43%) of the title compound as an oil. Mass spectrum (ESI, m/z): Calcd. for C$_{28}$H$_{39}$N$_5$O$_3$Si, 522.2 (M+H). found 522.3.

b) 5-Cyano-1H-imidazole-2-carboxylic acid [6-acetyl-2-(4,4-dimethyl-cyclohex-1-enyl)-pyridin-3-yl]-amide

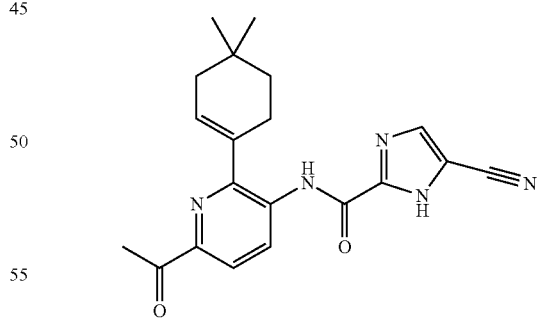

The title compound was prepared from 5-cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide (as prepared in the previous step, 12 mg, 0.023 mmol) according to the procedure in Example 1, step (g) (4.4 mg, 52%). Mass spectrum (ESI, m/z): Calcd. for C$_{20}$H$_{21}$N$_5$O$_2$, 364.1 (M+H). found 364.1.

c) 5-Cyano-1H-imidazole-2-carboxylic acid [2-(di-methyl-cyclohex-1-enyl)-6-(1-hydroxy-1-methyl-ethyl)-pyridin-3-yl]-amide

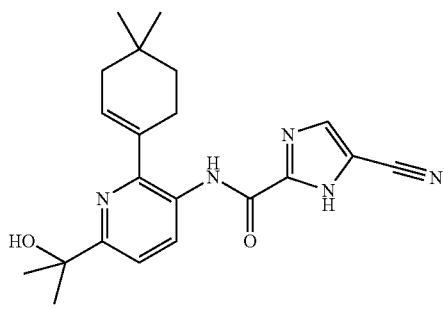

To a solution of 5-cyano-1H-imidazole-2-carboxylic acid [6-acetyl-2-(4,4-dimethyl-cyclohex-1-enyl)-pyridin-3-yl]-amide (as prepared in the previous step, 6 mg, 0.016 mmol) in THF (1 mL) was added methylmagnesium bromide (MeMgBr) (3 M in THF, 41 µL, 0.072 mmol). After 20 min another 2.5 equivalents of MeMgBr was added and the reaction was allowed to warm to room temperature and quenched with saturated aqueous $NaHCO_3$ (2 mL). The slurry was filtered through a 5-g Sep-Pak and concentrated in vacuo. The crude product was purified by silica gel chromatography (250-mg, 3-mL Supelco Si-tube, gradient $CHCl_3$-2% $CHCl_3$-MeOH) to afford 2.6 mg (43%) of the title compound as a white solid. $^1$H-NMR ($CD_3OD$; 400 MHz): δ 8.44 (d, 1H, J=8.5 Hz), 7.90 (s, 1H), 7.42 (d, 1H, J=8.5 Hz), 5.86 (s, 1H), 2.39-2.37 (m, 2H), 1.99-1.94 (m, 2H), 1.51 (t, 1H, J=6.3 Hz), 1.43 (s, 6H), 0.99 (s, 6H). Mass spectrum (ESI, m/z): Calcd. for $C_{21}H_{25}N_5O_2$, 380.2 (M+H). found 380.1.

d) 5-Cyano-1H-imidazole-2-carboxylic acid {2-(dimethyl-cyclohex-1-enyl)-6-[1-(2-methoxy-ethyl-amino)-1-methyl-ethyl]-pyridin-3-yl}-amide The title compound is prepared from 5-cyano-1H-imidazole-2-carboxylic acid [2-(4,4-dimethyl-cyclohex-1-enyl)-6-(1-hydroxy-1-methyl-ethyl)-pyridin-3-yl]-amide (as prepared in Example 59, step (e)), methoxyethylamine and thionyl chloride in DCM solvent according to the procedure in Example 14, step (e).

Example 60

5-Cyano-1H-imidazole-2-carboxylic acid [2-(4,4-dimethyl-cyclohex-1-enyl)-4-(2-morpholin-4-yl-ethyl)-phenyl]-amide hydrochloride

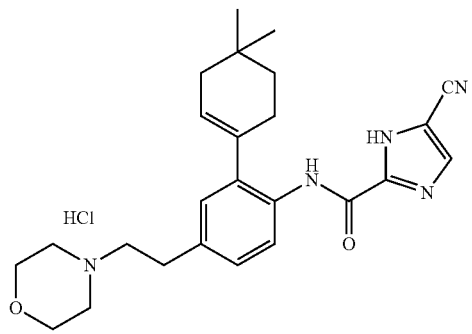 [SMILES: CC1(C)CC=C(c2cc(CCN3CCOCC3)ccc2NC(=O)c2ncc(C#N)[nH]2)CC1 ; Cl]

a) 2-(4,4-Dimethyl-cyclohex-1-enyl)-4-(2-morpholin-4-yl-ethyl)-phenylamine

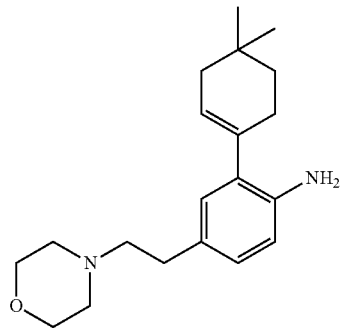 [SMILES: CC1(C)CC=C(c2cc(CCN3CCOCC3)ccc2N)CC1]

The title compound was prepared by Suzuki coupling of 2-bromo-4-(2-morpholin-4-yl-ethyl)-phenylamine (as prepared in Example 33, step (b)) and 4,4-dimethyl-1-cyclohexen-1-ylboronic acid according to the procedure in Example 1, step (e). Mass spectrum (ESI, m/z): Calcd. for $C_{20}H_{30}N_2O$, 315.2 (M+H). found 315.1.

b) 5-Cyano-1H-imidazole-2-carboxylic acid [2-(4,4-dimethyl-cyclohex-1-enyl)-4-(2-morpholin-4-yl-ethyl)-phenyl]-amide hydrochloride The title compound was prepared by coupling 4-cyano-1-(2-trimethylsilanyl-ethoxymethyl)-1H-imidazole-2-carboxylate potassium salt (as prepared in Example 1, step (d)) and 2-(4,4-dimethyl-cyclohex-1-enyl)-4-(2-morpholin-4-yl-ethyl)-phenylamine (as prepared in the previous step) according to the procedure in Example 34, step (c), followed by SEM deprotection according to the procedure in Example 34, step (d). The hydrochloride salt was prepared from the trifluoroacetic acid salt using a BioRad AG2-X8 resin, ion form. $^1$H-NMR (400 MHz, DMSO-$d_6$) δ 14.27 (br s, 1H), 10.58 (br s, 1H), 9.77 (s, 1H), 8.34 (s, 1H), 7.95 (d, J=8.2 Hz, 1H), 7.21 (dd, J=8.2, 1.9 Hz, 1H), 7.17 (d, J=1.9 Hz, 1H), 5.68 (m, 1H), 4.04-3.96 (m, 2H), 3.82-3.70 (m, 2H), 3.54-3.46 (m, 2H), 3.15-2.98 (m, 6H), 2.31-2.22 (m, 2H), 1.96 (m, 2H), 1.49 (t, J=6.2 Hz, 2H), 1.01 (s, 6H). Mass spectrum (ESI, m/z): Calcd. for $C_{25}H_{31}N_5O_2$, 434.2 (M+H). found 434.2.

Example 61

4-Cyano-1H-imidazole-2-carboxylic acid {2-(4,4-dimethyl-cyclohex-1-enyl)-4-[1-methyl-1-(2-morpholin-4-yl-ethoxy)-ethyl]-pheny}-amide

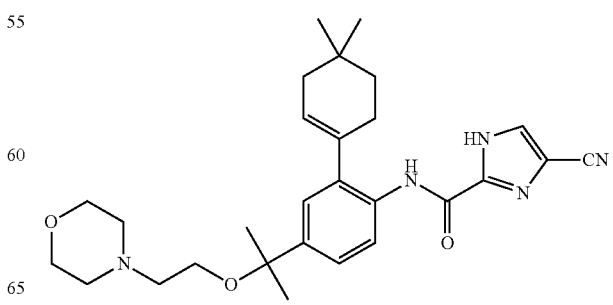

To a suspension of 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d), 50.0 mg, 0.132 mmol) in 1 mL of DCM at −15° C. was added oxalyl chloride (16 μL, 0.20 mmol) under Ar. After stirring at RT for 1 h, the mixture was cooled back to −15° C. To the reaction was added 2-hydroxylethylmorpholine (80 μL, 0.66 mmol) and the resulting mixture was warmed to RT and stirred for 16 h under Ar. Treated with EtOAc (30 mL), the mixture was washed with aqueous saturated NH$_4$Cl (10 mL), H$_2$O (10 mL) and brine (10 mL). The organic layer was dried over Na$_2$SO$_4$ and concentrated in vacuo. The residue was purified by silica gel chromatography (1-3% MeOH/DCM) to afford the title compound (29 mg, 44%) as a white solid. $^1$H-NMR (CDCl$_3$; 400 MHz): δ 9.68 (s, 1H), 8.31 (d, 1H, J=8.6 Hz), 7.72 (s, 1H), 7.37 (dd, 1H, J=8.6, 2.3 Hz), 7.21 (d, 1H, J=2.3 Hz), 5.77 (m, 1H), 3.71 (t, 4H, J=4.7 Hz), 3.34 (t, 2H, J=6.2 Hz), 2.61 (t, 2H, J=6.2 Hz), 2.54 (m, 4H), 2.25-2.31 (m, 2H), 2.07-2.13 (m, 2H), 1.59 (t, 2H, J=6.3 Hz), 1.52 (s, 6H), 1.11 (s, 6H). Mass spectrum (ESI, m/z): Calcd. for C$_{28}$H$_{37}$N$_5$O$_3$, 492.3 (M+H). found 492.0.

Example 62

4-Cyano-1H-imidazole-2-carboxylic acid (2-(4,4-dimethyl-cyclohex-1-enyl)-4-{1-[4-(2-hydroxy-ethyl)-piperazin-1-yl]-1-methyl-ethyl}-phenyl)-amide

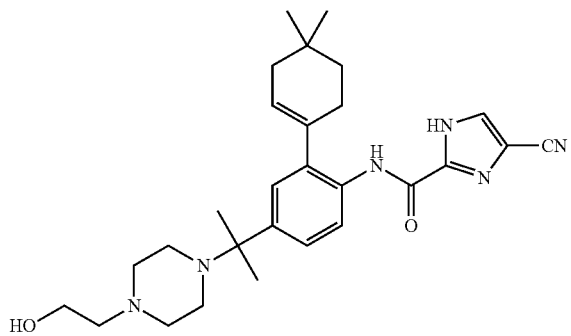 [SMILES: CC1(C)CC=C(c2cc(C(C)(C)N3CCN(CCO)CC3)ccc2NC(=O)c2nc(C#N)c[nH]2)CC1]

a) 1-(4-Amino-3-bromo-phenyl)-ethanone

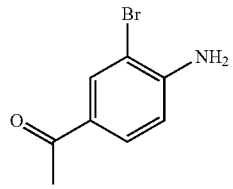

To a solution of 4-aminoacetophenone (5.67 g, 0.0419 mol) in 30 mL of CH$_3$CN at 0° C. was added N-bromosuccinimide (7.83 g, 0.0439 mol) in 20 mL of CH$_3$CN dropwise. The reaction was allowed to warm to room temperature and concentrated in vacuo after stirring 16 h. The crude residue was dissolved in EtOAc (100 mL), washed with saturated aqueous NaHCO$_3$ (1×100 mL), brine (1×100 mL) and dried (Na$_2$SO$_4$). The solvent was removed under vacuum to afford the title compound (7.62 g, 85%) as a yellow solid. Mass spectrum (ESI, m/z): Calcd. for C$_8$H$_8$BrNO, 213.9 (M+H). found 214.0.

b) 1-[4-Amino-3-(4,4-dimethyl-cyclohex-1-enyl)-phenyl]-ethanone

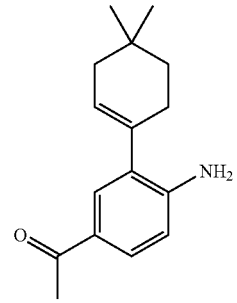 [SMILES: CC(=O)c1ccc(N)c(C2=CCC(C)(C)CC2)c1]

To a slurry of 1-(4-amino-3-bromo-phenyl)-ethanone (20.5 g, 0.960 mol, as prepared in the previous step), 2-dicyclohexylphosphino-2',6'-dimethoxy-1,1'-biphenyl (3.94 g, 9.60 mmol), and K$_3$PO$_4$ (61.0 g, 0.280 mol) in 250 mL of toluene was added 2-(4,4-dimethyl-cyclohex-1-enyl)-4,4,5,5-tetramethyl-[1,3,2]dioxaborolane (24.9 g, 0.100 mol) followed by Pd$_2$(dba)$_3$ (4.39 g, 4.80 mmol). The resultant mixture was heated to 100° C. with vigorous stirring. After 3 h, the reaction was filtered and concentrated in vacuo. Purification of the residue by column chromatography (20% EtOAc-hexane) afforded the title compound (15.0 g, 64%). Mass spectrum (ESI, m/z): Calcd. for C$_{16}$H$_{21}$NO, 244.1 (M+H). found 244.2.

c) 4-Cyano-1-(2-trimethylsilanyl-ethoxymethyl)-1H-imidazole-2-carboxylic acid [4-acetyl-2-(4,4-dimethyl-cyclohex-1-enyl)-phenyl]-amide

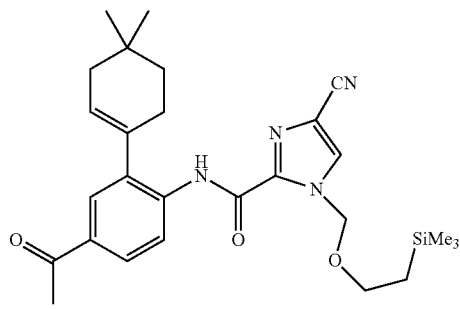 [SMILES: CC(=O)c1ccc(NC(=O)c2nc(C#N)cn2COCC[Si](C)(C)C)c(C2=CCC(C)(C)CC2)c1]

To a solution of 1-[4-amino-4,4-dimethyl-cyclohex-1-enyl)-phenyl]-ethanone (7.86 g, 0.0320 mol, as prepared in the previous step), 4-cyano-1-(2-trimethylsilanyl-ethoxymethyl)-1H-imidazole-2-carboxylate potassium salt (13.7 g, 0.0450 mol, as prepared in Example 1, step (d)), and PyBroP (22 g, 0.048 mol) in 120 mL of DMF was added DIEA (13.9 mL, 0.0800 mol) and the reaction was allowed to stir overnight. The reaction was then poured into 300 mL of water and stirred vigorously at 0° C. for 30 min and filtered. The solids were azeotropically dried by evaporation from 100 mL of toluene and then under vacuum. The crude oil was dissolved in 100 mL of DCM and triturated with hexanes to afford 8.20 g of the title compound. The mother liquor was concentrated and dissolved in 50 mL of DCM followed by trituration with hexanes to afford another 3.50 g affording a total of 11.7 g (75%) of the title compound. Mass spectrum (ESI, m/z): Calcd. for $C_{27}H_{36}N_4O_3Si$, 493.2 (M+H). found 493.1.

d) 4-Cyano-1H-imidazole-2-carboxylic acid [4-acetyl-2-(4,4-dimethyl-cyclohex-1-enyl)-phenyl]-amide

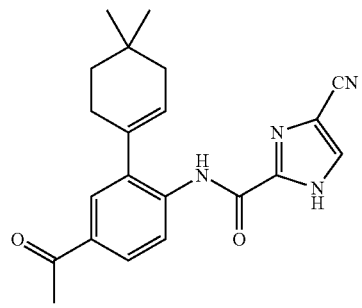 [SMILES: CC(=O)c1ccc(NC(=O)c2nc(C#N)c[nH]2)c(C2=CCC(C)(C)CC2)c1]

A solution of 4-cyano-1-(2-trimethylsilanyl-ethoxymethyl)-1H-imidazole-2-carboxylic acid [4-acetyl-2-(4,4-dimethyl-cyclohex-1-enyl)-phenyl]-amide (8.2 g, 0.016 mol, as prepared in the previous step) in 50 mL of DCM was treated with 6 mL of EtOH followed by 42 mL of TFA. The reaction was stirred for 1 h 45 min, at which time it was diluted with MeOH (100 mL), concentrated to half of the volume and diluted with diethyl ether (80 mL). The result was concentrated in vacuo and dried under vacuum overnight to afford the title compound as a yellow solid (6.00 g, 100%). Mass spectrum (ESI, m/z): Calcd. for $C_{21}H_{22}N_4O_2$, 363.1 (M+H). found 363.1.

e) 4-Cyano-1H-imidazole-2-carboxylic acid [2-(4,4-dimethyl-cyclohex-1-enyl)-4-(1-hydroxy-1-methyl-ethyl)phenyl]-amide

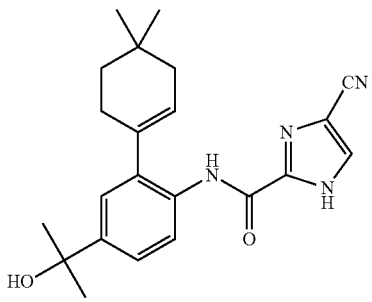 [SMILES: CC1(C)CC=C(c2cc(C(C)(C)O)ccc2NC(=O)c2nc(C#N)c[nH]2)CC1]

To a slurry of 4-cyano-1H-imidazole-2-carboxylic acid [4-acetyl-2-(4,4-dimethyl-cyclohex-1-enyl)-phenyl]-amide (6.00 g, 0.0160 mol) in 100 mL of THF at −78° C. was added a solution of MeMgBr (3.0 M in THF, 22 mL, 0.066 mol) via syringe over a 20-min period. The reaction was allowed to warm to ca. 0° C. over a 30-min period at which point there was no starting material evident by thin layer chromatography (10% MeOH—CHCl₃). The reaction was cooled to −78° C., quenched by the addition of saturated aqueous NH₄Cl (100 mL) and allowed to warm to 0° C. The mixture was extracted with ether (2×150 mL) and dried (Na₂SO₄).

The solvent was concentrated to afford the title compound as a white solid (6.40 g, 100%). The NMR and mass spectral data were identical to those for the compound produced in Example 14, step (d).

f) 4-Cyano-1H-imidazole-2-carboxylic acid (2-(4,4-dimethyl-cyclohex-1-enyl)-4-{1-[4-(2-hydroxy-ethyl)-piperazin-1-yl]-1-methyl-ethyl}-phenyl)-amide To a suspension of 4-cyano-1H-imidazole-2-carboxylic acid [2-(4,4-dimethyl-cyclohex-1-enyl)-4-(1-hydroxy-1-methyl-ethyl)-phenyl]-amide (as prepared in the previous step, 50.0 mg, 0.132 mmol) in 2 mL of DCM at −15° C. was added SOCl₂ (29 µL, 0.40 mmol) under Ar. After stirring at RT for 1 h, the mixture was cooled back to −15° C. To the reaction was added 2-hydroxylethylpiperazine (162 µL, 1.32 mmol). After stirring at −15° C. for 1 h, the resulting mixture was warmed to RT and stirred for 16 h under Ar. Treated with EtOAc (30 mL), the mixture was washed with H₂O (2×10 mL) and brine (10 mL). The organic layer was dried over Na₂SO₄ and concentrated in vacuo. The residue was purified by silica gel chromatography (2-6% MeOH/DCM) to afford the title compound (37.5 mg, 58%) as a white solid. ¹H-NMR (CD₃OD; 400 MHz): δ 8.12 (d, 1H, J=8.6 Hz), 7.93 (s, 1H), 7.42 (dd, 1H, J=8.6, 2.3 Hz), 7.34 (d, 1H, J=2.3 Hz), 5.72 (m, 1H), 3.70 (t, 2H, J=6.1 Hz), 2.52-2.77 (m, 10H), 2.25-2.32 (m, 2H), 2.04-2.10 (m, 2H), 1.59 (t, 2H, J=6.2 Hz), 1.38 (s, 6H), 1.08 (s, 6H). Mass spectrum (ESI, m/z): Calcd. for $C_{28}H_{38}N_6O_2$, 491.3 (M+H). found 491.0.

Example 63

4-Cyano-1H-imidazole-2-carboxylic acid (2-(4,4-dimethyl-cyclohex-1-enyl)-4-{1-[4-(2-hydroxy-ethyl)-piperazin-1-yl]-1-methyl-ethyl}-phenyl)-amide hydrochloride

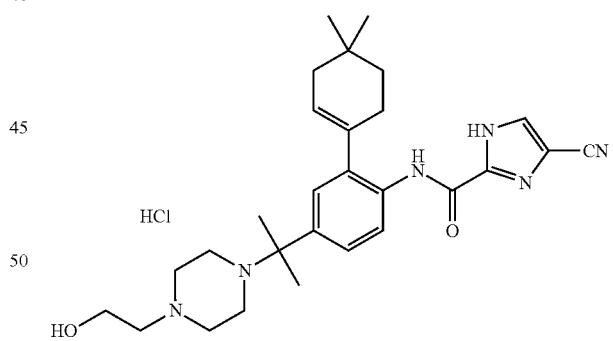

To a solution of 4-cyano-1H-imidazole-2-carboxylic acid (2-(4,4-dimethyl-cyclohex-1-enyl)-4-{1-[4-(2-hydroxy-ethyl)-piperazin-1-yl]-1-methyl-ethyl}-phenyl)-amide (as prepared in Example 62, 162.0 mg, 0.330 mmol) in 2 mL of EtOH was added a 2 N HCl ether solution (165 µL, 0.330 mmol). The mixture was stirred at RT for 0.5 h, 1 mL of diethyl ether (Et₂O) was added and the resulting mixture was heated at 60° C. for 1 min until the solution turned clear. The mixture was cooled down to RT and the solid was collected by filtration and washed with Et₂O. Upon drying in vacuo, the title compound (92 mg, 53%) was obtained as an off-white solid. ¹H-NMR (CD₃OD; 400 MHz): δ 8.42 (d, 1H, J=8.6 Hz), 8.04 (s, 1H), 7.70 (dd, 1H, J=8.6, 2.0 Hz), 7.64 (br s, 1H), 5.83 (m, 1H), 3.91 (m, 2H), 3.40-3.93 (m, 4H), 3.37 (m, 2H), 2.33-2.40 (m, 2H), 2.05-2.12 (m, 2H), 1.72-2.00 (br s, 6H), 1.62 (t, 2H, J=6.5 Hz), 1.07 (s, 6H). Mass spectrum (ESI, m/z): Calcd. for $C_{28}H_{38}N_6O_2$, 491.3 (M+H). found 491.1.

Example 64

(4-{1-[4-[(4-Cyano-1H-imidazole-2-carbonyl)-amino]-3-(4,4-dimethyl-cyclohex-1-enyl)-phenyl]-1-methyl-ethyl}-piperazin-1-yl)-acetic acid, sodium salt

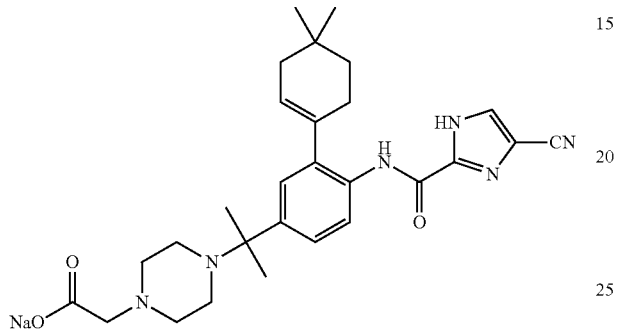

To a solution of (4-{1-[4-[(4-cyano-1H-imidazole-2-carbonyl)-amino]-3-(4,4-dimethyl-cyclohex-1-enyl)-phenyl]-1-methyl-ethyl}-piperazin-1-yl)-acetic acid ethyl ester (as prepared in Example 79, 72.0 mg, 0.135 mmol) in 5 mL of 1:1 THF/MeOH was added 6 N NaOH (225 µL, 1.35 mmol). After stirring at RT for 16 h, the mixture was washed with 1:2 EtOAc/hexane (3×10 mL). The aqueous layer was treated with 50 mL of brine and extracted with EtOAc (5×30 mL). The combined organic layers were washed with $H_2O$ (4×20 mL) and dried ($Na_2SO_4$). The organic solvent was evaporated in vacuo to give the title compound (66 mg, 92%) as a white solid. $^1$H-NMR (CD$_3$OD; 400 MHz): δ 8.14 (d, 1H, J=8.6 Hz), 7.85 (s, 1H), 7.44 (dd, 1H, J=8.6, 2.0 Hz), 7.34 (d, 1H, J=2.0 Hz), 5.72 (m, 1H), 3.43 (s, 2H), 3.00-3.19 (br s, 4H), 2.74 (br s, 4H), 2.24-2.34 (m, 2H), 2.05-2.11 (m, 2H), 1.58 (t, 2H, J=6.3 Hz), 1.41 (s, 6H), 1.07 (s, 6H). Mass spectrum (ESI, m/z): Calcd. for $C_{28}H_{35}N_6NaO_3$, 505.3 (M-Na+2H). found 504.9.

Example 65

4-Cyano-1H-imidazole-2-carboxylic acid {2-(4,4-dimethyl-cyclohex-1-enyl)-4-[1-(2-hydroxy-ethylamino)-1-methyl-ethyl]-pheny}-amide hydrochloride

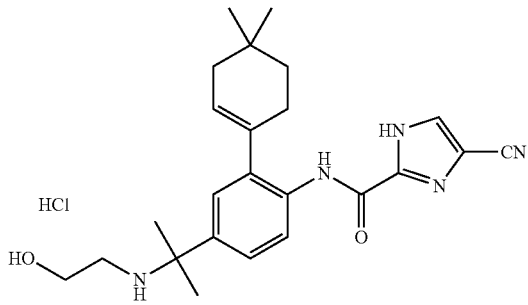 [SMILES: CC1(C)CC=C(c2cc(C(C)(C)NCCO)ccc2NC(=O)c2nc(C#N)c[nH]2)CC1 ; Cl]

The title compound was prepared from 4-cyano-1H-imidazole-2-carboxylic acid {2-(4,4-dimethyl-cyclohex-1-enyl)-4-[1-(2-hydroxy-ethylamino)-1-methyl-ethyl]-phenyl}-amide (as prepared in Example 78) and 2N HCl in ether according to the procedure as described in Example 63. $^1$H-NMR (CD$_3$OD; 400 MHz): δ 8.37 (d, 1H, J=8.6 Hz), 8.02 (s, 1H), 7.50 (dd, 1H, J=8.6, 2.3 Hz), 7.44 (d, 1H, J=2.3 Hz), 5.81 (m, 1H), 3.70 (t, 2H, J=5.1 Hz), 2.83 (t, 2H, J=5.1 Hz), 2.31-2.38 (m, 2H), 2.07-2.13 (m, 2H), 1.81 (s, 6H), 1.62 (t, 2H, J=6.3 Hz), 1.11 (s, 6H). Mass spectrum (ESI, m/z): Calcd. for $C_{24}H_{31}N_5O_2$, 422.3 (M+H). found 421.9.

Example 66

4-Cyano-1H-imidazole-2-carboxylic acid [2-cyclohex-1-enyl-4-(1-morpholin-4-ylmethyl-vinyl)-phenyl]-amide trifluoroacetic acid salt

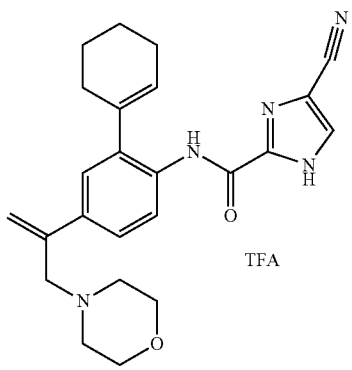 [SMILES: C=C(CN1CCOCC1)c1ccc(NC(=O)c2nc(C#N)c[nH]2)c(C2=CCCCC2)c1]

a) 4-Cyano-1-(2-trimethylsilanyl-ethoxymethyl)-1H-imidazole-2-carboxylic acid [2-cyclohex-1-enyl-4-(2-hydroxy-1-hydroxymethyl-ethyl)-phenyl]-amide

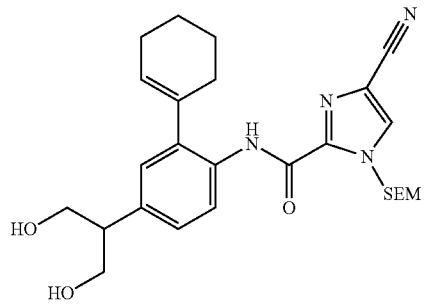 [SMILES: C[Si](C)(C)CCOCn1cc(C#N)nc1C(=O)Nc1ccc(C(CO)CO)cc1C1=CCCCC1]

To a solution of acetic acid 3-acetoxy-2-(4-{[4-cyano-1-(2-trimethylsilanyl-ethoxymethyl)-1H-imidazole-2-carbonyl]-amino}-3-cyclohex-1-enyl-phenyl)-propyl ester (580 mg, 1.00 mmol, as prepared in Example 12, step (c)) in isopropylalcohol (i-PrOH) (15 mL), 2N NaOH (1 mL, 2 mmol) was added. The reaction mixture was stirred at RT for 1 h, and DCM (200 mL) and water (200 mL) were added. The organic layer was separated, dried ($Na_2SO_4$) and concentrated. The residue was purified on silica (40% EtOAc-hexane) to obtain the title compound (312 mg, 63%). Mass spectrum (ESI, m/z): Calcd. for $C_{26}H_{36}N_4O_4Si$, 497.2 (M+H). found 497.0.

b) Methanesulfonic acid 2-(4-{[4-cyano-1-(2-trimethylsilanyl-ethoxymethyl)-1H-imidazole-2-carbonyl]-amino}-3-cyclohex-1-enyl-phenyl)-3-methanesulfonyloxy-propyl ester

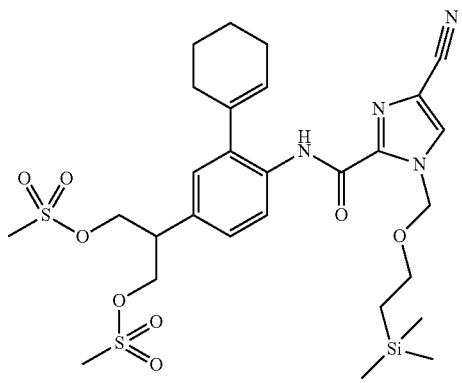 [SMILES: C[Si](C)(C)CCOCn1cc(C#N)nc1C(=O)Nc1ccc(C(COS(C)(=O)=O)COS(C)(=O)=O)cc1C1=CCCCC1]

A solution of 4-cyano-1-(2-trimethylsilanyl-ethoxymethyl)-1H-imidazole-2-carboxylic acid [2-cyclohex-1-enyl-4-(2-hydroxy-1-hydroxymethyl-ethyl)-phenyl]-amide (0.600 g, 1.21 mmol, as prepared in the previous step) in $CH_2Cl_2$ (25 mL) was cooled to 0° C. and was treated with $Et_3N$ (421 µL, 3.02 mmol) and methanesulfonyl chloride (190 µL, 2.42 mmol). The mixture was stirred at 0° C. for 2 h, diluted with $CH_2Cl_2$, and washed with water. The organic layer was dried over $MgSO_4$ and concentrated in vacuo. Silica gel chromatography of the residue with 25-50% EtOAc-hexane afforded the title compound (0.551 g, 70%) as a white solid. Mass spectrum (APCI, m/z): Calcd. for $C_{28}H_{40}N_4O_8S_2Si$, 653.2 (M+H). found 652.8.

c) 4-Cyano-1H-imidazole-2-carboxylic acid [2-cyclohex-1-enyl-4-(1-morpholin-4-ylmethyl-vinyl)-phenyl]-amide trifluoroacetic acid salt A solution of methanesulfonic acid 2-(4-{[4-cyano-1-(2-trimethylsilanyl-ethoxymethyl)-1H-imidazole-2-carbonyl]-amino}-3-cyclohex-1-enyl-phenyl)-3-methanesulfonyloxy-propyl ester (30.0 mg, 0.0460 mmol, as prepared in the previous step) in THF (1 mL) was treated with morpholine (200 µL, 2.29 mmol) and heated to 50° C. for 19 h. The mixture was diluted with EtOAc and washed with water. The organic layer was dried over $MgSO_4$ and concentrated in vacuo. The residue was treated with a solution of 20% TFA in $CH_2Cl_2$ (1 mL) at room temperature overnight. Purification of the residue by RP-HPLC (C18) with 10-80% $CH_3CN$ in 0.1% $TFA/H_2O$ over 25 min afforded 4.0 mg (15%) of the title compound as a white solid. $^1$H-NMR ($CD_3OD$; 400 MHz): δ 8.24 (d, 1H, J=8.0 Hz), 7.93 (s, 1H), 7.39 (dd, 1H, J=8.0, 2.0 Hz), 7.31 (d, 1H, 2.0 Hz), 5.80-5.76 (m, 1H), 5.74 (s, 1H), 5.56 (s, 1H), 4.22 (s, 2H), 3.96-3.55 (m, 4H), 3.37-3.04 (m, 4H), 2.26-2.16 (m, 4H), 1.82-1.67 (m, 4H). Mass spectrum (ESI, m/z): Calcd. for $C_{24}H_{27}N_5O_2$, 418.2 (M+H). found 418.4.

Example 67

4-Cyano-1H-imidazole-2-carboxylic acid (2-cyclohex-1-enyl-4-{1-[(2-methoxy-ethylamino)-methyl]-vinyl}-phenyl)-amide trifluoroacetic acid salt

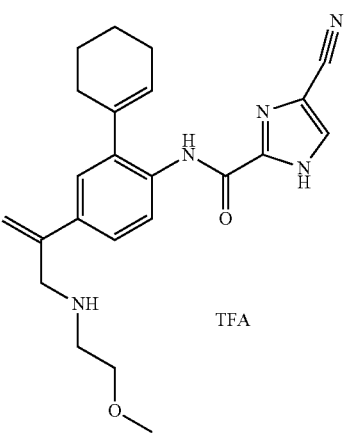 [SMILES: C=C(CNCCOC)c1ccc(NC(=O)c2nc(C#N)c[nH]2)c(C2=CCCCC2)c1 ; "TFA"]

The title compound was prepared from methanesulfonic acid 2-(4-{[4-cyano-1-(2-trimethylsilanyl-ethoxymethyl)-1H-imidazole-2-carbonyl]-amino}-3-cyclohex-1-enyl-phenyl)-3-methanesulfonyloxy-propyl ester (as prepared in Example 66, step (b)) and 2-methoxy-ethylamine according to the procedure of Example 66, step (c). $^1$H-NMR ($CD_3OD$; 400 MHz): δ 8.33 (d, 1H, J=8.8 Hz), 8.04 (s, 1H), 7.47 (dd, 1H, J=8.8 Hz, 2.0 Hz), 7.38 (dd, 1H, J=2.0 Hz), 5.93-5.86 (m, 1H), 5.76 (s, 1H), 5.53 (s, 1H), 4.19 (s, 2H), 3.71-3.65 (m, 2H), 3.42 (s, 3H), 3.30-3.25 (m, 2H), 2.37-2.28 (m, 4H), 1.95-1.79 (m, 4H). Mass spectrum (APCI, m/z): Calcd. for $C_{23}H_{27}N_5O_2$, 406.2 (M+H). found 406.2.

Example 68

4-Cyano-1H-imidazole-2-carboxylic acid [2-cyclohex-1-enyl-4-(1-methylaminomethyl-vinyl)-phenyl]-amide trifluoroacetic acid salt

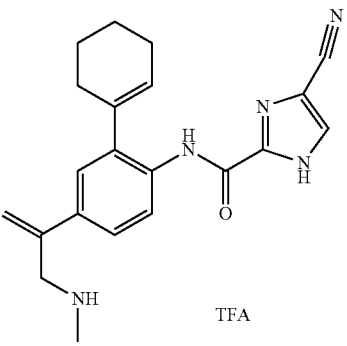 [SMILES: C=C(CNC)c1ccc(NC(=O)c2nc(C#N)c[nH]2)c(C2=CCCCC2)c1 ; "TFA"]

The title compound was prepared from methanesulfonic acid 2-(4-{[4-cyano-1-(2-trimethylsilanyl-ethoxymethyl)-1H-imidazole-2-carbonyl]-amino}-3-cyclohex-1-enyl-phenyl)-3-methanesulfonyloxy-propyl ester (as prepared in Example 66, step (b)) and methylamine solution in THF according to the procedure of Example 66, step (c). $^1$H-NMR ($CD_3OD$;

400 MHz): δ 8.33 (d, 1H, J=8.4 Hz), 8.03 (s, 1H), 7.46 (dd, 1H, J=8.4 Hz, 2.4 Hz), 7.37 (d, 1H, J=2.4 Hz), 5.91-5.85 (m, 1H), 5.74 (s, 1H), 5.49 (s, 1H), 4.14 (s, 2H), 2.73 (s, 3H), 2.35-2.26 (m, 4H), 1.93-1.77 (m, 4H). Mass spectrum (ESI, m/z): Calcd. for $C_{21}H_{23}N_5O$, 362.2 (M+H). found 362.3.

Example 69

4-Cyano-1H-imidazole-2-carboxylic acid {2-(4,4-dimethyl-cyclohex-1-enyl)-4-[1-(2-methoxy-ethyl-amino)-1-methyl-ethyl]-pheny}-amide hydrochloride salt

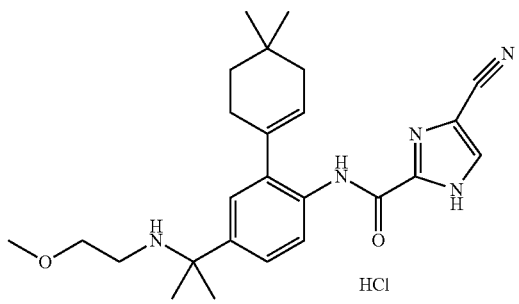 [SMILES: COCCNC(C)(C)c1ccc(NC(=O)c2nc(C#N)c[nH]2)c(C2=CCC(C)(C)CC2)c1 ; Cl]

A solution of 4-cyano-1H-imidazole-2-carboxylic acid {2-(4,4-dimethyl-cyclohex-1-enyl)-4-[1-(2-methoxy-ethyl-amino)-1-methyl-ethyl]-phenyl}-amide (750 mg, 1.72 mmol, as prepared in Example 20) in isopropanol (dissolved with heating) was treated with HCl (331 µL, 1.72 mmol, 5.2 M in isopropanol) at RT for 1 h. The resulting precipitate was filtered, washed with cold hexanes, and dried under high vacuum to afford the title compound (438 mg, 54%) as a white solid. $^1$H-NMR (CD$_3$OD; 400 MHz): δ 8.40 (d, 1H, J=9.2 Hz), 8.04 (s, 1H), 7.50 (dd, 1H, J=9.2, 2.8 Hz), 7.43 (d, 1H, J=2.8 Hz), 5.86-5.80 (m, 1H), 3.59-3.52 (m, 2H), 3.38 (s, 3H), 2.97-2.89 (m, 2H), 2.40-2.32 (m, 2H), 2.16-2.10 (m, 2H), 1.82 (s, 6H), 1.68-1.60 (m, 2H), 1.13 (s, 6H). Mass spectrum (APCI, m/z): Calcd. for $C_{25}H_{33}N_5O_2$, 436.3 (M+H). found 435.8.

Example 70

4-Cyano-1H-imidazole-2-carboxylic acid {2-(4,4-dimethyl-cyclohex-1-enyl)-4-[1-(4-methoxy-benzyl-sulfanyl)-1-methyl-ethyl]-pheny}-amide

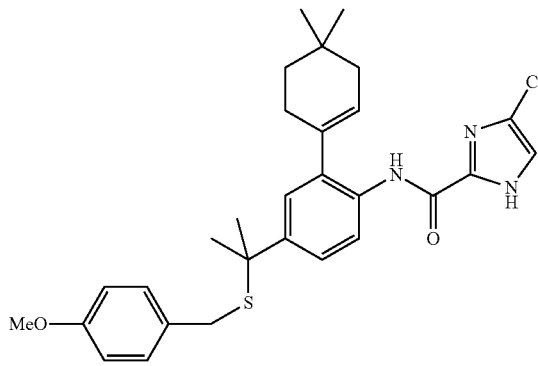

To a mixture of 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d), 86 mg, 0.22 mmol) and (4-methoxy-phenyl)-methanethiol (157 µL, 1.13 mmol) in 2 mL of DCM at 0° C. was added 175 µL (2.27 mmol) of TFA. The mixture was allowed to warm to room temperature overnight, at which time it was diluted with DCM (20 mL), washed with water (1×20 mL), dried (Na$_2$SO$_4$) and concentrated in vacuo. The residue was purified by preparative TLC on silica gel (5% methanol-CHCl$_3$) to afford the title compound (63 mg, 54%). $^1$H-NMR (CDCl$_3$; 400 MHz): δ 12.78 (br s, 1H), 9.75 (s, 1H), 8.32 (d, 1H, J=8.6 Hz), 7.75 (s, 1H), 7.51 (dd, 1H, J=7.5, 2.1 Hz), 7.41 (d, 1H, J=2.1 Hz), 7.04 (d, 2H, J=8.6 Hz), 6.75 (d, 2H, J=8.6 Hz), 5.80 (m, 1H), 3.75 (s, 3H), 3.41 (s, 2H), 2.31 (m, 2H), 2.13 (m, 2H), 1.72 (s, 6H), 1.61 (t, 2H, J=6.2 Hz), 1.12 (s, 6H).

Example 71

Thioacetic acid S-{1-[4-[(4-cyano-1H-imidazole-2-carbonyl)-amino]-3-(4,4-dimethyl-cyclohex-1-enyl)-phenyl]-1-methyl-ethyl}ester

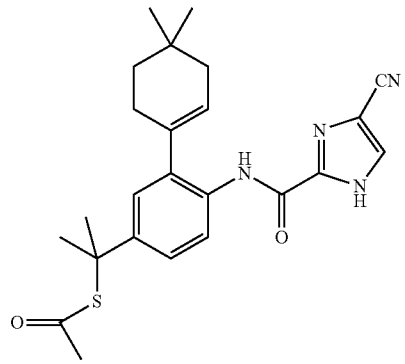 [SMILES: CC(=O)SC(C)(C)c1ccc(NC(=O)c2nc(C#N)c[nH]2)c(C2=CCC(C)(C)CC2)c1]

The title compound was prepared from 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d)) and thioacetic acid using the conditions described in Example 70. $^1$H-NMR (CDCl$_3$; 400 MHz): δ 9.73 (s, 1H), 8.29 (d, 1H, J=8.6 Hz), 7.74 (s, 1H), 7.49-7.47 (m, 1H), 7.35 (d, 1H, J=2.2 Hz), 5.79 (m, 1H), 2.32-2.28 (m, 2H), 2.20 (s, 3H), 2.11 (m, 2H), 1.86 (s, 6H), 1.59 (t, 2H, J=6.2 Hz), 1.11 (s, 6H).

Example 72

4-Cyano-1H-imidazole-2-carboxylic acid {2-(4,4-dimethyl-cyclohex-1-enyl)-4-[1-methyl-1-(pyridin-2-ylamino)-ethyl]-pheny}-amide

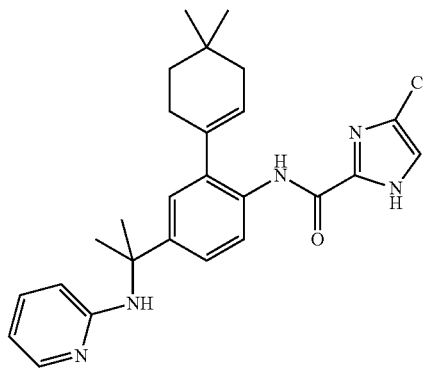

To a mixture of 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d), 120 mg, 0.317 mmol) and 2-aminopyridine (448 mg, 4.76 mmol) in 5 mL of DCM at 0° C. was added 244 µL (3.17 mmol) of TFA. The mixture was allowed to warm to room temperature, at which time it was cooled in an ice bath and filtered. The filtrate was concentrated in vacuo with MeOH (10 mL) and purified by preparative thin layer chromatography ((2×) with 10% MeOH—CHCl$_3$) to afford 2.5 mg (2%) of the title compound as a white solid. $^1$H-NMR (CDCl$_3$-CD$_3$OD; 400 MHz): δ 8.16 (d, 1H, J=8.6 Hz), 7.88 (m, 1H), 7.64 (s, 1H), 7.29 (m, 1H), 7.18 (d, 1H, J=2.0 Hz), 7.16-7.11 (m, 1H), 7.47-7.44 (m, 1H), 5.81 (d, 1H, J=8.6 Hz), 5.66 (m, 1H), 2.16-2.13 (m, 2H), 1.99 (m, 2H), 1.59 (s, 6H), 1.52-1.44 (m, 2H), 0.99 (s, 6H). Mass spectrum (ESI, m/z): Calcd. for C$_{27}$H$_{30}$N$_6$O 455.2 (M+H). found 455.1.

Example 73

4-Cyano-1H-imidazole-2-carboxylic acid {2-(4,4-dimethyl-cyclohex-1-enyl)-4-[1-methyl-1-(6-methyl-pyridin-2-ylamino)-ethyl]-pheny}-amide

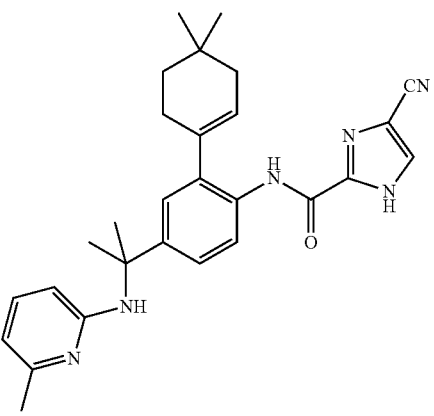 [SMILES: Cc1cccc(NC(C)(C)c2ccc(NC(=O)c3nc(C#N)c[nH]3)c(C3=CCC(C)(C)CC3)c2)n1]

The title compound was prepared from 4-cyano-1H-imidazole-2-carboxylic acid [2-(4,4-dimethyl-cyclohex-1-enyl)-4-(1-hydroxy-1-methyl-ethyl)-phenyl]-amide (as prepared in Example 14, step (d)) and 2-amino-6-methylpyridine using the conditions described in Example 72. $^1$H-NMR (CDCl$_3$-CD$_3$OD; 400 MHz): δ 8.26 (dd, 1H, J=8.6, 2.0 Hz), 7.76 (s, 1H), 7.54-7.49 (m, 1H), 7.28-7.22 (m, 1H), 7.14 (d, 1H, J=2.2 Hz), 6.58 (d, 1H, J=7.3 Hz), 6.07 (m, 1H), 5.67 (m, 1H), 2.46 (s, 3H), 2.20-2.14 (m, 2H), 2.00 (m, 2H), 1.71 (s, 6H), 1.51-1.48 (m, 2H), 1.00 (s, 6H). Mass spectrum (ESI, m/z): Calcd. for C$_{28}$H$_{32}$N$_6$O, 469.2 (M+H). found 469.1.

The following examples were produced according to procedures of previous examples with the corresponding reagents as indicated in the table below:

| | Example | Name | Structure | Procedure | Reagents |
|---|---|---|---|---|---|
| 74 | | 4-Cyano-1H-imidazole-2-carboxylic acid {2-(4,4-dimethyl-cyclohex-1-enyl)-4-[1-(4-ethyl-piperazin-1-yl)-1-methyl-ethyl]-phenyl}-amide | 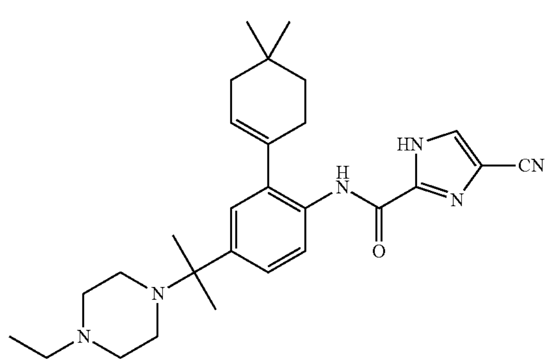 [SMILES: CCN1CCN(C(C)(C)c2ccc(NC(=O)c3nc(C#N)c[nH]3)c(C3=CCC(C)(C)CC3)c2)CC1] | 62 | |

(ESI-neg, m/z)

Calcd. for C$_{28}$H$_{38}$N$_6$O, 473.3

(M − H), found 473.5.

-continued

| Example | Name | Structure | Procedure | Reagents |
|---|---|---|---|---|
| 75 | 4-Cyano-1H-imidazole-2-carboxylic acid [4-[1-(4-acetyl-piperazin-1-yl)-1-methyl-ethyl]-2-(4,4-dimethyl-cyclohex-1-enyl)-phenyl]-amide | 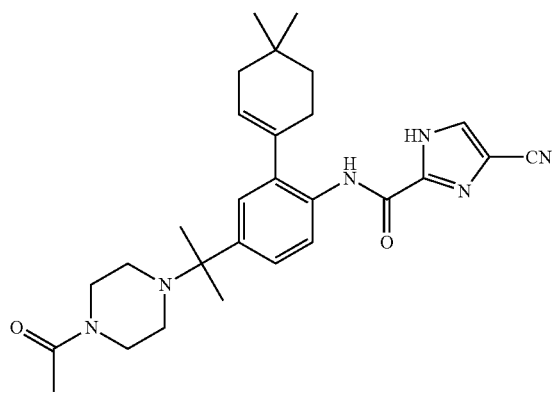 [SMILES: CC(=O)N1CCN(C(C)(C)c2ccc(NC(=O)c3nc(C#N)c[nH]3)c(C3=CCC(C)(C)CC3)c2)CC1]<br>(ESI-neg, m/z)<br>Calcd. for $C_{28}H_{36}N_6O_2$,<br>487.3 (M − H), found 487.5. | 62 | 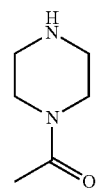 |
| 76 | 4-Cyano-1H-imidazole-2-carboxylic acid [4-[1-(2-acetylamino-ethylamino)-1-methyl-ethyl]-2-(4,4-dimethyl-cyclohex-1-enyl)-phenyl]-amide | 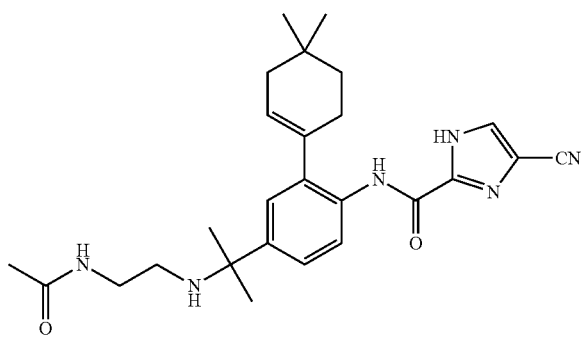 [SMILES: CC(=O)NCCNC(C)(C)c1ccc(NC(=O)c2nc(C#N)c[nH]2)c(C2=CCC(C)(C)CC2)c1]<br>(ESI, m/z)<br>Calcd. for $C_{26}H_{34}N_6O_2$,<br>463.3 (M + H), found 463.0. | 62 | 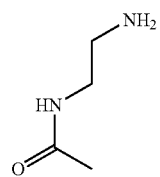 |
| 77 | 4-Cyano-1H-imidazole-2-carboxylic acid (2-(4,4-dimethyl-cyclohex-1-enyl)-4-{1-[4-(2-methoxy-ethyl)-piperazin-1-yl]-1-methyl-ethyl}-phenyl)-amide | 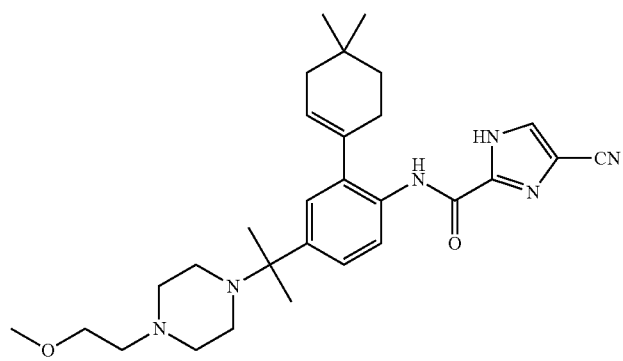 [SMILES: COCCN1CCN(C(C)(C)c2ccc(NC(=O)c3nc(C#N)c[nH]3)c(C3=CCC(C)(C)CC3)c2)CC1]<br>(ESI-neg, m/z)<br>Calcd. for $C_{29}H_{40}N_6O_2$,<br>503.3 (M − H), found 503.5. | 62 | 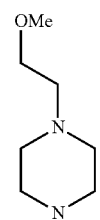 |

| Example | Name | Structure | Procedure | Reagents |
|---|---|---|---|---|
| 78 | 4-Cyano-1H-imidazole-2-carboxylic acid {2-(4,4-dimethyl-cyclohex-1-enyl)-4-[1-(2-hydroxy-ethylamino)-1-methyl-ethyl]-phenyl}-amide | (APCI, m/z) Calcd. for $C_{24}H_{31}N_5O_2$, 422.3 (M + H), found 421.7. | 62 | |
| 79 | (4-{1-[4-[(4-Cyano-1H-imidazole-2-carbonyl)-amino]-3-(4,4-dimethyl-cyclohex-1-enyl)-phenyl]-1-methyl-ethyl}-piperazin-1-yl)-acetic acid ethyl ester | (ESI, m/z) Calcd. for $C_{30}H_{40}N_6O_3$, 533.3 (M + H), found 533.0. | 62 | |
| 80 | 4-Cyano-1H-imidazole-2-carboxylic acid {2-(4,4-dimethyl-cyclohex-1-enyl)-4-[1-methyl-1-(2-pyrrolidin-1-yl-ethoxy)-ethyl]-phenyl}-amide | (ESI, m/z) Calcd. for $C_{28}H_{37}N_5O_2$, 476.3 (M + H), found 476.1. | 61 | |

The following examples are produced according to procedures of previous examples with the corresponding reagents as indicated in the table below:

| Example No. | Name | Structure | Procedure Reference | Reagents |
|---|---|---|---|---|
| 61 | 4-Cyano-1H-imidazole-2-carboxylic acid {2-(4,4-dimethyl-cyclohex-1-enyl)-4-[1-methyl-1-(2-morpholin-4-yl-ethoxy)-ethyl]-phenyl}-amide | 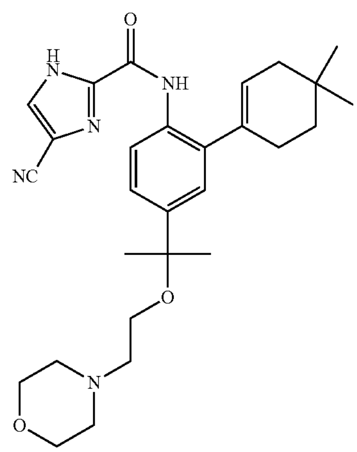 [SMILES: CC1(C)CC=C(c2cc(C(C)(C)OCCN3CCOCC3)ccc2NC(=O)c2nc(C#N)c[nH]2)CC1] | Example 52 | |
| 74 | 4-Cyano-1H-imidazole-2-carboxylic acid {2-(4,4-dimethyl-cyclohex-1-enyl)-4-[1-(4-ethyl-piperazin-1-yl)-1-methyl-ethyl]-phenyl}-amide | 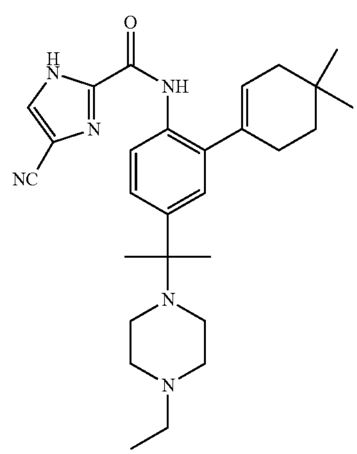 [SMILES: CCN1CCN(C(C)(C)c2ccc(NC(=O)c3nc(C#N)c[nH]3)c(C3=CCC(C)(C)CC3)c2)CC1] | Example 14, step (e) | |
| 75 | 4-Cyano-1H-imidazole-2-carboxylic acid [4-[1-(4-acetyl-piperazin-1-yl)-1-methyl-ethyl]-2-(4,4-dimethyl-cyclohex-1-enyl)-phenyl]-amide | 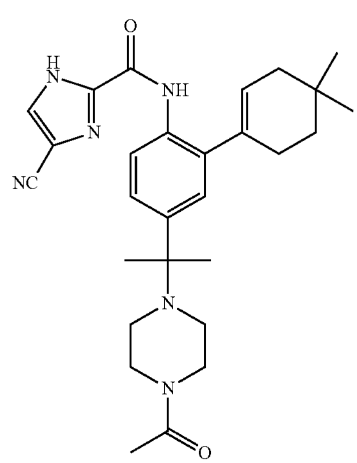 [SMILES: CC(=O)N1CCN(C(C)(C)c2ccc(NC(=O)c3nc(C#N)c[nH]3)c(C3=CCC(C)(C)CC3)c2)CC1] | Example 14, step (e) | |

-continued

| Example No. | Name | Structure | Procedure Reference | Reagents |
|---|---|---|---|---|
| 76 | 4-Cyano-1H-imidazole-2-carboxylic acid [4-[1-(2-acetylamino-ethylamino)-1-methyl-ethyl]-2-(4,4-dimethyl-cyclohex-1-enyl)-phenyl]-amide | 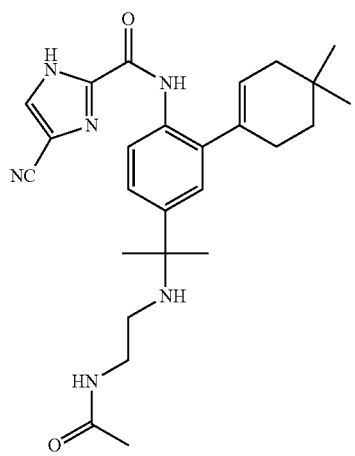 [SMILES: CC(=O)NCCNC(C)(C)c1ccc(NC(=O)c2nc(C#N)c[nH]2)c(C2=CCC(C)(C)CC2)c1] | Example 14, step (e) | 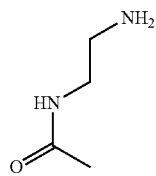 |
| 80 | 4-Cyano-1H-imidazole-2-carboxylic acid {2-(4,4-dimethyl-cyclohex-1-enyl)-4-[1-methyl-1-(2-pyrrolidin-1-yl-ethoxy)-ethyl]-phenyl}-amide | 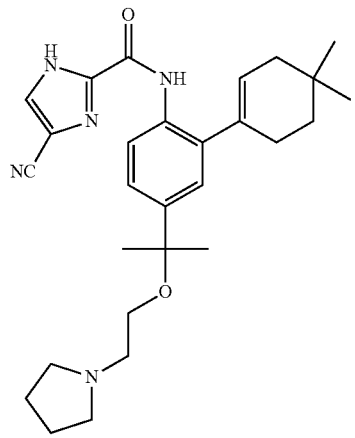 [SMILES: CC1(C)CC=C(c2cc(C(C)(C)OCCN3CCCC3)ccc2NC(=O)c2nc(C#N)c[nH]2)CC1] | Example 52 | 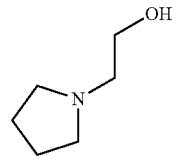 |
| 81 | 4-Cyano-1H-imidazole-2-carboxylic acid {2-(4,4-dimethyl-cyclohex-1-enyl)-4-[1-methyl-1-(2-pyrrolidin-1-yl-ethylamino)-ethyl]-phenyl}-amide | 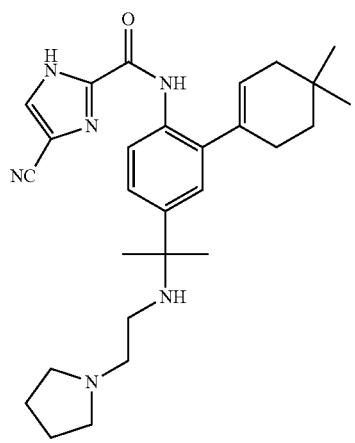 | Example 14, step (e) | 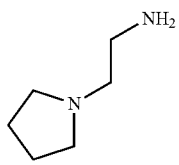 |

| Example No. | Name | Structure | Procedure Reference | Reagents |
|---|---|---|---|---|
| 82 | 4-Cyano-1H-pyrrole-2-carboxylic acid {2-(4,4-dimethyl-cyclohex-1-enyl)-4-[1-methyl-1-(2-pyrrolidin-1-yl-ethoxy)-ethyl]-phenyl}-amide | 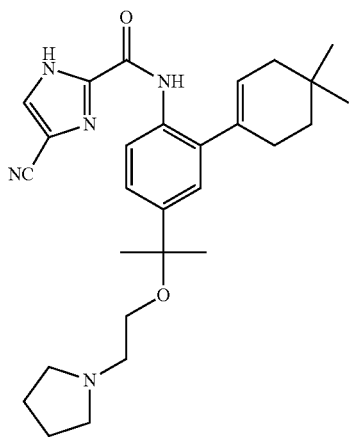 [SMILES: CC1(C)CC=C(c2cc(C(C)(C)OCCN3CCCC3)ccc2NC(=O)c2nc(C#N)c[nH]2)CC1] | Example 14, steps (b), (d); Example 52 | 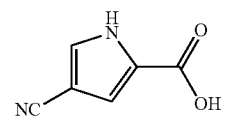 (Canadian J. Chem. 59, 2673 (1981)); 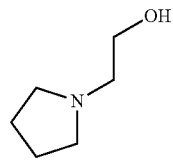 |
| 83 | 4-Cyano-1H-pyrrole-2-carboxylic acid {2-(4,4-dimethyl-cyclohex-1-enyl)-4-[1-methyl-1-(2-morpholin-4-yl-ethoxy)-ethyl]-phenyl}-amide | 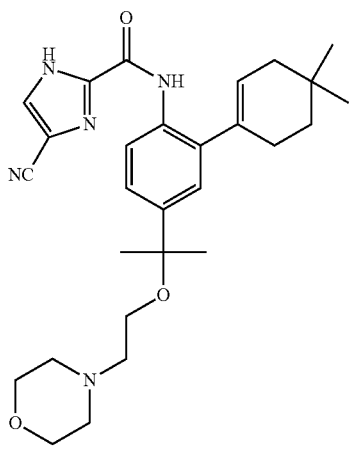 [SMILES: CC1(C)CC=C(c2cc(C(C)(C)OCCN3CCOCC3)ccc2NC(=O)c2nc(C#N)c[nH]2)CC1] | Example 14, steps (b), (d); Example 52 | 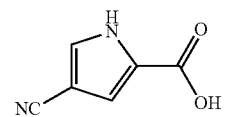 (Canadian J. Chem. 59, 2673 (1981)); 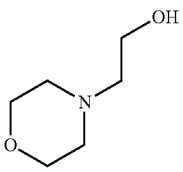 |
| 84 | 4-Cyano-1H-imidazole-2-carboxylic acid {2-cyclohex-1-enyl-4-[1 methyl-1-(3-pyrrolidin-1-yl-propoxy)-ethyl]-phenyl}-amide | 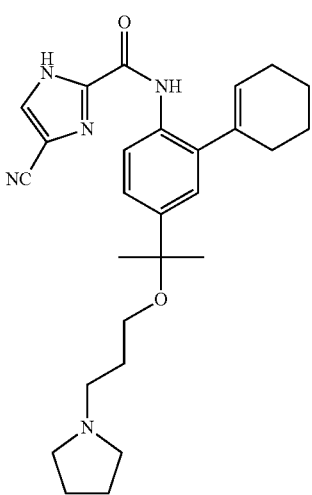 [SMILES: CC(C)(OCCCN1CCCC1)c1ccc(NC(=O)c2nc(C#N)c[nH]2)c(C2=CCCCC2)c1] | Example 14, step (a)-(d); Example 52 | 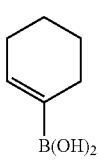 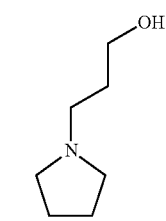 Bioorg Med Chem Lett, 15(1), 107-113; (2005) |

-continued

| Example No. | Name | Structure | Procedure Reference | Reagents |
|---|---|---|---|---|
| 85 | 4-Cyano-1H-imidazole-2-carboxylic acid {4-[1-(1,1-dioxo-1λ6-thiomorpholin-4-yl)-1-ethyl-propyl]-2-spiro[4.5]dec-7-en-8-yl-phenyl}-amide | 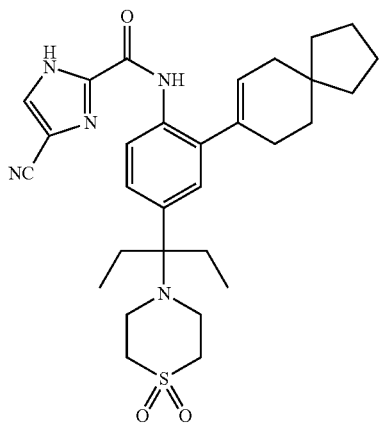 [SMILES: CCC(CC)(c1ccc(NC(=O)c2nc(C#N)c[nH]2)c(C2=CCC3(CCCC3)CC2)c1)N1CCS(=O)(=O)CC1] | Example 14, steps (a)-(e); Example 16 | Pentan-3-one; 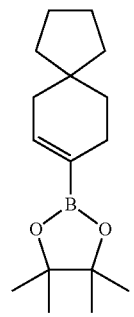 (WO2005063705) |
| 86 | 4-Cyano-1H-imidazole-2-carboxylic acid [4-[1-(4-ethyl-piperazin-1-yl)-1-methyl-ethyl]-2-(4-methyl-piperidin-1-yl)-phenyl]-amide | 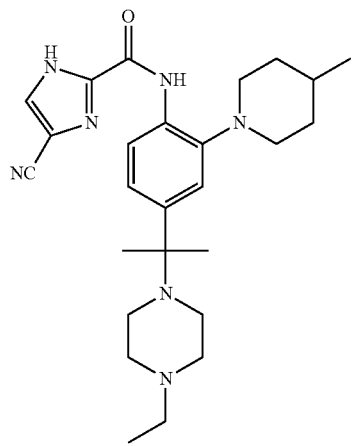 [SMILES: CCN1CCN(C(C)(C)c2ccc(NC(=O)c3nc(C#N)c[nH]3)c(N3CCC(C)CC3)c2)CC1] | Example 14, Steps (b)-(e), | 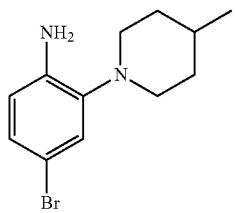 (US2005131022 A1) 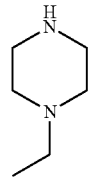 |
| 87 | 4-Cyano-1H-imidazole-2-carboxylic acid {2-(4-methyl-piperidin-1-yl)-4-[1-methyl-1-(2-pyrrolidin-1-yl-ethoxy)-ethyl]-phenyl}-amide | 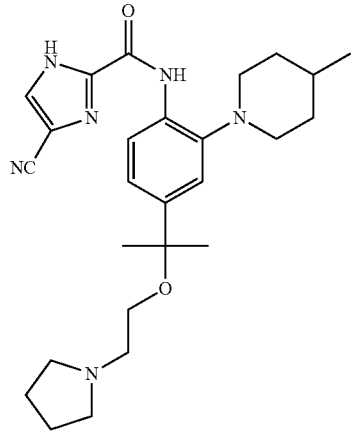 [SMILES: CC1CCN(c2cc(C(C)(C)OCCN3CCCC3)ccc2NC(=O)c2nc(C#N)c[nH]2)CC1] | Example 14, steps (b)-(d); Example 52 | 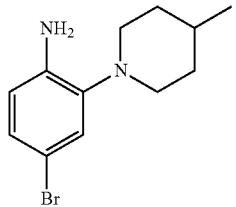 (US2005131022 A1); 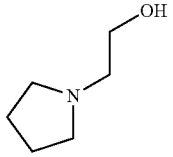 |

-continued

| Example No. | Name | Structure | Procedure Reference | Reagents |
|---|---|---|---|---|
| 88 | 4-Cyano-1H-pyrrole-2-carboxylic acid [4-[1-(4-acetyl-piperazin-1-yl)-1-ethyl-propyl]-2-(4-methyl-piperidin-1-yl)-phenyl]-amide | 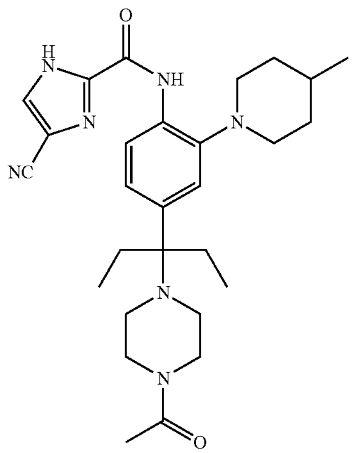 [SMILES: CCC(CC)(c1ccc(NC(=O)c2nc(C#N)c[nH]2)c(N2CCC(C)CC2)c1)N1CCN(C(C)=O)CC1] | Example 14, Steps (b), (d), (e) | (Canadian J. Chem. 59, 2673 (1981)); (US2005131022 A1); Pentan-3-one; |
| 89 | 4-Cyano-1H-imidazole-2-carboxylic acid [4-[1-(2-methoxy-ethylamino)-1-methyl-ethyl]-2-(4-methyl-piperidin-1-yl)-phenyl]-amide | 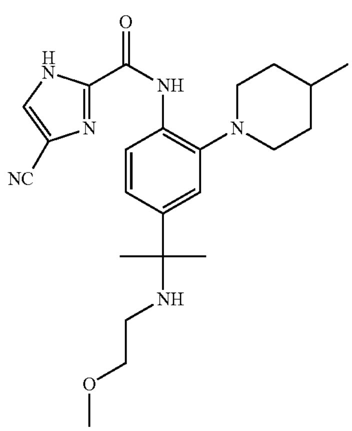 [SMILES: COCCNC(C)(C)c1ccc(NC(=O)c2nc(C#N)c[nH]2)c(N2CCC(C)CC2)c1] | Example 14, Steps (b)-(e) | (US2005131022 A1); |
| 90 | 4-Cyano-1H-pyrrole-2-carboxylic acid [4-[1-(2-methoxy-ethylamino)-1-methyl-ethyl]-2-(4-methyl-piperidin-1-yl)-phenyl]-amide | 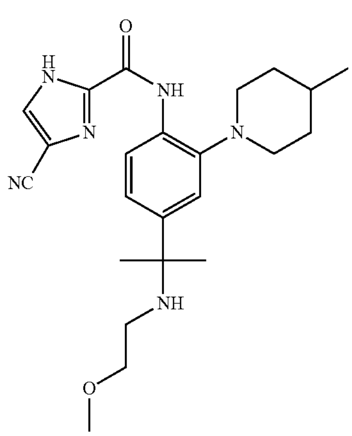 [SMILES: COCCNC(C)(C)c1ccc(NC(=O)c2nc(C#N)c[nH]2)c(N2CCC(C)CC2)c1] | Example 14, Steps (b), (d), (e) | (Canadian J. Chem. 59, 2673 (1981)); (US2005131022 A1); |

-continued

| Example No. | Name | Structure | Procedure Reference | Reagents |
|---|---|---|---|---|
| | | | | H₂N—CH₂CH₂—O—CH₃ |
| 91 | 2-[4-[(4-Cyano-1H-imidazole-2-carbonyl)-amino)-3-(4-methyl-piperidin-1-yl)-phenyl]-2-methyl-propionic acid | 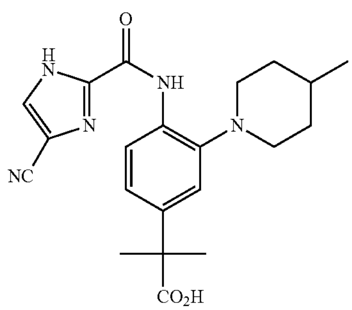 [SMILES: CC1CCN(c2cc(C(C)(C)C(=O)O)ccc2NC(=O)c2nc(C#N)c[nH]2)CC1] | Example 14, step (b); Example 13, step (a)-(c). | 2-amino-5-bromo-(4-methylpiperidin-1-yl)benzene (US2005131022 A1) |
| 92 | 2-[4-[(4-Cyano-1H-pyrrole-2-carbonyl)-amino]-3-(4-methyl-piperidin-1-yl)-phenyl]-2-methyl-propionic acid | 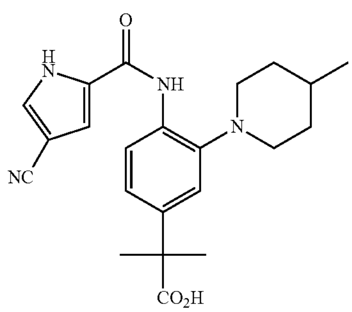 [SMILES: CC1CCN(c2cc(C(C)(C)C(=O)O)ccc2NC(=O)c2cc(C#N)c[nH]2)CC1] | Example 14, step (b); Example 13, step (a), (c). | 2-amino-5-bromo-(4-methylpiperidin-1-yl)benzene (US2005131022 A1); 4-cyano-1H-pyrrole-2-carboxylic acid (*Canadian J. Chem.* 59, 2673 (1981)) |
| 93 | 2-[4-[(5-Cyano-furan-2-carbonyl)-amino)-3-(4-methyl-piperidin-1-yl)-phenyl]-2-methyl-propionic acid | 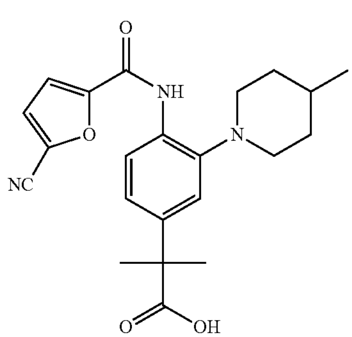 [SMILES: CC1CCN(c2cc(C(C)(C)C(=O)O)ccc2NC(=O)c2ccc(C#N)o2)CC1] | Example 14, step (b); Example 13, step (a), (c). | 5-cyano-furan-2-carboxylic acid (WO2004096795 A2); 2-amino-5-bromo-(4-methylpiperidin-1-yl)benzene (US2005131022 A1) |

-continued

| Example No. | Name | Structure | Procedure Reference | Reagents |
|---|---|---|---|---|
| 94 | 2-[4-[(4-Cyano-1H-pyrrole-2-carbonyl)-amino]-3-(4,4-dimethyl-cyclohex-1-enyl)-phenyl]-2-methyl-propionic acid | 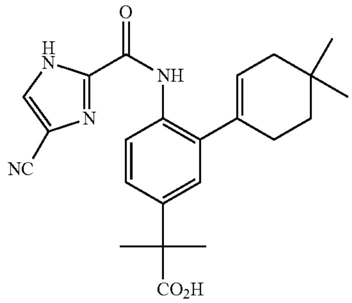 [SMILES: CC1(C)CC=C(c2cc(C(C)(C)C(=O)O)ccc2NC(=O)c2nc(C#N)c[nH]2)CC1] | Example 14, step (b); Example 13, step (a), (c). | (Canadian J. Chem. 59, 2673 (1981)) |
| 95 | 2-[4-[(5-Cyano-furan-2-carbonyl)-amino]-3-(4,4-dimethyl-cyclohex-1-enyl)-phenyl]-2-methyl-propionic acid | 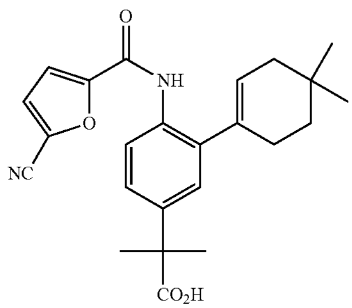 [SMILES: CC1(C)CC=C(c2cc(C(C)(C)C(=O)O)ccc2NC(=O)c2ccc(C#N)o2)CC1] | Example 14, step (b); Example 13, step (a), (c). | (WO2004096795 A2) |
| 96 | 4-Cyano-1H-imidazole-2-carboxylic acid {2-(4,4-dimethyl-cyclohex-1-enyl)-4-[2-(4-ethyl-piperazin-1-yl)-ethyl]-phenyl}-amide | 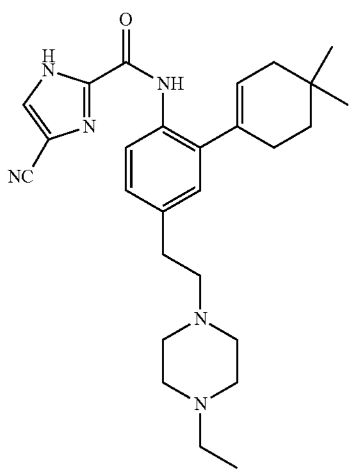 [SMILES: CCN1CCN(CCc2ccc(NC(=O)c3nc(C#N)c[nH]3)c(C3=CCC(C)(C)CC3)c2)CC1] | Example 33, steps (a)-(c); Example 25, steps (e) and (f) | |
| 97 | 4-Cyano-1H-imidazole-2-carboxylic acid [2-(4,4-dimethyl-cyclohex-1-enyl)-4-(2-thiomorpholin-4-yl-ethyl)-phenyl]-amide | 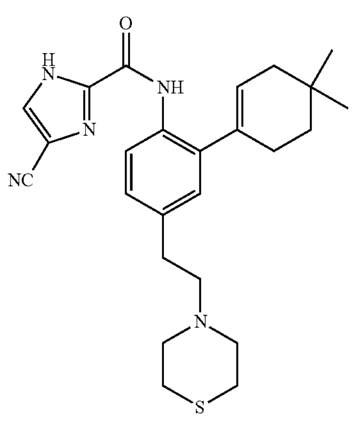 [SMILES: CC1(C)CC=C(c2cc(CCN3CCSCC3)ccc2NC(=O)c2nc(C#N)c[nH]2)CC1] | Ex. 33, steps (a)-(c); Ex. 25, steps (e) and (f) | |

-continued

| Example No. | Name | Structure | Procedure Reference | Reagents |
|---|---|---|---|---|
| 98 | 4-Cyano-1H-imidazole-2-carboxylic acid {2-(4,4-dimethyl-cyclohex-1-enyl)-4-[2-(1-oxo-1$\lambda^4$-thiomorpholin-4-yl)-ethyl]-phenyl}-amide | 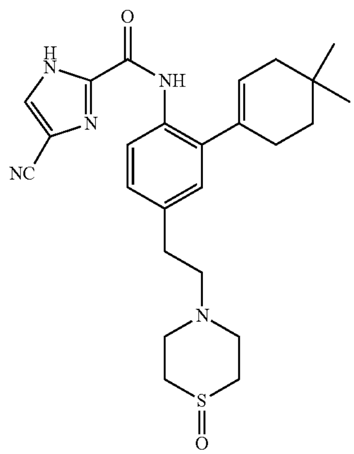 [SMILES: CC1(C)CC=C(c2cc(CCN3CCS(=O)CC3)ccc2NC(=O)c2nc(C#N)c[nH]2)CC1] | Ex. 33, steps (a)-(c); Ex. 25, steps (e) and (f); Ex. 15 | |
| 99 | 4-Cyano-1H-imidazole-2-carboxylic acid {2-(4,4-dimethyl-cyclohex-1-enyl)-4-[2-(1,1-dioxo-1$\lambda^6$-thiomorpholin-4-yl)-ethyl]-phenyl}-amide | 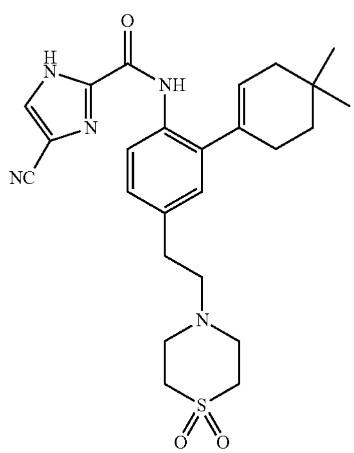 [SMILES: CC1(C)CC=C(c2cc(CCN3CCS(=O)(=O)CC3)ccc2NC(=O)c2nc(C#N)c[nH]2)CC1] | Ex. 33, steps (a)-(c); Ex. 25, steps (e) and (f); Ex. 15; Ex. 16 | |
| 100 | 4-Cyano-1H-imidazole-2-carboxylic acid [4-(2-imidazol-1-yl-ethyl)-2-spiro[4.5]dec-7-en-8-yl-phenyl]-amide | 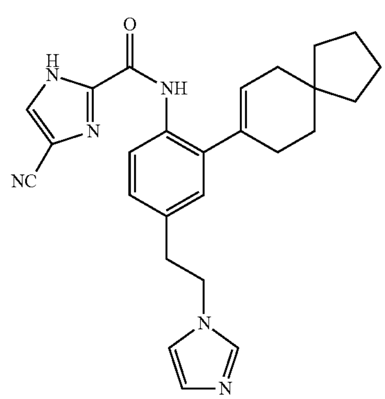 [SMILES: N#Cc1c[nH]c(C(=O)Nc2ccc(CCn3ccnc3)cc2C2=CCC3(CCCC3)CC2)n1] | Ex. 33, steps (a)-(c); Ex. 25, steps (e) and (f) | |

(WO2005063705)

-continued
| Example No. | Name | Structure | Procedure Reference | Reagents |
|---|---|---|---|---|
| 101 | 4-Cyano-1H-pyrrole-2-carboxylic acid {2-(4,4-dimethyl-cyclohex-1-enyl)-4-[2-(1,1-dioxo-1$\lambda^6$-thiomorpholin-4-yl)-ethyl] phenyl}-amide | 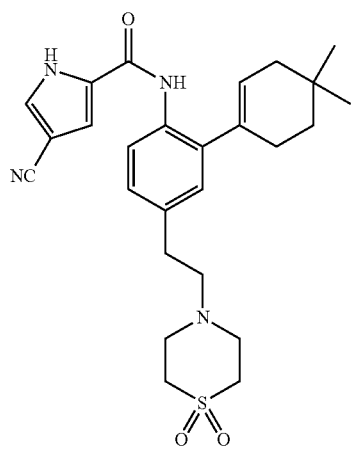 [SMILES: CC1(C)CC=C(c2cc(CCN3CCS(=O)(=O)CC3)ccc2NC(=O)c2cc(C#N)c[nH]2)CC1] | Ex. 33, steps (a)-(c); Ex. 34, step (c); Ex. 15; Ex. 16 | 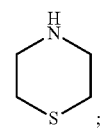 ; 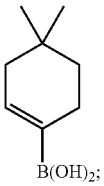 ; 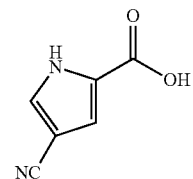 (Can. J. Chem. 59, 2673 (1981)) |
| 102 | 5-Cyano-furan-2-carboxylic acid [4-(2-imidazol-1-yl-ethyl)-2-spiro[4.5]dec-7-en-8-yl-phenyl)-amide | 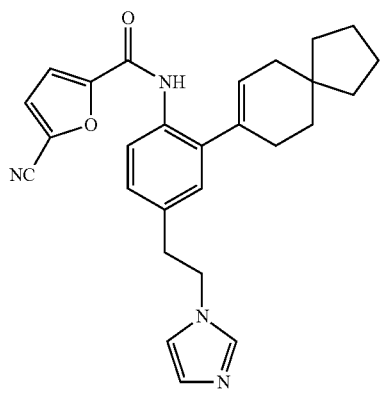 [SMILES: N#Cc1ccc(C(=O)Nc2ccc(CCn3ccnc3)cc2C2=CCC3(CCCC3)CC2)o1] | Ex. 33, steps (a)-(c); Ex. 43 | 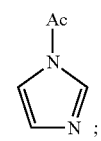 ; 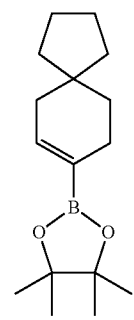 (WO2005063705); 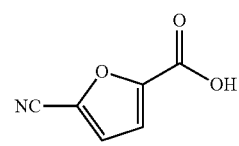 (WO2004096795 A2) |

-continued

| Example No. | Name | Structure | Procedure Reference | Reagents |
|---|---|---|---|---|
| 103 | 4-Cyano-1H-imidazole-2-carboxylic acid [2-(4,4-dimethyl-cyclohex-1-enyl)-4-(2-pyridin-2-yl-ethyl)-phenyl]-amide | 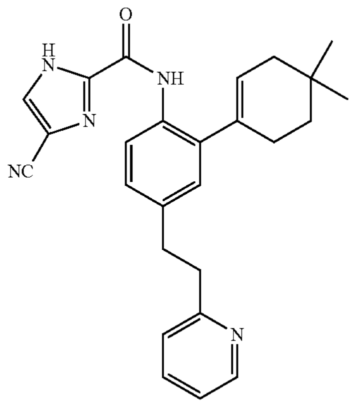 [SMILES: CC1(C)CC=C(c2cc(CCc3ccccn3)ccc2NC(=O)c2nc(C#N)c[nH]2)CC1] | Example 25, steps (c)-(f) | (EP 0 356 234 A2) |
| 104 | 4-Cyano-1H-imidazole-2-carboxylic acid {2-(4,4-dimethyl-cyclohex-1-enyl)-4-[2-(pyridin-2-ylamino)-ethyl]-phenyl}-amide | 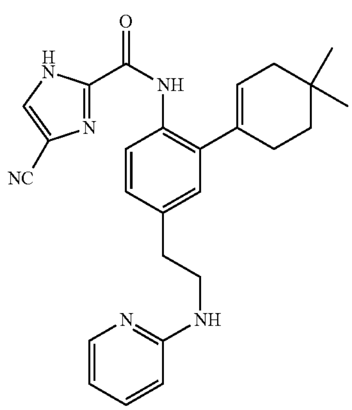 [SMILES: CC1(C)CC=C(c2cc(CCNc3ccccn3)ccc2NC(=O)c2nc(C#N)c[nH]2)CC1] | Example 33, steps (a)-(c); Example 25, steps (e) and (f) | |
| 105 | 4-Cyano-1H-imidazole-2-carboxylic acid [2-cyclohex-1-enyl-4-(4-methyl-piperazin-1-ylmethyl)-phenyl]-amide | 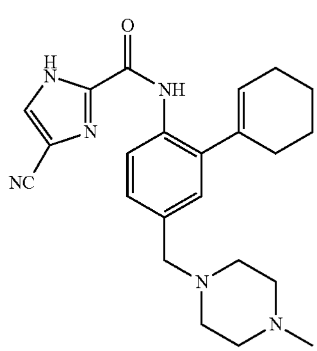 [SMILES: CN1CCN(Cc2ccc(NC(=O)c3nc(C#N)c[nH]3)c(C3=CCCCC3)c2)CC1] | Example 44, steps (a)-(b) | (Matrix Scientific); (Combi-Blocks, Inc.) |

| Example No. | Name | Structure | Procedure Reference | Reagents |
|---|---|---|---|---|
| 106 | 4-Cyano-1H-imidazole-2-carboxylic acid [2-(4,4-dimethyl-cyclohex-1-enyl)-4-(4-ethyl-piperazin-1-yl methyl) phenyl)-amide | 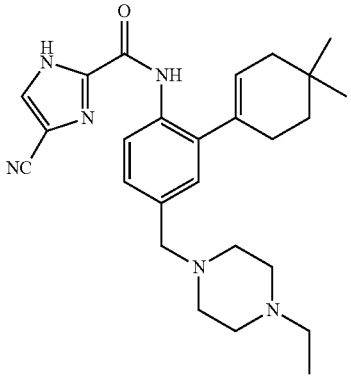 [SMILES: CCN1CCN(Cc2ccc(NC(=O)c3nc(C#N)c[nH]3)c(C3=CCC(C)(C)CC3)c2)CC1] | Ex. 44, steps (a)-(b) | <br>(Combi-Blocks, Inc.);<br><br>(Matrix Scientific) |
| 107 | 4-Cyano-1H-imidazole-2-carboxylic acid [2-(4,4-dimethyl-cyclohex-1-enyl)-4-thiomorpholin-4-ylmethyl-phenyl]-amide | 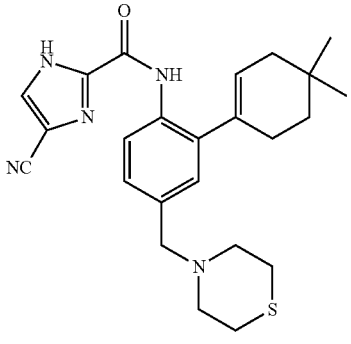 [SMILES: CC1(C)CC=C(c2cc(CN3CCSCC3)ccc2NC(=O)c2nc(C#N)c[nH]2)CC1] | Ex. 44, steps (a)-(b) | 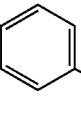<br>*Bioorganic & Medicinal Chemistry Letters*, 8(12), 1493-1498, (1998);<br><br>(Combi-Blocks, Inc.) |
| 108 | 4-Cyano-1H-imidazole-2-carboxylic acid [2-(4,4-dimethyl-cyclohex-1-enyl)-4-(1-oxo-1$\lambda^4$-thiomorpholin-4-ylmethyl)-phenyl]-amide | 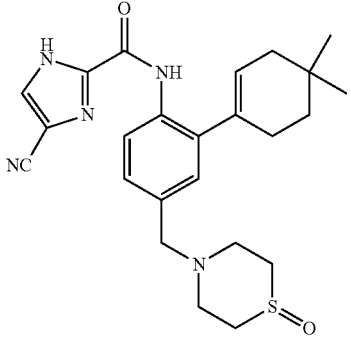 [SMILES: CC1(C)CC=C(c2cc(CN3CCS(=O)CC3)ccc2NC(=O)c2nc(C#N)c[nH]2)CC1] | Ex. 44, steps (a)-(b) | 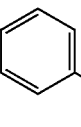<br>(WO2000018734); |

-continued

| Example No. | Name | Structure | Procedure Reference | Reagents |
|---|---|---|---|---|
| | | | | (Combi-Blocks, Inc.) |
| 109 | 4-Cyano-1H-imidazole-2-carboxylic acid [2-(4,4-dimethyl-cyclohex-1-enyl)-4-(1,1-dioxo-1$\lambda^6$-thiomorpholin-4-ylmethyl)-phenyl]-amide | 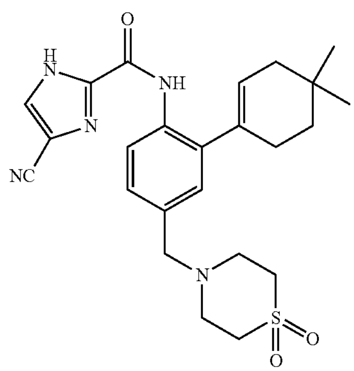 [SMILES: CC1(C)CC=C(c2cc(CN3CCS(=O)(=O)CC3)ccc2NC(=O)c2nc(C#N)c[nH]2)CC1] | Ex. 44, steps (a)-(b) | (Ryan Scientific); (Combi-Blocks, Inc.) |
| 110 | 4-Cyano-1H-pyrrole-2-carboxylic acid [2-(4,4-dimethyl-cyclohex-1-enyl)-4-(4-ethyl-piperazin-1-ylmethyl)-phenyl]-amide | 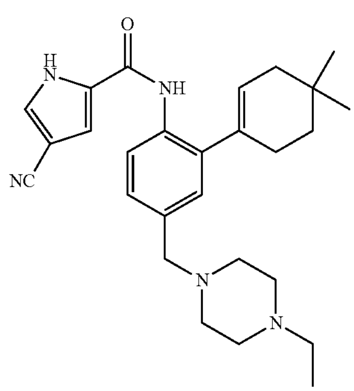 | Ex. 44, steps (a) Ex. 1, step (f) | (Matrix Scientific); (Canadian J. Chem. 59, 2673 (1981)) |

| Example No. | Name | Structure | Procedure Reference | Reagents |
|---|---|---|---|---|
| 111 | 5-Cyano-furan-2-carboxylic acid [2-(4,4-dimethyl-cyclohex-1-enyl)-4-(4-ethyl-piperazin-1-ylmethyl)-phenyl]-amide | 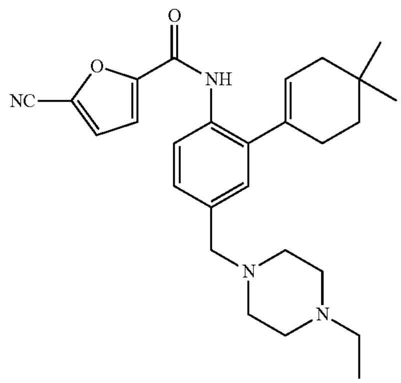 [SMILES: CCN1CCN(Cc2ccc(NC(=O)c3ccc(C#N)o3)c(C3=CCC(C)(C)CC3)c2)CC1] | Ex. 44, steps (a) Ex. 1, step (f) | (Matrix Scientific); 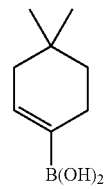 (Combi-Blocks, Inc.) (WO200409679) |
| 112 | 4-Cyano-1H-imidazole-2-carboxylic acid (4-morpholin-4-ylmethyl-2-piperidin-1-yl-phenyl)-amide | 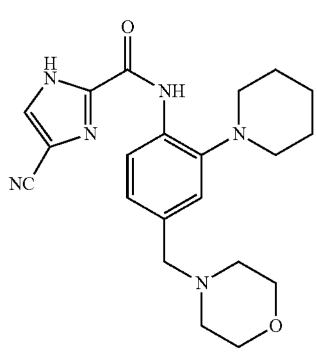 [SMILES: N#Cc1c[nH]c(C(=O)Nc2ccc(CN3CCOCC3)cc2N2CCCCC2)n1] | Ex. 55 step (a), Ex. 54 step (b), Ex. 1 steps (f)-(g) | (WO2003053972); 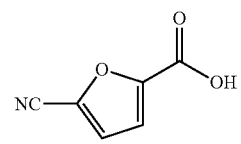 |

| Example No. | Name | Structure | Procedure Reference | Reagents |
|---|---|---|---|---|
| 113 | 4-Cyano-1H-pyrrole-2-carboxylic acid (4-morpholin-4-ylmethyl-2-piperidin-1-yl-phenyl)-amide | 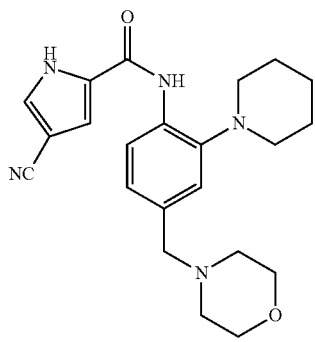 [SMILES: N#Cc1c[nH]c(C(=O)Nc2ccc(CN3CCOCC3)cc2N2CCCCC2)c1] | Ex. 55 step (a), Ex. 54 step (b), Ex. 1 step (f) | 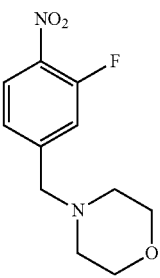 [SMILES: O=[N+]([O-])c1ccc(CN2CCOCC2)cc1F] (WO2003053972); 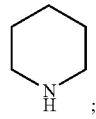 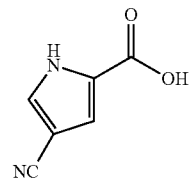 (*Canadian J. Chem.* 59, 2673 (1981)) |
| 114 | 5-Cyano-furan-2-carboxylic acid (4-morpholin-4-ylmethyl-2-piperidin-1-yl-phenyl)-amide | 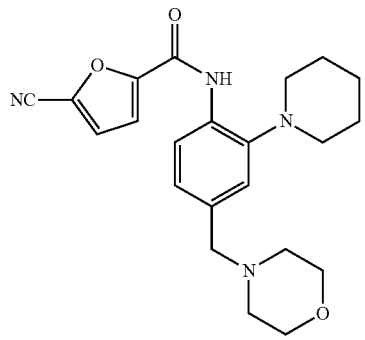 [SMILES: N#Cc1ccc(C(=O)Nc2ccc(CN3CCOCC3)cc2N2CCCCC2)o1] | Ex. 55 step (a), Ex. 54 step (b), Ex. 1 step (f) | 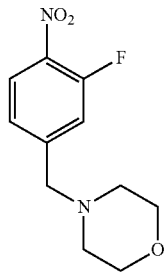 [SMILES: O=[N+]([O-])c1ccc(CN2CCOCC2)cc1F] (WO2003053972); 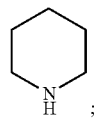 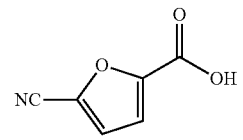 (WO200409679) |

-continued

| Example No. | Name | Structure | Procedure Reference | Reagents |
|---|---|---|---|---|
| 115 | 4-Cyano-1H-imidazole-2-carboxylic acid [2-(4,4-dimethyl-cyclohex-1-enyl)-4-(1-morpholin-4-yl-ethyl)-phenyl]-amide | 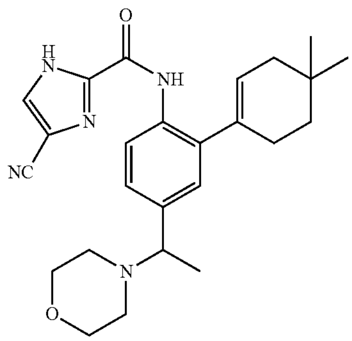 [SMILES: CC(c1ccc(NC(=O)c2nc(C#N)c[nH]2)c(C2=CCC(C)(C)CC2)c1)N1CCOCC1] | Ex 14, steps (d), (e). | Acetaldehyde, morpholine |
| 116 | 4-Cyano-1H-pyrrole-2-carboxylic acid [2-(4,4-dimethyl-cyclohex-1-enyl)-4-(1-morpholin-4-yl-ethyl)-phenyl]-amide | 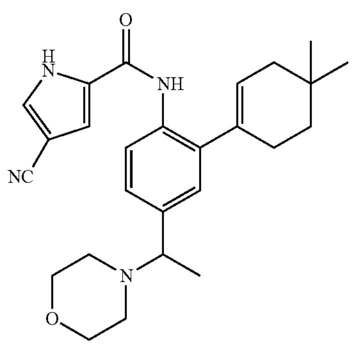 [SMILES: CC(c1ccc(NC(=O)c2cc(C#N)c[nH]2)c(C2=CCC(C)(C)CC2)c1)N1CCOCC1] | Ex 50, Ex 14, steps (a), (d), (e). | Acetaldehyde, morpholine |
| 117 | 4-Cyano-1H-imidazole-2-carboxylic acid [4-[1-(2-dimethylamino-ethoxy)-1-methyl-ethyl]-2-(4-methyl-piperidin-1-yl)-phenyl]-amide | 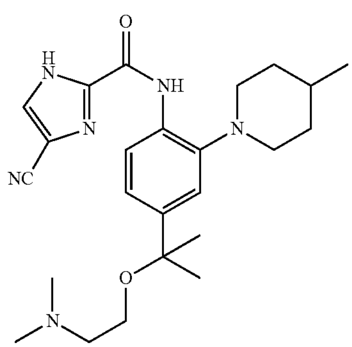 | Ex 1, steps (f)-(h), Ex. 52 | (US2005131022 A1); 2-dimethyl-aminoethanol |
| 118 | 4-Cyano-1H-pyrrole-2-carboxylic acid [4-[1-(2-dimethylamino-ethoxy)-1-methyl-ethyl]-2-(4-methyl-piperidin-1-yl)-phenyl]-amide | 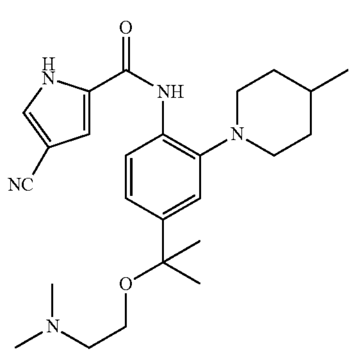 | Ex 50, Ex 1, step (h), Ex 52 | (US2005131022 A1); 2-dimethyl-aminoethanol |

| Example No. | Name | Structure | Procedure Reference | Reagents |
|---|---|---|---|---|
| 119 | 4-Cyano-1H-imidazole-2-carboxylic acid {2-(4,4-dimethyl-cyclohex-1-enyl)-4-[1-(2-imidazol-1-yl-ethoxy)-propyl]-phenyl}-amide | 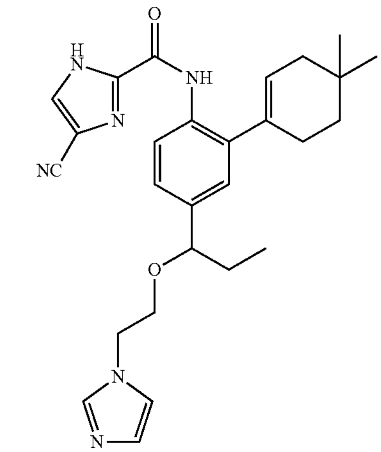 [SMILES: CCC(OCCn1ccnc1)c1ccc(NC(=O)c2nc(C#N)c[nH]2)c(C2=CCC(C)(C)CC2)c1] | Ex. 14, steps (d); Ex 52 | Propionaldehyde; 1-(2-hydroxyethyl) imidazole |
| 120 | 4-Cyano-1H-imidazole-2-carboxylic acid {4-[1-(4-ethyl-piperazin-1-yl)-ethyl)-2-spiro[4.5]dec-7-en-8-yl-phenyl}-amide | 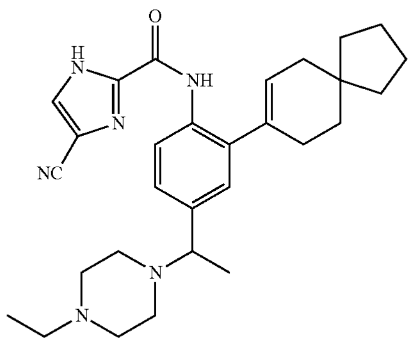 [SMILES: CCN1CCN(C(C)c2ccc(NC(=O)c3nc(C#N)c[nH]3)c(C3=CCC4(CCCC4)CC3)c2)CC1] | Ex. 1, steps (e)-(h); Ex 14 (e) | (WO2005063705); acetaldehyde; 1-ethyl-piperazine |
| 121 | 4-Cyano-1H-imidazole-2-carboxylic acid [4-(1-dimethylamino-ethyl)-2-spiro[4.5]dec-7-en-8-yl-phenyl]-amide | 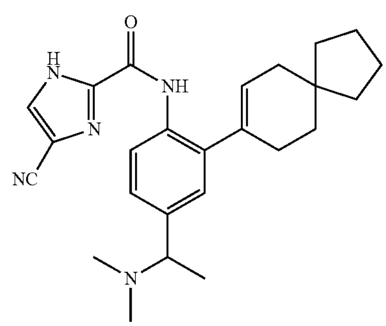 [SMILES: CC(c1ccc(NC(=O)c2nc(C#N)c[nH]2)c(C2=CCC3(CCCC3)CC2)c1)N(C)C] | Ex. 1, steps (e)-(h); Ex 14 (e) | (WO2005063705); acetaldehyde; dimethylamine |
| 122 | 4-Cyano-1H-imidazole-2-carboxylic acid {4-[1-(2-dimethylamino-ethoxy)-ethyl]-2-spiro[4.5]dec-7-en-8-yl-phenyl)-amide | 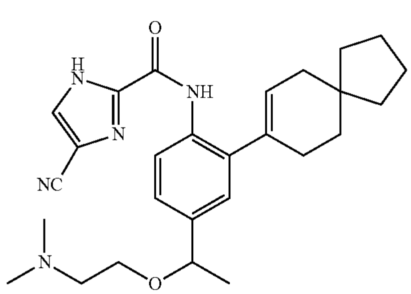 [SMILES: CC(OCCN(C)C)c1ccc(NC(=O)c2nc(C#N)c[nH]2)c(C2=CCC3(CCCC3)CC2)c1] | Ex. 1, steps (e)-(h); Ex 52 | |

-continued

| Example No. | Name | Structure | Procedure Reference | Reagents |
|---|---|---|---|---|
| | | | | (WO2005063705); acetaldehyde; 2-dimethyl-aminoethanol |
| 123 | 4-Cyano-1H-pyrrole-2-carboxylic acid {2-(4,4-dimethyl-cyclohex-1-enyl)-4-[1-(4-methyl-piperazin-1-yl)-ethyl]-phenyl}-amide | 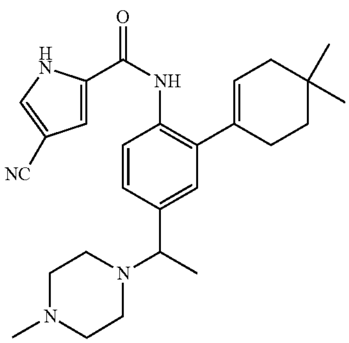 | Ex 50, Ex 14 step (a), (d), (e) | Acetaldehyde; 1-methyl-piperazine |
| 124 | 3-[4-[(4-Cyano-1H-pyrrole-2-carbonyl)-amino]-3-(4-methyl-piperidin-1-yl)-phenyl]-acrylic acid | 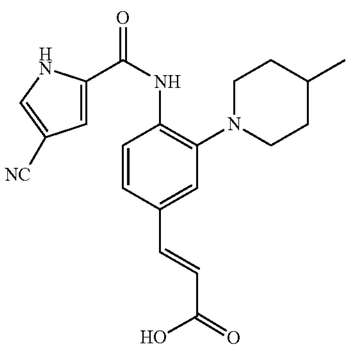 [SMILES: CC1CCN(c2cc(/C=C/C(=O)O)ccc2NC(=O)c2cc(C#N)c[nH]2)CC1] | Ex 50, Ex 48 step (a), (b) | (US2005131022 A1) |
| 125 | 3-[4-[(4-Cyano-1H-imidazole-2-carbonyl)-amino]-3-(4-methyl-piperidin-1-yl)-phenyl]-acrylic acid | 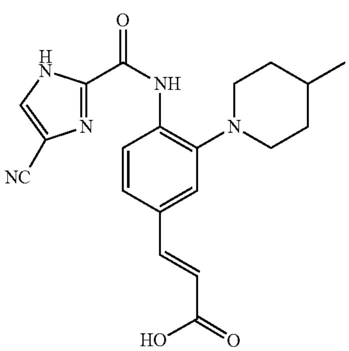 [SMILES: CC1CCN(c2cc(/C=C/C(=O)O)ccc2NC(=O)c2nc(C#N)c[nH]2)CC1] | Ex 1, steps (f), (g) Ex 48, steps (a), (b). | (US2005131022 A1) |
| 126 | 3-{3'-[(4-Cyano-1H-imidazole-2-carbonyl)-amino]-4-methyl-3,4,5,6-tetrahydro-2H-[1,2']bipyridinyl-6'-yl}-acrylic acid | 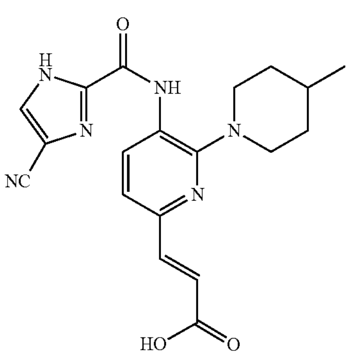 [SMILES: CC1CCN(c2nc(/C=C/C(=O)O)ccc2NC(=O)c2nc(C#N)c[nH]2)CC1] | Ex 1, steps(f), (g) Ex 48, steps (a), (b). | (Org. Prep. Proc. Int., 30, 709, (1998) |

-continued

| Example No. | Name | Structure | Procedure Reference | Reagents |
|---|---|---|---|---|
| 127 | 3-{3'-[(4-Cyano-1H-pyrrole-2-carbonyl)-amino]-4-methyl-3,4,5,6-tetrahydro-2H-[1,2']bipyridinyl-6'-yl}-acrylic acid | 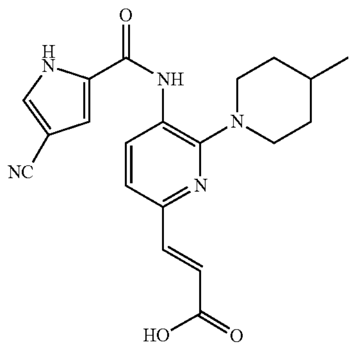 [SMILES: CC1CCN(c2nc(/C=C/C(=O)O)ccc2NC(=O)c2cc(C#N)c[nH]2)CC1] | Ex 50 Ex 48, steps (a), (b). (Org. Prep. Proc. Int., 30, 709, (1998) | |
| 128 | 4-Cyano-1H-imidazole-2-carboxylic acid {2-cyclohex-1-enyl-6-[1-methyl-1-(2-pyrrolidin-1-yl-ethoxy)-ethyl]-pyridin-3-yl}-amide | 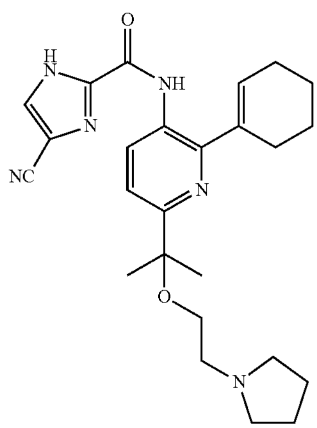 [SMILES: CC(C)(OCCN1CCCC1)c1ccc(NC(=O)c2nc(C#N)c[nH]2)c(C2=CCCCC2)n1] | Ex. 56, steps (a-e); Ex. 52 | (Combi-Blocks); |
| 129 | 4-Cyano-1H-imidazole-2-carboxylic acid {2-(4,4-dimethyl-cyclohex-1-enyl)-6-[1-methyl-1-(2-morpholin-4-yl-ethoxy)-ethyl]-pyridin-3-yl}-amide | 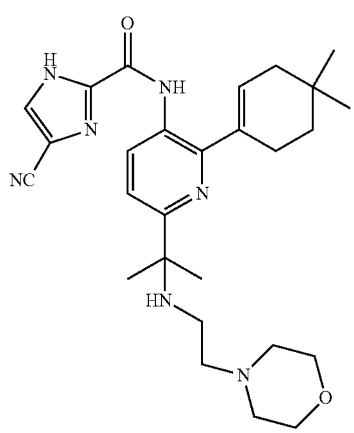 [SMILES: CC1(C)CC=C(c2nc(C(C)(C)NCCN3CCOCC3)ccc2NC(=O)c2nc(C#N)c[nH]2)CC1] | Ex. 56, steps (a-e); Ex. 14, step (e) | (Combi-Blocks); |

| Example No. | Name | Structure | Procedure Reference | Reagents |
|---|---|---|---|---|
| 130 | 4-Cyano-1H-imidazole-2-carboxylic acid {2-(4,4-diethyl-cyclohex-1-enyl)-6-[1-(3-dimethylamino-propoxy)-1-methyl-ethyl]-pyridin-3-yl}-amide | 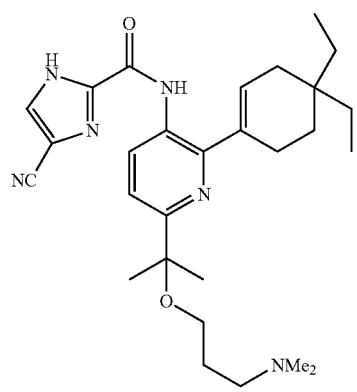 [SMILES: CCC1(CC)CC=C(c2nc(C(C)(C)OCCCN(C)C)ccc2NC(=O)c2nc(C#N)c[nH]2)CC1] | Ex. 56, steps (a-e) Ex. 52 | 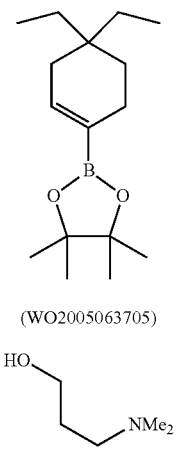<br>(WO2005063705) |
| 131 | 4-Cyano-1H-imidazole-2-carboxylic acid {6'-[1-(3-dimethylamino-propoxy)-1-methyl-ethyl]-3,4,5,6-tetrahydro-2H-[1,2']bipyridinyl-3'-yl}-amide | 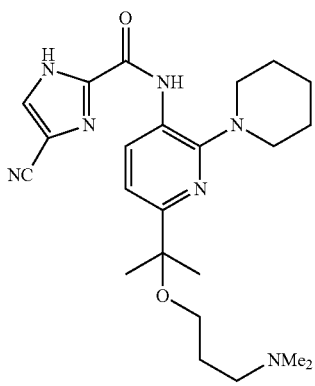 [SMILES: CN(C)CCCOC(C)(C)c1ccc(NC(=O)c2nc(C#N)c[nH]2)c(N2CCCCC2)n1] | Ex. 56, steps (c-e) Ex. 52 | 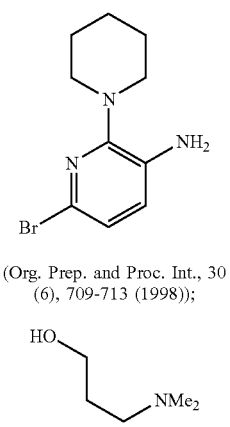<br>(Org. Prep. and Proc. Int., 30 (6), 709-713 (1998)); |
| 132 | 4-Cyano-1H-imidazole-2-carboxylic acid {6-[1-(3-dimethylamino-propoxy)-1-methyl-ethyl]-2-spiro[4.5]dec-7-en-8-yl-pyridin-3-yl}-amide | 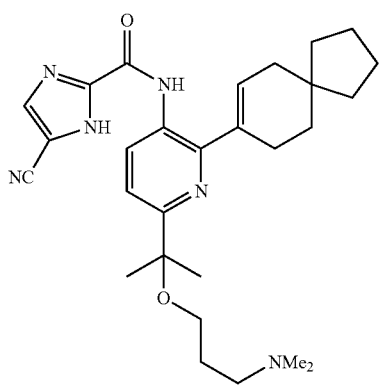 [SMILES: CN(C)CCCOC(C)(C)c1ccc(NC(=O)c2ncc(C#N)[nH]2)c(C2=CCC3(CCCC3)CC2)n1] | Ex. 56, steps (a), (b), (e); Ex. 55, step (d); Ex. 52 | 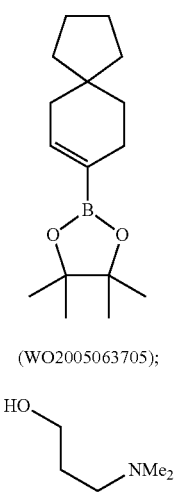<br>(WO2005063705); |

| Example No. | Name | Structure | Procedure Reference | Reagents |
|---|---|---|---|---|
| 133 | 4-Cyano-1H-imidazole-2-carboxylic acid [2-(4,4-dimethyl-cyclohex-1-enyl)-6-(1-methyl-1-piperidin-1-yl-ethyl)-pyridin-3-yl]-amide | 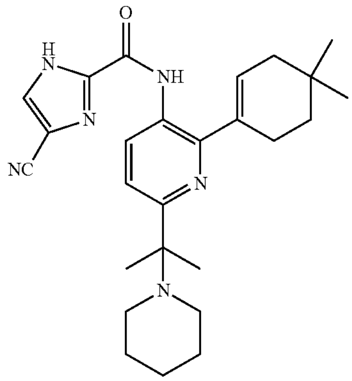 [SMILES: CC1(C)CC=C(c2nc(C(C)(C)N3CCCCC3)ccc2NC(=O)c2nc(C#N)c[nH]2)CC1] | Ex. 56, steps (a-e); Ex. 14, step (e) | B(OH)₂ (Combi-Blocks); |
| 134 | 4-Cyano-1H-imidazole-2-carboxylic acid {2-(4,4-dimethyl-cyclohex-1-enyl)-6-[1-(4-ethyl-piperazin-1-yl)-1-methyl-ethyl]-pyridin-3-yl}-amide | 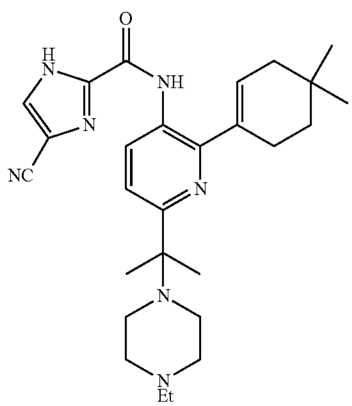 | Ex. 56, steps (a)-(e); Ex. 14, step (e) | B(OH)₂ (Combi-Blocks); |
| 135 | 4-Cyano-1H-imidazole-2-carboxylic acid {6-[1-methyl-1-(4-methyl-piperazin-1-yl)-ethyl]-2-spiro[4.5]dec-7-en-8-yl-pyridin-3-yl}-amide | 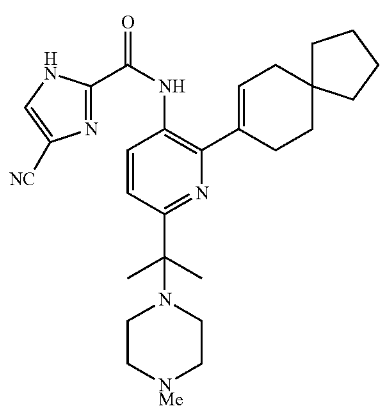 [SMILES: CN1CCN(C(C)(C)c2ccc(NC(=O)c3nc(C#N)c[nH]3)c(C3=CCC4(CCCC4)CC3)n2)CC1] | Ex. 56, steps (a)-(e); Ex. 14, step (e) | (WO2005063705); |

| Example No. | Name | Structure | Procedure Reference | Reagents |
|---|---|---|---|---|
| 136 | 4-Cyano-1H-pyrrole-2-carboxylic acid {6'-[1-methyl-1-(4-methyl-piperazin-1-yl)-ethyl]-3,4,5,6-tetrahydro-2H-[1,2']bipyridinyl-3'-yl}-amide | 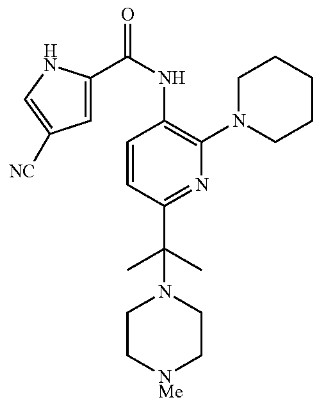 [SMILES: CN1CCN(C(C)(C)c2ccc(NC(=O)c3cc(C#N)c[nH]3)c(N3CCCCC3)n2)CC1] | Ex. 56, step (c); Ex. 14. step (e). | (Org. Prep. Proc. Int. 30 (6), 709-713, (1998)); |
| 137 | 4-Cyano-1H-imidazole-2-4-Cyano-1H-imidazole-2-carboxylic acid {2-(4,4-dimethyl-cyclohex-1-enyl)-6-[1-methyl-1-(4-methyl-piperazin-1-yl)-ethyl]-pyridin-3-yl}-amide | 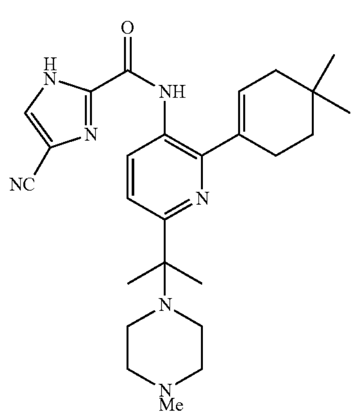 [SMILES: CN1CCN(C(C)(C)c2ccc(NC(=O)c3nc(C#N)c[nH]3)c(C3=CCC(C)(C)CC3)n2)CC1] | Ex. 56, steps (a)-(e); Ex. 14, step (e). | (Can. J. Chem. 59, 2673 (1981)); 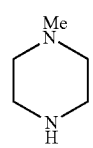 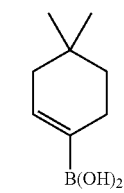 (Combi-Blocks) |

The following examples were made according to procedures described in this document, and other procedures known to those skilled in the art.

Example 138

4-Cyano-1H-imidazole-2-carboxylic acid {2-(4,4-dimethyl-cyclohex-1-enyl)-4-[1,1-dimethyl-2-(2-methylsulfanyl-ethylamino)-ethyl]-pheny}-amide

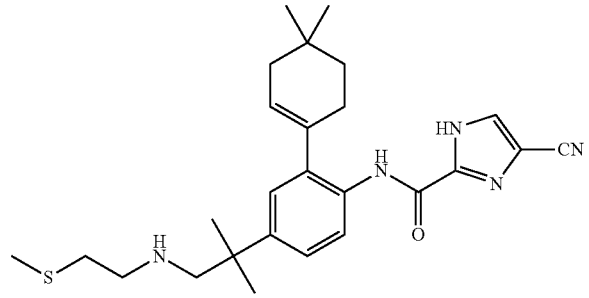 [SMILES: CSCCNCC(C)(C)c1ccc(NC(=O)c2nc(C#N)c[nH]2)c(C2=CCC(C)(C)CC2)c1]

a) 2-Methyl-2-(4-nitro-phenyl)-propan-1-ol

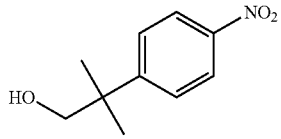

To a suspension of lithium aluminum hydride (1.00 g, 26.3 mmol) in 50 mL of THF at 0° C. was added 2-methyl-2-(4-nitro-phenyl)-propionic acid methyl ester (2.20 g, 9.86 mmol, Hartwig, et al, *J. Am. Chem. Soc*, 2004, 126, 5182) in 10 mL of THF dropwise. The resulting mixture was stirred at 0° C. for 3 h and treated with 1 mL of H$_2$O followed by 1 mL of 15% aq NaOH and 3 mL of H$_2$O. The solid was removed by filtration on Celite and the filtrate was concentrated in vacuo to give a light yellow oil (1.56 g, 81%). The product was used in the next step without further purification. $^1$H-NMR (CDCl$_3$; 400 MHz): δ 7.92 (d, 2H, J=8.6 Hz), 7.55 (d, 2H, J=8.6 Hz), 3.69 (s, 2H), 1.40 (s, 6H).

b) tert-Butyl-dimethyl-[2-methyl-2-(4-nitro-phenyl)-propoxy]-silane

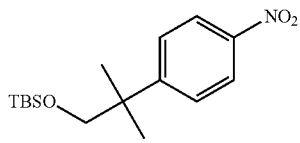 [SMILES: CC(C)(CO[Si](C)(C)C(C)(C)C)c1ccc([N+](=O)[O-])cc1]

To a mixture of 2-methyl-2-(4-nitro-phenyl)-propan-1-ol (as prepared in the previous step, 1.50 g, 7.68 mmol) and t-butyl-dimethylsilyl chloride (1.51 g, 9.99 mmol) in 60 mL of DCM was slowly added imidazole (3.09 g, 45.4 mmol).

After stirring at RT for 16 h, the mixture was treated with 40 mL of DCM and washed with H$_2$O (30 mL), 15% aqueous citric acid (30 mL) and brine (20 mL). The organic layer was dried (Na$_2$SO$_4$) and concentrated in vacuo. The residue was purified by flash chromatography on silica gel (0-5% EtOAc/hexane) to give 1.82 g (65%) of the title compound as a light brown oil. $^1$H-NMR (CDCl$_3$; 400 MHz): δ 7.85 (d, 2H, J=8.8 Hz), 7.52 (d, 2H, J=8.8 Hz), 3.59 (s, 2H), 1.35 (s, 6H), 0.86 (s, 9H), −0.04 (s, 6H).

c) 4-[2-(tert-Butyl-dimethyl-silanyloxy)-1,1-dimethyl-ethyl]-phenylamine

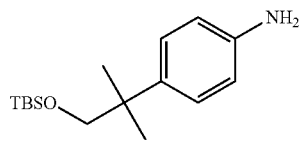 [SMILES: CC(C)(CO[Si](C)(C)C(C)(C)C)c1ccc(N)cc1]

A mixture of tert-butyl-dimethyl-[2-methyl-2-(4-nitro-phenyl)-propoxy]-silane (as prepared in the previous step, 1.70 g, 5.49 mmol) and 10% Pd/C (850 mg, 50 wt %) in 30 mL of EtOAc was stirred at RT under H$_2$ (balloon pressure) for 6 h. The Pd catalyst was removed by filtration on Celite and the filtrate was concentrated. The residue was purified by flash chromatography on silica gel (5-10% EtOAc/DCM) to give 1.43 g (93%) of the title compound as a light brown oil. Mass spectrum (ESI, m/z): Calcd. for C$_{16}$H$_{29}$NOSi, 280.2 (M+H). found 280.4.

d) 2-Bromo-4-[2-(tert-butyl-dimethyl-silanyloxy)-1,1-dimethyl-ethyl]-phenylamine

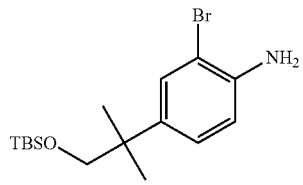 [SMILES: CC(C)(CO[Si](C)(C)C(C)(C)C)c1ccc(N)c(Br)c1]

To a solution of 4-[2-(tert-butyl-dimethyl-silanyloxy)-1,1-dimethyl-ethyl]-phenylamine (as prepared in the previous step, 1.41 g, 5.04 mmol) in 25 mL of DCM at 0° C. was slowly added N-bromosuccinimide (NBS) (898 mg, 5.04 mmol) in three portions over five minutes. After stirring at RT for 2 h, the mixture was treated with 50 mL of EtOAc and washed with H$_2$O (2×30 mL) and brine H$_2$O (20 mL). The organic layer was dried (Na$_2$SO$_4$) and concentrated in vacuo. The residue was purified by flash chromatography on silica gel (DCM) to give 1.59 g (88%) of the title compound as a light yellow oil. Mass spectrum (ESI, m/z): Calcd. for C$_{16}$H$_{28}$BrNOSi, 358.1 (M+H). found 358.4.

e) 4-[2-(tert-Butyl-dimethyl-silanyloxy)-1,1-dimethyl-ethyl]-2-(4,4-dimethyl-cyclohex-1-enyl)-phenylamine

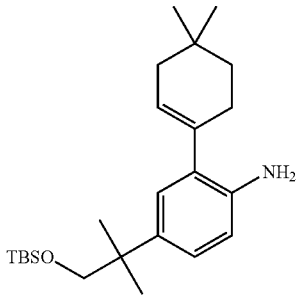 [SMILES: CC1(C)CC=C(c2cc(C(C)(C)CO[Si](C)(C)C(C)(C)C)ccc2N)CC1]

To a mixture of 2-bromo-4-[2-(tert-butyl-dimethyl-silanyloxy)-1,1-dimethyl-ethyl]-phenylamine (as prepared in the previous step, 1.50 g, 4.19 mmol), 4,4-dimethylcyclohexen-1-ylboronic acid (1.09 g, 4.61 mmol) and Pd(PPh$_3$)$_4$ (484 mg, 0.419 mmol) in 50 mL of 1,4-dioxane was added aqueous Na$_2$CO$_3$ (16.8 mL, 33.5 mmol, 2.0 M). The resulting mixture was stirred at 90° C. for 16 h under Ar. After cooling to RT, the mixture was treated with 150 mL of EtOAc and washed with H$_2$O (3×30 mL) and brine (30 mL). The organic layer was dried (Na$_2$SO$_4$) and concentrated in vacuo. The residue was purified by flash chromatography on silica gel (5-10% EtOAc/hexane) to afford 1.46 g (90%) of the title compound as a colorless oil. Mass spectrum (ESI, m/z): Calcd. for C$_{24}$H$_{41}$NOSi, 388.3 (M+H). found 388.3.

f) 4-Cyano-1-(2-trimethylsilanyl-ethoxymethyl)-1H-imidazole-2-carboxylic acid [4-[2-(tert-butyl-dimethyl-silanyloxy)-1,1-dimethyl-ethyl]-2-(4,4-dimethyl-cyclohex-1-enyl)-phenyl]-amide

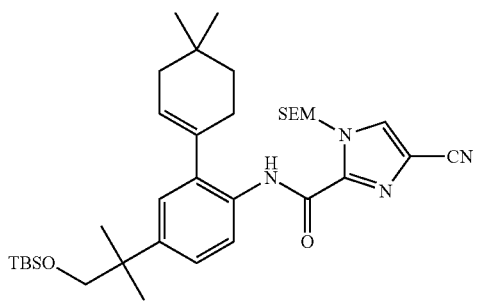 [SMILES: CC1(C)CC=C(c2cc(C(C)(C)CO[Si](C)(C)C(C)(C)C)ccc2NC(=O)c2nc(C#N)cn2COCC[Si](C)(C)C)CC1]

To a mixture of potassium 4-cyano-1-(2-trimethylsilanyl-ethoxymethyl)-1H-imidazole-2-carboxylate (as prepared in Example 1, step (d), 1.37 g, 4.49 mmol) and pyridine (363 µL, 4.49 mmol) in 15 mL of DCM at 0° C. was added SOCl$_2$ (328 µL, 4.49 mmol). After stirring at 0° C. for 0.5 h under Ar, the resulting mixture was warmed to RT and added to a solution of 4-[2-(tert-butyl-dimethyl-silanyloxy)-1,1-dimethyl-ethyl]-2-(4,4-dimethyl-cyclohex-1-enyl)-phenylamine (as prepared in the previous step, 1.45 g, 3.74 mmol) in 15 mL of DCM at 0° C. After stirring at 0° C. for 2 h under Ar, the reaction was warmed to RT. Treated with 100 mL of EtOAc, the mixture was washed with H$_2$O (20 mL), 10% aqueous citric acid (20 mL), aqueous saturated NaHCO$_3$ (20 mL) and brine (20 mL). The organic layer was dried over Na$_2$SO$_4$ and concentrated in vacuo. The residue was purified by silica gel chromatography (0-5% EtOAc/hexane) to afford the title compound (2.22 g, 93%) as a light brown oil. Mass spectrum (ESI, m/z): Calcd. for C$_{35}$H$_{56}$N$_4$O$_3$Si$_2$, 637.4 (M+H). found 637.2.

g) 4-Cyano-1H-imidazole-2-carboxylic acid [2-(4,4-dimethyl-cyclohex-1-enyl)-4-(2-hydroxy-1,1-dimethyl-ethyl)-phenyl]-amide

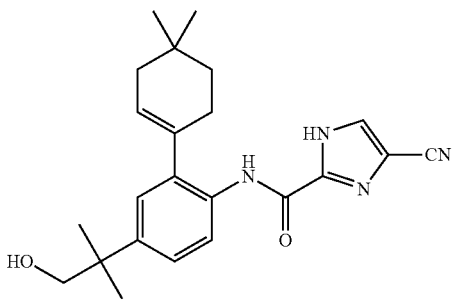 [SMILES: CC1(C)CC=C(c2cc(C(C)(C)CO)ccc2NC(=O)c2nc(C#N)c[nH]2)CC1]

A solution of 4-cyano-1-(2-trimethylsilanyl-ethoxymethyl)-1H-imidazole-2-carboxylic acid [4-[2-(tert-butyl-dimethyl-silanyloxy)-1,1-dimethyl-ethyl]-2-(4,4-dimethyl-cyclohex-1-enyl)-phenyl]-amide (as prepared in the previous step, 2.20 g, 3.45 mmol) and tetrabutylammonium fluoride hydrate (4.52 g, 17.3 mmol) in 25 mL of THF was stirred at 50° C. for 3 h. After cooling to RT, the mixture was treated with 100 mL of EtOAc and washed with saturated aqueous NH$_4$Cl (20 mL), H$_2$O (20 mL) and brine (20 mL). The organic layer was dried over Na$_2$SO$_4$ and concentrated in vacuo. The residue was purified by silica gel chromatography (0-4% MeOH/DCM) to afford the title compound (1.25 g, 92%) as a white solid. Mass spectrum (ESI, m/z): Calcd. for C$_{23}$H$_{28}$N$_4$O$_2$, 393.2 (M+H). found 393.2.

h) 4-Cyano-1H-imidazole-2-carboxylic acid [2-(4,4-dimethyl-cyclohex-1-enyl)-4-(1,1-dimethyl-2-oxo-ethyl)-phenyl]-amide

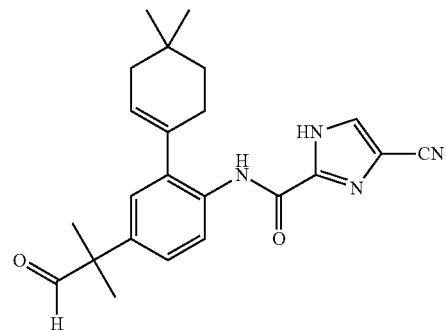 [SMILES: CC1(C)CC=C(c2cc(C(C)(C)C=O)ccc2NC(=O)c2nc(C#N)c[nH]2)CC1]

To a mixture of 4-cyano-1H-imidazole-2-carboxylic acid [2-(4,4-dimethyl-cyclohex-1-enyl)-4-(2-hydroxy-1,1-dimethyl-ethyl)-phenyl]-amide (as prepared in the previous step, 1.00 g, 2.55 mmol) and NaHCO$_3$ (1.07 g, 12.8 mmol) in 40 mL of DCM at 0° C. was added Dess-Martin periodinane (*Adv. Syn. Chem.*, 2004, 346, 111-124, 2.16 g, 5.10 mmol). After stirring at 0° C. for 0.5 h, the reaction was warmed to RT and continued to stir for 2 h. The mixture was treated with 100 mL of EtOAc and washed with 10% aqueous $Na_2S_2O_3$ (2×20 mL), aqueous saturated $NaHCO_3$ (20 mL), $H_2O$ (20 mL) and brine (10 mL). The organic layer was dried over $Na_2SO_4$ and concentrated in vacuo. The residue was purified by silica gel chromatography (0-3% MeOH/DCM) to afford the title compound (876 mg, 88%) as a white solid. Mass spectrum (ESI, m/z): Calcd. for $C_{23}H_{26}N_4O_2$, 391.2 (M+H). found 391.1.

i) 4-Cyano-1H-imidazole-2-carboxylic acid {2-(4,4-dimethyl-cyclohex-1-enyl)-4-[1,1-dimethyl-2-(2-methylsulfanyl-ethylamino)-ethyl]-phenyl}-amide To a mixture of 4-cyano-1H-imidazole-2-carboxylic acid [2-(4,4-dimethyl-cyclohex-1-enyl)-4-(1,1-dimethyl-2-oxo-ethyl)-phenyl]-amide (as prepared in the previous step, 60.0 mg, 0.154 mmol) and 2-methylsulfanyl-ethylamine (84 mg, 0.92 mmol) in 2 mL of 1,2-dichloroethane was added sodium triacetoxyborohydride (49.0 mg, 0.231 mmol). After stirring at RT for 3 h, the mixture was treated with EtOAc (40 mL) and washed with aqueous saturated $NaHCO_3$ (10 mL), $H_2O$ (10 mL) and brine (10 mL). The organic layer was dried over $Na_2SO_4$ and concentrated in vacuo. The residue was purified by silica gel chromatography (1-3% MeOH/DCM) to afford the title compound (45.0 mg, 63%) as a white solid. $^1$H-NMR (1:1 $CD_3OD/CDCl_3$; 400 MHz): δ 8.22 (d, 1H, J=8.6 Hz), 7.78 (s, 1H), 7.27 (dd, 1H, J=8.6, 2.0 Hz), 7.14 (d, 1H, J=2.0 Hz), 5.73 (m, 1H), 2.77 (s, 2H), 2.68 (t, 2H, J=6.3 Hz), 2.55 (t, 2H, J=6.3 Hz), 2.27 (m, 2H), 2.06 (m, 2H), 1.92 (s, 3H), 1.57 (t, 2H, J=6.3 Hz), 1.35 (s, 6H), 1.07 (s, 6H). Mass spectrum (ESI, m/z): Calcd. for $C_{26}H_{35}N_5OS$, 466.3 (M+H). found 466.2.

Example 139

4-Cyano-1H-imidazole-2-carboxylic acid {2-(4,4-dimethyl-cyclohex-1-enyl)-4-[2-(2-methanesulfonyl-ethylamino)-1,1-dimethyl-ethyl]phenyl}-amide

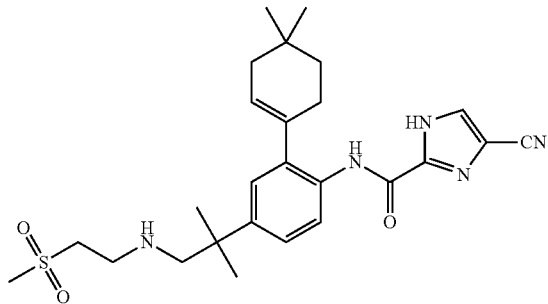 [SMILES: CC1(C)CC=C(c2cc(C(C)(C)CNCCS(C)(=O)=O)ccc2NC(=O)c2nc(C#N)c[nH]2)CC1]

To a solution of 4-cyano-1H-imidazole-2-carboxylic acid {2-(4,4-dimethyl-cyclohex-1-enyl)-4-[1,1-dimethyl-2-(2-methylsulfanyl-ethylamino)-ethyl]-phenyl}-amide (as prepared in Example 138, step (i), 38.0 mg, 0.0816 mmol) in 2 mL of DCM and 50 μL of i-PrOH at RT was added titanium (IV) isopropoxide (24.0 μL, 0.0816 mmol). The mixture was cooled to 0° C. and $H_2O_2$ (18.0 μL, 0.163 mmol, 30 wt % in $H_2O$) was added. After stirring at 0° C. for 0.5 h and at RT for 2 h, the mixture was treated with EtOAc (50 mL) and washed with aqueous saturated $NaHCO_3$ (10 mL), aqueous saturated $NH_4Cl$ (10 mL), brine (10 mL) and dried ($Na_2SO_4$). The organic layer was concentrated in vacuo and the residue was purified by silica gel chromatography (1-3% MeOH/DCM) to afford the title compound (39.8 mg, 98%) as a white solid. $^1$H-NMR (1:1 $CD_3OD/CDCl_3$; 400 MHz): δ 8.17 (d, 1H, J=8.6 Hz), 7.86 (s, 1H), 7.27 (d, 1H, J=8.6 Hz), 7.14 (br s, 1H), 5.73 (m, 1H), 3.12 (t, 2H, J=5.9 Hz), 2.99 (t, 2H, J=5.9 Hz), 2.86 (s, 3H), 2.76 (s, 2H), 2.28 (m, 2H), 2.07 (m, 2H), 1.58 (t, 2H, J=6.3 Hz), 1.33 (s, 6H), 1.07 (s, 6H). Mass spectrum (ESI, m/z): Calcd. for $C_{26}H_{35}N_5O_3S$, 498.3 (M+H). found 498.2.

Example 140

4-Cyano-1H-imidazole-2-carboxylic acid {2-(4,4-dimethyl-cyclohex-1-enyl)-4-[2-(2,2-dimethyl-tetrahydro-[1,3]dioxolo[4,5-c]pyrrol-5-yl)-1,1-dimethyl-ethyl]-phenyl}-amide

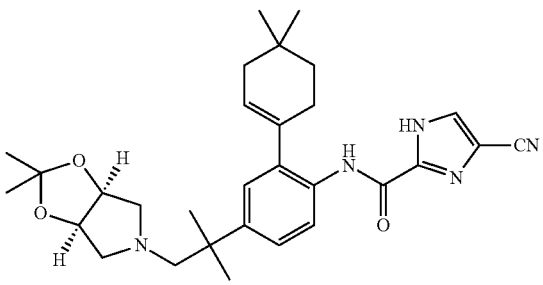 [SMILES: CC1(C)CC=C(c2cc(C(C)(C)CN3C[C@@H]4OC(C)(C)O[C@@H]4C3)ccc2NC(=O)c2nc(C#N)c[nH]2)CC1]

The title compound was prepared by the procedure of Example 138, step (i) using 4-cyano-1H-imidazole-2-carboxylic acid [2-(4,4-dimethyl-cyclohex-1-enyl)-4-(1,1-dimethyl-2-oxo-ethyl)-phenyl]-amide (as prepared in Example 138, step (h), 60.0 mg, 0.154 mmol) and 2,2-dimethyl-tetrahydro-[1,3]dioxolo[4,5-c]pyrrole (Couturier, M. et at, Organic Process Research & Development, 2002, 6, 42-48, 132 mg, 0.924 mmol). Silica gel chromatography (1-3% MeOH/DCM) afforded the title compound (49.3 mg, 63%) as a white solid. $^1$H-NMR (1:1 $CD_3OD$; 400 MHz): 8.13 (d, 1H, J=8.6 Hz), 7.98 (s, 1H), 7.32 (dd, 1H, J=8.6, 2.3 Hz), 7.21 (d, 1H, J=2.3 Hz), 5.73 (m, 1H), 4.48 (m, 2H), 2.70 (d, 2H, J=11.4 Hz), 2.59 (s, 2H), 2.31 (m, 2H), 2.08 (m, 2H), 1.98-2.04 (m, 2H), 1.59 (t, 2H, J=6.3 Hz), 1.44 (s, 3H), 1.34 (s, 6H), 1.23 (s, 3H), 1.09 (s, 6H). Mass spectrum (ESI, m/z): Calcd. for $C_{30}H_{39}N_5O_3$, 518.3 (M+H). found 518.3.

Example 141

4-Cyano-1H-imidazole-2-carboxylic acid [4-[2-(3,4-dihydroxy-pyrrolidin-1-yl)-1,1-dimethyl-ethyl]-2-(4,4-dimethyl-cyclohex-1-enyl)-phenyl]-amide hydrochloride

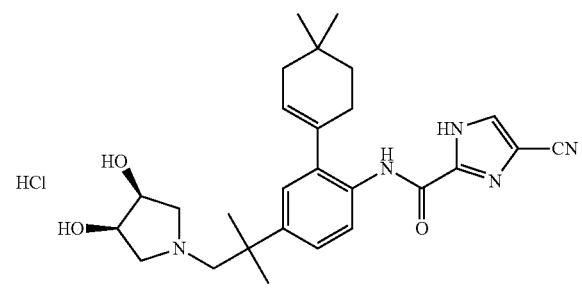 [SMILES: Cl ; CC1(C)CC=C(c2cc(C(C)(C)CN3C[C@@H](O)[C@@H](O)C3)ccc2NC(=O)c2nc(C#N)c[nH]2)CC1]

A solution of 4-cyano-1H-imidazole-2-carboxylic acid {2-(4,4-dimethyl-cyclohex-1-enyl)-4-[2-(2,2-dimethyl-tetrahydro-[1,3]dioxolo[4,5-c]pyrrol-5-yl)-1,1-dimethyl-ethyl]-phenyl}-amide (as prepared in Example 140, 42.0 mg, 0.0811 mmol) in 2 mL of 1:1 1N HCl/THF was stirred at 80° C. for 0.5 h. After cooling to RT, the mixture was treated with 40 mL of EtOAc and concentrated in vacuo to give the title compound (38.8 mg, 91%) as a colorless oil. $^1$H-NMR (1:1 CD$_3$OD; 400 MHz): 8.29 (d, 1H, J=8.6 Hz), 8.00 (s, 1H), 7.43 (dd, 1H, J=8.6, 2.3 Hz), 7.32 (d, 1H, J=2.3 Hz), 5.77 (m, 1H), 4.17 (m, 2H), 3.64 (s, 2H), 3.31-3.37 (m, 2H), 2.98-3.07 (m, 2H), 2.34 (m, 2H), 2.09 (m, 2H), 1.61 (t, 2H, J=6.3 Hz), 1.51 (s, 6H), 1.10 (s, 6H). Mass spectrum (ESI, m/z): Calcd. for C$_{27}$H$_{35}$N$_5$O$_3$, 478.3 (M+H). found 478.3.

The following compounds were prepared according to the examples as indicated:

| Example Number | Name | Structure | Procedure Reference | Mass Spectrum |
|---|---|---|---|---|
| 142 | 4-Cyano-1H-imidazole-2-carboxylic acid [2-(4,4-dimethyl-cyclohex-1-enyl)-4-(1,1-dimethyl-2-morpholin-4-yl-ethyl)-phenyl]-amide | 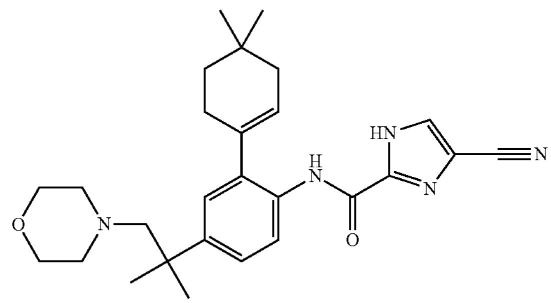 [SMILES: CC1(C)CC=C(c2cc(C(C)(C)CN3CCOCC3)ccc2NC(=O)c2nc(C#N)c[nH]2)CC1] | Ex 138, step (i) | (ESI, m/z) Calcd. for C$_{27}$H$_{35}$N$_5$O$_2$, 462.3 (M + H), found 462.3. |
| 143 | 4-Cyano-1H-imidazole-2-carboxylic acid [4-[2-(4-acetyl-piperazin-1-yl)-1,1-dimethyl-ethyl]-2-(4,4-dimethyl-cyclohex-1-enyl)-phenyl]-amide | 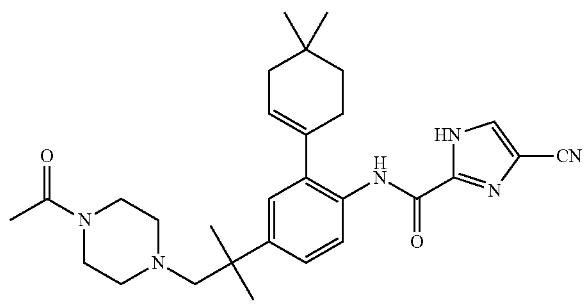 [SMILES: CC(=O)N1CCN(CC(C)(C)c2ccc(NC(=O)c3nc(C#N)c[nH]3)c(C3=CCC(C)(C)CC3)c2)CC1] | Ex 138, step (i) | (ESI, m/z) Calcd. for C$_{29}$H$_{38}$N$_6$O$_2$, 503.3 (M + H), found 503.3. |
| 144 | 4-Cyano-1H-imidazole-2-carboxylic acid [2-(4,4-dimethyl-cyclohex-1-enyl)-4-(1,1-dimethyl-2-thiomorpholin-4-yl-ethyl)-phenyl]-amide | 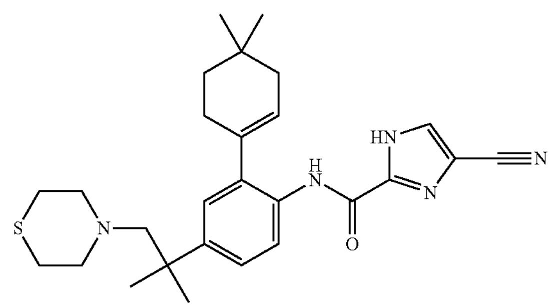 [SMILES: CC1(C)CC=C(c2cc(C(C)(C)CN3CCSCC3)ccc2NC(=O)c2nc(C#N)c[nH]2)CC1] | Ex 138, step (i) | (ESI, m/z) Calcd. for C$_{27}$H$_{35}$N$_5$OS, 478.3 (M + H), found 478.3. |
| 145 | 4-Cyano-1H-imidazole-2-carboxylic acid {2-(4,4-dimethyl-cyclohex-1-enyl)-4-[2-(1,1-dioxo-1λ$^6$-thiomorpholin-4-yl)-1,1-dimethyl-ethyl]-phenyl}-amide | 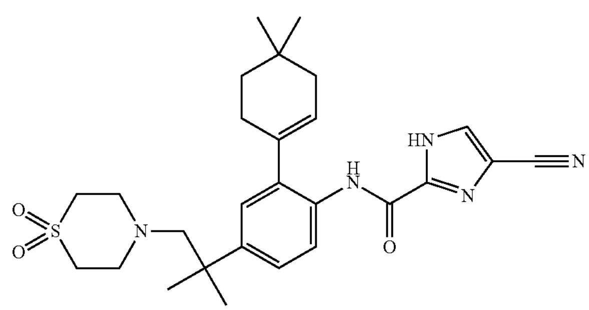 [SMILES: CC1(C)CC=C(c2cc(C(C)(C)CN3CCS(=O)(=O)CC3)ccc2NC(=O)c2nc(C#N)c[nH]2)CC1] | Ex 144, Ex 139 | (ESI, m/z) Calcd. for C$_{27}$H$_{35}$N$_5$O$_3$S, 510.3 (M + H), found 510.2. |

| Example Number | Name | Structure | Procedure Reference | Mass Spectrum |
|---|---|---|---|---|
| 146 | 4-Cyano-1H-imidazole-2-carboxylic acid (2-(4,4-dimethyl-cyclohex-1-enyl)-4-{2-[4-(2-hydroxy-ethyl)-piperazin-1-yl]-1,1-dimethyl-ethyl}-phenyl)-amide | 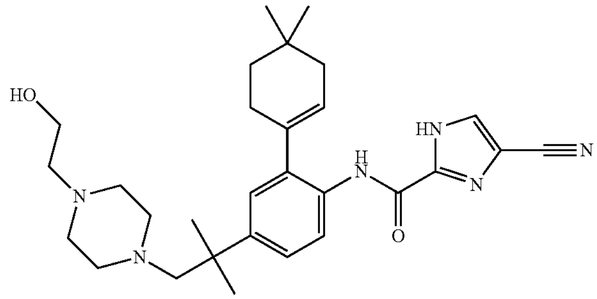 [SMILES: CC1(C)CC=C(c2cc(C(C)(C)CN3CCN(CCO)CC3)ccc2NC(=O)c2nc(C#N)c[nH]2)CC1] | Ex 138, step (i) | (ESI, m/z) Calcd. for $C_{29}H_{40}N_6O_2$, 505.3 (M + H), found 505.3. |
| 147 | 4-Cyano-1H-imidazole-2-carboxylic acid {2-(4,4-dimethyl-cyclohex-1-enyl)-4-[2-(2-methoxy-ethylamino)-1,1-dimethyl-ethyl]-phenyl}-amide | 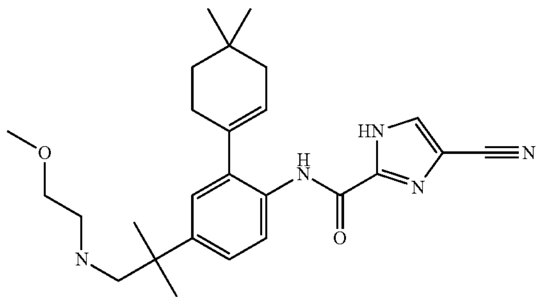 [SMILES: COCCNCC(C)(C)c1ccc(NC(=O)c2nc(C#N)c[nH]2)c(C2=CCC(C)(C)CC2)c1] | Ex 138, step (i) | (ESI, m/z) Calcd. for $C_{26}H_{35}N_5O_2$, 450.3 (M + H), found 450.2. |

35

The following examples were made according to procedures described in this document, and other procedures known to those skilled in the art.

| Example Number | Name | Structure | Procedure Reference | Reagents |
|---|---|---|---|---|
| 148 | 4-Cyano-1H-imidazole-2-carboxylic acid {2-(4,4-dimethyl-cyclohex-1-enyl)-4-[1-(3,5-dimethyl-piperazin-1-yl)-ethyl]-phenyl}-amide | 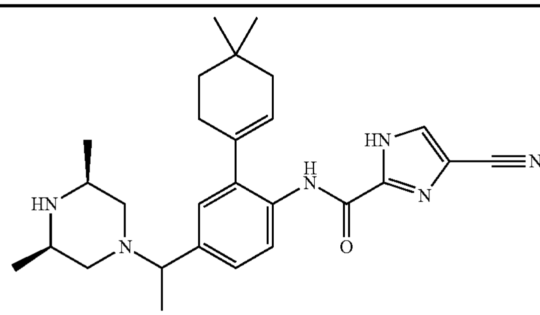 | Ex. 62, step (c); Ex. 138, step (i); Ex. 62, step (d) | |
| 149 | 4-Cyano-1H-imidazole-2-carboxylic acid [2-(dimethyl-cyclohex-1-enyl)-4-(1-methyl-1-piperidin-1-yl-ethyl)-phenyl]-amide | 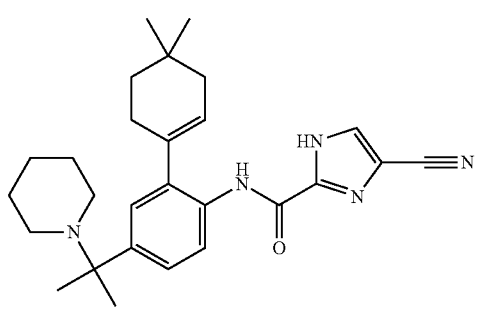 [SMILES: CC1(C)CC=C(c2cc(C(C)(C)N3CCCCC3)ccc2NC(=O)c2nc(C#N)c[nH]2)CC1] | Ex. 14, step (e) | piperidine |

Example 150

4-Cyano-1H-imidazole-2-carboxylic acid {2-(4,4-dimethyl-cyclohex-1-enyl)-4-[4-(2-hydroxy-ethyl)-piperazin-1-ylmethyl]-pheny}-amide trifluoroacetic acid salt

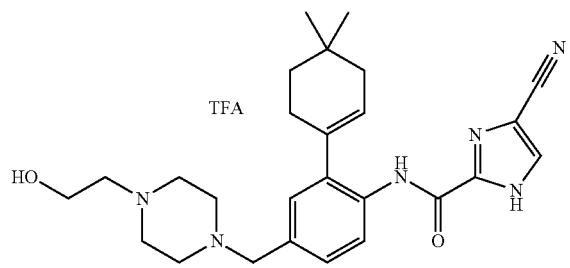 [SMILES: CC1(C)CC=C(c2cc(CN3CCN(CCO)CC3)ccc2NC(=O)c2nc(C#N)c[nH]2)CC1]

a) 2-[4-(4-Nitro-benzyl)-piperazin-1-yl]-ethanol hydrobromide

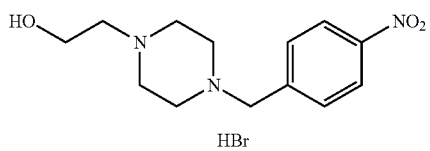 [SMILES: O=[N+]([O-])c1ccc(CN2CCN(CCO)CC2)cc1 ; Br]

A solution of 2-piperazin-1-yl-ethanol (5.10 g, 38.4 mmol) in EtOH (30 mL) was cooled to 0° C. and treated portionwise with 1-bromomethyl-4-nitro-benzene (8.30 g, 38.4 mmol). The mixture was allowed to warm to RT and stir at that temperature for 3 h. The mixture was filtered, and the solid was washed with EtOH and air-dried to afford the title compound (9.72 g, 73%) as a white solid. Mass spectrum (ESI, m/z): Calcd. for $C_{13}H_{19}N_3O_3$, 266.1 (M+H). found 266.2.

b) 1-[2-(tert-Butyl-dimethyl-silanyloxy)-ethyl]-4-(4-nitro-benzyl)-piperazine

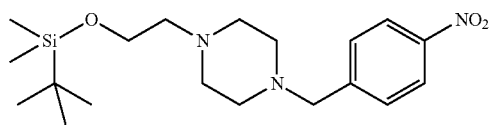

A suspension of 2-[4-(4-nitro-benzyl)-piperazin-1-yl]-ethanol hydrobromide (as prepared in the previous step, 1.00 g, 2.89 mmol) in DMF (3 mL) was treated with imidazole (688 mg, 10.1 mmol) and tert-butyl-chloro-dimethyl-silane (566 mg, 3.76 mmol) at RT for 3 h. The mixture was partitioned between EtOAc (50 mL) and brine (50 mL), and the layers were separated. The organic layer was washed with brine (3×40 mL). The combined aqueous layers were extracted with EtOAc (1×50 mL). The combined organic layers were dried over MgSO₄ and concentrated in vacuo. Purification of the residue on a 50-g Isolute SPE column on a FlashMaster system with 50% EtOAc-hexane afforded the title compound (1.03 g, 94%) as a pale yellow oil which solidified upon standing. Mass spectrum (ESI, m/z): Calcd. for $C_{19}H_{33}N_3O_3Si$, 380.2 (M+H). found 380.2.

c) 4-{4-[2-(tert-Butyl-dimethyl-silanyloxy)-ethyl]-piperazin-1-ylmethyl}-phenylamine

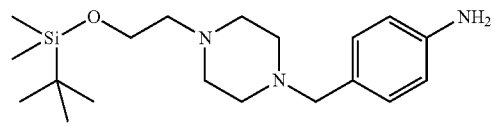 [SMILES: CC(C)(C)[Si](C)(C)OCCN1CCN(Cc2ccc([N+](=O)[O-])cc2)CC1]

A solution of 1-[2-(tert-butyl-dimethyl-silanyloxy)-ethyl]-4-(4-nitro-benzyl)-piperazine (as prepared in the previous step, 279 mg, 0.735 mmol) in MeOH (4 mL) and water (4 mL) was treated with solid NH₄Cl (393 mg, 7.35 mmol) and Zn powder (240 mg, 3.67 mmol). The mixture was stirred at 50° C. for 2 h and at RT for 16 h. The mixture was partitioned between EtOAc and water. The layers were separated, and the aqueous layer was extracted with EtOAc. The combined organic layers were dried over MgSO₄ and concentrated in vacuo. Purification of the residue on a 20-g Isolute SPE column on a FlashMaster system with EtOAc afforded the title compound (204 mg, 79%) as a yellow solid. Mass spectrum (ESI, m/z): Calcd. for $C_{19}H_{35}N_3OSi$, 350.3 (M+H). found 350.2.

d) 2-Bromo-4-{4-[2-(tert-butyl-dimethyl-silanyloxy)-ethyl]-piperazin-1-ylmethyl}-phenylamine

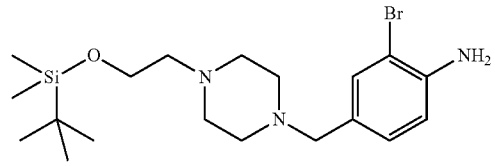 [SMILES: CC(C)(C)[Si](C)(C)OCCN1CCN(Cc2ccc(N)c(Br)c2)CC1]

A solution of 4-{4-[2-(tert-butyl-dimethyl-silanyloxy)-ethyl]-piperazin-1-ylmethyl}-phenylamine (as prepared in the previous step, 204 mg, 0.582 mmol) in CH₃CN (6 mL) was cooled to 0° C. and treated dropwise with NBS as a solution in CH₃CN (6 mL). The solvents were evaporated in vacuo. The residue was taken up in EtOAc and washed with satd aq NaHCO₃. The organic layer was dried over MgSO₄ and concentrated in vacuo. Purification of the residue on a 20-g Isolute SPE column on a FlashMaster system with 25-50% EtOAc-hexane afforded the title compound (80.9 mg, 32%) as an off-white solid. Mass spectrum (ESI, m/z): Calcd. for $C_{19}H_{34}N_3OSiBr$, 428.2/430.2 (M+H). found 428.1/430.0.

e) 4-{4-[2-(tert-Butyl-dimethyl-silanyloxy)-ethyl]-piperazin-1-ylmethyl}-2-(4,4-dimethyl-cyclohex-1-enyl)-phenylamine

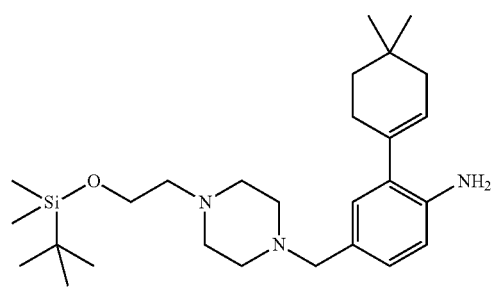 [SMILES: CC1(C)CC=C(c2cc(CN3CCN(CCO[Si](C)(C)C(C)(C)C)CC3)ccc2N)CC1]

A solution of 2-bromo-4-{4-[2-(tert-butyl-dimethyl-silanyloxy)-ethyl]-piperazin-1-ylmethyl}-phenylamine (as prepared in the previous step, 305 mg, 0.712 mmol) in DME (15 mL) was treated with LiCl (36.2 mg, 0.854 mmol), 4,4-dimethyl-cyclohex-1-enyl-4,4,5,5-tetramethyl-[1,3,2]dioxaborolane (202 mg, 8.54 mmol), and aqueous $Na_2CO_3$ (2.85 mL, 5.69 mmol, 2.0 M). The mixture was degassed via sonication, placed under Ar, treated with $Pd(PPh_3)_4$ (82.2 mg, 0.0712 mmol), and heated to 80° C. for 21 h. The mixture was concentrated in vacuo, and the residue was partitioned between EtOAc (60 mL) and water (60 mL). The layers were separated, and the organic layer was washed with brine (1×20 mL). The combined aqueous layers were extracted with EtOAc (2×20 mL). The combined organic layers were dried over $MgSO_4$ and concentrated in vacuo. Purification of the residue on a 20-g Isolute SPE column on a FlashMaster system with 50% EtOAc-hexane afforded the title compound (233 mg, 72%) as a light tan glassy solid. Mass spectrum (ESI, m/z): Calcd. for $C_{27}H_{47}N_3OSi$, 458.4 (M+H). found 458.1.

f) 4-Cyano-1-(2-trimethylsilanyl-ethoxymethyl)-1H-imidazole-2-carboxylic acid [4-{4-[2-(tert-butyl-dimethyl-silanyloxy)-ethyl]-piperazin-1-ylmethyl}-2-(4,4-dimethyl-cyclohex-1-enyl)-phenyl]-amide

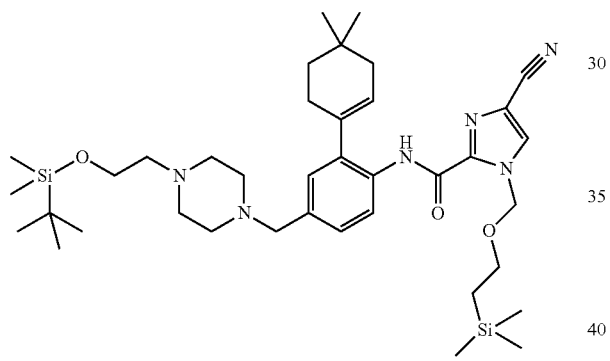

A solution of 4-{4-[2-(tert-butyl-dimethyl-silanyloxy)-ethyl]-piperazin-1-ylmethyl}-2-(4,4-dimethyl-cyclohex-1-enyl)-phenylamine (as prepared in the previous step, 233 mg, 0.590 mmol) in $CH_2Cl_2$ (10 mL) was treated with 4-cyano-1-(2-trimethylsilanyl-ethoxymethyl)-1H-imidazole-2-carboxylate potassium salt (as prepared in Example 1, step (d), 188 mg, 0.610 mmol), PyBroP (332 mg, 0.713 mmol), and DIEA (177 μL, 10.2 mmol) at RT for 1 h. The mixture was diluted with $CH_2Cl_2$ (40 mL) and washed with water (1×30 mL) and satd aq $NaHCO_3$ (1×30 mL). The combined aqueous layers were extracted with $CH_2Cl_2$ (1×30 mL). The combined organic layers were dried over $MgSO_4$ and concentrated in vacuo. Purification of the residue on a 20-g Isolute SPE column on a FlashMaster system with 10-25% EtOAc-hexane afforded the title compound (223 mg, 62%) as an off-white solid. Mass spectrum (ESI, m/z): Calcd. for $C_{38}H_{62}N_6O_3Si_2$, 707.4 (M+H). found 707.4.

g) 4-Cyano-1H-imidazole-2-carboxylic acid {2-(4,4-dimethyl-cyclohex-1-enyl)-4-[4-(2-hydroxy-ethyl)-piperazin-1-ylmethyl]-pheny}-amide trifluoroacetic acid salt A suspension of 4-cyano-1-(2-trimethylsilanyl-ethoxymethyl)-1H-imidazole-2-carboxylic acid [4-{4-[2-(tert-butyl-dimethyl-silanyloxy)-ethyl]-piperazin-1-ylmethyl}-2-(4,4-dimethyl-cyclohex-1-enyl)-phenyl]-amide (78.0 mg, 0.110 mmol) in DMF (2 mL) was heated to 60° C. and treated with tetrabutylammonium fluoride (TBAF) monohydrate (144 mg, 0.552 mmol). The mixture was stirred at 60° C. for 16 h, diluted with EtOAc (60 mL), and washed with brine (3×40 mL). The combined aqueous layers were extracted with EtOAc (1×20 mL). The combined organic layers were dried over $MgSO_4$ and concentrated in vacuo. Purification of the residue by RP-HPLC (C18) with 10-80% $CH_3CN$ in 0.1% $TFA/H_2O$ over 25 min afforded the title compound (59.1 mg, 93%) as a white solid. $^1H$-NMR ($CD_3OD$; 400 MHz): δ 8.27 (d, 1H, J=8.8 Hz), 8.03 (s, 1H), 7.34 (dd, 1H, J=8.8, 2.8 Hz), 7.27 (d, 1H, J=2.8 Hz), 5.81-5.75 (m, 1H), 3.90-3.81 (m, 4H), 3.44-3.25 (br s, 4H), 3.23-3.16 (m, 2H), 3.10-2.85 (br s, 4H), 2.38-2.29 (m, 2H), 2.14-2.06 (m, 2H), 1.66-1.58 (m, 2H), 1.11 (s, 6H). Mass spectrum (ESI, m/z): Calcd. for $C_{26}H_{34}N_6O_2$, 463.3 (M+H). found 463.2.

Example 151

4-Cyano-1H-imidazole-2-carboxylic acid [2-(4,4-dimethyl-cyclohex-1-enyl)-4-piperazin-1-ylmethyl-phenyl]-amide trifluoroacetic acid salt

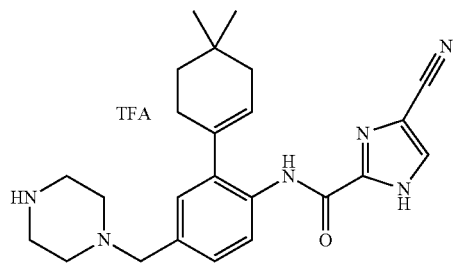 [SMILES: CC1(C)CC=C(c2cc(CN3CCNCC3)ccc2NC(=O)c2nc(C#N)c[nH]2)CC1]

a) 4-(4-Nitro-benzyl)-piperazine-1-carboxylic acid tert-butyl ester

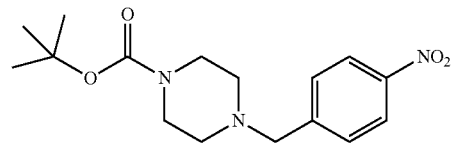 [SMILES: CC(C)(C)OC(=O)N1CCN(Cc2ccc([N+](=O)[O-])cc2)CC1]

A solution of piperazine-1-carboxylic acid tert-butyl ester (1.90 g, 10.2 mmol) and triethylamine (1.55 mL, 11.1 mmol) in $CH_3CN$ (9 mL) was treated with 1-bromomethyl-4-nitrobenzene (2.00 g, 9.26 mmol) as a solution in $CH_3CN$ (15 mL) at RT for 20 min. The mixture was concentrated in vacuo. The residue was taken up in $CH_2Cl_2$ (20 mL) and washed with water (1×20 mL). The aqueous layer was extracted with $CH_2Cl_2$ (2×20 mL), and the combined organic layers were washed with water (1×40 mL), dried over $MgSO_4$ and concentrated in vacuo. Purification of the residue on a 50-g Isolute SPE column on a FlashMaster system with 10-25% EtOAc-hexane afforded the title compound (2.82 g, 95%) as a white solid. Mass spectrum (ESI, m/z): Calcd. for $C_{16}H_{23}N_3O_4$, 322.2 (M+H). found 321.9.

b) 4-(4-Amino-benzyl)-piperazine-1-carboxylic acid tert-butyl ester

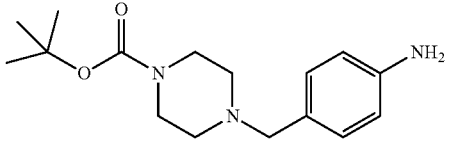

A solution of 4-(4-nitro-benzyl)-piperazine-1-carboxylic acid tert-butyl ester (2.82 g, 8.77 mmol) was hydrogenated on an H-Cube apparatus with a 5% Pd/C cartridge under the following conditions: flow rate=1 mL/min, heating column temperature=30° C., $H_2$ pressure=40 bar. The material was passed through the column twice more in order to complete the reaction. Solvents were evaporated in vacuo. Purification of the residue on a 50-g Isolute SPE column on a FlashMaster system with 25-50% EtOAc-hexane afforded the title compound (1.70 g, 67%) as a yellow solid. Mass spectrum (ESI, m/z): Calcd. for $C_{16}H_{25}N_3O_2$, 292.2 (M+H). found 292.1.

c) 4-(4-Amino-3-bromo-benzyl)-piperazine-1-carboxylic acid tert-butyl ester

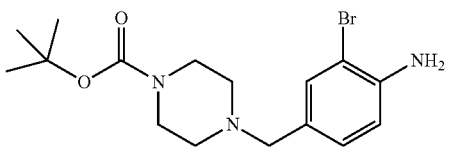 [SMILES: CC(C)(C)OC(=O)N1CCN(Cc2ccc(N)c(Br)c2)CC1]

The title compound was prepared as described in Example 150, step (d) using 4-(4-amino-benzyl)-piperazine-1-carboxylic acid tert-butyl ester (as prepared in the previous step). Mass spectrum (APCI, m/z): Calcd. for $C_{16}H_{24}N_3O_2Br$, 370.1/372.1 (M+H). found 370.3/372.0.

d) 4-[4-Amino-3-(4,4-dimethyl-cyclohex-1-enyl)-benzyl]-piperazine-1-carboxylic acid tert-butyl ester

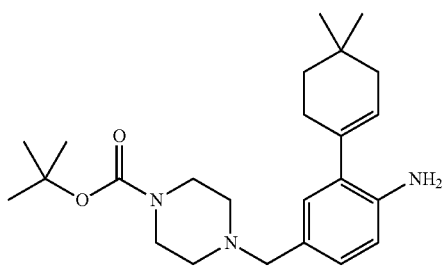 [SMILES: CC1(C)CC=C(c2cc(CN3CCN(C(=O)OC(C)(C)C)CC3)ccc2N)CC1]

The title compound was prepared as described in Example 150, step (e) using 4-(4-amino-3-bromo-benzyl)-piperazine-1-carboxylic acid tert-butyl ester (as prepared in the previous step). Mass spectrum (ESI, m/z): Calcd. for $C_{24}H_{37}N_3O_2$, 400.3 (M+H). found 400.1.

e) 4-[4-{[4-Cyano-1-(2-trimethylsilanyl-ethoxymethyl)-1H-imidazole-2-carbonyl]-amino}3-(4,4-dimethyl-cyclohex-1-enyl)-benzyl]-piperazine-1-carboxylic acid tert butyl ester

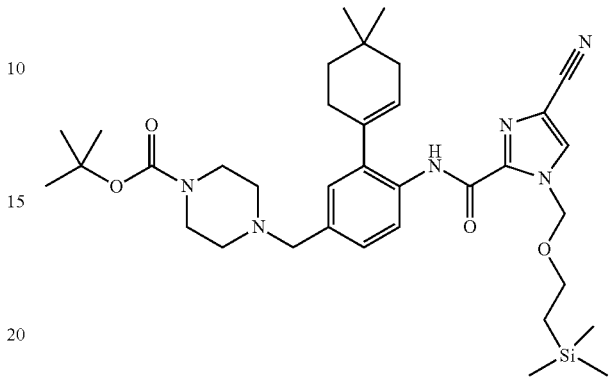

The title compound was prepared as described in Example 150, step (f) using 4-[4-amino-3-(4,4-dimethyl-cyclohex-1-enyl)-benzyl]-piperazine-1-carboxylic acid tert-butyl ester (as prepared in the previous step). Mass spectrum (APCI, m/z): Calcd. for $C_{35}H_{52}N_6O_4Si$, 649.4 (M+H). found 649.2.

f) 4-Cyano-1H-imidazole-2-carboxylic acid [2-(4,4-dimethyl-cyclohex-1-enyl)-4-piperazin-1-ylmethyl-phenyl]-amide trifluoroacetic acid salt The title compound was prepared as described in Example 150, step (g) using 4-[4-{[4-cyano-1-(2-trimethylsilanyl-ethoxymethyl)-1H-imidazole-2-carbonyl]-amino}3-(4,4-dimethyl-cyclohex-1-enyl)-benzyl]-piperazine-1-carboxylic acid tert butyl ester (as prepared in the previous step). $^1$H-NMR (CD$_3$OD; 400 MHz): δ 8.31-8.23 (m, 1H), 8.03 (s, 1H), 7.37-7.29 (m, 1H), 7.29-7.23 (m, 1H), 5.81-5.74 (m, 1H), 3.85 (s, 2H), 3.39-3.28 (m, 4H), 3.04-2.85 (m, 4H), 2.38-2.27 (m, 2H), 2.14-2.03 (m, 2H), 1.66-1.56 (m, 2H), 1.11 (s, 6H). Mass spectrum (ESI, m/z): Calcd. for $C_{24}H_{30}N_6O$, 419.3 (M+H). found 419.1.

IV. RESULTS

Fluorescence Polarization Competition Immunoassay

A fluorescence polarization competition immunoassay was used to measure compound inhibition of CSF-1R phosphorylation of tyrosine on a synthetic CSF-1R$_{555-568}$ peptide (SYEGNSYTFIDPTQ). The assay was performed in black 96-well microplates (Cat #42-000-0117, Molecular Devices, Sunnyvale, Calif.). To each well, 5 µL of compound (in 4% DMSO) were mixed with 2 µL of 3.5 nM CSF-1R, 25 mM MgCl$_2$ in assay buffer (100 mM HEPES (hydroxyethylpiperazineethylsodiumsulfonate), pH 7.5, 1 mM DTT (dithiothreitol), 0.01% Tween-20), and 2 µL of 1540 µM peptide in assay buffer. The kinase reaction was initiated by adding 1 µL of 10 mM ATP in assay buffer. The final concentrations in the 10 uL reaction mixture were 100 mM HEPES, pH 7.5, 1 mM DTT, 0.01% Tween-20, 2% DMSO, 308 µM SYEGNSYTFIDPTQ, 1 mM ATP, 5 mM MgCl$_2$, and 0.7 nM CSF-1R. Positive and negative control wells were included on each plate, where 4% DMSO in assay buffer was substituted for the compound; in addition, positive control wells received 1.2 µL of 50 mM EDTA (ethylenediaminetetraacetic acid) before the start of the reaction.

The plates were covered and incubated at room temperature for 80 min. Reactions were stopped by addition of 1.2 µL of 50 mM EDTA. Each well then received 10 µL of a 1:1:3 mixture of 10× anti-phosphotyrosine antibody, 10×PTK green tracer, and FP dilution buffer, respectively (Cat. # P2837, Invitrogen, Carlsbad, Calif.). The plates were covered, incubated for 30 min at room temperature, and the fluorescence polarization was read on an Analyst plate reader (Molecular Devices). Instrument settings were: 485 nm excitation, 530 nm emission, with a 505 nm cut-off filter; Z height: middle of well; G factor: 0.93. Under these conditions, the fluorescence polarization values for positive and negative controls were approximately 290 and 160, respectively, and were used to define 100% and 0% inhibition of the CSF-1R reaction. Reported $IC_{50}$ values are the mean of three of at least three determinations.

CSF-1-Driven Mouse Bone-Marrow Derived Macrophages Assay

Macrophages are derived by culturing mouse bone marrow in alpha-MEM supplemented with 10% FCS and 50 ng/ml recombinant mouse CSF-1 in bacteriologic dishes. On the sixth day, macrophages are detached from dishes, washed, and resuspended to 0.05 million cells/ml in alpha-MEM containing 10% FCS (fetal calf serum). One hundred ul of cell suspension are distributed per well into 96 well culture plates. Wells are further supplemented with the addition of 50 ul media containing 15 ng/ml CSF-1, 3 uM Indomethacin, and 3× of a dilution series of test compounds. The cells are cultured for 30 hrs at 37 degrees and 5% $CO_2$. During the final six hours, cultures are supplemented with an additional 30 ul of media containing a 1:500 dilution of bromodeoxyuridine (BrDU). At the end of the culture period, the plates are spun at 1000 RPM for 1 minute and 130 ul of media is removed with a pipet and replaced with 150 ul of fixative solution for 1 hour @ room temperature. The fixative is then dispelled from the plates and the plates allowed to air dry. Incorporation of BrDU into the fixed, dried cells is quantified using a specific ELISA.

Table 1 lists the assay results for representative compounds of the invention.

TABLE 1

| Example | 1 nM c-fms; peptide Pi assay - IC-50 (µM) | mCSF driven proliferation BMDM (Mouse) - IC-50 (µM) |
|---|---|---|
| 1 | 0.0047 | 0.0579 |
| 2 | 0.0329 | N/A |
| 3 | 0.0061 | 0.077 |
| 4 | 0.0124 | >0.3 |
| 5 | 0.0317 | >0.15 |
| 6 | 0.0086 | 0.0239 |
| 7 | 0.0027 | >0.05 |
| 8 | 0.0059 | >0.3 |
| 9 | 0.079 | N/A |
| 10 | 0.0017 | 0.0246 |
| 11 | >0.06 | N/A |
| 12 | 0.0044 | 0.0442 |
| 13 | 0.008 | >0.3 |
| 14 | 0.0093 | 0.059 |
| 15 | 0.0011 | 0.0058 |
| 16 | 0.0033 | 0.0085 |
| 17 | 0.0014 | 0.005 |
| 18 | 0.0018 | 0.0148 |
| 19 | 0.0072 | 0.04 |
|  |  | 0.0113 |
| 20 | 0.00044 | 0.0047 |
|  |  | 0.0048 |
| 21 | 0.0026 | 0.0119 |
|  | 0.0017 |  |
| 22 | 0.00094 | 0.0143 |
|  |  | 0.02 |
| 23 | 0.0029 | 0.0129 |
|  | 0.0051 | 0.0033 |
|  |  | 0.0031 |
|  |  | 0.0033 |
| 24 | 0.0012 | 0.0072 |
| 25 | 0.00774 | 0.1014 |
| 26 | 0.0032 | 0.0059 |
|  | 0.0037 | 0.0049 |
|  | 0.0036 | 0.04613 |
|  |  | 0.046 |
|  |  | 0.0059 |
| 27 | 0.0045 | 0.085 |
|  |  | 0.042 |
| 28 | 0.0094 | 0.0394 |
| 29 | 0.0029 | 0.0317 |
| 30 | 0.0056 | 0.0226 |
| 31 | 0.0026 | 0.0209 |
| 32 | 0.0128 | 0.0482 |
| 33 | >0.06 | N/A |
| 34 | 0.373 | N/A |
| 35 | >0.5 | N/A |
| 36 | >0.5 | N/A |
| 37 | ~0.3 | N/A |
| 38 | >0.06 | N/A |
| 39 | >0.06 | N/A |
| 40 | 0.0279 | N/A |
| 41 | 0.0082 | 0.3205 |
| 42 | 0.00143 | 0.0027 |
|  |  | 0.0012 |
| 43 | N/A | N/A |
| 44 | 0.0046 | 0.01636 |
|  |  | 0.0146 |
| 45 | 0.0006 | 0.0032 |
| 46 | 0.0025 | >0.3 |
| 47 | 0.0015 | 0.03388 |
| 48 | 0.0039 | >0.1 |
|  | 0.0053 | >1 |
| 49 | 0.026 | >0.3 |
| 50 | 0.06 | N/A |
| 51 | 0.0362 | N/A |
| 52 | 0.0056 | 0.001 |
|  | 0.0008 | 0.0033 |
| 53 | 0.0029 | >0.1 |
| 54 | 0.0024 | >0.1 |
| 55 | 0.05@0.002-2 (10 nM c-fms auto-Pi assay - IC-50) | N/A |
| 60 | 0.0008 | 0.0026 |
| 61 | 0.0019 | 0.024 |
| 62 | 0.00088 | 0.0057 |
| 63 | 0.00069 | 0.0087 |
| 64 | 0.00093 | 0.2 |
| 65 | N/A | 0.0081 |
| 66 | 0.0039 | 0.044 |
| 67 | 0.0013 | 0.018 |
| 68 | 0.0016 | 0.0093 |
| 69 | 0.00051 | 0.0019 |
| 70 | 0.14 | >0.3 |
| 71 | 0.033 | >0.3 |
| 72 | 0.019 | >0.2 |
| 73 | 0.0088 | >0.3 |
| 74 | 0.0015 | 0.0065 |
| 75 | 0.0017 | 0.013 |
| 76 | 0.00068 | 0.068 |
| 77 | 0.0013 | 0.0078 |
| 78 | N/A | 0.0081 |
| 79 | 0.002 | 0.023 |
| 80 | 0.0012 | 0.013 |

TABLE 1-continued

| Example | 1 nM c-fms; peptide Pi assay - IC-50 (μM) | mCSF driven proliferation BMDM (Mouse) - IC-50 (μM) |
|---|---|---|
| 138 | 0.0013 | 0.016 |
|  |  | 0.021 |
| 139 | 0.0016 | 0.016 |
|  |  | 0.019 |
| 140 | >0.1 | 0.031 |
| 141 | 0.018 | 0.0019 |
| 142 | 0.008 | 0.057 |
| 143 | 0.0057 | 0.029 |
| 144 | 0.036 | >0.1 |
| 145 | 0.0035 | 0.02 |
| 146 | 0.002 | 0.017 |
| 147 | 0.00064 | 0.012 |
|  |  | 0.018 |
|  |  | 0.0091 |
| 148 | 0.0017 | N/A |
| 149 | 0.0015 | 0.011 |
| 150 | 0.00075 | 0.016 |
|  |  | 0.0098 |
|  |  | 0.013 |
| 151 | 0.00082 | 0.0084 |
|  |  | 0.012 |

The term "N/A" in Table 1 means "not available".

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

We claim:

1. A compound of Formula I

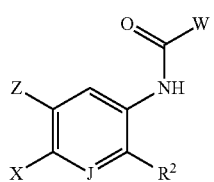

or a solvate, hydrate, tautomer or pharmaceutically acceptable salt thereof, wherein:

W is

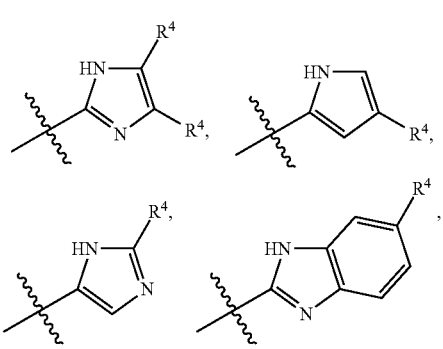

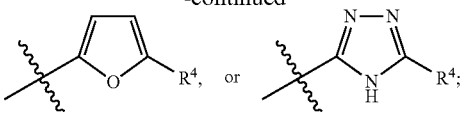

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$,

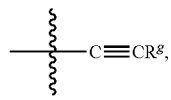

or CN;
wherein $R^d$ is H, or —$C_{(1-3)}$alkyl;
$R^e$ is H, or —$C_{(1-3)}$alkyl;
$R^f$ is H, or —$C_{(1-3)}$alkyl; and
$R^g$ is H, —$CH_2OH$, or —$CH_2CH_2OH$;
$R^2$ is cycloalkyl, spiro-substituted cycloalkenyl, heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;
Z is H, F, or $CH_3$;
J is N;
X is —$C_{(1-6)}$alkyl$R^1$, alkenyl, propenyl-$NA^1A^2$, —CH=CH—$CO_2R^a$ wherein said CH=CH bond includes both E and Z stereochemistry, —$C_{(1-4)}$alkyl$R^3R^{4a}$, or $CH_2$-heteroaryl-$C_{(1-4)}$alkyl-$R^1$;
wherein:
$R^1$ is —CN, —$SO_2NA^1A^2$, —$SO_2R^a$, —$SCH_2CH_2NA^1A^2$, —$SOCH_2CH_2NA^1A^2$, —$SO_2CH_2CH_2NA^1A^2$, —S—C(O)$C_{(1-4)}$alkyl, —S—$CH_2$-4-methoxy phenyl, —$OC_{(1-4)}$alkyl$NA^1A^2$, —$NA^1A^2$, —$NHSO_2R^a$, —$NHCOR^a$, —$NHSO_2CH_2CH_2NA^1A^2$, —$NHCOCH_2CH_2NA^1A^2$, —$CONH_2$, —$CONHCH_2CH_2CH_2OH$, —$CONHCH_2CH_2N(C_{(1-4)}alkyl)_2$, —$NHCONH_2$, —$NHCONHCH_2CH_2OH$, —$NHCOCONH_2$, —$NR_aCH_2CH_2NA^1A^2$, $CO_2R^a$, pyridyl, —$OCH_2CH_2OR^a$, —$OCH_2CH_2OCH_2CH_2NA^1A^2$, —$OCH_2CH_2NA^1CH_2CH_2OR^a$, —$NA^1CH_2CH_2OCH_2CH_2OR^a$, —$OCOR^a$, or —$CH_2OCOCH_3$;
$A^1$ is H or —$C_{(1-4)}$alkyl;
$A^2$ is —$C_{(1-4)}$alkyl, —$CH_2CH_2OR^a$, —$COR^a$, —$CH_2CH_2SC_{(1-4)}$alkyl, —$CH_2CH_2SOC_{(1-4)}$alkyl, pyridyl, 2-methyl pyridyl, —$CH_2CH_2OCH_2CH_2OR^a$, or —$CH_2CH_2SO_2C_{(1-4)}$alkyl;
alternatively, $A^1$ and $A^2$ may be taken together with their attached nitrogen to form a heterocyclic ring selected from the following:

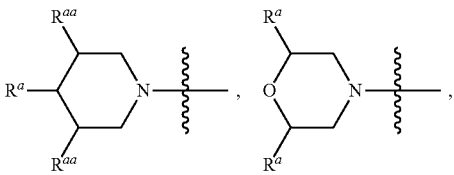

-continued

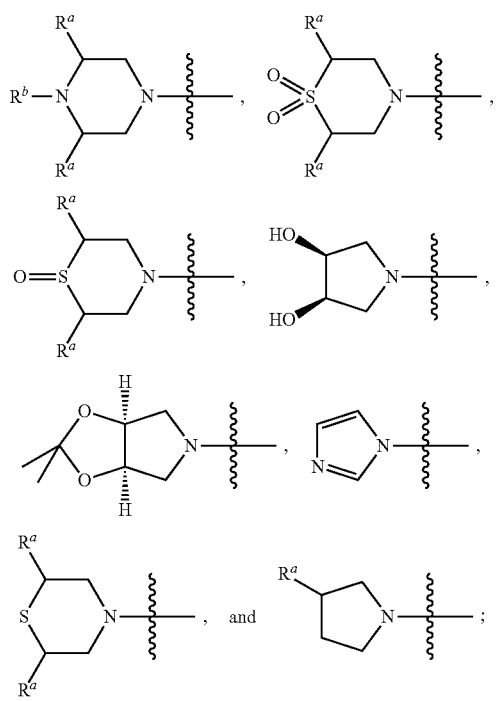

wherein:

$R^a$ is H or $C_{(1-4)}$alkyl;

$R^{aa}$ is H or $C_{(1-4)}$alkyl;

$R^b$ is H, —$C_{(1-4)}$alkyl, alkoxyether, —C(O)$C_{(1-4)}$alkyl, —$C_{(1-4)}$alkyl-OH, —$C_{(1-4)}$alkyl-O-$C_{(1-4)}$alkyl, —$C_{(1-4)}$alkyl-C(O)O-$C_{(1-4)}$alkyl, —$C_{(1-4)}$alkylC(O)OH, —$C_{(1-4)}$alkylC(O)ONa, or —$CH_2$C(O)$C_{(1-4)}$alkyl; and $R^3$ and $R^{4a}$ are independently —$CH_2OH$, —$OCH_3$, —$CH_2OCH_3$, —$CO_2H$, —$CO_2C_{(1-4)}$alkyl, OC(O)$C_{(1-4)}$alkyl, or —OH.

2. The compound of claim 1, wherein:

$R^2$ is

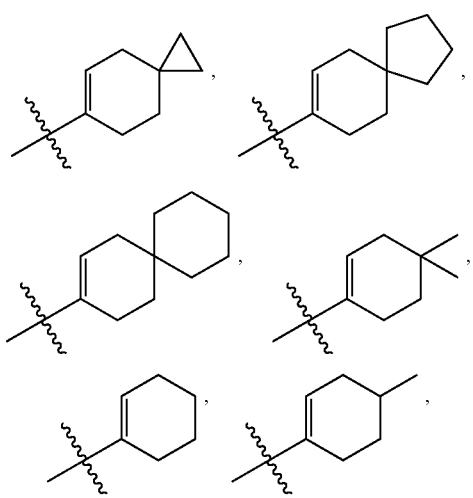

-continued

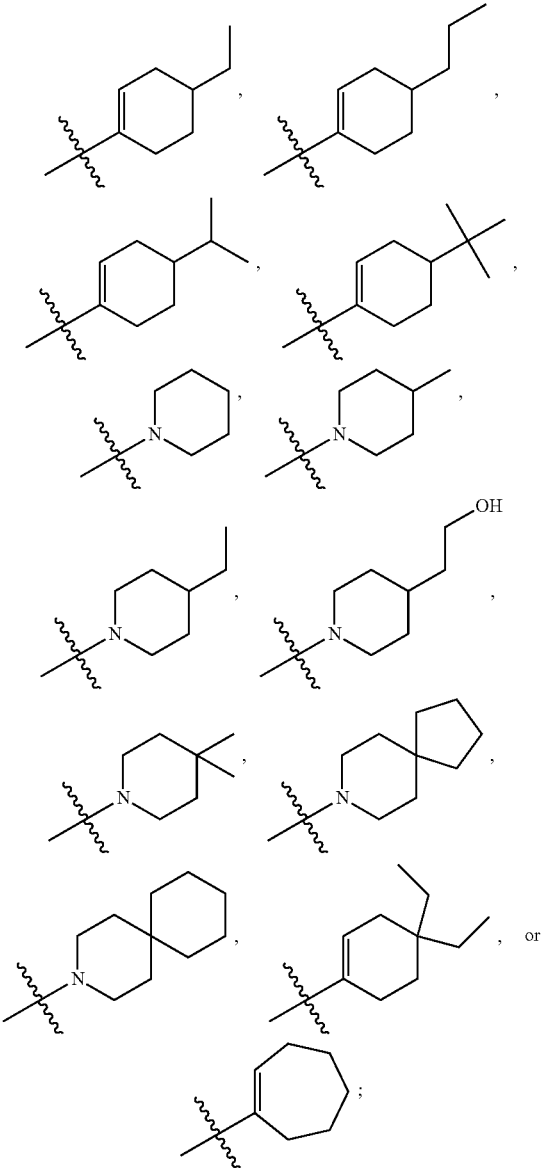

X is —$C_{(1-6)}$alkyl$R^1$, alkenyl, propenyl-$NA^1A^2$, —CH=CH—$CO_2R^a$, —$C_{(1-4)}$alkyl$R^3R^{4a}$, or —$CH_2$-heteroaryl-$C_{(1-4)}$alkyl-$R^1$;

wherein:

$R^1$ is —CN, —$SO_2NA^1A^2$, —$SO_2R^a$, —$SCH_2CH_2NA^1A^2$, —$SOCH_2CH_2NA^1A^2$, —$SO_2CH_2CH_2NA^1A^2$, —S—C(O)$C_{(1-4)}$alkyl, —S—$CH_2$-4-methoxy phenyl, —$OC_{(1-4)}$alkyl$NA^1A^2$, —$NA^1A^2$, —$NHSO_2CH_3$, —$NHCOCH_3$, —$CONH_2$, —$CONHCH_2CH_2CH_2OH$, —$CONHCH_2CH_2$$N(C_{(1-4)}alkyl)_2$, —$NHCONH_2$, —$NHCONHCH_2CH_2OH$, —$NHCOCONH_2$, —$NR_aCH_2CH_2NA^1A^2$, —$CO_2R^a$, pyridyl, —$OCOCH_3$, or —$CH_2OCOCH_3$;

$A^1$ is H or —$C_{(1-4)}$alkyl;

$A^2$ is —$C_{(1-4)}$alkyl, —$CH_2CH_2OR^a$, —$COR^a$, —$CH_2CH_2SC_{(1-4)}$alkyl, —$CH_2CH_2SOC_{(1-4)}$alkyl, pyridyl, 2-methyl pyridyl, or —$CH_2CH_2SO_2C_{(1-4)}$alkyl;

alternatively, $A^1$ and $A^2$ may be taken together with their attached nitrogen to form a heterocyclic ring selected from the following:

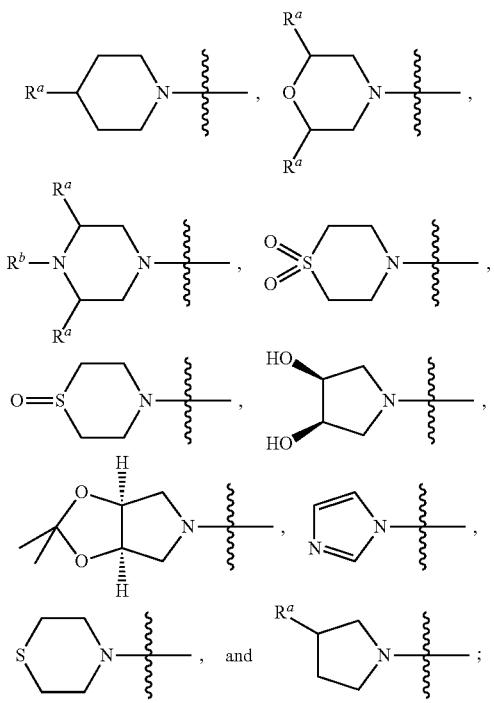

wherein:
  $R^a$ is H or $C_{(1-4)}$alkyl;
  $R^b$ is H, —$C_{(1-4)}$alkyl, alkoxyether, —C(O)$C_{(1-4)}$alkyl, —$C_{(1-4)}$alkyl-OH, —$C_{(1-4)}$alkyl-O-$C_{(1-4)}$alkyl, —$C_{(1-4)}$alkyl-C(O)O-$C_{(1-4)}$alkyl, —$C_{(1-4)}$alkylC(O)OH, —$C_{(1-4)}$alkylC(O)ONa, or —$CH_2C(O)C_{(1-4)}$alkyl; and
$R^3$ and $R^{4a}$ are independently —$CH_2OH$, —$OCH_3$, —$CH_2OCH_3$, —$CO_2H$, —$CO_2C_{(1-4)}$alkyl, —OC(O)$C_{(1-4)}$alkyl, or —OH.

3. The compound of claim 2 wherein:
$R^2$ is

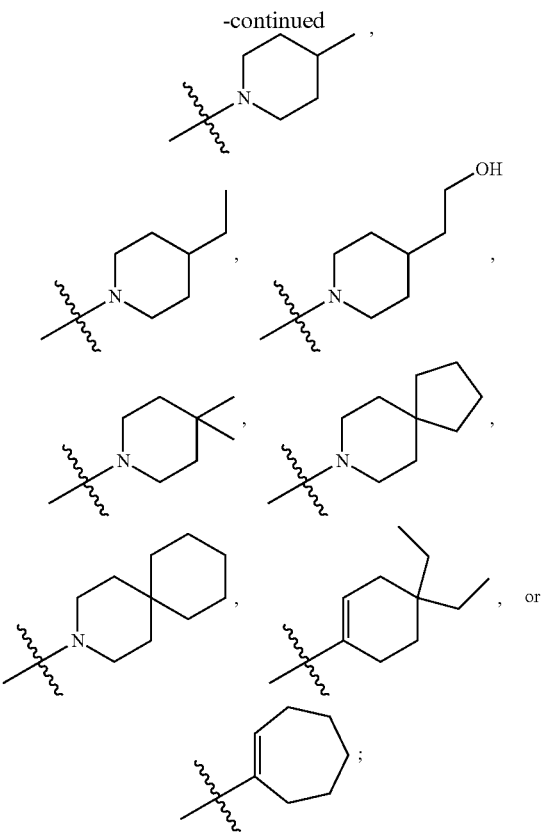

X is —$C_{(1-5)}$alkyl$R^1$, alkenyl, propenyl-$NA^1A^2$, —CH═CH—$CO_2R^a$, —$C_{(1-4)}$alkyl$R^3R^{4a}$, or —$CH_2$-heteroaryl-$C_{(1-4)}$alkyl-$R^1$;

wherein:
  $R^1$ is —CN, —$SO_2NA^1A^2$, —$SO_2R^a$, —$SCH_2CH_2NA^1A^2$, —$SOCH_2CH_2NA^1A^2$, —$SO_2CH_2CH_2NA^1A^2$, —S—C(O)$C_{(1-4)}$alkyl, —S—$CH_2$-4-methoxy phenyl, —$OC_{(1-4)}$alkyl$NA^1A^2$, —$NA^1A^2$, —$NHSO_2CH_3$, —$NHCOCH_3$, —$CONH_2$, —$CONHCH_2CH_2CH_2OH$, $CONHCH_2CH_2N(C_{(1-4)}$alkyl$)_2$, —$NHCONH_2$, —$NHCONHCH_2CH_2OH$, —$NHCOCONH_2$, —$NR_aCH_2CH_2NA^1A^2$, —$CO_2R^a$, pyridyl, —$OCOCH_3$, or —$CH_2OCOCH_3$;
  $A^1$ is H or —$C_{(1-4)}$alkyl;
  $A^2$ is —$C_{(1-4)}$alkyl, —$CH_2CH_2OR^a$, —$COR^a$, —$CH_2CH_2SC_{(1-4)}$alkyl, —$CH_2CH_2SOC_{(1-4)}$alkyl, pyridyl, 2-methyl pyridyl, or —$CH_2CH_2SO_2C_{(1-4)}$alkyl;
  alternatively, $A^1$ and $A^2$ may be taken together with their attached nitrogen to form a heterocyclic ring selected from the following:

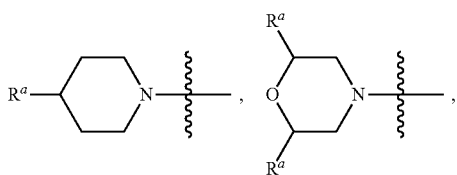

-continued

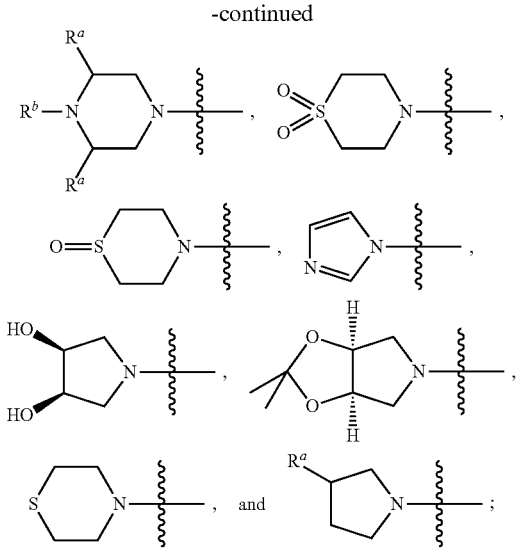

wherein:

$R^a$ is H or $C_{(1-4)}$alkyl;

$R^b$ is H, —$C_{(1-4)}$alkyl, alkoxyether, —C(O)$C_{(1-4)}$alkyl, —$C_{(1-4)}$alkyl-OH, —$C_{(1-4)}$alkyl-O-$C_{(1-4)}$alkyl, —$C_{(1-4)}$alkyl-C(O)O-$C_{(1-4)}$alkyl, —$C_{(1-4)}$alkylC(O)OH, —$C_{(1-4)}$alkylC(O)ONa, or —$CH_2C(O)$—$C_{(1-4)}$alkyl; and $R^3$ and $R^{4a}$ are independently —$CH_2OH$, —$OCH_3$, —$CH_2OCH_3$, —$CO_2H$, —$CO_2C_{(1-4)}$alkyl, OC(O)$C_{(1-4)}$alkyl, or —OH.

4. The compound of claim 3 wherein:

W is

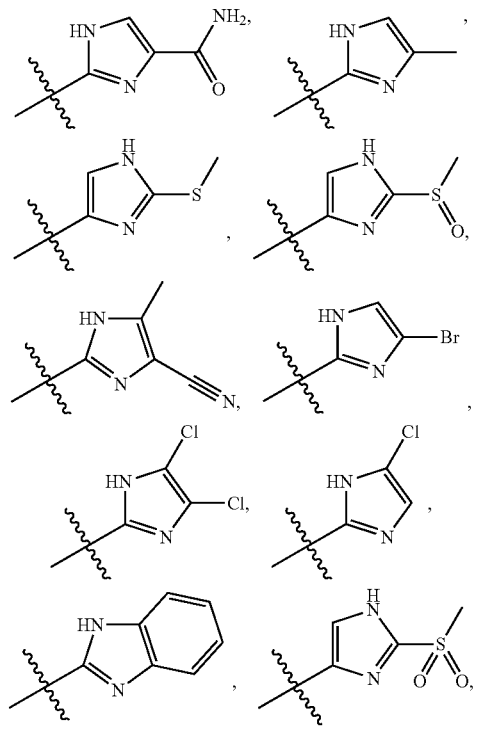

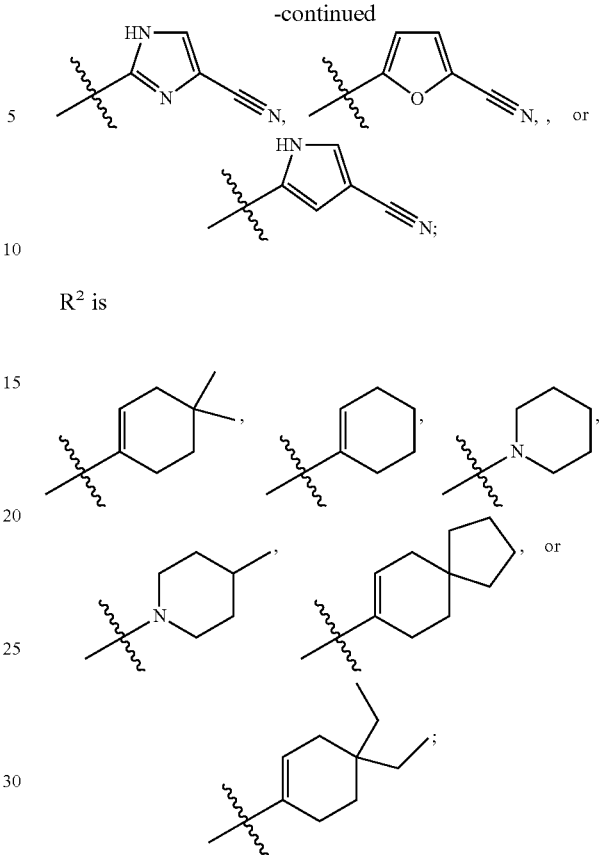

$R^2$ is

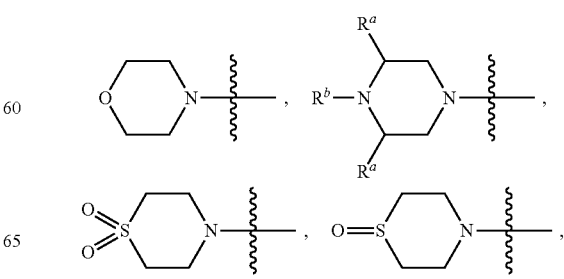

Z is H;

X is —$C_{(1-5)}$alkyl$R^1$, —CH=CH—$CO_2H$ wherein said CH=CH bond has E stereochemistry, —$C_{(1-4)}$alkyl$R^3R^{4a}$, propenyl-$NA^1A^2$, or propenyl;

wherein:

$R^1$ is —$SO_2NA^1A^2$, —S—C(O)$CH_3$, —S—$CH_2$-4-methoxy phenyl, —$OC_{(1-4)}$alkyl$NA^1A^2$, —$NA^1A^2$, —$NHCH_2CH_2NA^1A^2$, —$NHSO_2CH_3$, —$NHCOCH_3$, —$CONH_2$, —$CONHCH_2CH_2CH_2OH$, —$CONHCH_2CH_2N(CH_3)_2$, —$NHCONH_2$, —$NHCONHCH_2CH_2OH$, —$NHCOCONH_2$, —$CO_2R^a$, or pyridyl;

$A^1$ is H or —$C_{(1-4)}$alkyl;

$A^2$ is —$C_{(1-4)}$alkyl, —$CH_2CH_2OR^a$, —$COCH_3$, —$CH_2OCH_3$, —$CH_2CH_2SC_{(1-4)}$alkyl, pyridyl, 2-methyl pyridyl, or —$CH_2CH_2SO_2C_{(1-4)}$alkyl;

alternatively, $A^1$ and $A^2$ may be taken together with their attached nitrogen to form a heterocyclic ring selected from the following:

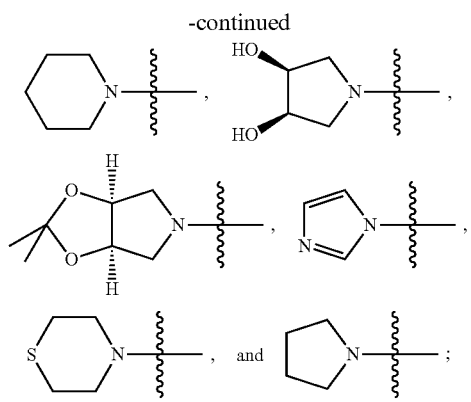

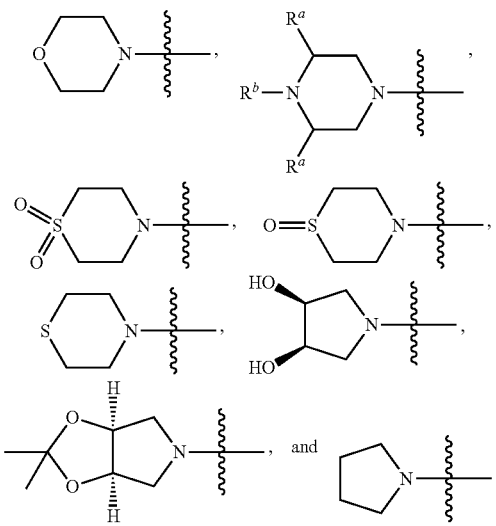

wherein:
$R^a$ is H or $C_{(1-4)}$alkyl;
$R^b$ is H, —$CH_2CH_2OH$, —$CH_2CH_2OCH_3$, —$CH_2C(O)OCH_2CH_3$, —$CH_2C(O)OH$, —$CH_2C(O)ONa$, —$C(O)CH_3$, or —$C_{(1-4)}$alkyl; and
$R^3$ and $R^{4a}$ are independently —$OCH_3$, —$CH_2OCH_3$, —$CO_2H$, —$OC(O)CH_3$, or —OH.

5. The compound of claim 4 wherein:
$R^2$ is

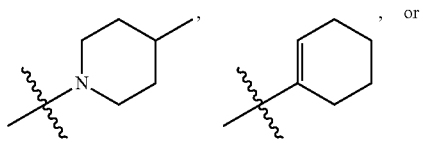

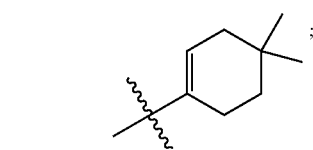

X is —$CH_2R^1$, —$CH_2CH_2R^1$, —$C(CH_3)_2R^1$, —CH=CH—$CO_2H$ wherein said CH=CH bond has E stereochemistry, —$C_{(1-4)}$alkyl$R^3R^{4a}$, propenyl-$NA^1A^2$, or propenyl;
wherein:
$R^1$ is —$SO_2NA^1A^2$, —S—$C(O)CH_3$, —S—$CH_2$-4-methoxy phenyl, —$OCH_2CH_2NA^1A^2$, —$NA^1A^2$, —$NHCH_2CH_2NA^1A^2$, —$NHSO_2CH_3$, —$NHCOCH_3$, —$CONH_2$, —$CONHCH_2CH_2OH$, —$CONHCH_2CH_2N(CH_3)_2$, —$NHCONH_2$, —$NHCONHCH_2CH_2OH$, —$NHCOCONH_2$, or —$CO_2R^a$;
$A^1$ is H or —$C_{(1-4)}$alkyl;
$A^2$ is —$C_{(1-4)}$alkyl, —$C(O)CH_3$, —$CH_2CH_2OCH_3$, —$CH_2CH_2OH$, —$CH_2CH_2SCH_3$, pyridyl, 2-methyl pyridyl, or —$CH_2CH_2SO_2CH_3$;
alternatively, $A^1$ and $A^2$ may be taken together with their attached nitrogen to form a heterocyclic ring selected from the following:

wherein:
$R^a$ is H, $CH_3$, or —$CH_2CH_3$
$R^b$ is H, $CH_2CH_2OH$, —$CH_2CH_2OCH_3$, —$CH_2C(O)OCH_2CH_3$;
—$CH_2C(O)OH$, —$CH_2C(O)ONa$, $CH_2CH_3$, $C(O)CH_3$, or $CH_3$; and
$R^3$ and $R^{4a}$ are independently, —$OCH_3$, —$CH_2OCH_3$, —$CO_2H$, —$OC(O)CH_3$, or —OH.

6. The compound of claim 1, wherein W is

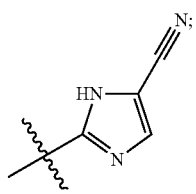 [SMILES: *c1ncc(C#N)[nH]1]

$R^2$ is

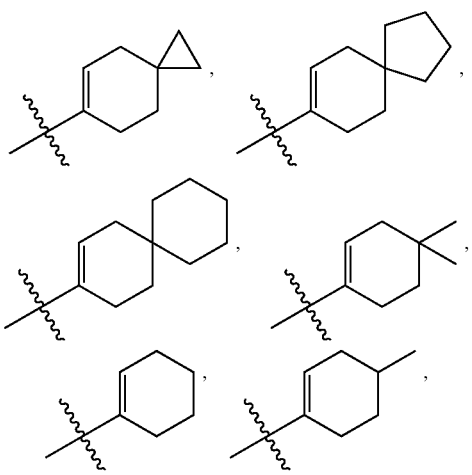

-continued

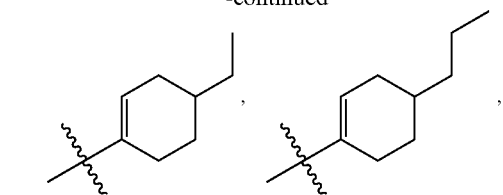

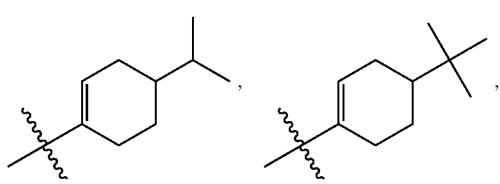

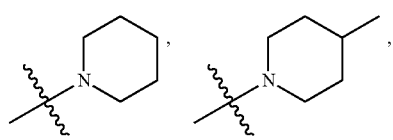

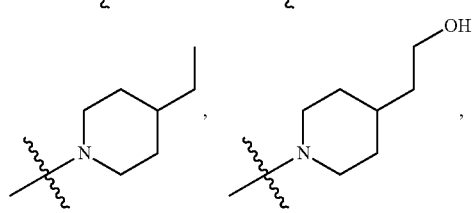

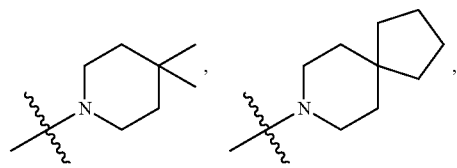

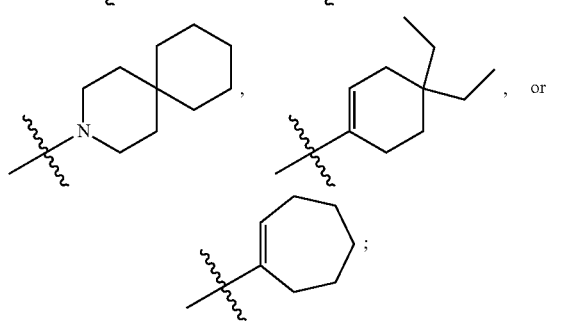

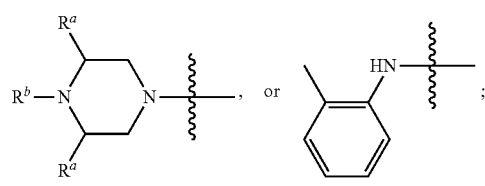

Z is H;
X is —C$_{(1-6)}$alkylR$^1$, or propenyl-NA$^1$A$^2$, wherein:
 R$^1$ is —NA$^1$A$^2$, —S—C(O)C$_{(1-4)}$alkyl, or —S—CH$_2$-4-methoxy phenyl, wherein A$^1$ and A$^2$ are taken together with their attached nitrogen to form a heterocyclic ring selected from wherein:
R$^a$ is H or C$_{(1-4)}$alkyl; and
R$^b$ is —C$_{(1-4)}$alkyl-OH, —C$_{(1-4)}$alkyl-O-C$_{(1-4)}$alkyl, —C$_{(1-4)}$alkyl-C(O)O-C$_{(1-4)}$alkyl, —C$_{(1-4)}$alkylC(O)OH, or —C$_{(1-4)}$alkylC(O)ONa.

7. A compound selected from the group consisting of:

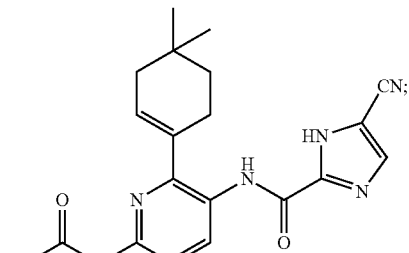

TFA 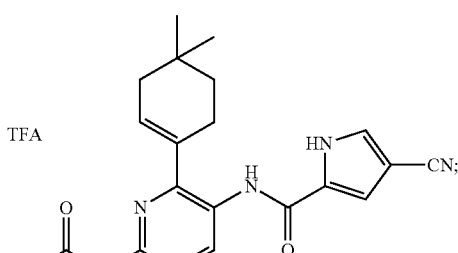

TFA 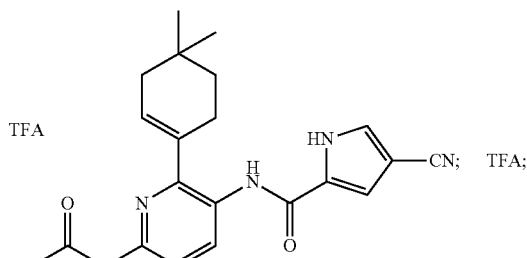 TFA;

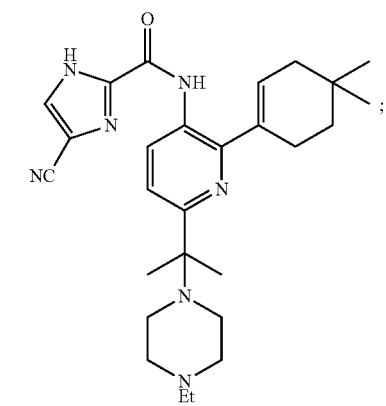

235

236

237
-continued
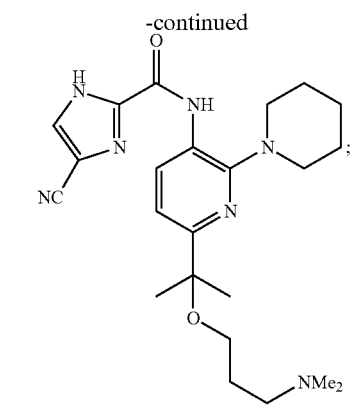
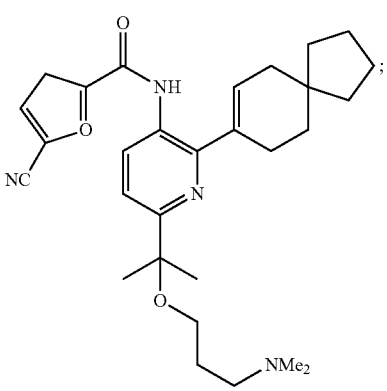
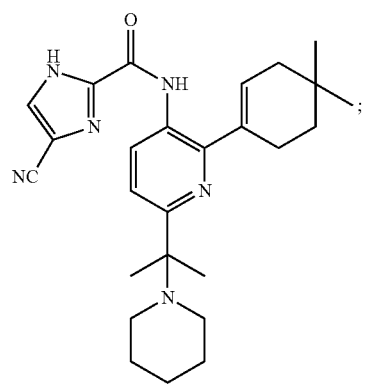
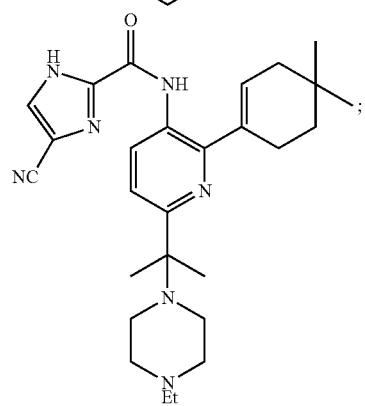
238
-continued
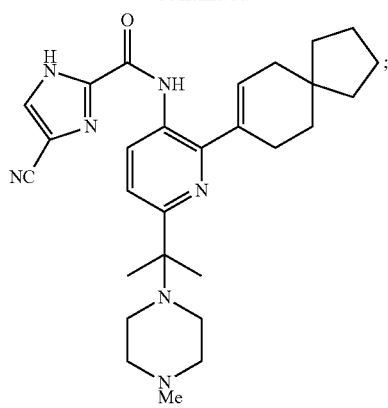
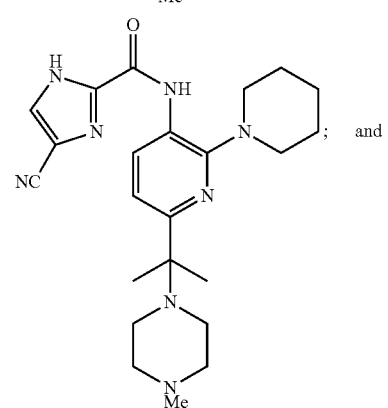; and
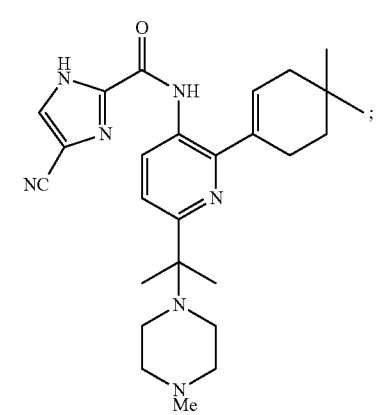 [SMILES: CN1CCN(C(C)(C)c2ccc(NC(=O)c3nc(C#N)c[nH]3)c(C3=CCC(C)(C)CC3)n2)CC1]
or a solvate, hydrate, tautomer or pharmaceutically acceptable salt thereof.
8. A compound of claim 7 selected from the group consisting of:
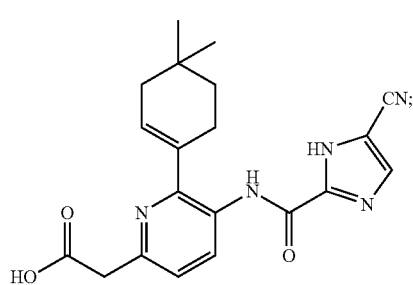

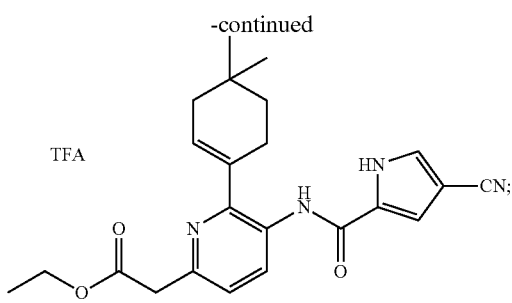

TFA

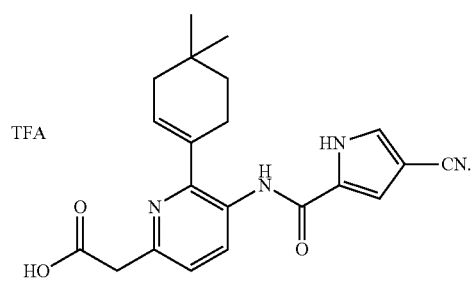 [SMILES: CC1(C)CC=C(c2nc(CC(=O)O)ccc2NC(=O)c2cc(C#N)c[nH]2)CC1]

TFA

9. A compound of Formula I

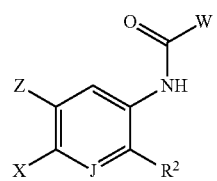

I wherein
W is

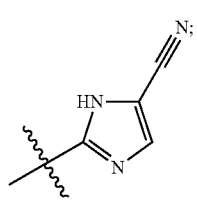 [SMILES: *c1ncc(C#N)[nH]1]

$R^2$ is

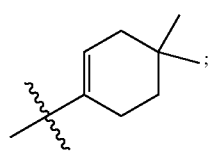 [SMILES: *C1=CCC(C)(C)CC1]

Z is H;
J is N;
X is —$C_{(1-6)}$alkyl$R^1$ wherein:
  $R^1$ is

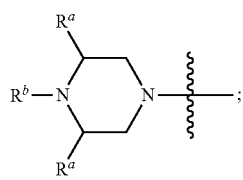

wherein:
  $R^a$ is H or $C_{(1-4)}$alkyl; and
  $R^b$ is —$C_{(1-4)}$alkyl-OH, —$C_{(1-4)}$alkyl-O-$C_{(1-4)}$alkyl, —$C_{(1-4)}$alkyl-C(O)O-$C_{(1-4)}$alkyl, —$C_{(1-4)}$alkylC(O)OH, or —$C_{(1-4)}$alkylC(O)ONa;
or a solvate, hydrate, tautomer or a pharmaceutically acceptable salt thereof.

10. The compound of claim 9, wherein
J is CH;
X is —$C_{(1-4)}$alkyl$R^1$ wherein:

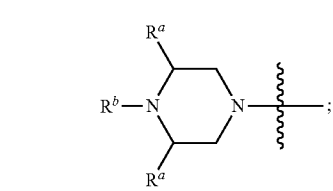

wherein:
  $R^a$ is H; and $R^b$ is —$C_{(1-4)}$alkyl-OH.

11. A pharmaceutical composition, comprising a compound of claim 1 and a pharmaceutically acceptable carrier.

12. A pharmaceutical dosage form comprising a pharmaceutically acceptable carrier and from about 0.5 mg to about 10 g of at least one compound of claim 1.

13. A dosage form according to claim 12 adapted for parenteral or oral administration.

14. A pharmaceutical composition, comprising a compound of claim 9 and a pharmaceutically acceptable carrier.

15. A pharmaceutical dosage form comprising a pharmaceutically acceptable carrier and from about 0.5 mg to about 10 g of at least one compound of claim 9.

16. A dosage form according to claim 15 adapted for parenteral or oral administration.

* * * * *